(12) United States Patent
Guo et al.

(10) Patent No.: US 10,820,582 B2
(45) Date of Patent: Nov. 3, 2020

(54) NON-HUMAN ANIMALS HAVING AN ENGINEERED IMMUNOGLOBULIN Λ LIGHT CHAIN LOCUS

(71) Applicant: Regeneron Pharmaceuticals, Inc., Tarrytown, NY (US)

(72) Inventors: Chunguang Guo, Thornwood, NY (US); Faith Harris, Mamaroneck, NY (US); Vera Voronina, Sleepy Hollow, NY (US); John McWhirter, Tarrytown, NY (US); Natasha Levenkova, New York, NY (US); Lynn Macdonald, Harrison, NY (US); Naxin Tu, Pleasantville, NY (US); Andrew J. Murphy, Croton-On-Hudson, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 19 days.

(21) Appl. No.: 15/803,513

(22) Filed: Nov. 3, 2017

(65) Prior Publication Data
US 2018/0125043 A1 May 10, 2018

Related U.S. Application Data

(60) Provisional application No. 62/567,932, filed on Oct. 4, 2017, provisional application No. 62/417,845, filed on Nov. 4, 2016.

(51) Int. Cl.
| *A01K 67/027* | (2006.01) |
| *C07K 16/00* | (2006.01) |
| *C12N 15/90* | (2006.01) |
| *C12N 15/85* | (2006.01) |

(52) U.S. Cl.
CPC .......... *A01K 67/0278* (2013.01); *C07K 16/00* (2013.01); *C12N 15/907* (2013.01); *A01K 2207/15* (2013.01); *A01K 2217/05* (2013.01); *A01K 2217/072* (2013.01); *A01K 2217/075* (2013.01); *A01K 2227/105* (2013.01); *A01K 2267/01* (2013.01); *C07K 2317/14* (2013.01); *C07K 2317/24* (2013.01); *C12N 2015/8518* (2013.01); *C12N 2800/30* (2013.01)

(58) Field of Classification Search
CPC ................................................. A01K 67/0278
See application file for complete search history.

(56) References Cited

U.S. PATENT DOCUMENTS

| 5,670,356 A | 9/1997 | Sherf et al. |
| 5,874,304 A | 2/1999 | Zolotukhin et al. |
| 6,586,251 B2 | 7/2003 | Economides et al. |
| 6,596,541 B2 | 7/2003 | Murphy et al. |
| 6,998,514 B2 | 2/2006 | Bruggemann |
| 7,105,348 B2 | 9/2006 | Murphy et al. |
| 7,435,871 B2 | 10/2008 | Green et al. |
| 8,502,018 B2 | 8/2013 | Murphy et al. |
| 8,642,835 B2 | 2/2014 | MacDonald et al. |
| 8,697,940 B2 | 4/2014 | MacDonald et al. |
| 8,791,323 B2 | 7/2014 | Murphy et al. |
| 9,006,511 B2 | 4/2015 | MacDonald et al. |
| 9,012,717 B2 | 4/2015 | MacDonald et al. |
| 9,029,628 B2 | 5/2015 | MacDonald et al. |
| 9,035,128 B2 | 5/2015 | MacDonald et al. |
| 9,066,502 B2 | 6/2015 | MacDonald et al. |
| 9,150,662 B2 | 10/2015 | MacDonald et al. |
| 9,163,092 B2 | 10/2015 | MacDonald et al. |
| 9,228,208 B2 | 1/2016 | Frendewey et al. |
| 2002/0088016 A1 | 7/2002 | Bruggemann |
| 2003/0217373 A1 | 11/2003 | Green et al. |
| 2011/0236378 A1 | 9/2011 | Green et al. |
| 2013/0096087 A1 | 4/2013 | Van Der Beek et al. |
| 2014/0235933 A1 | 8/2014 | Lee et al. |
| 2014/0283150 A1 | 9/2014 | Bradley et al. |
| 2015/0159174 A1 | 6/2015 | Frendewey et al. |

(Continued)

FOREIGN PATENT DOCUMENTS

| WO | WO-02/36789 A2 | 5/2002 |
| WO | WO-2011/163311 A1 | 12/2011 |

(Continued)

OTHER PUBLICATIONS

Garcia-Arocena D. (2014, The Jackson Laboratory, Same Mutation, Different Phenotype?) (Year: 2014).*
Heimain-Patterson et al. (2011, Amyotrophic Lateral Schlerosis, vol. 00, pp. 1-8) (Year: 2011).*
2004, Barthold S., Genetica, vol. 122, pp. 75-88 (Year: 2004).*
Tong et al. (2010, Nature, vol. 467(7312), pp. 211-213) (Year: 2010).*
Hong et al. (2012, Stem Cells and Development, vol. 21(9), pp. 1571-1586) (Year: 2012).*

(Continued)

*Primary Examiner* — Thaian N. Ton
*Assistant Examiner* — David A. Montanari
(74) *Attorney, Agent, or Firm* — Choate Hall & Stewart LLP; Stephanie L. Schonewald; Meaghan E. Bychowski

(57) ABSTRACT

Non-human animals (and/or non-human cells) and methods of using and making the same are provided, which non-human animals (and/or non-human cells) have a genome comprising human antibody-encoding sequences (i.e., immunoglobulin genes). Non-human animals described herein express antibodies that contain human Igλ light chains, in whole or in part. In particular, non-human animals provided herein are, in some embodiments, characterized by expression of antibodies that contain human Igλ light chains, in whole or in part, that are encoded by human Igλ light chain-encoding sequences inserted into an endogenous Igλ light chain locus of said non-human animals. Methods for producing antibodies from non-human animals are also provided.

21 Claims, 26 Drawing Sheets

Specification includes a Sequence Listing.

(56) References Cited

U.S. PATENT DOCUMENTS

| | | |
|---|---|---|
| 2015/0376628 A1 | 12/2015 | Schoenherr et al. |
| 2015/0376650 A1 | 12/2015 | Auerbach et al. |
| 2016/0060657 A1 | 3/2016 | Frendewey et al. |
| 2016/0177339 A1 | 6/2016 | Voronina et al. |

FOREIGN PATENT DOCUMENTS

| | | |
|---|---|---|
| WO | WO 2013/096142 A1 | 6/2013 |
| WO | WO-2018/128691 A1 | 7/2018 |

OTHER PUBLICATIONS

Altschul, S.F. and Gish, W., Local alignment statistics. Methods Enzymol, 266:460-80 (1996).
Altschul, S.F. et al., Basic local alignment search tool, J Mol Biol, 215(3):403-10 (1990).
Altschul, S.F. et al., Gapped BLAST and PSI-BLAST: a new generation of protein database search programs, Nucleic Acids Res, 25(17):3389-402 (1997).
Araki, K. et al., Site-specific recombination of a transgene in fertilized eggs by transient expression of Cre recombinase, Proc Natl Acad Sci USA, 92(1):160-4 (1995).
Asenbauer, H. and Klobeck, H.G., Tissue-specific deoxyribonuclease I-hypersensitive sites in the vicinity of the immunoglobulin C lambda cluster of man, Eur J Immunol, 26(1):142-50 (1996).
Auerbach, W. et al., Establishment and chimera analysis of 129/SvEv- and C57BL/6-derived mouse embryonic stem cell lines, Biotechniques, 29(5):1024-8, 1030, 1032 (2000).
Azzazy, H.M. and Highsmith, W.E. Jr., Phage display technology: clinical applications and recent innovations, Clin Biochem, 35(6):425-45 (2002).
Bruggemann et al., A repertoire of monoclonal antibodies with human heavy chains from transgenic mice, Proc. Natl. Acad. Sci. USA, 86: 6709-6713, 1989.
Bruggemann, M. et al., Human antibody production in transgenic mice: expression from 100 kb of the human IgH locus, Eur J Immunol, 21(5):1323-6 (1991).
Davies, N. et al., Creation of Mice Expressing Human Antibody Light Chains by Introduction of a Yeast Artificial Chromosome Containing the Core Region of the Human Immunoglobulin κ Locus, Nature Biotechnology 11:911-914, (1993).
Dechiara, T.M. et al., Producing fully ES cell-derived mice from eight-cell stage embryo injections, Methods Enzymol, 476:285-94 (2010).
Dechiara, T.M. et al., VelociMouse: fully ES cell-derived F0-generation mice obtained from the injection of ES cells into eight-cell-stage embryos, Methods Mol Biol, 530:311-24 (2009).
Dunham, I. et al., The DNA sequence of human chromosome 22, Nature, 402(6761):489-95 (1999).
Dymecki, S.M., Flp recombinase promotes site-specific DNA recombination in embryonic stem cells and transgenic mice, Proc Natl Acad Sci USA, 93(12):6191-6 (1996).
Festing, M.F. et al., Revised nomenclature for strain 129 mice, Mamm Genome, 10(8):836 (1999).
Fishwild, D.M. et al., High-avidity human IgG kappa monoclonal antibodies from a novel strain of minilocus transgenic mice, Nat Biotechnol, 14(7):845-51 (1996).
Frendewey, D. et al., The loss-of-allele assay for ES cell screening and mouse genotyping, Methods Enzymol, 476:295-307 (2010).
Gavilondo, J.V. and Larrick, J.W., Antibody engineering at the millennium, Biotechniques, 29(1):128-32 (2000).
Gonnett, G.H. et al., Exhaustive matching of the entire protein sequence database, Science, 256(5062):1443-5 (1992).
Green, L. et al., Antigen-specific human monoclonal antibodies from mice engineered with human Ig heavy and light chain YACs, Nat. Genet., 7(1):13-21 (1994).
Green, L. et al., Regulation of B cell development by variable gene complexity in mice reconstituted with human immunoglobulin yeast artificial chromosomes, J. Exp. Med., 188(3):483-495 (1998).
Gu, H. et al., Independent control of immunoglobulin switch recombination at individual switch regions evidenced through Cre-loxP-mediated gene targeting, Cell, 73(6):1155-64 (1993).
Hoogenboom, H.R., Designing and optimizing library selection strategies for generating high-affinity antibodies, Trends Biotechnol, 15(2):62-70 (1997).
Hoogenboon, H.R. and Chames, P., Natural and designer binding sites made by phage display technology, Immunol Today, 21(8):371-8 (2000).
Jakobovits, A. et al., Production of antigen-specific human antibodies from mice engineered with human heavy and light chain YACs, Ann Ny Acad Sci, 764:525-35 (1995).
Kellermann, S.A. and Green, L.L., Antibody discovery: the use of transgenic mice to generate human monoclonal antibodies for therapeutics, Curr Opin Biotechnol, 13(6):593-7 (2002).
Kim, U.J. et al., Construction and characterization of a human bacterial artificial chromosome library, Genomics, 34(2):213-8 (1996).
Lakso, M. et al., Targeted oncogene activation by site-specific recombination in transgenic mice, Proc Natl Acad Sci USA, 89(14):6232-6 (1992).
Lee, E.C. et al., Complete humanization of the mouse immunoglobulin loci enables efficient therapeutic antibody discovery, Nat Biotechnol, 32(4):356-63 (2014).
Little, M. et al., Of mice and men: hybridoma and recombinant antibodies, Immunol Today, 21(8):364-70 (2000).
Lonberg, N. et al., Antigen-specific Human Antibodies from Mice Comprising Four Distinct Genetic Modifications, Nature, 368:856-859, (1994).
Macdonald, L.E. et al., Precise and in situ genetic humanization of 6 Mb of mouse immunoglobulin genes, Proc Natl Acad Sci USA, 111(14):5147-52 (2014).
Mendez M.J., et al., Functional transplant of megabase human immunoglobulin loci recapitulates human antibody response in mice, Nat Genet. 15(2):146-56 (1997).
Moraes, J. et al., Genomic EcoRI polymorphism and cosmid sequencing reveal an insertion/deletion and a new IGLV5 allele in the human immunoglobulin lambda variable locus (22q11.2/IGLV), Immunogenetics, 55(1):10-5 (2003).
Murphy, A.J. et al., Mice with megabase humanization of their immunoglobulin genes generate antibodies as efficiently as normal mice. Proc Natl Acad Sci USA, 111(14):5153-8 (2014).
Nicholson, I.C. et al., Antibody Repertoires of Four- and Five-Feature Translocus Mice Carrying Human Immunoglobulin Heavy Chain and kappa and lambda light chain Yeast Artificial Chromosomes. Journal of Immunology 163(12):6898-6906 (1999).
O'Gorman, S. et al., Recombinase-mediated gene activation and site-specific integration in mammalian cells, Science, 251(4999):1351-5 (1991).
Orban, P.C. et al., Tissue- and site-specific DNA recombination in transgenic mice, Proc Natl Acad Sci USA, 89(15):6861-5 (1992).
Osborn, M.J. et al., High-affinity IgG antibodies develop naturally in Ig-knockout rats carrying germline human IgH/Igκ/IgΛ loci bearing the rat CH region, J Immunol, 190(4):1481-90 (2013).
Osoegawa, K. et al., A bacterial artificial chromosome library for sequencing the complete human genome, Genome Res, 11(3):483-96 (2001).
Osoegawa, K. et al., An improved approach for construction of bacterial artificial chromosome libraries, Genomics, 52(1):1-8 (1998).
Popov, A.V. et al., Assembly and extension of yeast artificial chromosomes to build up a large locus, Gene, 177(1-2):195-201 (1996).
Popov, et al., A Human Immunoglobulin I locus is Similarly Well Expressed in Mice and Humans, J. Exp. Med., 189(10):1611-1619(1999).
Poueymirou, W.T. et al., F0 generation mice fully derived from gene-targeted embryonic stem cells allowing immediate phenotypic analyses, Nat Biotechnol, 25(1):91-9 (2007).
Rajewsky, K. et al., Conditional gene targeting, J Clin Invest, 98(3):600-3 (1996).
Shizuya, H. et al., Cloning and stable maintenance of 300-kilobase-pair fragments of human DNA in *Escherichia coli* using an F-factor-based vector, Proc Natl Acad Sci USA, 89(18):8794-7 (1992).

(56) References Cited

OTHER PUBLICATIONS

Swiatek, P.J. and Gridley, T., Perinatal lethality and defects in hindbrain development in mice homozygous for a targeted mutation of the zinc finger gene Krox20, Genes Dev, 7(11):2071-84 (1993).
Taylor L.D. et al., Human immunoglobulin transgenes undergo rearrangement, somatic mutation and class switching in mice that lack endogenous IgM, Int Immunol. 6(4):579-91 (1994).
Taylor, L.D. et al., A Transgenic Mouse that Expresses a Diversity of Human Sequence Heavy and Light Chain Immunoglobulins, Nucleic Acid Research, 20(23):6287-6295 (1992).
Valenzuela, D.M., et al., High-throughput engineering of the mouse genome coupled with high-resolution expression analysis, Nat Biotechnol, 21(6):652-9 (2003).
Wagner S.D. et al., The diversity of antigen-specific monoclonal antibodies from transgenic mice bearing human immunoglobulin gene miniloci, Eur J Immunol. 24(11):2672-81 (1994).
Wagner, S.D. et al., Antibody expression from the core region of the human IgH locus reconstructed in transgenic mice using bacteriophage P1 clones, Genomics, 35(3):405-14 (1996).
Xian, J. et al., Comparison of the Performance of a Plasmid-Based Human IgK Minilocus and Yac-Based Human Igκ Transloci for the Production of Human Antibody Repertoires in Transgenic Mice, Transgenics, 2:333-343 (1998).
International Search Report for PCT/US2017/060006 (Non-Human Animals Having an Engineered Immunoglobulin Lambda Light Chain Locus, filed Nov. 3, 2017), issued by ISA/EP, 7 pages (dated Jun. 19, 2018).
Written Opinion for PCT/US2017/060006 (Non-Human Animals Having an Engineered Immunoglobulin Lambda Light Chain Locus, filed Nov. 3, 2017), issued by ISA/EP, 7 pages (dated Jun. 19, 2018).
Glassy, M. et al., Final Oral Progamme, The Twelfth International Conference on Human Antibodies & Hybridomas, 4 pages (May 10-12, 2006).
Glassy, M. et al., Second Circular and Provisional Conference Program, The Twelfth International Conference on Human Antibodies & Hybridomas, 8 pages (May 10-12, 2006).
Karow, Margaret, Making the VelocImmune mouse using Velocigene technology [abstract], Session 5: Molecular biology—II, Human Antibodies, 15:19-28 (2006).
Murphy, Andrew, Making the VelocImmune Mouse Using VelociGene Technology, Human Antibodies & Hybridomas, 31 pages (May 10-12, 2006).

* cited by examiner

Figure 11A mIgλ 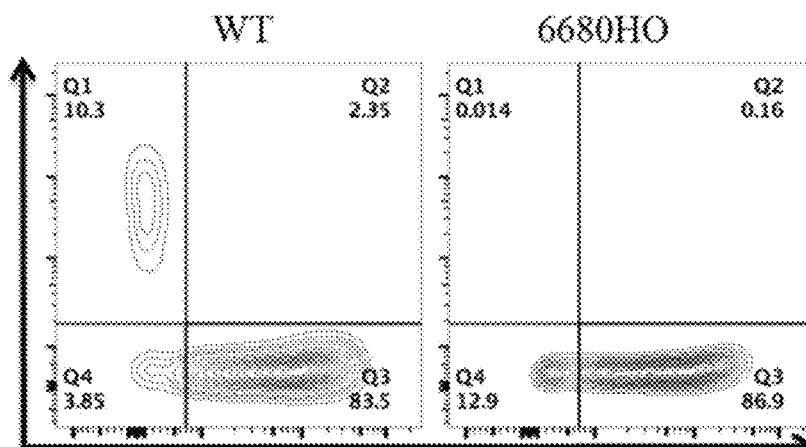
Figure 11B hIgλ 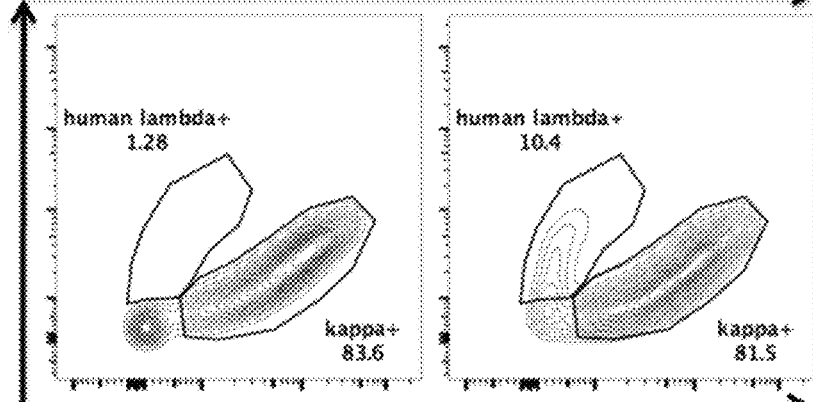
mIgκ

Figure 12A  mIgλ
Figure 12B  hIgλ
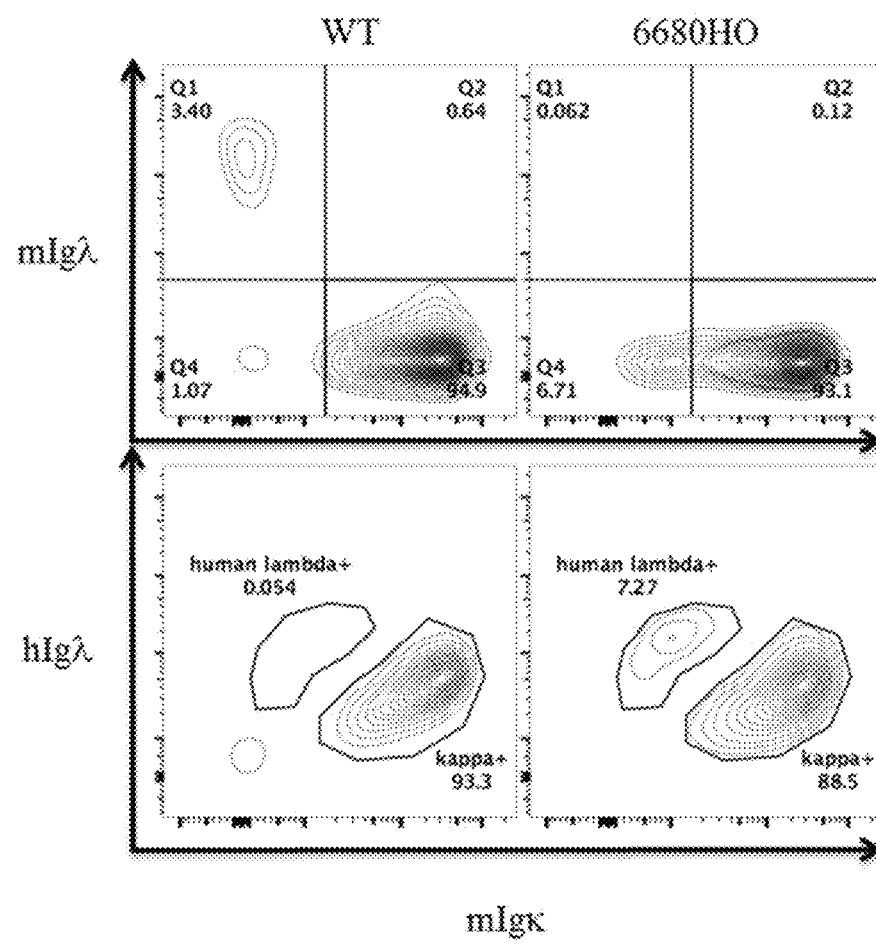
mIgκ

| spleen | 6571HET | 6571HO | 6597HET | 6680HET | 6680HO | 6680HO V1 HO Adam6 HO | 6889HET | 6889HO V1 HO Adam6 HO |
|---|---|---|---|---|---|---|---|---|
| % κC | 92 ± 0.4 | 81 ± 1.1 | 84 ± 0.4 | 87 ± 0.5 | 82 ± 2.2 | 67 ± 7.6 | 87 ± 0.7 | 59 ± 2.1 |
| % hum λC | 2.2 ± 0 | 7.1 ± 0.1 | 12.4 ± 0.5 | 9.9 ± 0.5 | 10 ± 1.1 | 29 ± 8.2 | 6.6 ± 0.3 | 37 ± 2.2 |

| immature BM | 6571HET | 6571HO | 6597HET | 6680HET | 6680HO | 6680HO V1 HO Adam6 HO | 6889HET | 6889HO V1 HO Adam6 HO |
|---|---|---|---|---|---|---|---|---|
| % κC | 88 ± 0.2 | 84 ± 1.6 | 86 ± 0.4 | 83 ± 1.3 | 77 ± 2.4 | 54 ± 13 | 80 ± 0.7 | 52 ± 3.2 |
| % hum λC | 3.3 ± 0.0 | 3.2 ± 0.3 | 7.2 ± 0.3 | 9.7 ± 1.2 | 12 ± 1.0 | 33 ± 8.6 | 7.3 ± 0.6 | 43 ± 2.8 |

| mature BM | 6571HET | 6571HO | 6597HET | 6680HET | 6680HO | 6680HO V1 HO Adam6 HO | 6889HET | 6889HO V1 HO Adam6 HO |
|---|---|---|---|---|---|---|---|---|
| % κC | 90 ± 0.8 | 92 ± 0.7 | 89 ± 0.5 | 92 ± 1.3 | 88 ± 1.2 | 76 ± 6.3 | 89 ± 0.5 | 66 ± 1.7 |
| % hum λC | 2.7 ± 0.0 | 5.6 ± 0.7 | 8.9 ± 0.5 | 7.6 ± 0.9 | 6.8 ± 0.8 | 16 ± 5.4 | 5.2 ± 0.4 | 31 ± 1.6 |

Figure 13

Mouse anti-human lambda

Goat anti-mouse lambda

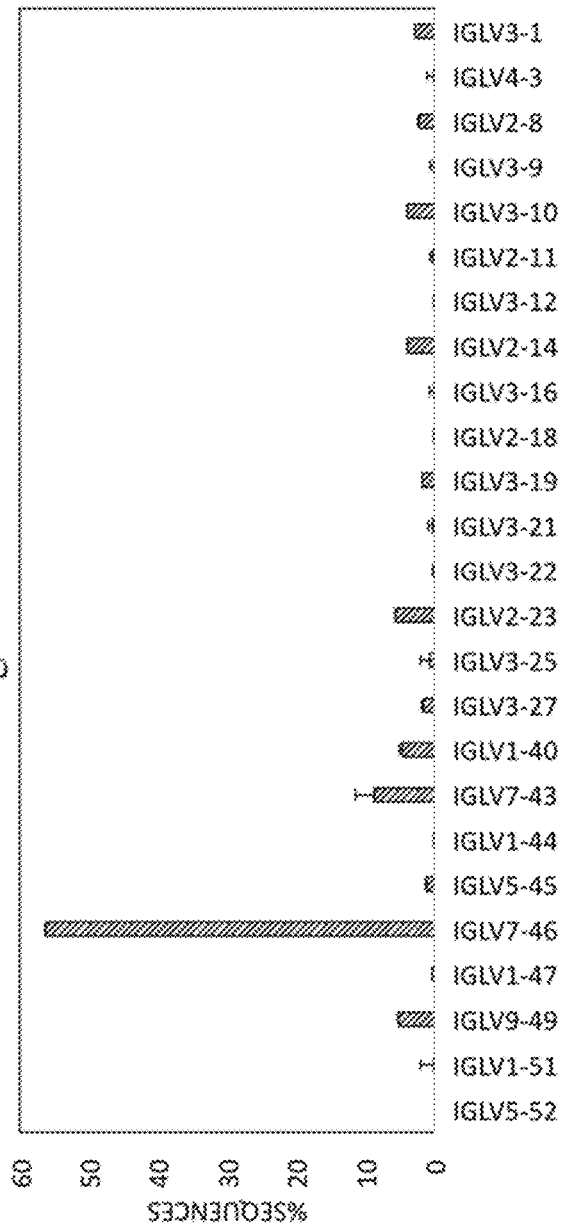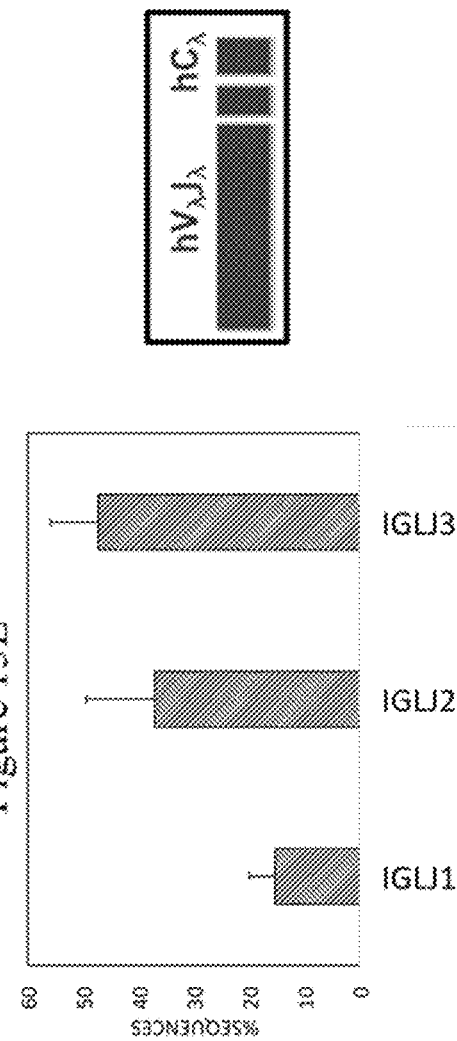

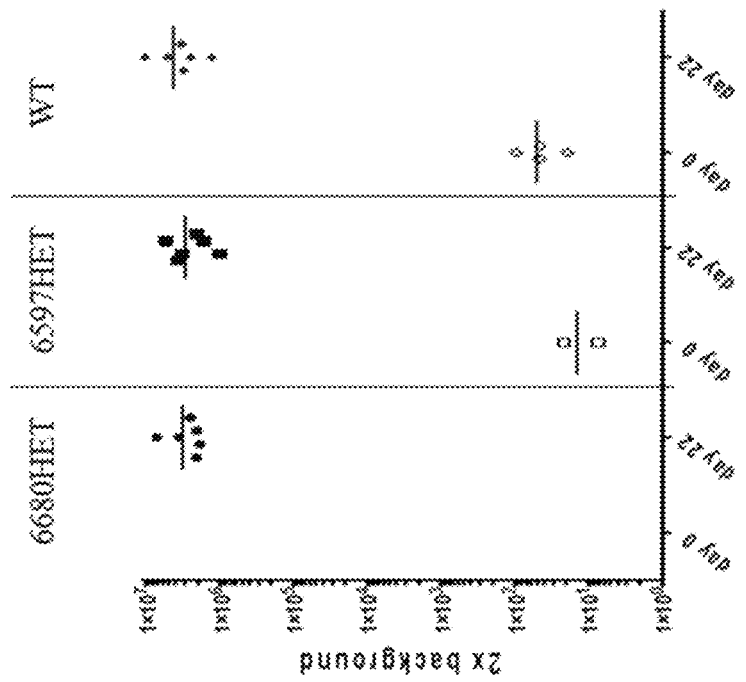
Figure 16A  Total IgG
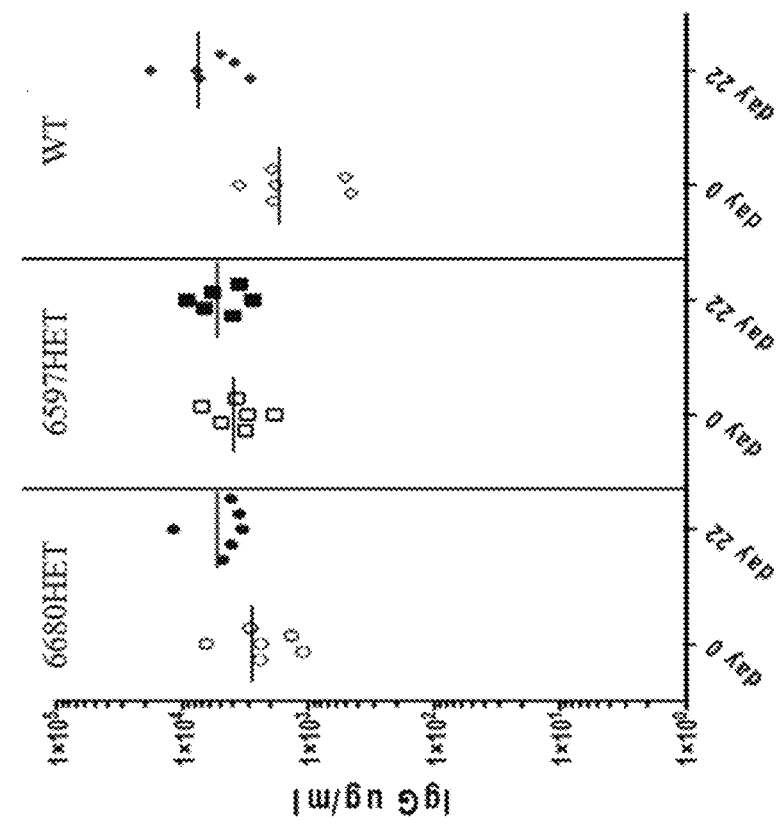
Figure 16B  Antigen-specific IgG

NON-HUMAN ANIMALS HAVING AN ENGINEERED IMMUNOGLOBULIN λ LIGHT CHAIN LOCUS

RELATED APPLICATIONS

This application claims the benefit of priority to U.S. Provisional Patent Application Ser. No. 62/417,845, filed Nov. 4, 2016, and U.S. Provisional Patent Application Ser. No. 62/567,932, filed Oct. 4, 2017, each of which is hereby incorporated by reference in its entirety.

SEQUENCE LISTING

The instant application contains a Sequence Listing which has been submitted electronically in ASCII format and is hereby incorporated by reference in its entirety. Said ASCII copy, created on Nov. 21, 2017, is named RPB-01801_SL.txt and is 41,337 bytes in size.

BACKGROUND

Human antibodies are the most rapidly growing class of therapeutics. Of the technologies that are currently used for their production, the development of transgenic animals (e.g., rodents) engineered with genetic material encoding human antibodies, in whole or in part, has revolutionized the field of human therapeutic monoclonal antibodies for the treatment of various diseases. Still, development of improved in vivo systems for generating human monoclonal antibodies that maximize human antibody repertoires in host transgenic animals is needed.

SUMMARY

In certain aspects, provided herein are improved in vivo systems for identifying and developing new antibody and antibody-based therapeutics that can be used for the treatment of a variety of diseases that affect humans. As disclosed herein, in certain embodiments the non-human animals (e.g., rodents) provided herein, having engineered immunoglobulin loci, in particular, engineered immunoglobulin (Ig)λ light chain loci and/or otherwise expressing, producing or containing antibody repertoires characterized by light chains having human Vλ regions, are useful, for example, for exploiting the diversity of human Vλ sequences in the identification and development of new antibody-based therapeutics. In some embodiments, non-human animals described herein provide improved in vivo systems for development of antibodies and/or antibody-based therapeutics for administration to humans. In some embodiments, non-human animals described herein provide improved in vivo systems for development of antibodies and/or antibody-based therapeutics that contain human Vλ domains characterized by improved performance as compared to antibodies and/or antibody-based therapeutics obtained from existing in vivo systems that contain human Vλ region sequences.

In certain aspects, provided herein is a non-human animal having an Igλ light chain locus that contains engineered immunoglobulin variable and constant regions; in some certain embodiments, further comprises engineered regulatory region (or sequence). As described herein, in certain embodiments the provided non-human animals, contain in their germline genome an Igλ light chain locus comprising an engineered Igλ light chain variable region characterized by the presence of one or more human Vλ gene segments, one or more human Jλ gene segments, one or more human Cλ region genes and a rodent Cλ region gene, which human Vλ, Jλ and Cλ gene segments are operably linked to each other and operably linked to said rodent Cλ region gene.

In some embodiments, provided non-human animals comprise an Igλ light chain locus that comprises at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24 or at least 25 human Vλ gene segments.

In some embodiments, provided non-human animals comprise an Igλ light chain locus that comprises 5 to 25, 5 to 24, 5 to 23, 5 to 22, 5 to 21, 5 to 20, 5 to 19, 5 to 18, 5 to 17, 5 to 16, 5 to 15, 5 to 14, 5 to 13, 5 to 12, 5 to 11, 5 to 10, 5 to 9, 5 to 8, 5 to 7, or 5 to 6 human Vλ gene segments. In some embodiments, provided non-human animals comprise an Igλ light chain locus that comprises 10 to 70, 10 to 69, 10 to 68, 10 to 67, 10 to 66, 10 to 65, 10 to 64, 10 to 63, 10 to 62, 10 to 61, 10 to 60, 10 to 59, 10 to 58, 10 to 57, 10 to 56, 10 to 55, 10 to 54, 10 to 53, 10 to 52, 10 to 51, 10 to 50, 10 to 49, 10 to 48, 10 to 47, 10 to 46, 10 to 45, 10 to 44, 10 to 43, 10 to 42, 10 to 41, 10 to 40, 10 to 39, 10 to 38, 10 to 37, 10 to 36, 10 to 35, 10 to 34, 10 to 33, 10 to 32, 10 to 31, 10 to 32, 10 to 31, 10 to 30, 10 to 29, 10 to 28, 10 to 27, 10 to 26, 10 to 25, 10 to 24, 10 to 23, 10 to 22, 10 to 21, 10 to 20, 10 to 19, 10 to 18, 10 to 17, 10 to 16, 10 to 15, 10 to 14, 10 to 13, 10 to 12, or 10 to 11 human Vλ gene segments.

In some embodiments, provided non-human animals comprise an Igλ light chain locus that comprises 6 to 25, 7 to 25, 8 to 25, 9 to 25, 10 to 25, 11 to 25, 12 to 25, 13 to 25, 14 to 25, 15 to 25, 16 to 25, 17 to 25, 18 to 25, 19 to 25, 20 to 25, 21 to 25, 22 to 25, 23 to 25, or 24 to 25 human Vλ gene segments. In some embodiments, provided non-human animals comprise an Igλ light chain locus that comprises 11 to 70, 12 to 70, 13 to 70, 14 to 70, 15 to 70, 16 to 70, 17 to 70, 18 to 70, 19 to 70, 20 to 70, 21 to 70, 22 to 70, 23 to 70, 24 to 70, 25 to 70, 26 to 70, 27 to 70, 28 to 70, 29 to 70, 30 to 70, 31 to 70, 32 to 70, 33 to 70, 34 to 70, 35 to 70, 36 to 70, 37 to 70, 38 to 70, 39 to 70, 40 to 70, 41 to 70, 42 to 70, 43 to 70, 44 to 70, 45 to 70, 46 to 70, 47 to 70, 48 to 70, 49 to 70, 50 to 70, 51 to 70, 52 to 70, 53 to 70, 54 to 70, 55 to 70, 56 to 70, 57 to 70, 58 to 70, 59 to 70, 60 to 70, 61 to 70, 62 to 70, 63 to 70, 64 to 70, 65 to 70, 66 to 70, 67 to 70, 68 to 70, or 69 to 70 human Vλ gene segments.

In some embodiments, provided non-human animals comprise an Igλ light chain locus that comprises 6 to 24, 7 to 23, 8 to 22, 9 to 21, 10 to 20, 11 to 19, 12 to 18, 13 to 17, 14 to 16, or 15 to 16 human Vλ gene segments. In some embodiments, provided non-human animals comprise an Igλ light chain locus that comprises 11 to 69, 12 to 68, 13 to 67, 14 to 66, 15 to 65, 16 to 64, 17 to 63, 18 to 62, 19 to 61, 20 to 60, 21 to 59, 22 to 58, 23 to 57, 24 to 56, 25 to 55, 26 to 54, 27 to 53, 28 to 52, 29 to 51, 30 to 50, 31 to 49, 32 to 48, 33 to 47, 34 to 48, 35 to 47, 36 to 46, 37 to 45, 38 to 44, 39 to 43, 40 to 42, or 41 to 42 human Vλ gene segments.

In certain embodiments, provided non-human animals comprise an Igλ light chain locus that comprises 5, 16 or 25 functional human Vλ gene segments. In certain embodiments, provided non-human animals comprise an Igλ light chain locus that comprises 10, 27 or 40 human Vλ gene segments. In certain embodiments, human Vλ gene segments include consecutive human Vλ gene segments as said human Vλ gene segments appear in a human Igλ light chain locus of a human cell.

In some embodiments, provided non-human animals comprise an Igλ light chain locus that comprises at least 5 human Jλ gene segments (e.g., but not limited to, 5 human Jλ gene segments, 6 human Jλ gene segments, 7 human Jλ gene segments, 8 human Jλ gene segments, etc.). In some embodiments, provided non-human animals comprise an Igλ light chain locus that comprises at least 4 human Cλ region genes (e.g., but not limited to, 4 human Cλ region genes, 5 human Cλ region genes, 6 human Cλ region genes, 7 human Cλ region genes, 8 human Cλ region genes, etc.). In certain embodiments, provided non-human animals comprise an Igλ light chain locus that comprises at least 25 human Vλ gene segments, at least 5 human Jλ gene segments and at least 4 human Cλ region genes at an endogenous Igλ light chain allele. In some embodiments, provided non-human animals comprise only one murine (e.g., mouse or rat) Cλ region gene (e.g., a mouse Cλ1 region gene or a mouse Cλ1 gene segment) at an endogenous non-human Igλ light chain locus. In some embodiments, said Igλ light chain locus further comprises a human Eλ region (or sequence) that is characterized by three sequence elements.

In some embodiments, provided non-human animals contain human Vλ, Jλ and Cλ gene segments at an endogenous non-human Igλ light chain locus in natural or germline configuration. In some embodiments, provided non-human animals contain human Vλ, Jλ and Cλ gene segments at an endogenous non-human Igλ light chain locus in a configuration that does not naturally appear in a human immunoglobulin λ light chain locus of the germline genome of a human cell.

In some embodiments, provided non-human animals contain a DNA sequence at an endogenous non-human Igλ light chain locus that includes a plurality of human Vλ, Jλ and Cλ coding sequences interspersed (or juxtaposed, associated, etc.) with non-coding human immunoglobulin λ light chain sequence. In some embodiments, provided non-human animals contain a DNA sequence at an endogenous non-human Igλ light chain locus that includes a plurality of human Vλ, Jλ and Cλ coding sequences interspersed with non-coding non-human (e.g., murine) immunoglobulin λ light chain sequence.

In some embodiments, provided non-human animals are characterized by expression of antibodies from endogenous non-human Igλ light chain loci in the germline genome of said non-human animals, which antibodies contain human Vλ domains and human or non-human Cλ domains. In some embodiments, provided non-human animals are characterized by an increased usage of human Vλ regions from engineered immunoglobulin λ light chain loci (e.g., a 60:40 κ:λ ratio) as compared to one or more reference engineered or wild-type non-human animals (e.g., but not limited to, a 95:5 κ:λ ratio).

In some embodiments, a non-human animal, non-human cell or non-human tissue is provided whose genome comprises an endogenous immunoglobulin λ light chain locus comprising insertion of one or more human Vλ gene segments, one or more human Jλ gene segments and one or more human Cλ gene segments, which human Vλ, Jλ and Cλ gene segments are operably linked to a non-human Cλ gene segment, and which endogenous immunoglobulin λ light chain locus further comprises one or more non-human immunoglobulin λ light chain enhancers (Eλ) and one or more human immunoglobulin λ light chain enhancers (Eλ).

In some embodiments, a non-human animal, non-human cell or non-human tissue is provided whose germline genome comprises an endogenous immunoglobulin λ light chain locus comprising: (a) one or more human Vλ gene segments, (b) one or more human Jλ gene segments, and (c) one or more human Cλ gene segments, wherein (a) and (b) are operably linked to (c) and a non-human Cλ gene segment, and wherein the endogenous immunoglobulin λ light chain locus further comprises: one or more non-human immunoglobulin λ light chain enhancers (Eλ), and one or more human immunoglobulin λ light chain enhancers (Eλ).

In some embodiments, an endogenous immunoglobulin λ light chain locus provided herein further comprises three human Eλs. In some embodiments, an endogenous immunoglobulin λ light chain locus further comprises one human Eλ characterized by the presence of three sequence elements. In some certain embodiments, an endogenous immunoglobulin λ light chain locus further comprises one human Eλ characterized by the presence of three sequence elements that act (or function) in modular fashion.

In some embodiments, an endogenous immunoglobulin λ light chain locus provided herein comprises two non-human Eλs. In some certain embodiments, an endogenous immunoglobulin λ light chain locus comprises two rodent Eλs. In some certain embodiments, an endogenous immunoglobulin λ light chain locus provided herein comprises two mouse Eλs. In some certain embodiments, an endogenous immunoglobulin λ light chain locus comprises a mouse Eλ and a mouse Eλ3-1. In some certain embodiments, an endogenous immunoglobulin λ light chain locus provided herein does not contain (or lacks) a mouse Eλ2-4. In some certain embodiments, an endogenous immunoglobulin λ light chain locus comprises two rat Eλs.

In some embodiments, an endogenous immunoglobulin λ light chain locus provided herein comprises a deletion of endogenous Vλ and Jλ gene segments, in whole or in part. In some certain embodiments, an endogenous immunoglobulin λ light chain locus provided herein comprises a deletion of Vλ2-Vλ3-Jλ2-Cλ2 gene segments and Vλ1-Jλ3-Cλ3-Jλ1 gene segments. In some certain embodiments, an endogenous immunoglobulin λ light chain locus comprises a deletion of Vλ2-Vλ3-Jλ2-Cλ2-Jλ4P-Cλ4P gene segments and Vλ1-Jλ3-Jλ3P-Cλ3-Jλ1 gene segments. In some embodiments, an endogenous immunoglobulin λ light chain locus provided herein comprises a deletion of a non-human Eλ2-4. In some certain embodiments, an endogenous immunoglobulin λ light chain locus provided herein comprises a deletion of Vλ2, Vλ3, Jλ2, Cλ2, Jλ4P, Cλ4P, Eλ2-4, Vλ1, Jλ3, Jλ3P, Cλ3 and Jλ1. In some certain embodiments, an endogenous immunoglobulin λ light chain locus provided herein comprises Cλ1, Eλ and Eλ3-1 as the only non-human gene segments or sequence elements present.

In some embodiments, an endogenous immunoglobulin λ light chain locus provided herein comprises insertion of the human Vλ gene segments Vλ4-69 to Vλ3-1, at least the human Jλ-Cλ gene segment pairs Jλ1-Cλ1, Jλ2-Cλ2, Jλ3-Cλ3, Jλ6-Cλ6, the human Jλ gene segment Jλ7 and a rodent Cλ1 gene segment. In some embodiments, an endogenous immunoglobulin λ light chain locus provided herein comprises insertion of the human Vλ gene segments Vλ5-52 to Vλ3-1, at least the human Jλ-Cλ gene segment pairs Jλ1-Cλ1, Jλ2-Cλ2, Jλ3-Cλ3, Jλ6-Cλ6, the human Jλ gene segment Jλ7 and a rodent Cλ1 gene segment. In some embodiments, an endogenous immunoglobulin λ light chain locus provided herein comprises insertion of the human Vλ gene segments Vλ5-52 to Vλ1-40 and Vλ3-27 to Vλ3-1, at least the human Jλ-Cλ gene segment pairs Jλ1-Cλ1, Jλ2-Cλ2, Jλ3-Cλ3, Jλ6-Cλ6, the human Jλ gene segment Jλ7 and a rodent Cλ1 gene segment. In some certain embodiments, the insertion includes human non-coding DNA that naturally appears between human Vλ5-52 to Vλ1-40 and Vλ3-27 to Vλ3-1, human non-coding DNA that naturally appears between human Jλ-Cλ gene segment pairs Jλ1-Cλ1, Jλ2-Cλ2, Jλ3-Cλ3 and Jλ6-Cλ6, and human non-coding DNA that naturally appears upstream (or 5') of human Jλ gene segment Jλ7.

In some embodiments, a non-human Cλ gene segment is or comprises a rodent Cλ gene segment. In some embodiments, a rodent Cλ gene segment is or comprises a murine (e.g., mouse or rat) Cλ gene segment. In some embodiments, a rodent Cλ gene segment is or comprises a rat Cλ gene segment. In some embodiments, a rodent Cλ gene segment is or comprises a mouse Cλ gene segment. In some certain embodiments, a rodent Cλ gene segment is a mouse Cλ1 gene segment.

In some embodiments, a mouse Cλ gene (or gene segment) comprises a sequence that is at least 50%, at least 55%, at least 60%, at least 65%, at least 70%, at least 75%, at least 80%, at least 85%, at least 90%, at least 95%, at least 98% identical or 100% identical to a mouse Cλ gene selected from the group consisting of a mouse Cλ1, mouse Cλ2 and a mouse Cλ3. In some embodiments, a mouse Cλ gene comprises a sequence that is substantially identical or identical to a mouse Cλ gene selected from the group consisting of a mouse Cλ1, mouse Cλ2 and a mouse Cλ3. In some certain embodiments, a mouse Cλ1 gene is or comprises SEQ ID NO:1. In some certain embodiments, a mouse Cλ2 gene is or comprises SEQ ID NO:3. In some certain embodiments, a mouse Cλ3 gene is or comprises SEQ ID NO:5. In some certain embodiments, a mouse Cλ gene comprises a sequence that is identical to a mouse Cλ1 gene.

In some embodiments, a mouse Cλ gene (or gene segment) comprises a sequence that is 50% to 100%, 55% to 100%, 60% to 100%, 65% to 100%, 70% to 100%, 75% to 100%, 80% to 100%, 85% to 100%, 90% to 100%, 95% to 100%, or 98% to 100% identical to a mouse Cλ gene selected from the group consisting of a mouse Cλ1, mouse Cλ2 and a mouse Cλ3.

In some embodiments, a mouse Cλ gene (or gene segment) comprises a sequence that is 50% to 98%, 50% to 95%, 50% to 90%, 50% to 85%, 50% to 80%, 50% to 75%, 50% to 70%, 50% to 65%, 50% to 60%, or 50% to 55% identical to a mouse Cλ gene selected from the group consisting of a mouse Cλ1, mouse Cλ2 and a mouse Cλ3.

In some embodiments, a mouse Cλ gene (or gene segment) comprises a sequence that is 55% to 98%, 60% to 95%, 65% to 90%, 70% to 85%, or 75% to 80%, identical to a mouse Cλ gene selected from the group consisting of a mouse Cλ1, mouse Cλ2 and a mouse Cλ3.

In some embodiments, a rat Cλ gene (or gene segment) comprises a sequence that is at least 50%, at least 55%, at least 60%, at least 65%, at least 70%, at least 75%, at least 80%, at least 85%, at least 90%, at least 95%, at least 98% identical, or 100% identical to a rat Cλ gene selected from the group consisting of a rat Cλ1, rat Cλ2, rat Cλ3 and a rat Cλ4 gene. In some embodiments, a rat Cλ gene comprises a sequence that is substantially identical or identical to a rat Cλ gene selected from the group consisting of a rat Cλ1, rat Cλ2, rat Cλ3 and a rat Cλ4 gene. In some certain embodiments, a rat Cλ1 gene is or comprises SEQ ID NO:7. In some certain embodiments, a rat Cλ2 gene is or comprises SEQ ID NO:9. In some certain embodiments, a rat Cλ3 gene is or comprises SEQ ID NO:11. In some certain embodiments, a rat Cλ4 gene is or comprises SEQ ID NO:13.

In some embodiments, a rat Cλ gene (or gene segment) comprises a sequence that is 50% to 100%, 55% to 100%, 60% to 100%, 65% to 100%, 70% to 100%, 75% to 100%, 80% to 100%, 85% to 100%, 90% to 100%, 95% to 100%, or 98% to 100% identical to a rat Cλ gene selected from the group consisting of a rat Cλ1, rat Cλ2, rat Cλ3 and a rat Cλ4 gene.

In some embodiments, a rat Cλ gene (or gene segment) comprises a sequence that is 50% to 98%, 50% to 95%, 50% to 90%, 50% to 85%, 50% to 80%, 50% to 75%, 50% to 70%, 50% to 65%, 50% to 60%, or 50% to 55% identical to a rat Cλ gene selected from the group consisting of a rat Cλ1, rat Cλ2, rat Cλ3 and a rat Cλ4 gene.

In some embodiments, a rat Cλ gene (or gene segment) comprises a sequence that is 55% to 98%, 60% to 95%, 65% to 90%, 70% to 85%, or 75% to 80%, identical to a rat Cλ gene selected from the group consisting of a rat Cλ1, rat Cλ2, rat Cλ3 and a rat Cλ4 gene.

In some embodiments of a provided non-human animal, non-human cell or non-human tissue, the germline genome or genome of said non-human animal, non-human cell or non-human tissue further comprises (i) an endogenous immunoglobulin heavy chain locus comprising insertion of one or more human $V_H$ gene segments, one or more human $D_H$ gene segments and one or more human $J_H$ gene segments, which human $V_H$, $D_H$ and $J_H$ gene segments are operably linked to a non-human immunoglobulin heavy chain constant region; or (ii) an endogenous immunoglobulin heavy chain locus comprising insertion of one or more human $V_H$ gene segments, one or more human $D_H$ gene segments and one or more human $J_H$ gene segments, which human $V_H$, $D_H$ and $J_H$ gene segments are operably linked to a non-human immunoglobulin heavy chain constant region, and an endogenous immunoglobulin κ light chain locus comprising insertion of one or more human Vκ gene segments and one or more human Jκ gene segments, which human Vκ and Jκ gene segments are operably linked to a non-human immunoglobulin Cκ region.

In some embodiments, the inserted one or more human $V_H$ gene segments, one or more human $D_H$ gene segments and one or more human $J_H$ gene segments replace non-human $V_H$, $D_H$ gene segments. In certain embodiments, the insertion includes human non-coding DNA that naturally appears between human $V_H$, $D_H$ and $J_H$ segments, and combinations thereof. In some embodiments, a non-human immunoglobulin heavy chain constant region is an endogenous non-human immunoglobulin heavy chain constant region. In some embodiments, an immunoglobulin heavy chain locus comprises insertion of the human $V_H$ gene segments from $V_H$3-74 to $V_H$6-1, the human $D_H$ gene segments from $D_H$1-1 to $D_H$7-27, and the human $J_H$ gene segments $J_H$1-$J_H$6. In certain embodiments, the insertion includes human non-coding DNA that naturally appears (occurs) between human $V_H$3-74 to $V_H$6-1, human non-coding DNA that naturally appears (occurs) between human $D_H$1-1 to $D_H$7-27, and human non-coding DNA that naturally appears (occurs) between human $J_H$1-$J_H$6. In some embodiments, an immunoglobulin heavy chain locus comprises insertion of all functional human $V_H$ gene segments, all functional human $D_H$ gene segments, and all functional human $J_H$ gene segments.

In some embodiments, an immunoglobulin heavy chain locus lacks an endogenous non-human Adam6 gene. In some embodiments, an immunoglobulin heavy chain locus further comprises an insertion of one or more nucleotide sequences encoding one or more non-human Adam6 polypeptides. In some embodiments, one or more nucleotide sequences encoding one or more rodent Adam6 polypeptides are inserted between a first and a second human $V_H$ gene segment. In some embodiments, a first human $V_H$ gene segment is human $V_H1$-2 and a second human $V_H$ gene segment is human $V_H6$-1. In some embodiments, one or more nucleotide sequences encoding one or more rodent Adam6 polypeptides are inserted between a human $V_H$ gene segment and a human $D_H$ gene segment. In some embodiments, one or more nucleotide sequences encoding one or more rodent Adam6 polypeptides are inserted in the place of a human Adam6 pseudogene.

In some embodiments, the inserted one or more human Vκ gene segments and one or more human Jκ gene segments replace non-human Vκ and Jκ gene segments. In some certain embodiments, the insertion includes human non-coding DNA that naturally appears between human Vκ and Jκ gene segments, and combinations thereof. In some embodiments, a non-human immunoglobulin Cκ region is an endogenous non-human Cκ region. In some embodiments, an immunoglobulin κ light chain locus comprises insertion of the proximal Vκ duplication, in whole or in part, of a human immunoglobulin κ light chain locus. In some embodiments, an immunoglobulin κ light chain locus comprises insertion of the human Vκ gene segments from Vκ2-40 to Vκ4-1 and the human Jκ gene segments from Jκ1-Jκ5. In some certain embodiments, the insertion includes human non-coding DNA that naturally appears between human Vκ2-40 to Vκ4-1, and human non-coding DNA that naturally appears between human Jκ1-Jκ5.

In some embodiments of a non-human animal, non-human cell or non-human tissue provided herein, the non-human animal, non-human cell or non-human tissue is heterozygous or homozygous for an immunoglobulin heavy chain locus as described herein (e.g., an endogenous immunoglobulin heavy chain locus as described herein).

In some embodiments of a non-human animal, non-human cell or non-human tissue provided herein, the non-human animal, non-human cell or non-human tissue is heterozygous or homozygous for an immunoglobulin κ light chain locus as described herein (e.g., an endogenous immunoglobulin κ light chain locus as described herein).

In some embodiments of a non-human animal, non-human cell or non-human tissue provided herein, the non-human animal, non-human cell or non-human tissue is heterozygous or homozygous for an immunoglobulin λ light chain locus as described herein (e.g., an endogenous immunoglobulin λ light chain locus as described herein).

In some embodiments of a non-human animal, non-human cell or non-human tissue provided herein, the germline genome of said non-human animal, non-human cell or non-human tissue further comprises insertion of one or more nucleotide sequences encoding one or more non-human Adam6 polypeptides, and the animal is heterozygous or homozygous for said insertion.

In some embodiments, a non-human cell is a non-human lymphocyte. In some embodiments, a non-human cell is selected from a B cell, dendritic cell, macrophage, monocyte and a T cell.

In some embodiments, a non-human cell is a non-human embryonic stem (ES) cell. In some embodiments, a non-human ES cell is a rodent ES cell. In certain embodiments, a rodent ES cell is a mouse ES cell (e.g., from a 129 strain, C57BL strain, BALB/c or a mixture thereof). In some certain embodiments, a rodent embryonic stem cell is a mouse embryonic stem cell and is a mixture of 129 and C57BL strains. In some certain embodiments, a rodent embryonic stem cell is a mouse embryonic stem cell and is a mixture of 129, C57BL and BALB/c strains.

In some embodiments, use of a non-human ES cell described herein to make a non-human animal is provided.

In certain embodiments, a non-human ES cell is a mouse ES cell and is used to make a mouse comprising engineered immunoglobulin λ light chain locus as described herein. In certain embodiments, a non-human ES cell is a rat ES cell and is used to make a rat comprising engineered immunoglobulin λ light chain locus as described herein.

In some embodiments, a non-human tissue is selected from adipose, bladder, brain, breast, bone marrow, eye, heart, intestine, kidney, liver, lung, lymph node, muscle, pancreas, plasma, serum, skin, spleen, stomach, thymus, testis, ovum, and a combination thereof.

In some embodiments, an immortalized cell made, generated, produced or obtained from an isolated non-human cell or tissue as described herein is provided.

In some embodiments, a non-human embryo made, generated, produced, or obtained from a non-human ES cell as described herein is provided. In some certain embodiments, a non-human embryo is a rodent embryo; in some embodiments, a mouse embryo; in some embodiments, a rat embryo.

In some embodiments, a kit comprising a non-human animal, non-human cell, non-human tissue, immortalized cell, non-human ES cell, or non-human embryo as described herein is provided.

In some embodiments, a kit as described herein for use in the manufacture and/or development of a drug (e.g., an antibody or fragment thereof) for therapy or diagnosis is provided.

In some embodiments, a kit as described herein for use in the manufacture and/or development of a drug (e.g., an antibody or fragment thereof) for the treatment, prevention or amelioration of a disease, disorder or condition is provided.

In some embodiments, a method of making a non-human animal whose germline genome comprises an engineered endogenous immunoglobulin λ light chain locus is provided, the method comprising (a) introducing a DNA fragment into a non-human embryonic stem cell, said DNA fragment comprising a nucleotide sequence that includes (i) one or more human Vλ gene segments, (ii) one or more human Jλ gene segments, and (iii) one or more human Cλ gene segments, wherein (i)-(iii) are operably linked to a non-human Cλ gene segment, and wherein the nucleotide sequence further comprises one or more human immunoglobulin λ light chain enhancers (Eλ); (b) obtaining the non-human embryonic stem cell generated in (a); and (c) creating a non-human animal using the non-human embryonic stem cell of (b).

In some embodiments, a method of making a non-human animal whose germline genome comprises an engineered endogenous immunoglobulin λ light chain locus is provided, which engineered endogenous immunoglobulin λ light chain locus comprises insertion of one or more human Vλ gene segments, one or more human Jλ gene segments and one or more human Cλ gene segments, which human Vλ and Jλ gene segments are operably linked to a non-human and/or human Cλ gene segment, and which endogenous immunoglobulin λ light chain locus further comprises one or more non-human immunoglobulin λ light chain enhancers (Eλ), and one or more human immunoglobulin λ light chain enhancers (Eλ), is provided, the method comprising modifying the germline genome of a non-human animal so that it comprises an engineered immunoglobulin λ light chain locus that includes insertion of one or more human Vλ gene segments, one or more human Jλ gene segments and one or more human Cλ gene segments, which human Vλ and Jλ gene segments are operably linked to a non-human and/or human Cλ gene segment, and which endogenous immunoglobulin λ light chain locus further comprises one or more rodent immunoglobulin λ light chain enhancers (Eλ), and one or more human immunoglobulin light chain enhancers (Eλ), thereby making said non-human animal.

In some embodiments of a method of making a non-human animal provided herein, one or more human Vλ gene segments include Vλ4-69 to Vλ3-1, Vλ5-52 to Vλ3-1 or Vλ3-27 to Vλ3-1. In some embodiments of a method of making a non-human animal, one or more human Vλ gene segments include Vλ5-52 to Vλ1-40 and/or Vλ3-27 to Vλ3-1. In some certain embodiments of a method of making a non-human animal, the one or more human Vλ gene segments include human non-coding DNA that naturally appears between human Vλ5-52 to Vλ1-40 and/or Vλ3-27 to Vλ3-1. In some embodiments of a method of making a non-human animal, one or more human Jλ gene segments and one or more human Cλ gene segments include the human Jλ-Cλ gene segment pairs Jλ1-Cλ1, Jλ2-Cλ2, Jλ3-Cλ3, Jλ6-Cλ6 and the human Jλ7 gene segment. In some certain embodiments of a method of making a non-human animal, the human Jλ-Cλ gene segment pairs Jλ1-Cλ1, Jλ2-Cλ2, Jλ3-Cλ3 and Jλ6-Cλ6 include human non-coding DNA that naturally appears between the human Jλ and Cλ gene segment pairs, and the human Jλ7 gene segment includes human non-coding DNA that naturally appears upstream (or 5') of human Jλ7.

In some certain embodiments of a method of making a non-human animal provided herein, insertion of the human Vλ gene segments Vλ5-52 to Vλ1-40 and Vλ3-27 to Vλ3-1 includes human non-coding DNA that naturally appears between the human Vλ gene segments, insertion of human Jλ-Cλ gene segment pairs Jλ1-Cλ1, Jλ2-Cλ2, Jλ3-Cλ3 and Jλ6-Cλ6 includes human non-coding DNA that naturally appears between the human Jλ-Cλ gene segment pairs, and insertion of the human Jλ7 gene segment includes human non-coding DNA that naturally appears upstream (or 5') of human Jλ7.

In some embodiments of a method of making a non-human animal provided herein, a non-human Cλ gene segment is a rodent Cλ gene segment; in some certain embodiments, a mouse Cλ1 gene segment.

In some embodiments of a method of making a non-human animal, a DNA fragment further comprises one or more selection markers. In some embodiments of a method of making a non-human animal, a DNA fragment further comprises one or more site-specific recombination sites. In some certain embodiments of a method of making a non-human animal provided herein, a DNA fragment further comprises one or more sets of site-specific recombination sites that recombine with the same recombinase. In some certain embodiments of a method of making a non-human animal, a DNA fragment further comprises one or more sets of site-specific recombination sites that recombine with different recombinases.

In some embodiments of a method of making a non-human animal provided herein, a DNA fragment is introduced into a non-human embryonic stem cell whose germline genome comprises (i) an endogenous immunoglobulin heavy chain locus comprising insertion of one or more human $V_H$ gene segments, one or more human $D_H$ gene segments and one or more human $J_H$ gene segments, which human $V_H$, $D_H$ and $J_H$ gene segments are operably linked to a non-human immunoglobulin heavy chain constant region; or (ii) an endogenous immunoglobulin heavy chain locus comprising insertion of one or more human $V_H$ gene segments, one or more human $D_H$ gene segments and one or more human $J_H$ gene segments, which human $V_H$, $D_H$ and $J_H$ gene segments are operably linked to a non-human immunoglobulin heavy chain constant region, and an endogenous immunoglobulin κ light chain locus comprising insertion of one or more human Vκ gene segments and one or more human Jκ gene segments, which human Vκ and Jκ gene segments are operably linked to a non-human immunoglobulin Cκ region.

In some embodiments of a method of making a non-human animal provided herein, a DNA fragment is introduced into a non-human embryonic stem cell whose germline genome comprises (i) a wild-type endogenous immunoglobulin heavy chain locus; or (ii) a wild-type endogenous immunoglobulin heavy chain locus and a wild-type endogenous immunoglobulin κ light chain locus; and wherein the method further comprises a step of breeding a mouse made, generated, produced or obtained from said non-human embryonic stem cell with a second mouse.

In some embodiments of a method of making a non-human animal provided herein, modifying the germline genome of a non-human animal so that it comprises an engineered immunoglobulin λ light chain locus is carried out in a non-human embryonic stem cell whose germline genome further comprises (i) an endogenous immunoglobulin heavy chain locus comprising insertion of one or more human $V_H$ gene segments, one or more human $D_H$ gene segments and one or more human $J_H$ gene segments, which human $V_H$, $D_H$ and $J_H$ gene segments are operably linked to a non-human immunoglobulin heavy chain constant region; or (ii) an endogenous immunoglobulin heavy chain locus comprising insertion of one or more human $V_H$ gene segments, one or more human $D_H$ gene segments and one or more human $J_H$ gene segments, which human $V_H$, $D_H$ and $J_H$ gene segments are operably linked to a non-human immunoglobulin heavy chain constant region, and an endogenous immunoglobulin κ light chain locus comprising insertion of one or more human Vκ gene segments and one or more human Jκ gene segments, which human Vκ and Jκ gene segments are operably linked to a non-human immunoglobulin Cκ region.

In some certain embodiments of a method of making a non-human animal provided herein, the insertion of one or more human $V_H$ gene segments, one or more human $D_H$ gene segments and one or more human $J_H$ gene segments includes human non-coding DNA that naturally appears between the one or more human $V_H$ gene segments, human non-coding DNA that naturally appears between the one or more human $D_H$ gene segments and human non-coding DNA that naturally appears between the one or more human $J_H$ gene segments. In some certain embodiments of a method of making a non-human animal provided herein, the insertion of one or more human Vκ gene segments and one or more human Jκ gene segments includes human non-coding DNA that naturally appears between the one or more human Vκ gene segments and human non-coding DNA that naturally appears between the one or more human Jκ gene segments.

In some embodiments of a method of making a non-human animal provided herein, modifying the germline genome of a non-human animal so that it comprises an engineered immunoglobulin λ light chain locus is carried out in a non-human embryonic stem cell whose germline genome comprises (i) a wild-type endogenous immunoglobulin heavy chain locus; or (ii) a wild-type endogenous immunoglobulin heavy chain locus and a wild-type endogenous immunoglobulin κ light chain locus; and wherein the method further comprises a step of breeding a mouse made, generated, produced or obtained from said non-human embryonic stem cell with a second mouse.

In some embodiments, a mouse as described herein has a germline genome comprising wild-type IgH and Igκ loci, homozygous or heterozygous humanized IgH and Igκ loci, which homozygous or heterozygous humanized IgH locus contains an inserted rodent Adam6-encoding sequence, or a homozygous or heterozygous humanized IgH locus (with or without insertion of Adam6-encoding sequence) and a homozygous or heterozygous inactivated Igκ locus.

In some embodiments, a non-human animal made, generated, produced, obtained or obtainable from a method as described herein is provided.

In some embodiments, a method of producing an antibody in a non-human animal is provided, the method comprising the steps of (a) immunizing a non-human animal as described herein with an antigen of interest, (b) maintaining the non-human animal under conditions sufficient that the rodent produces an immune response to the antigen of interest, and (c) recovering an antibody from the non-human animal, or a non-human cell, that binds the antigen of interest. In some embodiments, the antibody comprises a human lambda light chain variable domain.

In some embodiments, a method of producing a nucleic acid encoding a human lambda light chain variable domain in a non-human animal is provided, the method comprising the steps of (a) immunizing a non-human animal as described herein with an antigen of interest, (b) maintaining the non-human animal under conditions sufficient that the rodent produces an immune response to the antigen of interest, and (c) recovering a nucleic acid encoding a human lambda light chain variable domain from the non-human animal, or a non-human cell. In some embodiments, the method further comprises recovering a nucleic acid encoding a human heavy chain variable domain from the non-human animal, or a non-human cell.

In some embodiments of a method of producing an antibody or a nucleic acid in a non-human animal, a non-human cell is a B cell. In some embodiments of a method of producing an antibody or a nucleic acid in a non-human animal, a non-human cell is a hybridoma.

In some embodiments of a method of producing an antibody in a non-human animal, an antibody recovered from a rodent, or a rodent cell, that binds the antigen of interest comprises a human heavy chain variable domain and a human lambda light chain variable domain.

In some embodiments a of a method of producing an antibody or a nucleic acid in a non-human animal, a human heavy chain variable domain includes a rearranged human $V_H$ gene segment selected from the group consisting of $V_H$3-74, $V_H$3-73, $V_H$3-72, $V_H$2-70, $V_H$1-69, $V_H$3-66, $V_H$3-64, $V_H$4-61, $V_H$4-59, $V_H$1-58, $V_H$3-53, $V_H$5-51, $V_H$3-49, $V_H$3-48, $V_H$1-46, $V_H$1-45, $V_H$3-43, $V_H$4-39, $V_H$4-34, $V_H$3-33, $V_H$4-31, $V_H$3-30, $V_H$4-28, $V_H$2-26, $V_H$1-24, $V_H$3-23, $V_H$3-21, $V_H$3-20, $V_H$1-18, $V_H$3-15, $V_H$3-13, $V_H$3-11, $V_H$3-9, $V_H$1-8, $V_H$3-7, $V_H$2-5, $V_H$7-4-1, $V_H$4-4, $V_H$1-3, $V_H$1-2 and $V_H$6-1.

In some embodiments a of a method of producing an antibody or a nucleic acid in a non-human animal, a human lambda light chain variable domain includes a rearranged human Vλ gene segment selected from the group consisting of Vλ4-69, Vλ8-61, Vλ4-60, Vλ6-57, Vλ10-54, Vλ5-52, Vλ1-51, Vλ9-49, Vλ1-47, Vλ7-46, Vλ5-45, Vλ1-44, Vλ7-43, Vλ1-40, Vλ5-39, Vλ5-37, Vλ1-36, Vλ3-27, Vλ3-25, Vλ2-23, Vλ3-22, Vλ3-21, Vλ3-19, Vλ2-18, Vλ3-16, Vλ2-14, Vλ3-12, Vλ2-11, Vλ3-10, Vλ3-9, Vλ2-8, Vλ4-3 and Vλ3-1.

In some embodiments, a method of inducing an antigen-specific immune response in a non-human animal is provided, the method comprising the steps of (a) immunizing a non-human animal as described herein with an antigen of interest, (b) maintaining the non-human animal under conditions sufficient that the rodent produces an immune response to the antigen of interest.

In some embodiments, a non-human animal is provided whose germline genome comprises a homozygous endogenous immunoglobulin λ light chain locus comprising insertion of (i) human Vλ gene segments Vλ4-69 to Vλ3-1, Vλ5-52 to Vλ3-1, Vλ3-27 to Vλ3-1, or Vλ5-52 to Vλ1-40 and Vλ3-27 to Vλ3-1, (ii) human Jλ-Cλ gene segment pairs Jλ1-Cλ1, Jλ2-Cλ2, Jλ3-Cλ3 and Jλ6-Cλ6, (iii) human Jλ gene segment Jλ7, and (iv) three human immunoglobulin λ light chain enhancers (or a human immunoglobulin λ light chain enhancer having three sequence elements); wherein (i)-(iv) are operably linked to each other and the insertion is upstream of a non-human Cλ gene segment, and wherein the endogenous immunoglobulin λ light chain locus lacks an endogenous non-human immunoglobulin Eλ2-4.

In some embodiments, a non-human animal is provided whose germline genome comprises a homozygous endogenous immunoglobulin λ light chain locus comprising: (i) human Vλ gene segments Vλ5-52 to Vλ1-40 and Vλ3-27 to Vλ3-1, (ii) human Jλ-Cλ gene segment pairs Jλ1-Cλ1, Jλ2-Cλ2, Jλ3-Cλ3 and Jλ6-Cλ6, (iii) human Jλ gene segment Jλ7, and (iv) three human immunoglobulin λ light chain enhancers (or a human immunoglobulin λ light chain enhancer having three sequence elements); wherein (i)-(iv) are operably linked to each other and (i)-(iii) are upstream (or 5') of a non-human Cλ gene segment, and wherein the endogenous immunoglobulin light chain locus lacks an endogenous non-human immunoglobulin Eλ2-4, the human Vλ gene segments Vλ5-52 to Vλ1-40 and Vλ3-27 to Vλ3-1 includes human non-coding DNA that naturally appears between the human Vλ gene segments, the human Jλ-Cλ gene segments pairs Jλ1-Cλ1, Jλ2-Cλ2, Jλ3-Cλ3 and Jλ6-Cλ6 includes human non-coding DNA that naturally appears between the human Jλ-Cλ gene segments pairs, and the human Jλ gene segment Jλ7 includes human non-coding DNA that naturally appears upstream (or 5') of human Jλ7.

In some certain embodiments of a provided non-human animal, a non-human Cλ gene (or gene segment) is a mouse Cλ1 gene (or gene segment). In some certain embodiments of a provided non-human animal, an endogenous immunoglobulin λ light chain locus further comprises endogenous non-human immunoglobulin λ light chain enhancers Eλ and Eλ3-1. In some certain embodiments of a provided non-human animal, an endogenous immunoglobulin λ light chain locus comprises a deletion of endogenous non-human Vλ2-Vλ3-Jλ2-Cλ2-Jλ4P-Cλ4P gene segments and Vλ1-Jλ3-Jλ3P-Cλ3-Jλ1 gene segments.

In some embodiments, a non-human animal, non-human cell or non-human tissue as described herein is provided for use in the manufacture and/or development of a drug (e.g., an antibody or fragment thereof) for therapy or diagnosis.

In some embodiments, a non-human animal, non-human cell or non-human tissue as described herein is provided for use in the manufacture of a medicament for the treatment, prevention or amelioration of a disease, disorder or condition.

In some embodiments, use of a non-human animal, non-human cell or non-human tissue as described herein in the manufacture and/or development of a drug or vaccine for use in medicine, such as use as a medicament, is provided.

In some embodiments, use of a non-human animal or cell as described herein in the manufacture and/or development of an antibody or fragment thereof is provided.

In various embodiments, a provided non-human animal, non-human cell or non-human tissue as described herein is a rodent, rodent cell or rodent tissue; in some embodiments, a mouse, mouse cell or mouse tissue; in some embodiments, a rat, rat cell or rat tissue. In some embodiments, a mouse, mouse cell or mouse tissue as described herein comprises a genetic background that includes a 129 strain, a BALB/c strain, a C57BL/6 strain, a mixed 129×C57BL/6 strain or combinations thereof.

As used in this application, the terms "about" and "approximately" are used as equivalents. Any numerals used in this application with or without about or approximately are meant to cover any normal fluctuations appreciated by one of ordinary skill in the relevant art.

BRIEF DESCRIPTION OF THE DRAWING

The Drawing included herein, which is composed of the following Figures, is for illustration purposes only and not for limitation.

FIGS. 11A and 11B show representative contour plots indicating immature bone marrow (CD19$^+$IgM$^+$B220$^{int}$-gated) showing expression of mouse Igλ (mIgλ, y-axis), mouse Igκ (mIgκ, x-axis) or human Igλ (hIgλ, y-axis) from mice homozygous for insertion of the 6680 targeting vector (6680HO) and wild-type littermates (WT).

FIGS. 12A and 12B show representative contour plots indicating mature bone marrow (CD19$^+$IgM$^+$B220$^{int}$-gated) showing expression of mouse Igλ (mIgλ, y-axis), mouse Igκ (mIgκ, x-axis) or human Igλ (hIgλ, y-axis) from mice homozygous for insertion of the 6680 targeting vector (6680HO) and wild-type littermates (WT).

FIG. 13 shows representative mean percent of Igκ-expressing (% κ C) and human Igλ-expressing (% hum λ C) B cells in spleen, immature bone marrow (immature BM) and mature bone marrow (mature BM) from selected engineered mouse strains as described herein. Data is presented as mean values with standard deviation also indicated. 6680HO/VI HO/Adam6 HO: an engineered mouse strain containing a homozygous engineered Igλ light chain locus designed to contain 25 functional human Vλ gene segments, four functional human Jλ-Cλ gene segment pairs and a human Jλ7 gene segment operably linked to a rodent Cλ region (e.g., a mouse Cλ1 region), which Igλ light chain locus further includes two endogenous Igλ enhancer regions (or sequences) and a modular human Igλ enhancer region (or sequence, see above); and homozygous humanized IgH and Igκ loci, which homozygous humanized IgH locus contained an inserted rodent Adam6-encoding sequence (see, e.g., U.S. Pat. Nos. 8,642,835 and 8,697,940; hereby incorporated by reference in their entireties); 6889HO/VI HO/Adam6 HO: an engineered mouse strain containing a homozygous engineered Igλ light chain locus containing 25 functional human Vλ gene segments, four functional human Jλ-Cλ gene segment pairs and a human Jλ7 gene segment operably linked to a rodent Cλ region (e.g., a mouse Cλ1 region), which Igλ light chain locus further includes two endogenous Igλ enhancer regions (or sequences) and a modular human Igλ enhancer region (or sequence, see above); and homozygous humanized IgH and Igκ loci, which homozygous humanized IgH locus contained an inserted rodent Adam6-encoding sequence (see, e.g., U.S. Pat. Nos. 8,642,835 and 8,697,940; hereby incorporated by reference in their entireties). Number of mice for each genotype cohort shown included at least three and up to eight animals per group.

FIGS. 15D and 15E show representative human Vλ (FIG. 15D) and human Jλ (FIG. 15E) gene segment usage in human Cλ-primed sequences amplified from RNA isolated from splenocytes harvested from 6889HO/VI HO/Adam6 HO mice (n=6).

FIGS. 16A and 16B show representative total IgG (A) and antigen-specific IgG (B) titers in serum at days 0 and 22 collected from immunized mice heterozygous for insertion of the 6597 (6597HET, n=6) or 6680 (6680HET, n=6) targeting vectors and immunized wild-type controls (WT, n=6).

BRIEF DESCRIPTION OF SELECTED SEQUENCES IN THE SEQUENCE LISTING

Figure 1:
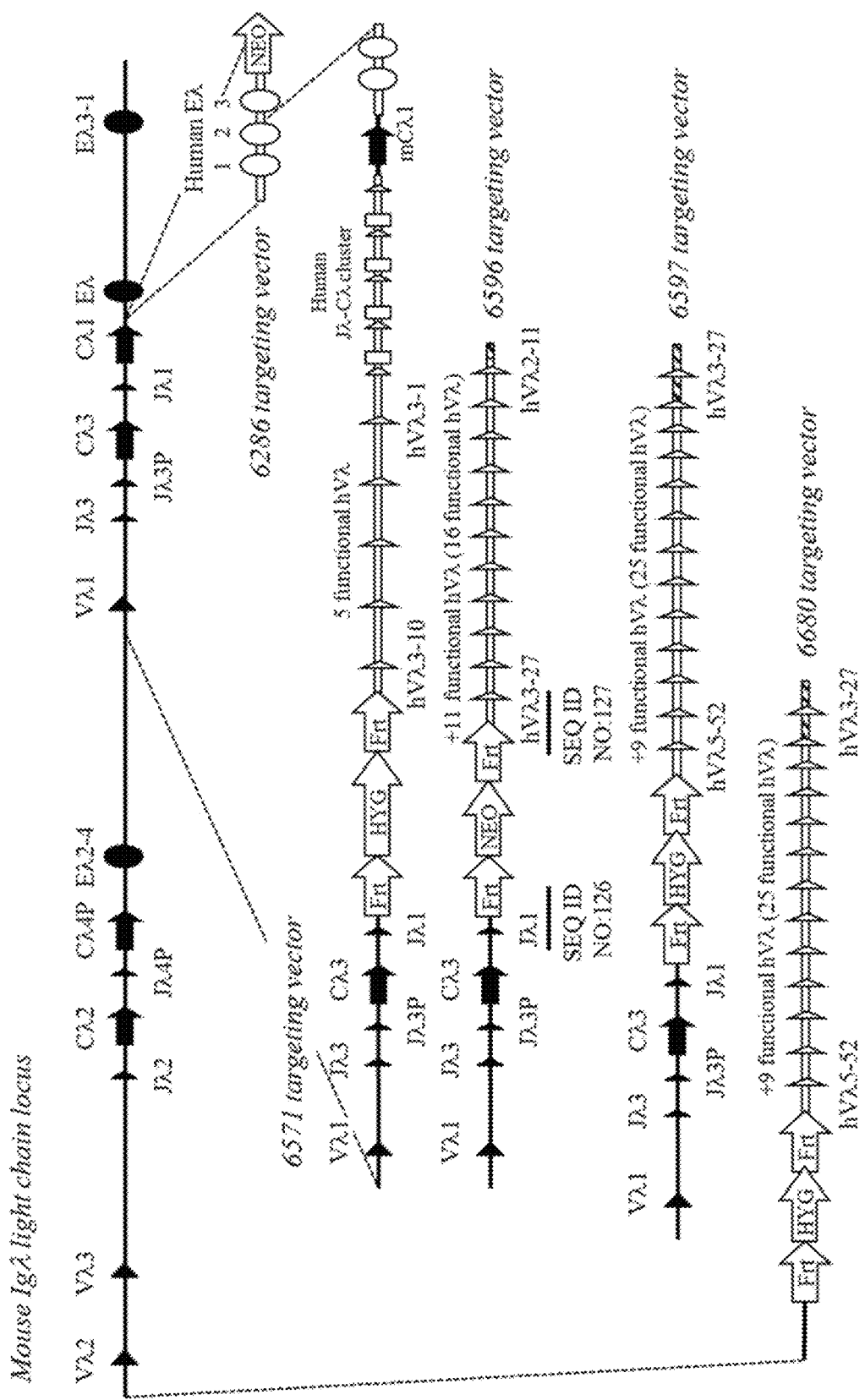
FIG. 1 shows a schematic illustration, not to scale, of an exemplary strategy for construction of an engineered endogenous Igλ light chain locus in a rodent characterized by the presence of a plurality of human Vλ, Jλ and Cλ coding sequences that are operably linked to each other and operably linked to a rodent Cλ region (or rodent Cλ gene). As depicted, five separate targeting vectors (6286, 6571, 6596, 6597 and 6680) are shown with various amounts of genetic material from a human Igλ light chain locus and are sequentially inserted into an endogenous rodent (e.g., mouse) Igλ light chain locus (shown at the top). A first targeting vector (6286) was inserted downstream of a rodent Cλ1 region and constructed to contain a modular human Igλ enhancer (Eλ) region (or sequence) characterized by three sequence elements. A second targeting vector (6571) was inserted upstream of a rodent Cλ1 region and was engineered to contain five functional human Vλ gene segments, four functional human Jλ-Cλ gene segment pairs and a human Jλ7 gene segment (Human Jλ1-Cλ1-Jλ2-Cλ2-Jλ3-Cλ3-Jλ4-Cλ4-Jλ5-Cλ5-Jλ6-Cλ6-Jλ7). Third (6596) and fourth (6597) targeting vectors included further sets of additional human Vλ gene segments (eleven and nine, respectively) that sequentially add to the total human Vλ gene segment content of the endogenous mouse Igλ light chain locus after successful targeting of the first targeting vector. Both targeting vectors included regions of overlap (striped filled rectangles) on the 3' ends to facilitate homologous recombination with the 5' end of the preceding targeting vector once integrated into the endogenous mouse Igλ light chain locus. An alternative fifth targeting vector (6680) is also shown that has the same genetic material as the 6597 targeting vector except that this alternative targeting vector included a 5' homology arm having a sequence that is identical to the sequence 5' (or upstream) of a rodent Vλ2 gene segment, thereby facilitating deletion of endogenous Vλ2-Vλ3-Jλ2-Cλ2-Jλ4P-Cλ4P-Eλ2-4-Vλ1-Jλ3-Jλ3P-Cλ3-Jλ1 gene segments upon homologous recombination with the targeting vector. Unless otherwise indicated, closed symbols indicate rodent gene segments and/or sequences, while open symbols indicate human gene segments and/or sequences. Site-specific recombination recognition sites (e.g., loxP, Frt) flanking selection cassettes (HYG: Hygromycin resistance gene [HYG$^R$] under transcriptional control of a ubiquitin promoter; NEO: Neomycin resistance gene [NEO$^R$] under transcriptional control of a ubiquitin promoter) are also shown. Selected nucleotide junction locations are marked with a line below each junction and each indicated by SEQ ID NO.

Mouse Cλ1 DNA (SEQ ID NO: 1):
GCCAGCCCAAGTCTTCGCCATCAGTCACCCTGTTTCCACCTTCCTCTGA
AGAGCTCGAGACTAACAAGGCCACACTGGTGTGTACGATCACTGATTTC
TACCCAGGTGTGGTGACAGTGGACTGGAAGGTAGATGGTACCCCTGTCA
CTCAGGGTATGGAGACAACCCAGCCTTCCAAACAGAGCAACAACAAGTA
CATGGCTAGCAGCTACCTGACCCTGACAGCAAGAGCATGGGAAAGGCAT
AGCAGTTACAGCTGCCAGGTCACTCATGAAGGTCACACTGTGGAGAAGA
GTTTGTCCCGTGCTGACTGTTCC Mouse Cλ1 amino acid (SEQ ID NO: 2):
GQPKSSPSVTLFPPSSEELETNKATLVCTITDFYPGVVTVDWKVDGTPV
TQGMETTQPSKQSNNKYMASSYLTLTARAWERHSSYSCQVTHEGHTVEK
SLSRADCS Mouse Cλ2 DNA (SEQ ID NO: 3):
GTCAGCCCAAGTCCACTCCCACTCTCACCGTGTTTCCACCTTCCTCTGA
GGAGCTCAAGGAAAACAAAGCCACACTGGTGTGTCTGATTTCCAACTTT
TCCCCGAGTGGTGTGACAGTGGCCTGGAAGGCAAATGGTACACCTATCA
CCCAGGGTGTGGACACTTCAAATCCCACCAAAGAGGGCAACAAGTTCAT
GGCCAGCAGCTTCCTACATTTGACATCGGACCAGTGGAGATCTCACAAC
AGTTTTACCTGTCAAGTTACACATGAAGGGGACACTGTGGAGAAGAGTC
TGTCTCCTGCAGAATGTCTC Mouse Cλ2 amino acid (SEQ ID NO: 4):
GQPKSTPTLTVFPPSSEELKENKATLVCLISNFSPSGVTVAWKANGTPI
TQGVDTSNPTKEGNKFMASSFLHLTSDQWRSHNSFTCQVTHEGDTVEKS
LSPAECL Mouse Cλ3 DNA (SEQ ID NO: 5):
GTCAGCCCAAGTCCACTCCCACACTCACCATGTTTCCACCTTCCCCTGA
GGAGCTCCAGGAAAACAAAGCCACACTCGTGTGTCTGATTTCCAATTTT
TCCCCAAGTGGTGTGACAGTGGCCTGGAAGGCAAATGGTACACCTATCA
CCCAGGGTGTGGACACTTCAAATCCCACCAAAGAGGACAACAAGTACAT
GGCCAGCAGCTTCTTACATTTGACATCGGACCAGTGGAGATCTCACAAC
AGTTTTACCTGCCAAGTTACACATGAAGGGGACACTGTGGAGAAGAGTC
TGTCTCCTGCAGAATGTCTC Mouse Cλ3 amino acid (SEQ ID NO: 6):
GQPKSTPTLTMFPPSPEELQENKATLVCLISNFSPSGVTVAWKANGTPI
TQGVDTSNPTKEDNKYMASSFLHLTSDQWRSHNSFTCQVTHEGDTVEKS
LSPAECL Rat Cλ1 DNA (SEQ ID NO: 7):
GTCAGCCCAAGTCCACTCCCACACTCACAGTATTTCCACCTTCAACTGA
GGAGCTCCAGGGAAACAAAGCCACACTGGTGTGTCTGATTTCTGATTTC
TACCCGAGTGATGTGGAAGTGGCCTGGAAGGCAAATGGTGCACCTATCT
CCCAGGGTGTGGACACTGCAAATCCCACCAAACAGGGCAACAAATACAT
CGCCAGCAGCTTCTTACGTTTGACAGCAGAACAGTGGAGATCTCGCAAC -continued

AGTTTTACCTGCCAAGTTACACATGAAGGGAACACTGTGGAGAAGAGTC

TGTCTCCTGCAGAATGTGTC

Rat Cλ1 amino acid (SEQ ID NO: 8):
GQPKSTPTLTVFPPSTEELQGNKATLVCLISDFYPSDVEVAWKANGAPI

SQGVDTANPTKQGNKYIASSFLRLTAEQWRSRNSFTCQVTHEGNTVEKS

LSPAECV

Rat Cλ2 DNA (SEQ ID NO: 9):
ACCAACCCAAGGCTACGCCCTCAGTCACCCTGTTCCCACCTTCCTCTGA

AGAGCTCAAGACTGACAAGGCTACACTGGTGTGTATGGTGACAGATTTC

TACCCTGGTGTTATGACAGTGGTCTGGAAGGCAGATGGTACCCCTATCA

CTCAGGGTGTGGAGACTACCCAGCCTTTCAAACAGAACAACAAGTACAT

GGCTACCAGCTACCTGCTTTTGACAGCAAAAGCATGGGAGACTCATAGC

AATTACAGCTGCCAGGTCACTCACGAAGAGAACACTGTGGAGAAGAGTT

TGTCCCGTGCTGAGTGTTCC

Rat Cλ2 amino acid (SEQ ID NO: 10):
DQPKATPSVTLFPPSSEELKTDKATLVCMVTDFYPGVMTVVWKADGTPI

TQGVETTQPFKQNNKYMATSYLLLTAKAWETHSNYSCQVTHEENTVEKS

LSRAECS

Rat Cλ3 DNA (SEQ ID NO: 11):
GTCAGCCCAAGTCCACTCCCACACTCACAGTATTTCCACCTTCAACTGA

GGAGCTCCAGGGAAACAAAGCCACACTGGTGTGTCTGATTTCTGATTTC

TACCCGAGTGATGTGGAAGTGGCCTGGAAGGCAAATGGTGCACCTATCT

CCCAGGGTGTGGACACTGCAAATCCCACCAAACAGGGCAACAAATACAT

CGCCAGCAGCTTCTTACGTTTGACAGCAGAACAGTGGAGATCTCGCAAC

AGTTTTACCTGCCAAGTTACACATGAAGGGAACACTGTGGAAAAGAGTC

TGTCTCCTGCAGAGTGTGTC

Rat Cλ3 amino acid (SEQ ID NO: 12):
GQPKSTPTLTVFPPSTEELQGNKATLVCLISDFYPSDVEVAWKANGAPI

SQGVDTANPTKQGNKYIASSFLRLTAEQWRSRNSFTCQVTHEGNTVEKS

LSPAECV

Rat Cλ4 DNA (SEQ ID NO: 13):
ACCAACCCAAGGCTACGCCCTCAGTCACCCTGTTCCCACCTTCCTCTGA

AGAGCTCAAGACTGACAAGGCTACACTGGTGTGTATGGTGACAGATTTC

TACCCTGGTGTTATGACAGTGGTCTGGAAGGCAGATGGTACCCCTATCA

CTCAGGGTGTGGAGACTACCCAGCCTTTCAAACAGAACAACAAGTACAT

GGCTACCAGCTACCTGCTTTTGACAGCAAAAGCATGGGAGACTCATAGC

AATTACAGCTGCCAGGTCACTCACGAAGAGAACACTGTGGAGAAGAGTT

TGTCCCGTGCTGAGTGTTCC

Rat Cλ4 amino acid (SEQ ID NO: 14):
DQPKATPSVTLFPPSSEELKTDKATLVCMVTDFYPGVMTVVWKADGTPI

TQGVETTQPFKQNNKYMATSYLLLTAKAWETHSNYSCQVTHEENTVEKS

LSRAECS

Definitions

The scope of the present invention is defined by the claims appended hereto and is not limited by certain embodiments described herein; those skilled in the art, reading the present specification, will be aware of various modifications that may be equivalent to such described embodiments, or otherwise within the scope of the claims.

In general, terms used herein are in accordance with their understood meaning in the art, unless clearly indicated otherwise. Explicit definitions of certain terms are provided below; meanings of these and other terms in particular instances throughout this specification will be clear to those skilled in the art from context. Additional definitions for the following and other terms are set forth throughout the specification. Patent and non-patent literature references cited within this specification, or relevant portions thereof, are incorporated herein by reference in their entireties.

Administration: as used herein, includes the administration of a composition to a subject or system (e.g., to a cell, organ, tissue, organism, or relevant component or set of components thereof). The skilled artisan will appreciate that route of administration may vary depending, for example, on the subject or system to which the composition is being administered, the nature of the composition, the purpose of the administration, etc. For example, in certain embodiments, administration to an animal subject (e.g., to a human or a rodent) may be bronchial (including by bronchial instillation), buccal, enteral, interdermal, intra-arterial, intradermal, intragastric, intramedullary, intramuscular, intranasal, intraperitoneal, intrathecal, intravenous, intraventricular, mucosal, nasal, oral, rectal, subcutaneous, sublingual, topical, tracheal (including by intratracheal instillation), transdermal, vaginal and/or vitreal. In some embodiments, administration may involve intermittent dosing. In some embodiments, administration may involve continuous dosing (e.g., perfusion) for at least a selected period of time.

Amelioration: as used herein, includes the prevention, reduction or palliation of a state, or improvement of the state of a subject. Amelioration includes but does not require complete recovery or complete prevention of a disease, disorder or condition.

Approximately: as applied to one or more values of interest, includes to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Biologically active: as used herein, refers to a characteristic of any agent that has activity in a biological system, in vitro or in vivo (e.g., in an organism). For instance, an agent that, when present in an organism, has a biological effect within that organism is considered to be biologically active. In particular embodiments, where a protein or polypeptide is biologically active, a portion of that protein or polypeptide that shares at least one biological activity of the protein or polypeptide is typically referred to as a "biologically active" portion.

Comparable: as used herein, refers to two or more agents, entities, situations, sets of conditions, etc. that may not be identical to one another but that are sufficiently similar to permit comparison there between so that conclusions may reasonably be drawn based on differences or similarities observed. Persons of ordinary skill in the art will understand, in context, what degree of identity is required in any given circumstance for two or more such agents, entities, situations, sets of conditions, etc. to be considered comparable.

Conservative: as used herein, refers to instances when describing a conservative amino acid substitution, including a substitution of an amino acid residue by another amino acid residue having a side chain R group with similar chemical properties (e.g., charge or hydrophobicity). In general, a conservative amino acid substitution will not substantially change the functional properties of interest of a protein, for example, the ability of a receptor to bind to a ligand. Examples of groups of amino acids that have side chains with similar chemical properties include: aliphatic side chains such as glycine (Gly, G), alanine (Ala, A), valine (Val, V), leucine (Leu, L), and isoleucine (Ile, I); aliphatic-hydroxyl side chains such as serine (Ser, S) and threonine (Thr, T); amide-containing side chains such as asparagine (Asn, N) and glutamine (Gln, Q); aromatic side chains such as phenylalanine (Phe, F), tyrosine (Tyr, Y), and tryptophan (Trp, W); basic side chains such as lysine (Lys, K), arginine (Arg, R), and histidine (His, H); acidic side chains such as aspartic acid (Asp, D) and glutamic acid (Glu, E); and sulfur-containing side chains such as cysteine (Cys, C) and methionine (Met, M). Conservative amino acids substitution groups include, for example, valine/leucine/isoleucine (Val/Leu/Ile, V/L/I), phenylalanine/tyrosine (Phe/Tyr, F/Y), lysine/arginine (Lys/Arg, K/R), alanine/valine (Ala/Val, A/V), glutamate/aspartate (Glu/Asp, E/D), and asparagine/glutamine (Asn/Gln, N/Q). In some embodiments, a conservative amino acid substitution can be a substitution of any native residue in a protein with alanine, as used in, for example, alanine scanning mutagenesis. In some embodiments, a conservative substitution is made that has a positive value in the PAM250 log-likelihood matrix disclosed in Gonnet, G. H. et al., 1992, Science 256:1443-1445. In some embodiments, a substitution is a moderately conservative substitution wherein the substitution has a nonnegative value in the PAM250 log-likelihood matrix.

Control: as used herein, refers to the art-understood meaning of a "control" being a standard against which results are compared. Typically, controls are used to augment integrity in experiments by isolating variables in order to make a conclusion about such variables. In some embodiments, a control is a reaction or assay that is performed simultaneously with a test reaction or assay to provide a comparator. A "control" also includes a "control animal." A "control animal" may have a modification as described herein, a modification that is different as described herein, or no modification (i.e., a wild-type animal). In one experiment, a "test" (i.e., a variable being tested) is applied. In a second experiment, the "control," the variable being tested is not applied. In some embodiments, a control is a historical control (i.e., of a test or assay performed previously, or an amount or result that is previously known). In some embodiments, a control is or comprises a printed or otherwise saved record. A control may be a positive control or a negative control.

Derived from: when used concerning a rearranged variable region gene or a variable domain "derived from" an unrearranged variable region and/or unrearranged variable region gene segments refers to the ability to trace the sequence of the rearranged variable region gene or variable domain back to a set of unrearranged variable region gene segments that were rearranged to form the rearranged variable region gene that expresses the variable domain (accounting for, where applicable, splice differences and somatic mutations). For example, a rearranged variable region gene that has undergone somatic mutation does not change the fact that it is derived from the unrearranged variable region gene segments.

Disruption: as used herein, refers to the result of a homologous recombination event with a DNA molecule (e.g., with an endogenous homologous sequence such as a gene or gene locus). In some embodiments, a disruption may achieve or represent an insertion, deletion, substitution, replacement, missense mutation, or a frame-shift of a DNA sequence(s), or any combination thereof. Insertions may include the insertion of entire genes or gene fragments, e.g., exons, which may be of an origin other than the endogenous sequence (e.g., a heterologous sequence). In some embodiments, a disruption may increase expression and/or activity of a gene or gene product (e.g., of a polypeptide encoded by a gene). In some embodiments, a disruption may decrease expression and/or activity of a gene or gene product. In some embodiments, a disruption may alter sequence of a gene or an encoded gene product (e.g., an encoded polypeptide). In some embodiments, a disruption may truncate or fragment a gene or an encoded gene product (e.g., an encoded polypeptide). In some embodiments, a disruption may extend a gene or an encoded gene product. In some such embodiments, a disruption may achieve assembly of a fusion polypeptide. In some embodiments, a disruption may affect level, but not activity, of a gene or gene product. In some embodiments, a disruption may affect activity, but not level, of a gene or gene product. In some embodiments, a disruption may have no significant effect on level of a gene or gene product. In some embodiments, a disruption may have no significant effect on activity of a gene or gene product. In some embodiments, a disruption may have no significant effect on either level or activity of a gene or gene product.

Determining, measuring, evaluating, assessing, assaying and analyzing: are used interchangeably herein to refer to any form of measurement, and include determining if an element is present or not. These terms include both quantitative and/or qualitative determinations. Assaying may be relative or absolute. "Assaying for the presence of" can be determining the amount of something present and/or determining whether or not it is present or absent.

Endogenous locus or endogenous gene: as used herein, refers to a genetic locus found in a parent or reference organism prior to introduction of a disruption, deletion, replacement, alteration, or modification as described herein. In some embodiments, an endogenous locus has a sequence found in nature. In some embodiments, an endogenous locus is a wild-type locus. In some embodiments, an endogenous locus is an engineered locus. In some embodiments, a reference organism is a wild-type organism. In some embodiments, a reference organism is an engineered organism. In some embodiments, a reference organism is a laboratory-bred organism (whether wild-type or engineered).

Endogenous promoter: as used herein, refers to a promoter that is naturally associated, e.g., in a wild-type organism, with an endogenous gene.

Engineered: as used herein refers, in general, to the aspect of having been manipulated by the hand of man. For example, in some embodiments, a polynucleotide may be considered to be "engineered" when two or more sequences that are not linked together in that order in nature are manipulated by the hand of man to be directly linked to one another in the engineered polynucleotide. In some particular such embodiments, an engineered polynucleotide may comprise a regulatory sequence that is found in nature in operative association with a first coding sequence but not in operative association with a second coding sequence, is linked by the hand of man so that it is operatively associated with the second coding sequence. Alternatively, or additionally, in some embodiments, first and second nucleic acid sequences that each encode polypeptide elements or domains that in nature are not linked to one another may be linked to one another in a single engineered polynucleotide. Comparably, in some embodiments, a cell or organism may be considered to be "engineered" if it has been manipulated so that its genetic information is altered (e.g., new genetic material not previously present has been introduced, or previously present genetic material has been altered or removed). As is common practice and is understood by persons of skill in the art, progeny of an engineered polynucleotide or cell are typically still referred to as "engineered" even though the actual manipulation was performed on a prior entity. Furthermore, as will be appreciated by persons of skill in the art, a variety of methodologies are available through which "engineering" as described herein may be achieved. For example, in some embodiments, "engineering" may involve selection or design (e.g., of nucleic acid sequences, polypeptide sequences, cells, tissues, and/or organisms) through use of computer systems programmed to perform analysis or comparison, or otherwise to analyze, recommend, and/or select sequences, alterations, etc.). Alternatively, or additionally, in some embodiments, "engineering" may involve use of in vitro chemical synthesis methodologies and/or recombinant nucleic acid technologies such as, for example, nucleic acid amplification (e.g., via the polymerase chain reaction) hybridization, mutation, transformation, transfection, etc., and/or any of a variety of controlled mating methodologies. As will be appreciated by those skilled in the art, a variety of established such techniques (e.g., for recombinant DNA, oligonucleotide synthesis, and tissue culture and transformation (e.g., electroporation, lipofection, etc.) are well known in the art and described in various general and more specific references that are cited and/or discussed throughout the present specification. See e.g., Sambrook et al., Molecular Cloning: A Laboratory Manual 2nd ed., Cold Spring Harbor Laboratory Press, Cold Spring Harbor, N.Y., 1989 and Principles of Gene Manipulation: An Introduction to Genetic Manipulation, 5th Ed., ed. By Old, R. W. and S. B. Primrose, Blackwell Science, Inc., 1994.

Functional: as used herein, refers to a form or fragment of an entity (e.g., a gene or gene segment) that exhibits a particular property (e.g., forms part of a coding sequence) and/or activity. For example, in the context of immunoglobulins, variable domains are encoded by unique gene segments (i.e., V, D and/or J) that are assembled (or recombined) to form functional coding sequences. When present in the genome, gene segments are organized in clusters, although variations do occur. A "functional" gene segment is a gene segment represented in an expressed sequence (i.e., a variable domain) for which the corresponding genomic DNA has been isolated (i.e., cloned) and identified by sequence. Some immunoglobulin gene segment sequences contain open reading frames and are considered functional although not represented in an expressed repertoire, while other immunoglobulin gene segment sequences contain mutations (e.g., point mutations, insertions, deletions, etc.) resulting in a stop codon and/or truncated sequence which subsequently render(s) such gene segment sequences unable to perform the property/ies and/or activity/ies associated with a non-mutated sequence(s). Such sequences are not represented in expressed sequences and, therefore, categorized as pseudogenes.

Gene: as used herein, refers to a DNA sequence in a chromosome that codes for a product (e.g., an RNA product and/or a polypeptide product). In some embodiments, a gene includes coding sequence (i.e., sequence that encodes a particular product). In some embodiments, a gene includes non-coding sequence. In some particular embodiments, a gene may include both coding (e.g., exonic) and non-coding (e.g., intronic) sequence. In some embodiments, a gene may include one or more regulatory sequences (e.g., promoters, enhancers, etc.) and/or intron sequences that, for example, may control or impact one or more aspects of gene expression (e.g., cell-type-specific expression, inducible expression, etc.). For the purpose of clarity, we note that, as used in the present disclosure, the term "gene" generally refers to a portion of a nucleic acid that encodes a polypeptide or fragment thereof; the term may optionally encompass regulatory sequences, as will be clear from context to those of ordinary skill in the art. This definition is not intended to exclude application of the term "gene" to non-protein-coding expression units but rather to clarify that, in most cases, the term as used in this document refers to a polypeptide-coding nucleic acid.

Heterologous: as used herein, refers to an agent or entity from a different source. For example, when used in reference to a polypeptide, gene, or gene product present in a particular cell or organism, the term clarifies that the relevant polypeptide, gene, or gene product: 1) was engineered by the hand of man; 2) was introduced into the cell or organism (or a precursor thereof) through the hand of man (e.g., via genetic engineering); and/or 3) is not naturally produced by or present in the relevant cell or organism (e.g., the relevant cell type or organism type). "Heterologous" also includes a polypeptide, gene or gene product that is normally present in a particular native cell or organism, but has been altered or modified, for example, by mutation or placement under the control of non-naturally associated and, in some embodiments, non-endogenous regulatory elements (e.g., a promoter).

Host cell: as used herein, refers to a cell into which a nucleic acid or protein has been introduced. Persons of skill upon reading this disclosure will understand that such terms refer not only to the particular subject cell, but also is used to refer to the progeny of such a cell. Because certain modifications may occur in succeeding generations due to either mutation or environmental influences, such progeny may not, in fact, be identical to the parent cell, but are still included within the scope of the phrase "host cell." In some embodiments, a host cell is or comprises a prokaryotic or eukaryotic cell. In general, a host cell is any cell that is suitable for receiving and/or producing a heterologous nucleic acid or protein, regardless of the Kingdom of life to which the cell is designated. Exemplary cells include those of prokaryotes and eukaryotes (single-cell or multiple-cell), bacterial cells (e.g., strains of *Escherichia coli, Bacillus* spp., *Streptomyces* spp., etc.), mycobacteria cells, fungal cells, yeast cells (e.g., *Saccharomyces cerevisiae, Schizosaccharomyces pombe, Pichia pastoris, Pichia methanolica,* etc.), plant cells, insect cells (e.g., SF-9, SF-21, baculovirus-infected insect cells, Trichoplusia ni, etc.), non-human animal cells, human cells, or cell fusions such as, for example, hybridomas or quadromas. In some embodiments, a cell is a human, monkey, ape, hamster, rat, or mouse cell. In some embodiments, a cell is eukaryotic and is selected from the following cells: CHO (e.g., CHO K1, DXB-11 CHO, Veggie-CHO), COS (e.g., COS-7), retinal cell, Vero, CV1, kidney (e.g., HEK293, 293 EBNA, MSR 293, MDCK, HaK, BHK), HeLa, HepG2, WI38, MRC 5, Colo205, HB 8065, HL-60, (e.g., BHK21), Jurkat, Daudi, A431 (epidermal), CV-1, U937, 3T3, L cell, C127 cell, SP2/0, NS-0, MMT 060562, Sertoli cell, BRL 3A cell, HT1080 cell, myeloma cell, tumor cell, and a cell line derived from an aforementioned cell. In some embodiments, a cell comprises one or more viral genes, e.g., a retinal cell that expresses a viral gene (e.g., a PER.C6® cell). In some embodiments, a host cell is or comprises an isolated cell. In some embodiments, a host cell is part of a tissue. In some embodiments, a host cell is part of an organism.

Identity: as used herein in connection with a comparison of sequences, refers to identity as determined by a number of different algorithms known in the art that can be used to measure nucleotide and/or amino acid sequence identity. In some embodiments, identities as described herein are determined using a ClustalW v. 1.83 (slow) alignment employing an open gap penalty of 10.0, an extend gap penalty of 0.1, and using a Gonnet similarity matrix (MACVECTOR™10.0.2, MacVector Inc., 2008).

In vitro: as used herein refers to events that occur in an artificial environment, e.g., in a test tube or reaction vessel, in cell culture, etc., rather than within a multi-cellular organism.

In vivo: as used herein refers to events that occur within a multi-cellular organism, such as a human and/or a non-human animal. In the context of cell-based systems, the term may be used to refer to events that occur within a living cell (as opposed to, for example, in vitro systems).

Isolated: as used herein, refers to a substance and/or entity that has been (1) separated from at least some of the components with which it was associated when initially produced (whether in nature and/or in an experimental setting), and/or (2) designed, produced, prepared, and/or manufactured by the hand of man. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated agents are separated from 10% to 100%, 15%-100%, 20%-100%, 25%-100%, 30%-100%, 35%-100%, 40%-100%, 45%-100%, 50%-100%, 55%-100%, 60%-100%, 65%-100%, 70%-100%, 75%-100%, 80%-100%, 85%-100%, 90%-100%, 95%-100%, 96%-100%, 97%-100%, 98%-100%, or 99%-100% of the other components with which they were initially associated. In some embodiments, isolated agents are separated from 10% to 100%, 10%-99%, 10%-98%, 10%-97%, 10%-96%, 10%-95%, 10%-90%, 10%-85%, 10%-80%, 10%-75%, 10%-70%, 10%-65%, 10%-60%, 10%-55%, 10%-50%, 10%-45%, 10%-40%, 10%-35%, 10%-30%, 10%-25%, 10%-20%, or 10%-15% of the other components with which they were initially associated. In some embodiments, isolated agents are separated from 11% to 99%, 12%-98%, 13%-97%, 14%-96%, 15%-95%, 20%-90%, 25%-85%, 30%-80%, 35%-75%, 40%-70%, 45%-65%, 50%-60%, or 55%-60% of the other components with which they were initially associated. In some embodiments, isolated agents are about 80%, about 85%, about 90%, about 91%, about 92%, about 93%, about 94%, about 95%, about 96%, about 97%, about 98%, about 99%, or more than about 99% pure. In some embodiments, isolated agents are 80%-99%, 85%-99%, 90%-99%, 95%-99%, 96%-99%, 97%-99%, or 98%-99% pure. In some embodiments, isolated agents are 80%-99%, 80%-98%, 80%-97%, 80%-96%, 80%-95%, 80%-90%, or 80%-85% pure. In some embodiments, isolated agents are 85%-98%, 90%-97%, or 95%-96% pure. In some embodiments, a substance is "pure" if it is substantially free of other components. In some embodiments, as will be understood by those skilled in the art, a substance may still be considered "isolated" or even "pure", after having been combined with certain other components such as, for example, one or more carriers or excipients (e.g., buffer, solvent, water, etc.); in such embodiments, percent isolation or purity of the substance is calculated without including such carriers or excipients. To give but one example, in some embodiments, a biological polymer such as a polypeptide or polynucleotide that occurs in nature is considered to be "isolated" when: a) by virtue of its origin or source of derivation is not associated with some or all of the components that accompany it in its native state in nature; b) it is substantially free of other polypeptides or nucleic acids of the same species from the species that produces it in nature; or c) is expressed by or is otherwise in association with components from a cell or other expression system that is not of the species that produces it in nature. Thus, for instance, in some embodiments, a polypeptide that is chemically synthesized, or is synthesized in a cellular system different from that which produces it in nature, is considered to be an "isolated" polypeptide. Alternatively, or additionally, in some embodiments, a polypeptide that has been subjected to one or more purification techniques may be considered to be an "isolated" polypeptide to the extent that it has been separated from other components: a) with which it is associated in nature; and/or b) with which it was associated when initially produced.

Locus or loci: as used herein, refers to a specific location(s) of a gene (or significant sequence), DNA sequence, polypeptide-encoding sequence, or position on a chromosome of the genome of an organism. For example, an "immunoglobulin locus" may refer to the specific location of an immunoglobulin gene segment (e.g., V, D, J or C), immunoglobulin gene segment DNA sequence, immunoglobulin gene segment-encoding sequence, or immunoglobulin gene segment position on a chromosome of the genome of an organism that has been identified as to where such a sequence resides. An "immunoglobulin locus" may comprise a regulatory element of an immunoglobulin gene segment, including, but not limited to, an enhancer, a promoter, 5' and/or 3' regulatory sequence or region, or a combination thereof. An "immunoglobulin locus" may comprise DNA that normally resides between gene segments in a wild-type locus, but the DNA itself lacks an immunoglobulin gene segment (e.g., an immunoglobulin DNA sequence that naturally resides between a group of V gene segments and a group of J gene segments, an immunoglobulin DNA sequence that naturally resides between a group of J gene segments and a constant region gene, or an immunoglobulin DNA sequence that naturally resides 3' of a constant region gene). Persons of ordinary skill in the art will appreciate that chromosomes may, in some embodiments, contain hundreds or even thousands of genes and demonstrate physical co-localization of similar genetic loci when comparing between different species. Such genetic loci can be described as having shared synteny.

Non-human animal: as used herein, refers to any vertebrate organism that is not a human. In some embodiments, a non-human animal is a cyclostome, a bony fish, a cartilaginous fish (e.g., a shark or a ray), an amphibian, a reptile, a mammal, and a bird. In some embodiments, a non-human animal is a mammal. In some embodiments, a non-human mammal is a primate, a goat, a sheep, a pig, a dog, a cow, or a rodent. In some embodiments, a non-human animal is a rodent such as a rat or a mouse.

Nucleic acid: as used herein, refers to any compound and/or substance that is or can be incorporated into an oligonucleotide chain. In some embodiments, a "nucleic acid" is a compound and/or substance that is or can be incorporated into an oligonucleotide chain via a phosphodiester linkage. As will be clear from context, in some embodiments, "nucleic acid" refers to individual nucleic acid residues (e.g., nucleotides and/or nucleosides); in some embodiments, "nucleic acid" refers to an oligonucleotide chain comprising individual nucleic acid residues. In some embodiments, a "nucleic acid" is or comprises RNA; in some embodiments, a "nucleic acid" is or comprises DNA. In some embodiments, a "nucleic acid" is, comprises, or consists of one or more natural nucleic acid residues. In some embodiments, a "nucleic acid" is, comprises, or consists of one or more nucleic acid analogs. In some embodiments, a nucleic acid analog differs from a "nucleic acid" in that it does not utilize a phosphodiester backbone. For example, in some embodiments, a "nucleic acid" is, comprises, or consists of one or more "peptide nucleic acids", which are known in the art and have peptide bonds instead of phosphodiester bonds in the backbone. Alternatively, or additionally, in some embodiments, a "nucleic acid" has one or more phosphorothioate and/or 5'-N-phosphoramidite linkages rather than phosphodiester bonds. In some embodiments, a "nucleic acid" is, comprises, or consists of one or more natural nucleosides (e.g., adenosine, thymidine, guanosine, cytidine, uridine, deoxyadenosine, deoxythymidine, deoxyguanosine, and deoxycytidine). In some embodiments, a "nucleic acid" is, comprises, or consists of one or more nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, 2-thiocytidine, methylated bases, intercalated bases, and combinations thereof). In some embodiments, a "nucleic acid" comprises one or more modified sugars (e.g., 2'-fluororibose, ribose, 2'-deoxyribose, arabinose, and hexose) as compared with those in natural nucleic acids. In some embodiments, a "nucleic acid" has a nucleotide sequence that encodes a functional gene product such as an RNA or polypeptide. In some embodiments, a "nucleic acid" includes one or more introns. In some embodiments, a "nucleic acid" includes one or more exons. In some embodiments, a "nucleic acid" is prepared by one or more of isolation from a natural source, enzymatic synthesis by polymerization based on a complementary template (in vivo or in vitro), reproduction in a recombinant cell or system, and chemical synthesis. In some embodiments, a "nucleic acid" is at least, e.g., but not limited to, 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, 20, 225, 250, 275, 300, 325, 350, 375, 400, 425, 450, 475, 500, 600, 700, 800, 900, 1000, 1500, 2000, 2500, 3000, 3500, 4000, 4500, 5000 or more residues long. In some embodiments, a "nucleic acid" is single stranded; in some embodiments, a "nucleic acid" is double stranded. In some embodiments, a "nucleic acid" has a nucleotide sequence comprising at least one element that encodes, or is the complement of a sequence that encodes, a polypeptide. In some embodiments, a "nucleic acid" has enzymatic activity.

Operably linked: as used herein, refers to a juxtaposition wherein the components described are in a relationship permitting them to function in their intended manner. For example, unrearranged variable region gene segments are "operably linked" to a contiguous constant region gene if the unrearranged variable region gene segments are capable of rearranging to form a rearranged variable region gene that is expressed in conjunction with the constant region gene as a polypeptide chain of an antigen binding protein. A control sequence "operably linked" to a coding sequence is ligated in such a way that expression of the coding sequence is achieved under conditions compatible with the control sequences. "Operably linked" sequences include both expression control sequences that are contiguous with a gene of interest and expression control sequences that act in trans or at a distance to control a gene of interest (or sequence of interest). The term "expression control sequence" includes polynucleotide sequences, which are necessary to affect the expression and processing of coding sequences to which they are ligated. "Expression control sequences" include: appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance polypeptide stability; and when desired, sequences that enhance polypeptide secretion. The nature of such control sequences differs depending upon the host organism. For example, in prokaryotes, such control sequences generally include promoter, ribosomal binding site and transcription termination sequence, while in eukaryotes typically such control sequences include promoters and transcription termination sequence. The term "control sequences" is intended to include components whose presence is essential for expression and processing, and can also include additional components whose presence is advantageous, for example, leader sequences and fusion partner sequences.

Physiological conditions: as used herein, refers to its art-understood meaning referencing conditions under which cells or organisms live and/or reproduce. In some embodiments, the term includes conditions of the external or internal milieu that may occur in nature for an organism or cell system. In some embodiments, physiological conditions are those conditions present within the body of a human or non-human animal, especially those conditions present at and/or within a surgical site. Physiological conditions typically include, e.g., a temperature range of 20-40° C., atmospheric pressure of 1, pH of 6-8, glucose concentration of 1-20 mM, oxygen concentration at atmospheric levels, and gravity as it is encountered on earth. In some embodiments, conditions in a laboratory are manipulated and/or maintained at physiologic conditions. In some embodiments, physiological conditions are encountered in an organism.

Polypeptide: as used herein, refers to any polymeric chain of amino acids. In some embodiments, a polypeptide has an amino acid sequence that occurs in nature. In some embodiments, a polypeptide has an amino acid sequence that does not occur in nature. In some embodiments, a polypeptide has an amino acid sequence that contains portions that occur in nature separately from one another (i.e., from two or more different organisms, for example, human and non-human portions). In some embodiments, a polypeptide has an amino acid sequence that is engineered in that it is designed and/or produced through action of the hand of man. In some embodiments, a polypeptide has an amino acid sequence encoded by a sequence that does not occur in nature (e.g., a sequence that is engineered in that it is designed and/or produced through action of the hand of man to encode said polypeptide).

Recombinant: as used herein, is intended to refer to polypeptides that are designed, engineered, prepared, expressed, created or isolated by recombinant means, such as polypeptides expressed using a recombinant expression vector transfected into a host cell, polypeptides isolated from a recombinant, combinatorial human polypeptide library (Hoogenboom, H. R., 1997, TIB Tech. 15:62-70; Azzazy, H. and W. E. Highsmith, 2002, Clin. Biochem. 35:425-45; Gavilondo, J. V. and J. W. Larrick, 2002, Bio-Techniques 29:128-45; Hoogenboom H., and P. Chames, 2000, Immunol. Today 21:371-8), antibodies isolated from an animal (e.g., a mouse) that is transgenic for human immunoglobulin genes (see e.g., Taylor, L. D. et al., 1992, Nucl. Acids Res. 20:6287-95; Kellermann, S-A. and L. L. Green, 2002, Curr. Opin. Biotechnol. 13:593-7; Little, M. et al., 2000, Immunol. Today 21:364-70; Osborn, M. J. et al., 2013, J. Immunol. 190:1481-90; Lee, E-C. et al., 2014, Nat. Biotech. 32(4):356-63; Macdonald, L. E. et al., 2014, Proc. Natl. Acad. Sci. U.S.A. 111(14):5147-52; Murphy, A. J. et al., 2014, Proc. Natl. Acad. Sci. U.S.A. 111(14):5153-8) or polypeptides prepared, expressed, created or isolated by any other means that involves splicing selected sequence elements to one another. In some embodiments, one or more of such selected sequence elements is found in nature. In some embodiments, one or more of such selected sequence elements is designed in silico. In some embodiments, one or more such selected sequence elements result from mutagenesis (e.g., in vivo or in vitro) of a known sequence element, e.g., from a natural or synthetic source. For example, in some embodiments, a recombinant polypeptide is comprised of sequences found in the genome of a source organism of interest (e.g., human, mouse, etc.). In some embodiments, a recombinant polypeptide has an amino acid sequence that resulted from mutagenesis (e.g., in vitro or in vivo, for example, in a non-human animal), so that the amino acid sequences of the recombinant polypeptides are sequences that, while originating from and related to polypeptides sequences, may not naturally exist within the genome of a non-human animal in vivo.

Reference: as used herein, refers to a standard or control agent, animal, cohort, individual, population, sample, sequence or value against which an agent, animal, cohort, individual, population, sample, sequence or value of interest is compared. In some embodiments, a reference agent, animal, cohort, individual, population, sample, sequence or value is tested and/or determined substantially simultaneously with the testing or determination of an agent, animal, cohort, individual, population, sample, sequence or value of interest. In some embodiments, a reference agent, animal, cohort, individual, population, sample, sequence or value is a historical reference, optionally embodied in a tangible medium. In some embodiments, a reference may refer to a control. A "reference" also includes a "reference animal." A "reference animal" may have a modification as described herein, a modification that is different as described herein or no modification (i.e., a wild-type animal). Typically, as would be understood by persons of skill in the art, a reference agent, animal, cohort, individual, population, sample, sequence or value is determined or characterized under conditions comparable to those utilized to determine or characterize an agent, animal (e.g., a mammal), cohort, individual, population, sample, sequence or value of interest.

Replacement: as used herein, refers to a process through which a "replaced" nucleic acid sequence (e.g., a gene) found in a host locus (e.g., in a genome) is removed from that locus, and a different, "replacement" nucleic acid is located in its place. In some embodiments, the replaced nucleic acid sequence and the replacement nucleic acid sequences are comparable to one another in that, for example, they are homologous to one another and/or contain corresponding elements (e.g., protein-coding elements, regulatory elements, etc.). In some embodiments, a replaced nucleic acid sequence includes one or more of a promoter, an enhancer, a splice donor site, a splice acceptor site, an intron, an exon, an untranslated region (UTR); in some embodiments, a replacement nucleic acid sequence includes one or more coding sequences. In some embodiments, a replacement nucleic acid sequence is a homolog or variant (e.g., mutant) of the replaced nucleic acid sequence. In some embodiments, a replacement nucleic acid sequence is an ortholog or homolog of the replaced sequence. In some embodiments, a replacement nucleic acid sequence is or comprises a human nucleic acid sequence. In some embodiments, including where the replacement nucleic acid sequence is or comprises a human nucleic acid sequence, the replaced nucleic acid sequence is or comprises a rodent sequence (e.g., a mouse or rat sequence). In some embodiments, including where the replacement nucleic acid sequence is or comprises a human nucleic acid sequence, the replaced nucleic acid sequence is or comprises a human sequence. In some embodiments, a replacement nucleic acid sequence is a variant or mutant (i.e., a sequence that contains one or more sequence differences, e.g., substitutions, as compared to the replaced sequence) of the replaced sequence. The nucleic acid sequence so placed may include one or more regulatory sequences that are part of source nucleic acid sequence used to obtain the sequence so placed (e.g., promoters, enhancers, 5'- or 3'-untranslated regions, etc.). For example, in various embodiments, a replacement is a substitution of an endogenous sequence with a heterologous sequence that results in the production of a gene product from the nucleic acid sequence so placed (comprising the heterologous sequence), but not expression of the endogenous sequence; a replacement is of an endogenous genomic sequence with a nucleic acid sequence that encodes a polypeptide that has a similar function as a polypeptide encoded by the endogenous sequence (e.g., the endogenous genomic sequence encodes a non-human variable domain polypeptide, in whole or in part, and the DNA fragment encodes one or more human variable domain polypeptides, in whole or in part). In various embodiments, an endogenous non-human immunoglobulin gene segment or fragment thereof is replaced with a human immunoglobulin gene segment or fragment thereof.

Substantially: as used herein, refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Substantial homology: as used herein, refers to a comparison between amino acid or nucleic acid sequences. As will be appreciated by those of ordinary skill in the art, two sequences are generally considered to be "substantially homologous" if they contain homologous residues in corresponding positions. Homologous residues may be identical residues. Alternatively, homologous residues may be non-identical residues with appropriately similar structural and/or functional characteristics. For example, as is well known by those of ordinary skill in the art, certain amino acids are typically classified as "hydrophobic" or "hydrophilic" amino acids, and/or as having "polar" or "non-polar" side chains. Substitution of one amino acid for another of the same type may often be considered a "homologous" substitution. Typical amino acid categorizations are summarized in the table below.

| Alanine | Ala | A | Nonpolar | Neutral | 1.8 |
|---|---|---|---|---|---|
| Arginine | Arg | R | Polar | Positive | −4.5 |
| Asparagine | Asn | N | Polar | Neutral | −3.5 |
| Aspartic acid | Asp | D | Polar | Negative | −3.5 |
| Cysteine | Cys | C | Nonpolar | Neutral | 2.5 |
| Glutamic acid | Glu | E | Polar | Negative | −3.5 |
| Glutamine | Gln | Q | Polar | Neutral | −3.5 |
| Glycine | Gly | G | Nonpolar | Neutral | −0.4 |
| Histidine | His | H | Polar | Positive | −3.2 |
| Isoleucine | Ile | I | Nonpolar | Neutral | 4.5 |
| Leucine | Leu | L | Nonpolar | Neutral | 3.8 |
| Lysine | Lys | K | Polar | Positive | −3.9 |
| Methionine | Met | M | Nonpolar | Neutral | 1.9 |
| Phenylalanine | Phe | F | Nonpolar | Neutral | 2.8 |
| Proline | Pro | P | Nonpolar | Neutral | −1.6 |
| Serine | Ser | S | Polar | Neutral | −0.8 |
| Threonine | Thr | T | Polar | Neutral | −0.7 |
| Tryptophan | Trp | W | Nonpolar | Neutral | −0.9 |
| Tyrosine | Tyr | Y | Polar | Neutral | −1.3 |
| Valine | Val | V | Nonpolar | Neutral | 4.2 |

| Ambiguous Amino Acids | 3-Letter | 1-Letter |
|---|---|---|
| Asparagine or aspartic acid | Asx | B |
| Glutamine or glutamic acid | Glx | Z |
| Leucine or Isoleucine | Xle | J |
| Unspecified or unknown amino acid | Xaa | X |

As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul, S. F. et al., 1990, J. Mol. Biol., 215(3): 403-10; Altschul, S. F. et al., 1996, Meth. Enzymol. 266:460-80; Altschul, S. F. et al., 1997, Nucleic Acids Res., 25:3389-402; Baxevanis, A. D. and B. F. F. Ouellette (eds.) Bioinformatics: A Practical Guide to the Analysis of Genes and Proteins, Wiley, 1998; and Misener et al. (eds.) Bioinformatics Methods and Protocols, Methods in Molecular Biology, Vol. 132, Humana Press, 1998. In addition to identifying homologous sequences, the programs mentioned above typically provide an indication of the degree of homology. In some embodiments, two sequences are considered to be substantially homologous if at least, e.g., but not limited to, 50%, 55%, 60%, 65%, 70%, 75%, 80%, 85%, 90%, 91%, 92%, 93%, 94%, 95%, 96%, 97%, 98%, 99% or more of their corresponding residues are homologous over a relevant stretch of residues. In some embodiments, the relevant stretch is a complete sequence. In some embodiments, the relevant stretch is at least 9, 10, 11, 12, 13, 14, 15, 16, 17 or more residues. In some embodiments, the relevant stretch includes contiguous residues along a complete sequence. In some embodiments, the relevant stretch includes discontinuous residues along a complete sequence, for example, noncontiguous residues brought together by the folded conformation of a polypeptide or a portion thereof. In some embodiments, the relevant stretch is at least, e.g., but not limited to, 10, 15, 20, 25, 30, 35, 40, 45, 50, or more residues.

Substantial identity: as used herein, refers to a comparison between amino acid or nucleic acid sequences. As will be appreciated by those of ordinary skill in the art, two sequences are generally considered to be "substantially identical" if they contain identical residues in corresponding positions. As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul, S. F. et al., 1990, J. Mol. Biol., 215(3): 403-10; Altschul, S. F. et al., 1996, Meth. Enzymol. 266:460-80; Altschul, S. F. et al., 1997, Nucleic Acids Res., 25:3389-402; Baxevanis, A. D. and B. F. F. Ouellette (eds.) Bioinformatics: A Practical Guide to the Analysis of Genes and Proteins, Wiley, 1998; and Misener et al. (eds.) Bioinformatics Methods and Protocols, Methods in Molecular Biology, Vol. 132, Humana Press, 1998. In addition to identifying identical sequences, the programs mentioned above typically provide an indication of the degree of identity. In some embodiments, two sequences are considered to be substantially identical if at least 50%, 55%, 60%, 65%, 70%, 75%, 80%, 85%, 90%, 91%, 92%, 93%, 94%, 95%, 96%, 97%, 98%, 99% or more of their corresponding residues are identical over a relevant stretch of residues. In some embodiments, a relevant stretch of residues is a complete sequence. In some embodiments, a relevant stretch of residues is, e.g., but not limited to, at least 10, 15, 20, 25, 30, 35, 40, 45, 50, or more residues.

Targeting construct or targeting vector: as used herein, refers to a polynucleotide molecule that comprises a targeting region. A targeting region comprises a sequence that is identical or substantially identical to a sequence in a target cell, tissue or animal and provides for integration of the targeting construct into a position within the genome of the cell, tissue or animal via homologous recombination. Targeting regions that target using site-specific recombinase recognition sites (e.g., loxP or Frt sites) are also included and described herein. In some embodiments, a targeting construct as described herein further comprises a nucleic acid sequence or gene of particular interest, a selectable marker, control and/or regulatory sequences, and other nucleic acid sequences that allow for recombination mediated through exogenous addition of proteins that aid in or facilitate recombination involving such sequences. In some embodiments, a targeting construct as described herein further comprises a gene of interest in whole or in part, wherein the gene of interest is a heterologous gene that encodes a polypeptide, in whole or in part, that has a similar function as a protein encoded by an endogenous sequence. In some embodiments, a targeting construct as described herein further comprises a humanized gene of interest, in whole or in part, wherein the humanized gene of interest encodes a polypeptide, in whole or in part, that has a similar function as a polypeptide encoded by an endogenous sequence. In some embodiments, a targeting construct (or targeting vector) may comprise a nucleic acid sequence manipulated by the hand of man. For example, in some embodiments, a targeting construct (or targeting vector) may be constructed to contain an engineered or recombinant polynucleotide that contains two or more sequences that are not linked together in that order in nature yet manipulated by the hand of man to be directly linked to one another in the engineered or recombinant polynucleotide.

Transgene or transgene construct: as used herein, refers to a nucleic acid sequence (encoding e.g., a polypeptide of interest, in whole or in part) that has been introduced into a cell by the hand of man such as by the methods described herein. A transgene could be partly or entirely heterologous, i.e., foreign, to the transgenic animal or cell into which it is introduced. A transgene can include one or more transcriptional regulatory sequences and any other nucleic acid, such as introns or promoters, which may be necessary for expression of a selected nucleic acid sequence.

Transgenic animal, transgenic non-human animal or $Tg^+$: are used interchangeably herein and refer to any non-naturally occurring non-human animal in which one or more of the cells of the non-human animal contain heterologous nucleic acid and/or gene encoding a polypeptide of interest, in whole or in part. For example, in some embodiments, a "transgenic animal" or "transgenic non-human animal" refers to an animal or non-human animal that contains a transgene or transgene construct as described herein. In some embodiments, a heterologous nucleic acid and/or gene is introduced into the cell, directly or indirectly by introduction into a precursor cell, by way of deliberate genetic manipulation, such as by microinjection or by infection with a recombinant virus. The term genetic manipulation does not include classic breeding techniques, but rather is directed to introduction of recombinant DNA molecule(s). This molecule may be integrated within a chromosome, or it may be extrachromosomally replicating DNA. The term "$Tg^+$" includes animals that are heterozygous or homozygous for a heterologous nucleic acid and/or gene, and/or animals that have single or multi-copies of a heterologous nucleic acid and/or gene.

Variant: as used herein, refers to an entity that shows significant structural identity with a reference entity, but differs structurally from the reference entity in the presence or level of one or more chemical moieties as compared with the reference entity. In many embodiments, a "variant" also differs functionally from its reference entity. In general, whether a particular entity is properly considered to be a "variant" of a reference entity is based on its degree of structural identity with the reference entity. As will be appreciated by persons of skill in the art, any biological or chemical reference entity has certain characteristic structural elements. A "variant", by definition, is a distinct chemical entity that shares one or more such characteristic structural elements. To give but a couple examples, a polypeptide may have a characteristic sequence element comprised of a plurality of amino acids having designated positions relative to one another in linear or three-dimensional space and/or contributing to a particular biological function, or a nucleic acid may have a characteristic sequence element comprised of a plurality of nucleotide residues having designated positions relative to on another in linear or three-dimensional space. In another example, a "variant polypeptide" may differ from a reference polypeptide as a result of one or more differences in amino acid sequence and/or one or more differences in chemical moieties (e.g., carbohydrates, lipids, etc.) covalently attached to the polypeptide backbone. In some embodiments, a "variant polypeptide" shows an overall sequence identity with a reference polypeptide that is at least 85%, 86%, 87%, 88%, 89%, 90%, 91%, 92%, 93%, 94%, 95%, 96%, 97%, or 99%. Alternatively, or additionally, in some embodiments, a "variant polypeptide" does not share at least one characteristic sequence element with a reference polypeptide. In some embodiments, a reference polypeptide has one or more biological activities. In some embodiments, a "variant polypeptide" shares one or more of the biological activities of the reference polypeptide. In some embodiments, a "variant polypeptide" lacks one or more of the biological activities of the reference polypeptide. In some embodiments, a "variant polypeptide" shows a reduced level of one or more biological activities as compared with the reference polypeptide. In many embodiments, a polypeptide of interest is considered to be a "variant" of a parent or reference polypeptide if the polypeptide of interest has an amino acid sequence that is identical to that of the parent but for a small number of sequence alterations at particular positions. Typically, fewer than 20%, 15%, 10%, 9%, 8%, 7%, 6%, 5%, 4%, 3%, or 2% of the residues in the variant are substituted as compared with the parent. In some embodiments, a "variant" has, e.g., but not limited to, 10, 9, 8, 7, 6, 5, 4, 3, 2, or 1 substituted residue(s) as compared with a parent. Often, a "variant" has a very small number (e.g., fewer than 5, 4, 3, 2, or 1) number of substituted functional residues (i.e., residues that participate in a particular biological activity). Furthermore, a "variant" typically has not more than, e.g., but not limited to, 5, 4, 3, 2, or 1 additions or deletions, and often has no additions or deletions, as compared with the parent. Moreover, any additions or deletions are typically fewer than about 25, about 20, about 19, about 18, about 17, about 16, about 15, about 14, about 13, about 10, about 9, about 8, about 7, about 6, and commonly are fewer than about 5, about 4, about 3, or about 2 residues. In some embodiments, a parent or reference polypeptide is one found in nature. As will be understood by persons of ordinary skill in the art, a plurality of variants of a particular polypeptide of interest may commonly be found in nature, particularly when the polypeptide of interest is an infectious agent polypeptide.

Vector: as used herein, refers to a nucleic acid molecule capable of transporting another nucleic acid to which it is associated. In some embodiment, vectors are capable of extra-chromosomal replication and/or expression of nucleic acids to which they are linked in a host cell such as a eukaryotic and/or prokaryotic cell. Vectors capable of directing the expression of operably linked genes are referred to herein as "expression vectors."

Wild-type: as used herein, refers to an entity having a structure and/or activity as found in nature in a "normal" (as contrasted with mutant, diseased, altered, etc.) state or context. Those of ordinary skill in the art will appreciate that wild-type genes and polypeptides often exist in multiple different forms (e.g., alleles).

DETAILED DESCRIPTION OF CERTAIN EMBODIMENTS

In certain aspects, provided herein, among other things, are engineered non-human animals having heterologous genetic material encoding human variable domains and, in some embodiments, human constant domains, which heterologous genetic material comprises human Vλ Jλ and Cλ gene sequences (i.e., gene segments) and other human sequences that provide for proper rearrangement and expression of antibodies having a human portion and a non-human portion or antibodies having a sequence that is substantially or substantially all human. In various embodiments, provided engineered non-human animals contain heterologous genetic material that is inserted in such a way so that antibodies containing light chains that have a human Vλ domain and a human or non-human Cλ domain are expressed in the antibody repertoire of the non-human animal. Further, provided engineered non-human animals contain heterologous genetic material that is inserted in such a way so that antibodies containing light chains that have a human Vλ domain and a human or non-human Cλ domain are expressed from engineered Igλ light chain loci that include human and non-human Igλ enhancer regions (or sequences) in the germline genome of the non-human animal.

Without wishing to be bound by any particular theory, it is contemplated that embodiments of the non-human animals as described herein provide an improved in vivo system that exploits the expression of antibodies containing human Vλ domains for the production of therapeutic antibodies. It is also contemplated that embodiments of the non-human animals as described herein, in some embodiments, provide alternative engineered forms of Igλ light chain loci that contain heterologous genetic material for the development of human antibody-based therapeutics (e.g., human monoclonal antibodies, multi-specific binding agents, scFvs, fusion polypeptides, etc.) to disease targets that are associated with biased antibody responses (e.g., antibody responses characterized by an overwhelming proportion of either κ or λ light chains). Thus, embodiments of the non-human animals as described herein are particularly useful for the development of human antibodies against targets associated with poor immunogenicity (e.g., viruses) due, in part, to skewed antibody repertoires and/or responses.

In particular, in certain aspects the present disclosure describes the production of a non-human animal (e.g., a rodent, such as a rat or mouse) having a germline genome that contains an engineered Igλ light chain locus that is, in some embodiments, characterized by the introduction of a plurality of human Vλ, Jλ and Cλ gene sequences in operable linkage to a non-human Cλ region resulting in the expression of antibodies that contain light chains that include a human Vλ domain and a human or non-human Cλ domain. As described herein, the production of such an engineered Igλ light chain locus results in the expression of antibodies that contain light chains that include a human Vλ domain and a human or non-human Cλ domain from said engineered Igλ light chain locus in the germline genome of the non-human animal. The germline genome of provided non-human animals, in some embodiments, further comprises (1) humanized IgH and Igκ loci or (2) a humanized IgH locus and functionally silenced or otherwise rendered non-functional Igκ light chain loci. Provided non-human animals, as described herein, express antibody repertoires that contain Igλ light chains that include human Vλ domains.

In some embodiments, non-human animals as described herein contain human and non-human Igλ light chain sequences within a single Igλ light chain locus. In some embodiments, non-human animals as described herein contain human Igλ and murine (e.g., mouse or rat) Igλ light chain sequences within an Igλ light chain locus. In many embodiments of non-human animals as described herein, non-human Igλ light chain sequences are or comprise murine sequences (e.g., mouse or rat).

In some embodiments, Igλ light chain sequences include intergenic DNA that is of human and/or murine (e.g., mouse or rat) origin. In some embodiments, Igλ light chain sequences include intergenic DNA that is synthetic and based on a source sequence that is of human or murine (e.g., mouse or rat) origin. In some embodiments, said intergenic DNA is of the same immunoglobulin locus in which the intergenic DNA is so placed, inserted, positioned or engineered (e.g., Igλ intergenic DNA in an Igλ light chain locus). In some certain embodiments, non-human animals as described herein contain an engineered Igλ light chain locus that contains intergenic DNA that includes Igλ light chain sequence(s) of non-human origin (e.g., mouse or rat Igλ light chain sequence).

In various embodiments, a humanized IgH locus contains a plurality of human $V_H$, $D_H$ and $J_H$ gene segments operably linked to a non-human IgH constant region (e.g., an endogenous non-human IgH constant region that includes one or more IgH constant region genes such as, for example, IgM, IgG, etc.). In various embodiments, a humanized Igκ light chain locus contains a plurality of human Vκ and Jκ gene segments operably linked to a non-human Igκ constant region. In some embodiments, provided non-human animals have a germline genome that includes the immunoglobulin loci (or alleles) depicted in a Drawing provided herein (e.g., see FIGS. 1, 2, 3 and/or 4). Such engineered non-human animals provide a source of human antibodies and human antibody fragments, and/or nucleic acids encoding such human antibodies and human antibody fragments, and provide an improved in vivo system suitable for exploiting human Vλ sequences for the production of human therapeutic antibodies.

As described herein, in certain embodiments non-human animals are provided having a genome that contains a plurality of human λ light chain gene segments (e.g., Vλ, Jλ and Cλ) in the place of non-human immunoglobulin λ light chain gene segments at endogenous immunoglobulin light chain loci, and include human non-coding intergenic DNA between the human variable region gene segments. In some embodiments, non-human animals provided herein have a genome that further comprises human heavy (i.e., $V_H$, $D_H$ and $J_H$) and κ light chain (e.g., Vκ and Jκ) variable region gene segments in the place of non-human heavy (i.e., $V_H$, $D_H$ and $J_H$) and κ light chain (e.g., Vκ and Jκ) variable region gene segments at endogenous immunoglobulin heavy and κ light chain loci, respectively. In many embodiments, human immunoglobulin gene segments (heavy and/or light) are engineered with human intergenic DNA (i.e., human non-coding immunoglobulin intergenic DNA) that is naturally associated with said gene segments (i.e., non-coding genomic DNA associated with said gene segments that naturally appears in a human immunoglobulin locus of a human cell). Such intergenic DNA includes, for example, promoters, leader sequences and recombination signal sequences that allow for proper recombination and expression of the human gene segments in the context of variable domains of antibodies. Persons of skill understand that non-human immunoglobulin loci also contain such non-coding intergenic DNA and that, upon reading this disclosure, other human or non-human intergenic DNA can be employed in constructing such engineered immunoglobulin loci resulting in the same expression of human variable domains in the context of antibodies in the non-human animal. Such similar engineered immunoglobulin loci need only contain the human coding sequences (i.e., exons) of the desired human gene segments, or combination of human gene segments, to achieve expression of antibodies that contain human variable domains.

Various aspects of certain embodiments are described in detail in the following sections, each of which can apply to any aspect or embodiment as described herein. The use of sections is not for limitation, and the use of "or" means "and/or" unless stated otherwise.

Antibody Repertoires in Non-Human Animals

Immunoglobulins (also called antibodies) are large (~150 kD), Y-shaped glycoproteins that are produced by B cells of a host immune system to neutralize foreign antigens (e.g., viruses, bacteria, etc.). Each immunoglobulin (Ig) is composed of two identical heavy chains and two identical light chains, each of which has two structural components: a variable domain and a constant domain. The heavy and light chain variable domains differ in antibodies produced by different B cells, but are the same for all antibodies produced by a single B cell or B cell clone. The heavy and light chain variable domains of each antibody together comprise the antigen-binding region (or antigen-binding site). Immunoglobulins can exist in different varieties that are referred to as isotypes or classes based on the heavy chain constant regions (or domains) that they contain. The heavy chain constant domain is identical in all antibodies of the same isotype, but differs in antibodies of different isotypes. The table below summarizes the nine antibody isotypes in mouse and man (human).

| Mouse | Human |
|---|---|
| IgM | IgM |
| IgD | IgD |
| IgG1 | IgG1 |
| IgG2a | IgG2 |
| IgG2b | IgG3 |
| IgG2c | IgG4 |
| IgG3 | IgE |
| IgE | IgA1 |
| IgA | IgA2 |

Additional isotypes have been identified in other species. Isotypes confer specialized biological properties on the antibody due to the different structural characteristics among the different isotypes and are found in different locations (cells, tissues, etc.) within an animal body. Initially, B cells produce IgM and IgD with identical antigen-binding regions. Upon activation, B cells switch to different isotypes by a process referred to as class switching, which involves a change of the constant domain of the antibody produced by the B cell while the variable domains remain the same, thereby preserving antigen specificity of the original antibody (B cell).

Two separate loci (Igκ and Igλ) contain the gene segments that encode the light chains of antibodies, and exhibit both allelic and isotypic exclusion. The expression ratios of $κ^+$ to $λ^+$ B cells vary among species. For example, humans demonstrate a ratio of about 60:40 (κ:λ). In mice and rats, a ratio of 95:5 (κ:λ) is observed. Interestingly, the κ:λ ratio observed in cats (5:95) is opposite of mice and rats. Several studies have been conducted to elucidate the possible reasons behind these observed ratios and have proposed that both the complexity of the locus (i.e., number of gene segments, in particular, V gene segments) and the efficiency of gene segment rearrangement as rationale. The human immunoglobulin λ light chain locus extends over 1,000 kb and contains approximately 70 Vλ gene segments (29 to 33 functional) and seven Jλ-Cλ gene segment pairs (four to five functional) organized into three clusters (see, e.g., FIG. 1 of U.S. Pat. No. 9,006,511). The majority of the observed Vλ regions in the expressed antibody repertoire are encoded by gene segments contained within the most proximal cluster (i.e., cluster A). The mouse immunoglobulin λ light chain locus is strikingly different than the human locus and, depending on the strain, contains only a few Vλ and Jλ gene segments organized in two distinct gene clusters (see, e.g., FIG. 2 of U.S. Pat. No. 9,006,511).

Development of therapeutic antibodies for the treatment of various human diseases has largely been centered on the creation of engineered non-human animal lines, in particular, engineered rodent lines, harboring varying amounts of genetic material in their genomes corresponding to human immunoglobulin genes (reviewed in, e.g., Brüggemann, M. et al., 2015, Arch. Immunol. Ther. Exp. 63:101-8). Initial efforts in creating such transgenic rodent lines focused on integration of portions of human immunoglobulin loci that could, by themselves, support recombination of gene segments and production of heavy and/or light chains that were entirely human while having endogenous immunoglobulin loci inactivated (see e.g., Brüggemann, M. et al., 1989, Proc. Nat. Acad. Sci. U.S.A. 86:67-09-13; Brüggemann, M. et al., 1991, Eur. J. Immunol. 21:1323-6; Taylor, L. D. et al., 1992, Nucl. Acids Res. 20:6287-6295; Davies, N. P. et al., 1993, Biotechnol. 11:911-4; Green, L. L. et al., 1994, Nat. Genet. 7:13-21; Lonberg, N. et al., 1994, Nature 368:856-9; Taylor, L. D. et al., 1994, Int. Immunol. 6:579-91; Wagner, S. D. et al., 1994, Eur. J. Immunol. 24:2672-81; Fishwild, D. M. et al., 1996, Nat. Biotechnol. 14:845-51; Wagner, S. D. et al., 1996, Genomics 35:405-14; Mendez, M. J. et al., 1997, Nat. Genet. 15:146-56; Green, L. L. et al., 1998, J. Exp. Med. 188:483-95; Xian, J. et al., 1998, Transgenics 2:333-43; Little, M. et al., 2000, Immunol. Today 21:364-70; Kellermann, S. A. and L. L. Green, 2002, Cur. Opin. Biotechnol. 13:593-7). In particular, some efforts have included integration of human Igλ light chain sequences (see, e.g., U.S. Patent Application Publication Nos. 2002/0088016 A1, 2003/0217373 A1 and 2011/0236378 A1; U.S. Pat. Nos. 6,998,514 and 7,435,871; Nicholson, I. C. et al., 1999, J. Immunol. 163:6898-906; Popov, A. V et al., 1999, J. Exp. Med. 189(10):1611-19). Such efforts have focused on the random integration of yeast artificial chromosomes containing human Vλ, Jλ and Cλ sequences thereby creating mouse strains that express fully human λ light chains (i.e., human variable and human constant). More recent efforts have employed similar strategies using constructs that also contain human Vλ, Jλ and Cλ sequences (Osborn, M. J. et al., 2013, J. Immunol. 190:1481-90; Lee, E-C. et al., 2014, Nat. Biotech. 32(4):356-63).

Yet other efforts have included the specific insertion of human Vλ and Jλ gene segments into endogenous rodent Ig light chain loci (κ and λ) so that said human Vλ and Jλ gene segments are operably linked to endogenous Ig light chain constant regions (see, e.g., U.S. Pat. Nos. 9,006,511, 9,012, 717, 9,029,628, 9,035,128, 9,066,502, 9,150,662 and 9,163, 092; all of which are incorporated herein by reference in their entireties). In such animals, all of the human Vλ gene segments from clusters A and B and either one or four human Jλ gene segments were inserted into endogenous Igκ and Igλ light chain loci. As a result, several different human Vλ and Jλ gene segments demonstrated proper rearrangement at both engineered rodent Ig light chain loci to form functional human Vλ domains that were expressed in the context of both Cκ and Cλ regions in light chains of the rodent antibody repertoire (see, e.g., Table 7 and FIGS. 11-13 of U.S. Pat. No. 9,006,511). In particular, mice having engineered Igκ light chain loci harboring human Vλ and Jλ gene segments demonstrated a κ:λ ratio of about 1:1 in the splenic compartment (see, e.g., Table 4 of U.S. Pat. No. 9,006,511). Indeed, both engineered mouse strains (i.e., engineered Igκ or engineered Igλ light chain loci) demonstrated that human Vλ domains could be expressed from endogenous Ig light chain loci in rodents, which normally display a large bias in light chain expression (see above).

The present invention is based on the recognition that other engineered Ig light chain locus structures can be produced to maximize usage of human Vλ and Jλ gene segments in antibody repertoires to therapeutic targets in non-human animals, in particular, as compared to non-human animals that contain an Igλ light chain locus that lacks the complexity and robust quality (e.g., mice and rats) normally associated with a human Igλ light chain locus (i.e., that appears in a human cell). Such alternative engineered Ig light chain locus structures provide the capacity for unique antibody repertoires resulting from their design.

The present disclosure describes, among other things, the successful production of a non-human animal whose germline genome contains an engineered endogenous Igλ light chain locus comprising a plurality of human Vλ, Jλ and Cλ gene segments in operable linkage to a non-human Igλ light chain constant region. In particular, the present disclosure specifically demonstrates the successful production of an engineered non-human animal that expresses antibodies having human variable domains and non-human constant domains, which antibodies include light chains that contain a human Vλ domain. As described herein, expression of such light chains is achieved by insertion of said plurality of human Vλ, Jλ and Cλ gene segments into an endogenous Igλ light chain locus (or allele). Also, as described herein, provided non-human animals are, in some embodiments, engineered so that expression of light chains that contain endogenous Vλ domains is inactivated (e.g., by gene deletion). Thus, the present disclosure, in at least some embodiments, embraces the development of an improved in vivo system for the production of human antibodies by providing an engineered non-human animal containing an alternatively engineered Igλ light chain locus that results in an expressed antibody repertoire containing human Vλ domains.

DNA Inserts

Typically, a polynucleotide molecule containing human Igλ light chain sequences (e.g., Vλ Jλ Cλ and Igλ enhancers) or portion(s) thereof is inserted into a vector, preferably a DNA vector, in order to replicate the polynucleotide molecule in a host cell.

Human Igλ light chain sequences can be cloned directly from known sequences or sources (e.g., libraries) or synthesized from germline sequences designed in silico based on published sequences available from GenBank or other publically available databases (e.g., IMGT). Alternatively, bacterial artificial chromosome (BAC) libraries can provide immunoglobulin DNA sequences of interest (e.g., human Vλ gene segments, human Jλ-Cλ gene segment pairs, human Eλ regions or sequences, and combinations thereof). BAC libraries can contain an insert size of 100-150 kb and are capable of harboring inserts as large as 300 kb (Shizuya, et al., 1992, Proc. Natl. Acad. Sci., USA 89:8794-8797; Swiatek, et al., 1993, Genes and Development 7:2071-2084; Kim, et al., 1996, Genomics 34 213-218; incorporated herein by reference in their entireties). For example, a human BAC library harboring average insert sizes of 164-196 kb has been described (Osoegawa, K. et al., 2001, Genome Res. 11(3):483-96; Osoegawa, K. et al., 1998, Genomics 52:1-8, Article No. GE985423). Human and mouse genomic BAC libraries have been constructed and are commercially available (e.g., ThermoFisher). Genomic BAC libraries can also serve as a source of immunoglobulin DNA sequences as well as transcriptional control regions.

Alternatively, immunoglobulin DNA sequences may be isolated, cloned and/or transferred from yeast artificial chromosomes (YACs). For example, the nucleotide sequence of the human Igλ light chain locus has been determined (see, e.g., Dunham, I. et al., 1999, Nature 402:489-95). Further, YACs have previously been employed to assemble a human Igλ light chain locus transgene (see, e.g., Popov, A. V. et al., 1996, Gene 177:195-201; Popov, A. V. et al., 1999, J. Exp. Med. 189(10):1611-19). An entire Igλ light chain locus (human or rodent) can be cloned and contained within several YACs. If multiple YACs are employed and contain regions of overlapping homology, they can be recombined within yeast host strains to produce a single construct representing the entire locus or desired portions of the locus (e.g., a region to targeted with a targeting vector). YAC arms can be additionally modified with mammalian selection cassettes by retrofitting to assist in introducing the constructs into embryonic stems cells or embryos by methods known in the art and/or described herein.

DNA and amino acid sequences of human Igλ light chain gene segments for use in constructing an engineered Igλ light chain locus as described herein may be obtained from published databases (e.g., GenBank, IMGT, etc.) and/or published antibody sequences. DNA inserts containing human Igλ light chain gene segments, in some embodiments, comprise one or more human Igλ light chain enhancer sequences (or regions). DNA inserts, in some embodiments, comprise a human Igλ light chain enhancer sequence (or region) that includes one or more sequence elements, e.g., one, two, three, etc. In some certain embodiments, DNA inserts comprise a human Igλ light chain enhancer sequence (or region), referred to as a human Eλ having three distinct sequence elements. Thus, in some embodiments, a human Eλ as described herein is modular and one or more sequence elements function together as an enhancer sequence (or region). In some certain embodiments, DNA inserts containing human Igλ light chain enhancer sequences comprise human Igλ light chain enhancer sequences operably linked to a non-human Igλ light chain sequence (e.g., a non-human Igλ light chain constant region sequence). In some certain embodiments, DNA inserts containing human Igλ light chain enhancer sequences comprise human Igλ light chain enhancer sequences operably linked to a non-human Igλ light chain sequence (e.g., a non-human Igλ light chain constant region sequence) and operably linked to one or more human Vλ gene segments, one or more human Jλ-Cλ gene segment pairs and/or one or more human Jλ gene segments. In some certain embodiments, DNA inserts containing human Igλ light chain enhancer sequences comprise human Igλ light chain enhancer sequences operably linked to a non-human Igλ light chain sequence (e.g., a non-human Igλ light chain constant region sequence), one or more human Vλ gene segments, one or more human Jλ gene segments and one or more human Cλ gene segments.

DNA inserts can be prepared using methods known in the art. For example, a DNA insert can be prepared as part of a larger plasmid. Such preparation allows the cloning and selection of the correct constructions in an efficient manner as is known in the art. DNA inserts containing human Igλ light chain sequences, in whole or in part, as described herein can be located between convenient restriction sites on the plasmid so that they can be easily isolated from the remaining plasmid sequences for incorporation into a desired non-human animal.

Various methods employed in preparation of plasmids and transformation of host organisms are known in the art. For other suitable expression systems for both prokaryotic and eukaryotic cells, as well as general recombinant procedures, see Principles of Gene Manipulation: An Introduction to Genetic Manipulation, 5th Ed., ed. By Old, R. W. and S. B. Primrose, Blackwell Science, Inc., 1994 and Molecular Cloning: A Laboratory Manual, 2nd Ed., ed. by Sambrook, J. et al., Cold Spring Harbor Laboratory Press: 1989.

Targeting Vectors

Targeting vectors can be employed to introduce a DNA insert into a genomic target locus and comprise a DNA insert and homology arms that flank said DNA insert. Targeting vectors can be in linear form or in circular form, and they can be single-stranded or double-stranded. Targeting vectors can be deoxyribonucleic acid (DNA) or ribonucleic acid (RNA). For ease of reference, homology arms are referred to herein as 5' and 3' (i.e., upstream and downstream) homology arms. This terminology relates to the relative position of the homology arms to a DNA insert within a targeting vector. 5' and 3' homology arms correspond to regions within a targeted locus or to a region within another targeting vector, which are referred to herein as "5' target sequence" and "3' target sequence," respectively. In some embodiments, homology arms can also function as a 5' or a 3' target sequence.

In some embodiments, methods described herein employ two, three or more targeting vectors that are capable of recombining with each other. In various embodiments, targeting vectors are large targeting vectors (LTVEC) as described elsewhere herein. In such embodiments, first, second, and third targeting vectors each comprise a 5' and a 3' homology arm. The 3' homology arm of the first targeting vector comprises a sequence that overlaps with the 5' homology arm of the second targeting vector (i.e., overlapping sequences), which allows for homologous recombination between first and second LTVECs.

In the case of double targeting methods, a 5' homology arm of a first targeting vector and a 3' homology arm of a second targeting vector are homologous to corresponding segments within a target genomic locus (i.e., a target sequence) which promotes homologous recombination of the first and the second targeting vectors with corresponding genomic segments and modifies the target genomic locus.

In the case of triple targeting methods, a 3' homology arm of a second targeting vector comprises a sequence that overlaps with a 5' homology arm of a third targeting vector (i.e., overlapping sequences), which allows for homologous recombination between the second and the third LTVEC. The 5' homology arm of the first targeting vector and the 3' homology arm of the third targeting vector are homologous to corresponding segments within the target genomic locus (i.e., the target sequence), which promotes homologous recombination of the first and the third targeting vectors with the corresponding genomic segments and modifies the target genomic locus.

A homology arm and a target sequence or two homology arms "correspond" or are "corresponding" to one another when the two regions share a sufficient level of sequence identity to one another to act as substrates for a homologous recombination reaction. The term "homology" includes DNA sequences that are either identical or share sequence identity to a corresponding sequence. The sequence identity between a given target sequence and the corresponding homology arm found on a targeting vector (i.e., overlapping sequence) or between two homology arms can be any degree of sequence identity that allows for homologous recombination to occur. To give but one example, an amount of sequence identity shared by a homology arm of a targeting vector (or a fragment thereof) and a target sequence of another targeting vector or a target sequence of a target genomic locus (or a fragment thereof) can be, e.g., but not limited to, at least 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity, such that the sequences undergo homologous recombination.

Moreover, a corresponding region of homology between a homology arm and a corresponding target sequence can be of any length that is sufficient to promote homologous recombination at the target genomic locus. For example, a given homology arm and/or corresponding target sequence can comprise corresponding regions of homology that are, e.g., but not limited to, at least about 5-10 kb, 5-15 kb, 5-20 kb, 5-25 kb, 5-30 kb, 5-35 kb, 5-40 kb, 5-45 kb, 5-50 kb, 5-55 kb, 5-60 kb, 5-65 kb, 5-70 kb, 5-75 kb, 5-80 kb, 5-85 kb, 5-90 kb, 5-95 kb, 5-100 kb, 100-200 kb, or 200-300 kb in length or more (such as described elsewhere herein) such that a homology arm has sufficient homology to undergo homologous recombination with a corresponding target sequence(s) within a target genomic locus of the cell or within another targeting vector. In some embodiments, a given homology arm and/or corresponding target sequence comprise corresponding regions of homology that are, e.g., but not limited to, at least about 10-100 kb, 15-100 kb, 20-100 kb, 25-100 kb, 30-100 kb, 35-100 kb, 40-100 kb, 45-100 kb, 50-100 kb, 55-100 kb, 60-100 kb, 65-100 kb, 70-100 kb, 75-100 kb, 80-100 kb, 85-100 kb, 90-100 kb, or 95-100 kb in length or more (such as described elsewhere herein) such that a homology arm has sufficient homology to undergo homologous recombination with a corresponding target sequence(s) within a target genomic locus of the cell or within another targeting vector.

Overlapping sequences of a 3' homology arm of a first targeting vector and a 5' homology arm of a second targeting vector or of a 3' homology arm of a second targeting vector and a 5' homology arm of a third targeting vector can be of any length that is sufficient to promote homologous recombination between said targeting vectors. For example, a given overlapping sequence of a homology arm can comprise corresponding overlapping regions that are at least about 1-5 kb, 5-10 kb, 5-15 kb, 5-20 kb, 5-25 kb, 5-30 kb, 5-35 kb, 5-40 kb, 5-45 kb, 5-50 kb, 5-55 kb, 5-60 kb, 5-65 kb, 5-70 kb, 5-75 kb, 5-80 kb, 5-85 kb, 5-90 kb, 5-95 kb, 5-100 kb, 100-200 kb, or 200-300 kb in length or more such that an overlapping sequence of a homology arm has sufficient homology to undergo homologous recombination with a corresponding overlapping sequence within another targeting vector. In some embodiments, a given overlapping sequence of a homology arm comprises an overlapping region that is at least about 1-100 kb, 5-100 kb, 10-100 kb, 15-100 kb, 20-100 kb, 25-100 kb, 30-100 kb, 35-100 kb, 40-100 kb, 45-100 kb, 50-100 kb, 55-100 kb, 60-100 kb, 65-100 kb, 70-100 kb, 75-100 kb, 80-100 kb, 85-100 kb, 90-100 kb, or 95-100 kb in length or more such that an overlapping sequence of a homology arm has sufficient homology to undergo homologous recombination with a corresponding overlapping sequence within another targeting vector. In some embodiments, an overlapping sequence is from 1-5 kb, inclusive. In some embodiments, an overlapping sequence is from about 1 kb to about 70 kb, inclusive. In some embodiments, an overlapping sequence is from about 10 kb to about 70 kb, inclusive. In some embodiments, an overlapping sequence is from about 10 kb to about 50 kb, inclusive. In some embodiments, an overlapping sequence is at least 10 kb. In some embodiments, an overlapping sequence is at least 20 kb. For example, an overlapping sequence can be from about 1 kb to about 5 kb, inclusive, from about 5 kb to about 10 kb, inclusive, from about 10 kb to about 15 kb, inclusive, from about 15 kb to about 20 kb, inclusive, from about 20 kb to about 25 kb, inclusive, from about 25 kb to about 30 kb, inclusive, from about 30 kb to about 35 kb, inclusive, from about 35 kb to about 40 kb, inclusive, from about 40 kb to about 45 kb, inclusive, from about 45 kb to about 50 kb, inclusive, from about 50 kb to about 60 kb, inclusive, from about 60 kb to about 70 kb, inclusive, from about 70 kb to about 80 kb, inclusive, from about 80 kb to about 90 kb, inclusive, from about 90 kb to about 100 kb, inclusive, from about 100 kb to about 120 kb, inclusive, from about 120 kb to about 140 kb, inclusive, from about 140 kb to about 160 kb, inclusive, from about 160 kb to about 180 kb, inclusive, from about 180 kb to about 200 kb, inclusive, from about 200 kb to about 220 kb, inclusive, from about 220 kb to about 240 kb, inclusive, from about 240 kb to about 260 kb, inclusive, from about 260 kb to about 280 kb, inclusive, or about 280 kb to about 300 kb, inclusive. To give but one example, an overlapping sequence can be from about 20 kb to about 60 kb, inclusive. Alternatively, an overlapping sequence can be at least 1 kb, at least 5 kb, at least 10 kb, at least 15 kb, at least 20 kb, at least 25 kb, at least 30 kb, at least 35 kb, at least 40 kb, at least 45 kb, at least 50 kb, at least 60 kb, at least 70 kb, at least 80 kb, at least 90 kb, at least 100 kb, at least 120 kb, at least 140 kb, at least 160 kb, at least 180 kb, at least 200 kb, at least 220 kb, at least 240 kb, at least 260 kb, at least 280 kb, or at least 300 kb.

Homology arms can, in some embodiments, correspond to a locus that is native to a cell (e.g., a targeted locus), or alternatively they can correspond to a region of a heterologous or exogenous segment of DNA that was integrated into the genome of the cell, including, for example, transgenes, expression cassettes, or heterologous or exogenous regions of DNA. Alternatively, homology arms can, in some embodiments, correspond to a region on a targeting vector in a cell. In some embodiments, homology arms of a targeting vector may correspond to a region of a yeast artificial chromosome (YAC), a bacterial artificial chromosome (BAC), a human artificial chromosome, or any other engineered region contained in an appropriate host cell. Still further, homology arms of a targeting vector may correspond to or be derived from a region of a BAC library, a cosmid library, or a P1 phage library. In some certain embodiments, homology arms of a targeting vector correspond to a locus that is native, heterologous, or exogenous to a prokaryote, a yeast, a bird (e.g., chicken), a non-human mammal, a rodent, a human, a rat, a mouse, a hamster a rabbit, a pig, a bovine, a deer, a sheep, a goat, a cat, a dog, a ferret, a primate (e.g., marmoset, rhesus monkey), a domesticated mammal, an agricultural mammal, or any other organism of interest. In some embodiments, homology arms correspond to a locus of the cell that is not targetable using a conventional method or that can be targeted only incorrectly or only with significantly low efficiency in the absence of a nick or double-strand break induced by a nuclease agent (e.g., a Cas protein). In some embodiments, homology arms are derived from synthetic DNA.

In some embodiments, one of the 5' or 3' homology arms of a targeting vector(s) corresponds to a targeted genomic locus while the other of the 5' or 3' homology arms corresponds to a region on another targeting vector.

In some embodiments, 5' and 3' homology arms of a targeting vector(s) correspond to a targeted genome. Alternatively, homology arms can be from a related genome. For example, a targeted genome is a mouse genome of a first strain, and targeting arms are from a mouse genome of a second strain, wherein the first strain and the second strain are different. In certain embodiments, homology arms are from the genome of the same animal or are from the genome of the same strain, e.g., the targeted genome is a mouse genome of a first strain, and the targeting arms are from a mouse genome from the same mouse or from the same strain.

A homology arm of a targeting vector can be of any length that is sufficient to promote a homologous recombination event with a corresponding target sequence, including, for example, at least 1-5 kb, inclusive, 5-10 kb, inclusive, 5-15 kb, inclusive, 5-20 kb, inclusive, 5-25 kb, inclusive, 5-30 kb, inclusive, 5-35 kb, inclusive, 5-40 kb, inclusive, 5-45 kb, inclusive, 5-50 kb, inclusive, 5-55 kb, inclusive, 5-60 kb, inclusive, 5-65 kb, inclusive, 5-70 kb, inclusive, 5-75 kb, inclusive, 5-80 kb, inclusive, 5-85 kb, inclusive, 5-90 kb, inclusive, 5-95 kb, inclusive, 5-100 kb, inclusive, 100-200 kb, inclusive, or 200-300 kb, inclusive, in length or greater. In some embodiments, a homology arm of a targeting vector has a length that is sufficient to promote a homologous recombination event with a corresponding target sequence that is at least 1-100 kb, inclusive, 5-100 kb, inclusive, 10-100 kb, inclusive, 15-100 kb, inclusive, 20-100 kb, inclusive, 25-100 kb, inclusive, 30-100 kb, inclusive, 35-100 kb, inclusive, 40-100 kb, inclusive, 45-100 kb, inclusive, 50-100 kb, inclusive, 55-100 kb, inclusive, 60-100 kb, inclusive, 65-100 kb, inclusive, 70-100 kb, inclusive, 75-100 kb, inclusive, 80-100 kb, inclusive, 85-100 kb, inclusive, 90-100 kb, inclusive, or 95-100 kb, inclusive, in length or greater. As described herein, large targeting vectors can employ targeting arms of greater length.

Nuclease agents (e.g., CRISPR/Cas systems) can be employed in combination with targeting vectors to facilitate the modification of a target locus (e.g., an Igλ light chain locus). Such nuclease agents may promote homologous recombination between a targeting vector and a target locus. When nuclease agents are employed in combination with a targeting vector, the targeting vector can comprise 5' and 3' homology arms corresponding to 5' and 3' target sequences located in sufficient proximity to a nuclease cleavage site so as to promote the occurrence of a homologous recombination event between target sequences and homology arms upon a nick or double-strand break at the nuclease cleavage site. The term "nuclease cleavage site" includes a DNA sequence at which a nick or double-strand break is created by a nuclease agent (e.g., a Cas9 cleavage site). Target sequences within a targeted locus that correspond to 5' and 3' homology arms of a targeting vector are "located in sufficient proximity" to a nuclease cleavage site if the distance is such as to promote the occurrence of a homologous recombination event between 5' and 3' target sequences and homology arms upon a nick or double-strand break at the recognition site. Thus, in certain embodiments, target sequences corresponding to 5' and/or 3' homology arms of a targeting vector are within one nucleotide of a given recognition site or are within at least 10 nucleotides to about 14 kb of a given recognition site. In some embodiments, a nuclease cleavage site is immediately adjacent to at least one or both of the target sequences.

The spatial relationship of target sequences that correspond to homology arms of a targeting vector and a nuclease cleavage site can vary. For example, target sequences can be located 5' to a nuclease cleavage site, target sequences can be located 3' to a recognition site, or target sequences can flank a nuclease cleavage site.

Combined use of a targeting vector (including, for example, a large targeting vector) with a nuclease agent can result in an increased targeting efficiency compared to use of a targeting vector alone. For example, when a targeting vector is used in conjunction with a nuclease agent, targeting efficiency of a targeting vector can be increased by at least two-fold, at least three-fold, at least four-fold, at least five-fold, at least six-fold, at least seven-fold, at least eight-fold, at least nine-fold, at least ten-fold or within a range formed from these integers, such as 2-10-fold when compared to use of a targeting vector alone.

Some targeting vectors are "large targeting vectors" or "LTVECs," which includes targeting vectors that comprise homology arms that correspond to and are derived from nucleic acid sequences larger than those typically used by other approaches intended to perform homologous recombination in cells. A LTVEC can be, for example, at least 10 kb in length, or the sum total of a 5' homology arm and a 3' homology arm can be, for example, at least 10 kb. LTVECs also include targeting vectors comprising DNA inserts larger than those typically used by other approaches intended to perform homologous recombination in cells. For example, LTVECs make possible the modification of large loci that cannot be accommodated by traditional plasmid-based targeting vectors because of their size limitations. For example, a targeted locus can be (i.e., 5' and 3' homology arms can correspond to) a locus of a cell that is not targetable using a conventional method or that can be targeted only incorrectly or only with significantly low efficiency in the absence of a nick or double-strand break induced by a nuclease agent (e.g., a Cas protein).

In some embodiments, methods described herein employ two or three LTVECs that are capable of recombining with each other and with a target genomic locus in a three-way or a four-way recombination event. Such methods make possible the modification of large loci that cannot be achieved using a single LTVEC.

Examples of LTVECs include vectors derived from a bacterial artificial chromosome (BAC), a human artificial chromosome, or a yeast artificial chromosome (YAC). Examples of LTVECs and methods for making them are described, e.g., in U.S. Pat. Nos. 6,586,251, 6,596,541 and 7,105,348; and International Patent Application Publication No. WO 2002/036789, each of which is incorporated herein by reference in its entirety. LTVECs can be in linear form or in circular form.

LTVECs can be of any length, including, for example, from about 20 kb to about 300 kb, inclusive, from about 20 kb to about 50 kb, inclusive, from about 50 kb to about 75 kb, inclusive, from about 75 kb to about 100 kb, inclusive, from about 100 kb to 125 kb, inclusive, from about 125 kb to about 150 kb, inclusive, from about 150 kb to about 175 kb, inclusive, from about 175 kb to about 200 kb, inclusive, from about 200 kb to about 225 kb, inclusive, from about 225 kb to about 250 kb, inclusive, from about 250 kb to about 275 kb, inclusive, or from about 275 kb to about 300 kb, inclusive. Alternatively, a LTVEC can be at least 10 kb, at least 15 kb, at least 20 kb, at least 30 kb, at least 40 kb, at least 50 kb, at least 60 kb, at least 70 kb, at least 80 kb, at least 90 kb, at least 100 kb, at least 150 kb, at least 200 kb, at least 250 kb, at least 300 kb, at least 350 kb, at least 400 kb, at least 450 kb, or at least 500 kb or greater. The size of a LTVEC can, in some embodiments, be too large to enable screening of targeting events by conventional assays, e.g., southern blotting and long-range (e.g., 1 kb to 5 kb) PCR.

In some embodiments, a LTVEC comprises a DNA insert ranging from about 5 kb to about 200 kb, inclusive, from about 5 kb to about 10 kb, inclusive, from about 10 kb to about 20 kb, inclusive, from about 20 kb to about 30 kb, inclusive, from about 30 kb to about 40 kb, inclusive, from about 40 kb to about 50 kb, inclusive, from about 60 kb to about 70 kb, inclusive, from about 80 kb to about 90 kb, inclusive, from about 90 kb to about 100 kb, inclusive, from about 100 kb to about 110 kb, inclusive, from about 120 kb to about 130 kb, inclusive, from about 130 kb to about 140 kb, inclusive, from about 140 kb to about 150 kb, inclusive, from about 150 kb to about 160 kb, inclusive, from about 160 kb to about 170 kb, inclusive, from about 170 kb to about 180 kb, inclusive, from about 180 kb to about 190 kb, inclusive, or from about 190 kb to about 200 kb, inclusive. In some embodiments, a DNA insert can range from about 5 kb to about 10 kb, inclusive, from about 10 kb to about 20 kb, inclusive, from about 20 kb to about 40 kb, inclusive, from about 40 kb to about 60 kb, inclusive, from about 60 kb to about 80 kb, inclusive, from about 80 kb to about 100 kb, inclusive, from about 100 kb to about 150 kb, inclusive, from about 150 kb to about 200 kb, inclusive, from about 200 kb to about 250 kb, inclusive, from about 250 kb to about 300 kb, inclusive, from about 300 kb to about 350 kb, inclusive, or from about 350 kb to about 400 kb, inclusive. In some embodiments, a LTVEC comprises a DNA insert ranging from about 400 kb to about 450 kb, inclusive, from about 450 kb to about 500 kb, inclusive, from about 500 kb to about 550 kb, inclusive, from about 550 kb to about 600 kb, inclusive, about 600 kb to about 650 kb, inclusive, from about 650 kb to about 700 kb, inclusive, from about 700 kb to about 750 kb, inclusive, or from about 750 kb to about 800 kb, inclusive.

In some embodiments, the sum total of a 5' homology arm and a 3' homology arm of a LTVEC is at least 10 kb. In some embodiments, a 5' homology arm of a LTVEC(s) ranges from about 1 kb to about 100 kb, inclusive, and/or a 3' homology arm of a LTVEC(s) ranges from about 1 kb to about 100 kb, inclusive. The sum total of 5' and 3' homology arms can be, for example, from about 1 kb to about 5 kb, inclusive, from about 5 kb to about 10 kb, inclusive, from about 10 kb to about 20 kb, inclusive, from about 20 kb to about 30 kb, inclusive, from about 30 kb to about 40 kb, inclusive, from about 40 kb to about 50 kb, inclusive, from about 50 kb to about 60 kb, inclusive, from about 60 kb to about 70 kb, inclusive, from about 70 kb to about 80 kb, inclusive, from about 80 kb to about 90 kb, inclusive, from about 90 kb to about 100 kb, inclusive, from about 100 kb to about 110 kb, inclusive, from about 110 kb to about 120 kb, inclusive, from about 120 kb to about 130 kb, inclusive, from about 130 kb to about 140 kb, inclusive, from about 140 kb to about 150 kb, inclusive, from about 150 kb to about 160 kb, inclusive, from about 160 kb to about 170 kb, inclusive, from about 170 kb to about 180 kb, inclusive, from about 180 kb to about 190 kb, inclusive, or from about 190 kb to about 200 kb, inclusive. Alternatively, each homology arm can, in some embodiments, be at least 5 kb, at least 10 kb, at least 15 kb, at least 20 kb, at least 30 kb, at least 40 kb, at least 50 kb, at least 60 kb, at least 70 kb, at least 80 kb, at least 90 kb, at least 100 kb, at least 110 kb, at least 120 kb, at least 130 kb, at least 140 kb, at least 150 kb, at least 160 kb, at least 170 kb, at least 180 kb, at least 190 kb, or at least 200 kb. Likewise, the sum total of the 5' and 3' homology arms can, in some embodiments, be at least 5 kb, at least 10 kb, at least 15 kb, at least 20 kb, at least 30 kb, at least 40 kb, at least 50 kb, at least 60 kb, at least 70 kb, at least 80 kb, at least 90 kb, at least 100 kb, at least 110 kb, at least 120 kb, at least 130 kb, at least 140 kb, at least 150 kb, at least 160 kb, at least 170 kb, at least 180 kb, at least 190 kb, or at least 200 kb.

In some embodiments, a LTVEC and DNA insert are designed to allow for a deletion of an endogenous sequence at a target locus from about 5 kb to about 10 kb, inclusive, from about 10 kb to about 20 kb, inclusive, from about 20 kb to about 40 kb, inclusive, from about 40 kb to about 60 kb, inclusive, from about 60 kb to about 80 kb, inclusive, from about 80 kb to about 100 kb, inclusive, or from about 100 kb to about 150 kb, inclusive, from about 150 kb to about 200 kb, inclusive, from about 200 kb to about 300 kb, inclusive, from about 300 kb to about 400 kb, inclusive, from about 400 kb to about 500 kb, inclusive, from about 500 kb to about 600 kb, inclusive, from about 600 kb to about 700 kb, inclusive, from about 700 kb to about 800 kb, inclusive, or from about 500 kb to about 1 Mb, inclusive, from about 1 Mb to about 1.5 Mb, inclusive, from about 1.5 Mb to about 2 Mb, inclusive, from about 2 Mb to about 2.5 Mb, inclusive, or from about 2.5 Mb to about 3 Mb, inclusive. Alternatively, a deletion can be from about 3 Mb to about 4 Mb, inclusive, from about 4 Mb to about 5 Mb, inclusive, from about 5 Mb to about 10 Mb, inclusive, from about 10 Mb to about 20 Mb, inclusive, from about 20 Mb to about 30 Mb, inclusive, from about 30 Mb to about 40 Mb, inclusive, from about 40 Mb to about 50 Mb, inclusive, from about 50 Mb to about 60 Mb, inclusive, from about 60 Mb to about 70 Mb, inclusive, from about 70 Mb to about 80 Mb, inclusive, from about 80 Mb to about 90 Mb, inclusive, or from about 90 Mb to about 100 Mb, inclusive. Alternatively, a deletion can be at least 10 kb, at least 20 kb, at least 30 kb, at least 40 kb, at least 50 kb, at least 60 kb, at least 70 kb, at least 80 kb, at least 90 kb, at least 100 kb, at least 150 kb, at least 200 kb, at least 250 kb, at least 300 kb, at least 350 kb, at least 400 kb, at least 450 kb, or at least 500 kb or greater.

In some embodiments, a LTVEC and DNA insert are designed to allow for an insertion into a target locus of an exogenous nucleic acid sequence ranging from about 5 kb to about 10 kb, inclusive, from about 10 kb to about 20 kb, inclusive, from about 20 kb to about 40 kb, inclusive, from about 40 kb to about 60 kb, inclusive, from about 60 kb to about 80 kb, inclusive, from about 80 kb to about 100 kb, inclusive, from about 100 kb to about 150 kb, inclusive, from about 150 kb to about 200 kb, inclusive, from about 200 kb to about 250 kb, inclusive, from about 250 kb to about 300 kb, inclusive, from about 300 kb to about 350 kb, inclusive, or from about 350 kb to about 400 kb, inclusive. Alternatively, an insertion can, in some embodiments, be from about 400 kb to about 450 kb, inclusive, from about 450 kb to about 500 kb, inclusive, from about 500 kb to about 550 kb, inclusive, from about 550 kb to about 600 kb, inclusive, about 600 kb to about 650 kb, inclusive, from about 650 kb to about 700 kb, inclusive, from about 700 kb to about 750 kb, inclusive, or from about 750 kb to about 800 kb, inclusive. Alternatively, an insertion can be, in some embodiments, at least 10 kb, at least 20 kb, at least 30 kb, at least 40 kb, at least 50 kb, at least 60 kb, at least 70 kb, at least 80 kb, at least 90 kb, at least 100 kb, at least 150 kb, at least 200 kb, at least 250 kb, at least 300 kb, at least 350 kb, at least 400 kb, at least 450 kb, or at least 500 kb or greater.

In yet other cases, a DNA insert and/or a region of an endogenous locus being altered, deleted, targeted, modified, engineered, etc., is at least 100, 200, 300, 400, 500, 600, 700, 800, or 900 nucleotides or at least 1 kb, 2 kb, 3 kb, 4 kb, 5 kb, 6 kb, 7 kb, 8 kb, 9 kb, 10 kb, 11 kb, 12 kb, 13 kb, 14 kb, 15 kb, 16 kb, 17 kb, 18 kb, 19 kb, 20 kb or greater. In some embodiments, a DNA insert and/or a region of an endogenous locus being altered, deleted, targeted, modified, engineered, etc. is nucleotides to 20 kb, 200 nucleotides to 20 kb, 300 nucleotides to 20 kb, 400 nucleotides to 20 kb, 500 nucleotides to 20 kb, 600 nucleotides to 20 kb, 700 nucleotides to 20 kb, 800 nucleotides to 20 kb, 900 nucleotides to 20 kb, 1 kb to 20 kb, 2 kb to 20 kb, 3 kb to 20 kb, 4 kb to 20 kb, 5 kb to 20 kb, 6 kb to 20 kb, 7 kb to 20 kb, 8 kb to 20 kb, 9 kb to 20 kb, 10 kb to 20 kb, 11 kb to 20 kb, 12 kb to 20 kb, 13 kb to 20 kb, 14 kb to 20 kb, 15 kb to 20 kb, 16 kb to 20 kb, 17 kb to 20 kb, 18 kb to 20 kb, or 19 kb to 20 kb. In some embodiments, a DNA insert and/or a region of an endogenous locus being altered, deleted, targeted, modified, engineered, etc. is 100 nucleotides to 19 kb, 100 nucleotides to 18 kb, 100 nucleotides to 17 kb, 100 nucleotides to 16 kb, 100 nucleotides to 15 kb, 100 nucleotides to 14 kb, 100 nucleotides to 13 kb, 100 nucleotides to 12 kb, 100 nucleotides to 11 kb, 100 nucleotides to 10 kb, 100 nucleotides to 9 kb, 100 nucleotides to 8 kb, 100 nucleotides to 7 kb, 100 nucleotides to 6 kb, 100 nucleotides to 5 kb, 100 nucleotides to 4 kb, 100 nucleotides to 3 kb, 100 nucleotides to 2 kb, 100 nucleotides to 1 kb, 100 nucleotides to 900 nucleotides, 100 nucleotides to 800 nucleotides, 100 nucleotides to 700 nucleotides, 100 nucleotides to 600 nucleotides, 100 nucleotides to 500 nucleotides, 100 nucleotides to 400 nucleotides, 100 nucleotides to 300 nucleotides, or 100 nucleotides to 200 nucleotides. In some embodiments, a DNA insert and/or a region of an endogenous locus being altered, deleted, targeted, modified, engineered, etc. is 200 nucleotides to 19 kb, 300 nucleotides to 18 kb, 400 nucleotides to 17 kb, 500 nucleotides to 16 kb, 600 nucleotides to 15 kb, 700 nucleotides to 14 kb, 800 nucleotides to 13 kb, 900 nucleotides to 12 kb, 1 kb to 11 kb, 2 kb to 10 kb, 3 kb to 9 kb, 4 kb to 8 kb, 5 kb to 7 kb, or 5 kb to 6 kb.

Provided Non-Human Animals

In certain aspects, non-human animals are provided that express antibodies that contain light chains that include a human Igλ light chain sequence, in whole or in part, resulting from integration of genetic material that corresponds to at least a portion of a human Igλ light chain locus, and which encodes at least a human Vλ domain (i.e., a rearranged human Vλ-Jλ sequence), in the place of corresponding non-human Igλ light chain sequences in the germline genome of the non-human animal. Suitable examples described herein include, but are not limited to, rodents, in particular, rats or mice.

A human Igλ light chain sequence, in some embodiments, comprises genetic material from a human Igλ light chain locus, wherein the human Igλ light chain sequence encodes an immunoglobulin light chain that comprises the encoded portion of the genetic material from the human Igλ light chain locus. In some embodiments, a human Igλ light chain sequence as described herein comprises at least one human Vλ gene segment and at least one human Jλ gene segment, and one or more sequences necessary to promote rearrangement (e.g., recombination signal sequence[s]) of said at least one human Vλ gene segment with said at least one human Jλ gene segment to form a functional rearranged human Vλ-Jλ sequence that encodes a human Vλ domain. In many embodiments, a human Igλ light chain sequence comprises a plurality of human Vλ gene segments and one or more sequences necessary to promote rearrangement of said human Vλ gene segments with at least one human Jλ gene segment. In many embodiments, a human Igλ light chain sequence as described herein is a genomic sequence of a human Igλ light chain locus (e.g., isolated and/or cloned from a bacterial artificial chromosome) and contains a plurality of human Vλ gene segments in germline configuration. In some embodiments, a human Igλ light chain sequence comprises human Vλ, Jλ and Cλ sequences in germline configuration (i.e., as said human Vλ, Jλ and Cλ sequences appear in an Igλ light chain locus in a human cell). In some embodiments, a human Igλ light chain sequence is or comprises a human sequence that appears in the Drawing (e.g., see FIGS. 1-4). In some embodiments, a human Igλ light chain sequence encodes an Igλ light chain polypeptide, in whole or in part, which Igλ light chain polypeptide appears in an immunoglobulin, in particular, an immunoglobulin that is expressed by a human B cell. Non-human animals, embryos, cells and targeting constructs for making non-human animals, non-human embryos, and cells containing said human Igλ light chain sequence in the place of a corresponding non-human Igλ light chain sequence (e.g., an endogenous rodent Igλ light chain locus) are also provided.

In some embodiments, a human Igλ light chain sequence is inserted in the place of a corresponding non-human Igλ light chain sequence within the germline genome of a non-human animal. In some embodiments, a human Igλ light chain sequence is inserted upstream of a non-human Igλ light chain sequence (e.g., a non-human Igλ light chain constant region sequence). In some embodiments, a human Igλ light chain sequence is inserted in the midst of one or more non-human Igλ light chain sequences so that said human Igλ light chain sequence is juxtaposed by non-human Igλ light chain sequences (e.g., see FIGS. 1, 2, 3 and/or 4).

In some embodiments, one or more non-human Igλ light chain sequences (or portion thereof) of non-human Igλ light chain locus are not deleted. In some embodiments, one or more non-human Igλ light chain sequences (e.g., Vλ, Jλ and/or Cλ) of a non-human Igλ light chain locus are altered, displaced, disrupted, deleted or replaced with, among other things, a human Igλ light chain sequence as described herein (e.g., a sequence that includes one or more human Vλ gene segments, one or more human Jλ gene segments, one or more human Cλ gene segments, or combinations thereof) operably linked to a non-human Igλ light chain constant region, and one or more enhancer and/or regulatory element (s) of a non-human Igλ light chain locus. In some embodiments, all or substantially all of a non-human Igλ light chain locus is replaced with one or more human Igλ light chain sequences (as described herein) that is operably linked to a non-human Igλ light chain constant region and one or more non-human Igλ light chain enhancer and/or regulatory element(s) of a non-human Igλ light chain locus. In some certain embodiments, one or more non-human Igλ light chain constant region genes are not deleted or replaced in a non-human animal that includes a human Igλ light chain sequence as described herein. To give but one non-limiting example, in the instance of an insertion of a human Igλ light chain sequence that is inserted into a non-human Igλ light chain locus, said insertion is made in manner to maintain the integrity of non-human Igλ light chain sequences near the insertion point (e.g., a non-human Igλ light chain constant region and/or a non-human Igλ light chain enhancer region or sequence). Thus, such non-human animals have a wild-type Igλ light chain constant region. In some embodiments, a non-human Igλ light chain locus that is altered, displaced, disrupted, deleted, replaced or engineered with one or more human Igλ light chain sequences as described herein is a murine (e.g., mouse or rat) Igλ light chain locus. In some embodiments, a human Igλ light chain sequence is inserted into one copy (i.e., allele) of a non-human Igλ light chain locus of the two copies of said non-human Igλ light chain locus, giving rise to a non-human animal that is heterozygous with respect to the human Igλ light chain sequence. In some embodiments, a non-human animal is provided that is homozygous for an Igλ light chain locus that includes a human Igλ light chain sequence as described herein.

In some embodiments, an engineered non-human Igλ light chain locus as described herein comprises human Vλ, Jλ and Cλ gene segments operably linked to a non-human Igλ light chain constant region and one or more non-human Igλ light chain enhancers and/or regulatory elements. In some embodiments, an engineered non-human Igλ light chain locus as described herein comprises human Vλ, Jλ and Cλ gene segments operably linked to a non-human Igλ light chain constant region, one or more non-human Igλ light chain enhancers and/or regulatory elements and one or more human Igλ light chain enhancers and/or regulatory elements.

In some embodiments, a non-human animal contains an engineered Igλ light chain locus as described herein that is randomly integrated into its genome (e.g., as part of a randomly integrated human Igλ light chain sequence). Thus, such non-human animals can be described as having a human Igλ light chain transgene containing a plurality of human Vλ, Jλ and/or Cλ gene segments configured such that said human Vλ, Jλ and/or Cλ gene segments are capable of rearrangement and encoding an Igλ light chain, in whole or in part, of an antibody in the expressed repertoire of the non-human animal. An engineered Igλ light chain locus or transgene as described herein can be detected using a variety of methods including, for example, PCR, Western blot, Southern blot, restriction fragment length polymorphism (RFLP), or a gain or loss of allele assay. In some embodiments, a non-human animal as described herein is heterozygous with respect to an engineered Igλ light chain locus as described herein. In some embodiments, a non-human animal as described herein is hemizygous with respect to an engineered Igλ light chain locus as described herein. In some embodiments, a non-human animal as described herein contains one or more copies of an engineered Igλ light chain locus or transgene as described herein. In some embodiments, a non-human animal as described herein contains an Igλ light chain locus as depicted in the Drawing (e.g., see FIGS. 1, 2, 3 and/or 4).

In some embodiments, compositions and methods for making non-human animals whose germline genome comprises an engineered Igλ light chain locus that includes one or more human Igλ light chain sequences (e.g., human Vλ, Jλ and/or Cλ gene segments) in the place of non-human Igλ light chain sequences, including human Igλ light chain encoding sequences that include specific polymorphic forms of human Vλ, Jλ and/or Cλ segments (e.g., specific V and/or J alleles or variants) are provided, including compositions and methods for making non-human animals that express antibodies comprising Igλ light chains that contain human variable domains and human or non-human constant domains, assembled from an Igλ light chain locus that contains human Vλ, Jλ and Cλ segments operably linked to a non-human Igλ light chain constant region. In some embodiments, compositions and methods for making non-human animals that express such antibodies under the control of an endogenous enhancer(s) and/or an endogenous regulatory sequence(s) are also provided. In some embodiments, compositions and methods for making non-human animals that express such antibodies under the control of a heterologous enhancer(s) and/or a heterologous regulatory sequence(s) are also provided.

In certain embodiments, methods described herein include inserting a sequence encoding a human Igλ light chain, in whole or in part, upstream of a non-human Igλ light chain constant region (e.g., a murine Cλ region) so that an antibody is expressed, which antibody is characterized by the presence of a light chain that contains at least a human Vλ domain and, in some embodiments, a human Vλ and Cλ domain, and is expressed both on the surface of B cells and in the blood serum of a non-human animal.

In some embodiments, methods include serial insertion of genetic material corresponding to a human Igλ light chain locus. In some embodiments, genetic material corresponding to a human Igλ light chain locus can be synthetic or genomic (e.g., cloned from a bacterial artificial chromosome). In some embodiments, genetic material corresponding to a human Igλ light chain locus can be designed from published sources and/or bacterial artificial chromosomes so that said genetic material contains human Vλ, Jλ and/or Cλ segments in an orientation that is different from that which appears in a human Igλ light chain locus yet said genetic material still contains sequences to support rearrangement of said human Vλ, Jλ and/or Cλ segments to encode a functional Igλ light chain. To give but one example, genetic material corresponding to a human Igλ light chain locus can be designed using the guidance provided herein to construct a human Igλ light chain sequence that contains human Vλ, Jλ and/or Cλ segments in an order and/or arrangement that is different than that which appears in a human Igλ light chain locus of a human cell. In such an example, content of human Vλ, Jλ and/or Cλ segments would be equivalent to the corresponding segments in a human cell, however, the order and arrangement would be different. When constructing a human Igλ light chain locus for generation of a non-human animal as described herein the requisite recombination signal sequences can be configured so that the human segments can correctly rearrange and form a functional Igλ light chain. Guidance for germline configuration of human Igλ light chain segments and sequences necessary for proper recombination can be found in Molecular Biology of B Cells, London: Elsevier Academic Press, 2004, Ed. Honjo, T., Alt, F. W., Neuberger, M. Chapters 4 (pp. 37-59) and 5 (61-82); incorporated herein by reference in their entireties.

In some embodiments, serial insertion includes multiple insertions of portions of heterologous genetic material in a single ES cell clone. In some embodiments, serial insertion includes sequential insertions of portions of heterologous genetic material in successive ES cell clones.

In some embodiments, methods include insertion of about 11,822 bp of DNA downstream of a murine (e.g., mouse or rat) Cλ1 region so that said DNA is operably linked to said murine (e.g., mouse or rat) Cλ1 region, which DNA includes one or more human Igλ light chain enhancer regions (or sequences). In some certain embodiments, methods include insertion of about 11,822 bp of DNA that comprises three human Igλ light chain enhancer regions (or sequences), which said three human Igλ light chain enhancer regions (or sequences) are inserted downstream of said murine (e.g., mouse or rat) Cλ1 region.

In some embodiments, methods include insertion of about 125,473 bp of DNA upstream of a murine (e.g., mouse or rat) Cλ1 region so that said DNA is operably linked to said murine (e.g., mouse or rat) Cλ1 region, which DNA includes human Vλ gene segments Vλ3-10, Vλ3-9, Vλ2-8, Vλ4-3, Vλ3-1, human Jλ-Cλ segment pairs Jλ1-Cλ1, Jλ2-Cλ2, Jλ3-Cλ3, Jλ6-Cλ6 and human Jλ gene segment Jλ7. In some certain embodiments, methods include insertion of about 11,822 bp of DNA that comprises one or more human Igλ light chain enhancer regions (or sequences), which one or more human Igλ light chain enhancer regions (or sequences) are inserted downstream of said murine (e.g., mouse or rat) Cλ1 region.

In some embodiments, methods include insertion of about 171,458 bp of DNA upstream of a murine (e.g., mouse or rat) Cλ1 region so that said DNA is operably linked to said murine (e.g., mouse or rat) Cλ1 region, which DNA includes human Vλ gene segments Vλ2-11, Vλ3-12, Vλ2-14, Vλ3-16, Vλ3-19, Vλ3-21, Vλ3-22, Vλ2-23, Vλ3-25 and Vλ3-27. In some certain embodiments, methods include insertion of about 171,458 bp of DNA upstream of a human Vλ3-10 gene segment that is operably linked to a murine (e.g., mouse or rat) Cλ1 region, which DNA includes human Vλ gene segments Vλ2-11, Vλ3-12, Vλ2-14, Vλ3-16, Vλ3-19, Vλ3-21, Vλ3-22, Vλ2-23, Vλ3-25 and Vλ3-27.

In some embodiments, methods include insertion of about 121,188 bp of DNA upstream of a murine (e.g., mouse or rat) Cλ1 region so that said DNA is operably linked to said murine (e.g., mouse or rat) Cλ1 region, which DNA includes human Vλ gene segments Vλ3-27, Vλ1-36, Vλ5-37, Vλ5-39, Vλ1-40, Vλ7-43, Vλ1-44, Vλ5-45, Vλ7-46, Vλ1-47, Vλ9-49, Vλ1-51 and Vλ5-52. In some certain embodiments, methods include insertion of about 121,188 bp of DNA upstream of a human Vλ3-27 gene segment that is operably linked to a murine (e.g., mouse or rat) Cλ1 region, which DNA includes human Vλ gene segments Vλ3-27, Vλ1-36, Vλ5-37, Vλ5-39, Vλ1-40, Vλ7-43, Vλ1-44, Vλ5-45, Vλ7-46, Vλ1-47, Vλ9-49, Vλ1-51 and Vλ5-52.

In some embodiments, methods include insertion of about 121,188 bp of DNA upstream of a murine (e.g., mouse or rat) Cλ1 region so that said DNA is operably linked to said murine (e.g., mouse or rat) Cλ1 region, which DNA includes human Vλ gene segments Vλ3-27, Vλ1-36, Vλ5-37, Vλ5-39, Vλ1-40, Vλ7-43, Vλ1-44, Vλ5-45, Vλ7-46, Vλ1-47, Vλ9-49, Vλ1-51 and Vλ5-52, and which DNA includes a homology arm that includes a sequence that is 5' of a mouse Vλ2 gene segment. In some certain embodiments, methods include insertion of about 121,188 bp of DNA upstream of a human Vλ3-27 gene segment that is operably linked to a murine (e.g., mouse or rat) Cλ1 region, which DNA includes human Vλ gene segments Vλ3-27, Vλ1-36, Vλ5-37, Vλ5-39, Vλ1-40, Vλ7-43, Vλ1-44, Vλ5-45, Vλ7-46, Vλ1-47, Vλ9-49, Vλ1-51 and Vλ5-52, and which DNA includes a homology arm that includes a mouse sequence that is 5' of a mouse Vλ2 gene segment to direct deletion of a mouse Igλ genomic sequence (e.g., a Igλ light chain locus) upon homologous recombination with said DNA fragment.

Insertion of additional human Vλ, Jλ and/or Cλ gene segments may be achieved using methods described herein to further supplement the diversity of an engineered Igλ light chain locus. For example, in some embodiments, methods can include insertion of about 300 kb of DNA upstream of a murine (e.g., mouse or rat) Cλ1 region so that said DNA is operably linked to said murine (e.g., mouse or rat) Cλ1 region, which DNA includes human Vλ gene segments Vλ10-54, Vλ6-57, Vλ4-60, Vλ8-61 and Vλ4-69. In such embodiments, said DNA is inserted upstream of a human Vλ5-52 gene segment that is operably linked to a murine (e.g., mouse or rat) Cλ1 region, which DNA includes human Vλ gene segments Vλ10-54, Vλ6-57, Vλ4-60, Vλ8-61 and Vλ4-69. In some certain embodiments, said DNA includes a human VpreB gene. Additional human Vλ segments described above may be cloned directly from commercially available BAC clones and arranged in smaller DNA fragment using recombinant techniques described herein or otherwise known in the art. Alternatively, additional human Vλ gene segments described above can be synthesized into a DNA fragment and added to an engineered Igλ light chain locus as described above. Likewise, additional human Jλ and/or Cλ gene segments may be obtained from commercially available BAC clones or synthesized directly from published sequences. Also, endogenous Igλ light chain enhancer regions (or sequences) may be deleted from an engineered Igλ light chain locus as described herein. An exemplary illustration that shows an engineered Igλ light chain locus of non-human animals as described herein is set forth in any one of FIGS. 1, 2, 3 and 4.

Where appropriate, a human Igλ light chain sequence (i.e., a sequence containing human Vλ, Jλ and/or Cλ gene segments) encoding an Igλ light chain, in whole or in part, may separately be modified to include codons that are optimized for expression in a non-human animal (e.g., see U.S. Pat. Nos. 5,670,356 and 5,874,304). Codon optimized sequences are synthetic sequences, and preferably encode the identical polypeptide (or a biologically active fragment of a full length polypeptide which has substantially the same activity as the full length polypeptide) encoded by the non-codon optimized parent polynucleotide. In some embodiments, a human Igλ light chain sequence encoding an Igλ light chain, in whole or in part, may separately include an altered sequence to optimize codon usage for a particular cell type (e.g., a rodent cell). For example, the codons of each nucleotide sequence to be inserted into the genome of a non-human animal (e.g., a rodent) may be optimized for expression in a cell of the non-human animal. Such a sequence may be described as a codon-optimized sequence.

In some embodiments, insertion of a nucleotide sequence encoding a human Igλ light chain, in whole or in part, employs a minimal modification of the germline genome of a non-human animal as described herein and results in expression of antibodies comprising light chains that are human, in whole or in part. Methods for generating engineered non-human animals, including knockouts and knock-ins, are known in the art (see, e.g., Gene Targeting: A Practical Approach, Joyner, ed., Oxford University Press, Inc., 2000). For example, generation of transgenic rodents may optionally involve disruption of the genetic loci of one or more endogenous rodent genes (or gene segments) and introduction of one or more heterologous genes (or gene segments or nucleotide sequences) into the rodent genome, in some embodiments, at the same location as an endogenous rodent gene (or gene segments). In some embodiments, a nucleotide sequence encoding a human Igλ light chain, in whole or in part, is introduced upstream of a murine (e.g., mouse or rat) Igλ light chain constant region gene of a randomly inserted Igλ light chain transgene in the germline genome of a rodent. In some embodiments, a nucleotide sequence encoding a human Igλ light chain, in whole or in part, is introduced upstream of a murine (e.g., mouse or rat) Igλ light chain constant region gene of an endogenous Igλ light chain locus in the germline genome of a rodent; in some certain embodiments, an endogenous Igλ light chain locus is altered, modified, or engineered to contain human Igλ gene segments (e.g., Vλ, Jλ and/or Cλ) operably linked to a rodent Cλ1 region.

Figure 2:
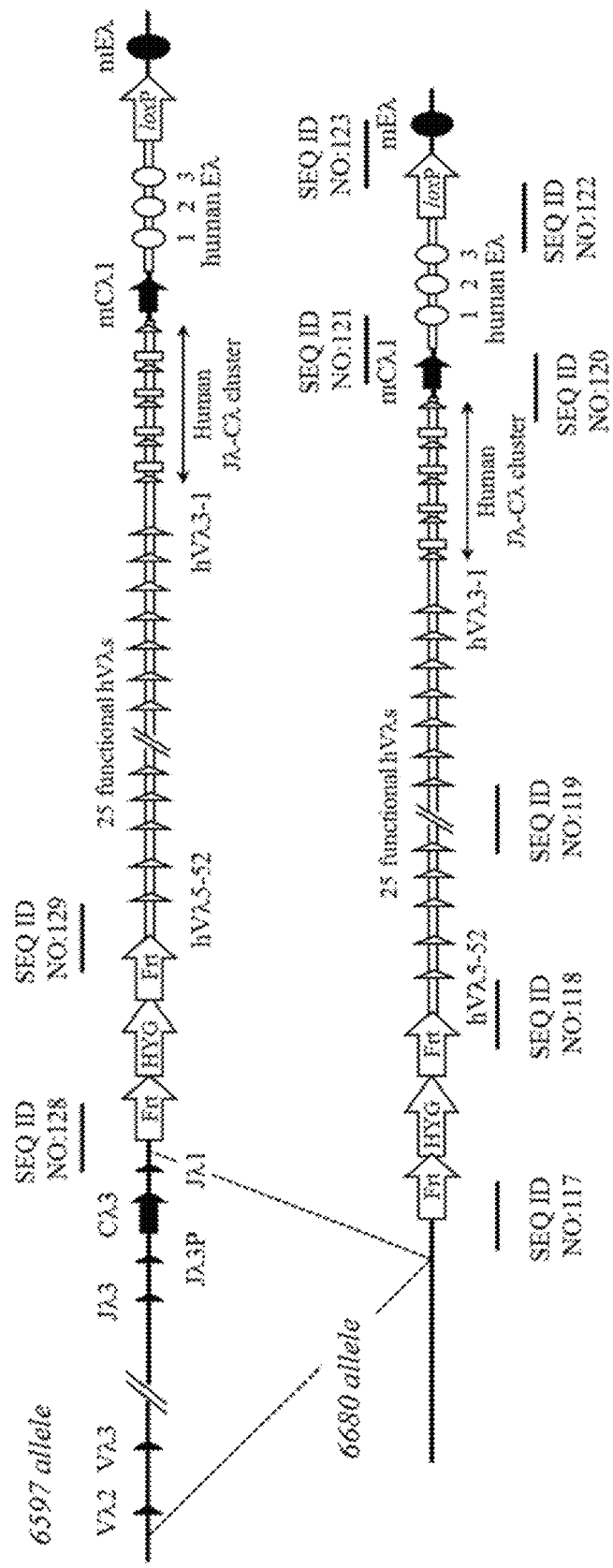
FIG. 2 shows a schematic illustration, not to scale, of exemplary rodent Igλ light chain alleles after sequential insertion of targeting vectors described in Example 1. 6597 allele: an Igλ light chain allele that contains 25 functional human Vλ gene segments, four functional human Jλ-Cλ gene segment pairs and a human Jλ7 gene segment operably linked to a rodent Cλ region (e.g., a mouse Cλ1 region), and which Igλ light chain locus further includes endogenous Vλ-Jλ-Cλ gene segments, three (i.e., E2.4, E and E3.1) endogenous Igλ enhancer regions (or sequences) and a modular human Igλ enhancer region (or sequence) characterized by three sequence elements. 6680 allele: an Igλ light chain allele after site-specific deletion of endogenous Vλ-Jλ-Cλ gene segments and Igλ enhancer Eλ2-4, which Igλ light chain allele contains 25 functional human Vλ gene segments, four functional human Jλ-Cλ gene segment pairs and a human Jλ7 gene segment operably linked to a rodent Cλ region (e.g., a mouse Cλ1 region), which Igλ light chain locus further includes two (i.e., E and E3.1) endogenous Igλ enhancer regions (or sequences) and a modular human Igλ enhancer region (or sequence, see above). Unless otherwise indicated, closed symbols indicate rodent gene segments and/or sequences, while open symbols indicate human gene segments and/or sequences. Site-specific recombination recognition sites (e.g., Frt) flanking selection cassettes (HYG: Hygromycin resistance gene [HYG$^R$] under transcriptional control of a ubiquitin promoter) are shown. Dashed lines indicate deleted region between two illustrated Igλ alleles. Selected nucleotide junction locations are marked with a line below each junction and each indicated by SEQ ID NO.

A schematic illustration (not to scale) of exemplary engineered Igλ light chain loci is provided in FIGS. 1-4. In particular, FIGS. 1 and 3 sets forth exemplary strategies for construction of engineered Igλ light chain loci characterized by insertion of nucleotide sequences containing a plurality of human Vλ, Jλ and Cλ segments. As illustrated in FIG. 1, a DNA fragment containing a human Eλ sequence (or region) is inserted downstream of a rodent Cλ region via homologous recombination. This DNA fragment contains a Neomycin selection cassette (e.g., a Neomycin resistance gene [NEO$^R$] flanked by loxP recombination recognition sites) positioned 3' to the human Eλ sequence, which contains three human Eλ elements engineered downstream (or 3') of the rodent Cλ1 region. Also illustrated in FIG. 1 is a DNA fragment containing a first portion of human Vλ segments, a set of human Jλ-Cλ segment pairs (e.g., human Jλ1-Cλ1, Jλ2-Cλ2, Jλ3-C13, Jλ6-Cλ6) and a human Jλ7 segment is inserted upstream of a rodent Cλ1 region via homologous recombination. As illustrated a Hygromycin selection cassette (e.g., a Hygromycin resistance gene [HYG$^R$] flanked by Frt recombination recognition sites) is positioned on the 5' end of the targeting vector and upstream of the human Igλ light chain sequence contained in the targeting vector. The Hygromycin selection cassette is removed via homologous recombination with subsequent targeting vectors described in the example section below. The targeting vector is then electroporated into rodent embryonic stem (ES) cells to create a rodent whose germline genome comprises the engineered Igλ light chain locus. Once a positive rodent ES cell clone is confirmed, the other depicted targeting vectors are electroporated in successive fashion and confirmed at each step to complete construction of the engineered Igλ light chain locus (see FIG. 2). The final targeting vector may be designed with (6680 targeting vector) or without (6597 targeting vector) a homology arm that directs deletion of endogenous Igλ light chain segments via homologous recombination resulting in two potential engineered Igλ light chain alleles (FIG. 2). Additionally, any remaining selection cassette may be deleted as desired via recombinase-mediated deletion. An alternative strategy for inserting additional human Vλ gene segments into an engineered Igλ light chain locus using guide RNAs (gRNAs) is set forth in FIG. 3.

Once a human Igλ light chain sequence is inserted upstream of a non-human Igλ light chain constant region of a BAC clone, a targeting vector for integration into an Igλ light chain locus is created. The BAC clone targeted with a human Igλ light chain sequence for creating a targeting vector can contain 5' and/or 3' flanking genomic DNA of murine (e.g., mouse or rat) origin. Alternatively, or additionally, a BAC clone targeted with a human Igλ light chain sequence for creating a targeting vector can contain 5' and/or 3' flanking genomic DNA of human origin so that a region of overlap with a human Igλ light chain sequence is created. In this way, successive targeting of multiple engineered BAC clones is enabled (e.g., see FIG. 1). The final targeting vectors are incorporated into an Igλ light chain locus in the genome of a non-human cell (e.g., a rodent embryonic stem cell). In some embodiments, targeting vectors as described herein are incorporated into an Igλ light chain locus in the germline genome of a non-human cell that further contains human $V_H$, $D_H$ and $J_H$ genomic DNA (e.g., containing a plurality of human $V_H$, $D_H$ and $J_H$ gene segments) operably linked with one or more IgH constant region genes and/or human Vκ and Jκ genomic DNA (e.g., containing a plurality of human Vκ and Jκ gene segments) operably linked with an Igκ constant region gene (e.g., see U.S. Pat. Nos. 8,502,018, 8,642,835, 8,697,940 and 8,791,323, incorporated herein by reference in their entireties).

A targeting vector is introduced into rodent (e.g., mouse) embryonic stem cells by electroporation so that the sequence contained in the targeting vector is inserted into the genome of the rodent embryonic stem cells and results in the capacity of a non-human cell or non-human animal (e.g., a mouse) that expresses antibodies having human Igλ light chains, in whole or in part. As described herein, a transgenic rodent is generated where an engineered Igλ light chain locus has been created in the germline of the rodent genome (e.g., an endogenous Igλ light chain locus containing a human Igλ light chain sequence operably linked to an endogenous rodent Cλ region as described herein). Antibodies are expressed on the surface of rodent B cells and in the serum of said rodent, which antibodies are characterized by light chains having human Vλ domains and, in some embodiments, human Vλ and Cλ domains. When an endogenous Igλ light chain locus in the germline of the rodent genome is not targeted by the targeting vector, an engineered Igλ light chain locus is preferably inserted at a location other than that of an endogenous rodent Igλ light chain locus (e.g., randomly inserted transgene).

Creation of an engineered Igλ light chain locus in a non-human animal as described above provides an engineered rodent strain that produces antibodies that include Igλ light chains expressed from such an engineered Igλ light chain locus having a human Vλ domain, and in some embodiments, human Vλ and Cλ domains. Leveraged with the presence of an engineered IgH locus that includes a plurality of human $V_H$, $D_H$ and $J_H$ gene segments operably linked to IgH constant region genes, an engineered rodent strain that produces antibodies and antibody components for the development of human antibody-based therapeutics is created. Thus, a single engineered rodent strain is realized that has the capacity to provide an alternative in vivo system for exploiting human Vλ domains for the development of new antibody-based medicines to treat human disease.

In some embodiments, the genome of a non-human animal as described herein further comprises (e.g., via crossbreeding or multiple gene targeting strategies) one or more human immunoglobulin heavy and/or light chain variable regions as described in U.S. Pat. Nos. 8,502,018, 8,642,835, 8,697,940 and 8,791,323; all of which are incorporated herein by reference in their entireties. Alternatively, the engineered Igλ light chain locus as described herein can be engineered into an embryonic stem cell comprising humanized IgH and/or Igκ loci, or a non-human animal comprising engineered Igλ light chain locus described herein may be bred with another non-human animal comprising humanized IgH and/or Igκ loci. Various such animals comprising humanized IgH and/or Igκ loci are known, e.g., a VELOCIMMUNE® strain (see, e.g., U.S. Pat. Nos. 8,502, 018 and/or 8,642,835; incorporated herein by reference in their entireties), a XENOMOUSE™ strain (see, e.g., Mendez, M. J. et al., 1997, Nat. Genetics 15(2):146-56 and Jakobovits, A. et al., 1995, Ann. NY Acad. Sci. 764:525-35). Homozygosity of the engineered Igλ light chain locus as described herein can subsequently be achieved by breeding. Alternatively, in the case of a randomly inserted engineered Igλ light chain transgene (described above), rodent strains can be selected based on, among other things, expression of human Vλ domains from the transgene.

Alternatively, and/or additionally, in some embodiments, the germline genome of a non-human animal as described herein further comprises a deleted, inactivated, functionally silenced or otherwise non-functional endogenous Igκ light chain locus. Genetic modifications to delete or render non-functional a gene or genetic locus may be achieved using methods described herein and/or methods known in the art.

A transgenic founder non-human animal can be identified based upon the presence of an engineered Igλ light chain locus in its germline genome and/or expression of antibodies having a human Igλ light chain sequence, in whole or in part, in tissues or cells of the non-human animal. A transgenic founder non-human animal can then be used to breed additional non-human animals carrying the engineered Igλ light chain locus thereby creating a cohort of non-human animals each carrying one or more copies of an engineered Igλ light chain locus. Moreover, transgenic non-human animals carrying an engineered Igλ light chain locus as described herein can further be bred to other transgenic non-human animals carrying other transgenes (e.g., human immunoglobulin genes) as desired.

In some embodiments, transgenic non-human animals may also be produced to contain selected systems that allow for regulated, directed, inducible and/or cell-type specific expression of the transgene or integrated sequence(s). For example, non-human animals as described herein may be engineered to contain a sequence encoding a human Igλ light chain, in whole or in part, of an antibody that is/are conditionally expressed (e.g., reviewed in Rajewski, K. et al., 1996, J. Clin. Invest. 98(3):600-3). Exemplary systems include the Cre/loxP recombinase system of bacteriophage P1 (see, e.g., Lakso, M. et al., 1992, Proc. Natl. Acad. Sci. U.S.A. 89:6232-6) and the FLP/Frt recombinase system of *S. cerevisiae* (O'Gorman, S. et al, 1991, Science 251:1351-5). Such animals can be provided through the construction of "double" transgenic animals, e.g., by mating two transgenic animals, one containing a transgene comprising a selected modification (e.g., an engineered Igλ light chain locus as described herein) and the other containing a transgene encoding a recombinase (e.g., a Cre recombinase).

Non-human animals as described herein may be prepared as described above, or using methods known in the art, to comprise additional human, humanized or otherwise engineered genes, oftentimes depending on the intended use of the non-human animal. Genetic material of such human, humanized or otherwise engineered genes may be introduced through the further alteration of the genome of cells (e.g., embryonic stem cells) having the genetic modifications or alterations as described above or through breeding techniques known in the art with other genetically modified or engineered strains as desired. In some embodiments, non-human animals as described herein are prepared to further comprise transgenic human IgH and/or Igκ light chain genes or gene segments (see e.g., Murphy, A. J. et al., (2014) Proc. Natl. Acad. Sci. U.S.A. 111(14):5153-5158; U.S. Pat. Nos. 8,502,018; 8,642,835; 8,697,940; 8,791,323; and U.S. Patent Application Publication No. 2013/0096287 A1; incorporated herein by reference in their entireties).

In some embodiments, non-human animals as described herein may be prepared by introducing a targeting vector described herein into a cell from a modified strain. To give but one example, a targeting vector, as described above, may be introduced into a VELOCIMMUNE® mouse. VELOCIMMUNE® mice express antibodies that have fully human variable domains and mouse constant domains. In some embodiments, non-human animals as described herein are prepared to further comprise human immunoglobulin genes (variable and/or constant region genes). In some embodiments, non-human animals as described herein comprise an engineered Igλ light chain locus as described herein and genetic material from a heterologous species (e.g., humans), wherein the genetic material encodes, in whole or in part, one or more human heavy and/or Igκ light chain variable domains.

For example, as described herein, non-human animals comprising an engineered Igλ light chain locus as described herein may further comprise (e.g., via cross-breeding or multiple gene targeting strategies) one or more modifications as described in Murphy, A. J. et al., (2014) Proc. Natl. Acad. Sci. U.S.A. 111(14):5153-8; Macdonald, L. E. et al., 2014, Proc. Natl. Acad. Sci. U.S.A. 111(14):5147-52; U.S. Pat. Nos. 8,502,018, 8,642,835, 8,697,940 and 8,791,323; all of which are incorporated herein by reference in their entirety. In some embodiments, a rodent comprising an engineered Igλ light chain locus as described herein is crossed to a rodent comprising a humanized IgH and/or Igκ light chain variable region locus (see, e.g., U.S. Pat. Nos. 8,502,018, 8,642,835, 8,697,940 and/or 8,791,323; incorporated herein by reference in their entireties). In some embodiments, a rodent comprising an engineered Igλ light chain locus as described herein is crossed to a rodent comprising a humanized IgH variable region locus (see, e.g., U.S. Pat. Nos. 8,502,018, 8,642,835, 8,697,940 and/or 8,791,323; incorporated herein by reference in their entireties) and an inactivated endogenous Igκ light chain locus (see, e.g., U.S. Pat. Nos. 9,006,511, 9,012,717, 9,029,628, 9,035,128, 9,066,502, 9,150,662 and 9,163,092, incorporated herein by reference in their entireties).

Although embodiments describing the construction of an engineered Igλ light chain locus in a mouse (i.e., a mouse with an engineered Igλ light chain locus characterized by the presence of a plurality of human Vλ, Jλ and Cλ gene segments operably linked with a mouse Cλ region so that antibodies containing human Igλ light chains, in whole or in part, are expressed) are extensively discussed herein, other non-human animals that comprise an engineered Igλ light chain locus are also provided. Such non-human animals include any of those which can be genetically modified to express antibodies as described herein, including, e.g., mammals, e.g., mouse, rat, rabbit, pig, bovine (e.g., cow, bull, buffalo), deer, sheep, goat, chicken, cat, dog, ferret, primate (e.g., marmoset, rhesus monkey), etc. For example, for those non-human animals for which suitable genetically modifiable ES cells are not readily available, other methods are employed to make a non-human animal comprising the genetic modification. Such methods include, e.g., modifying a non-ES cell genome (e.g., a fibroblast or an induced pluripotent cell) and employing somatic cell nuclear transfer (SCNT) to transfer the genetically modified genome to a suitable cell, e.g., an enucleated oocyte, and gestating the modified cell (e.g., the modified oocyte) in a non-human animal under suitable conditions to form an embryo.

Methods for modifying the germline genome of a non-human animal (e.g., a pig, cow, rodent, chicken, etc. genome) include, e.g., employing a zinc finger nuclease (ZFN), a transcription activator-like effector nuclease (TALEN), or a Cas protein (i.e., a CRISPR/Cas system) to include engineered Igλ light chain locus as described herein. Guidance for methods for modifying the germline genome of a non-human animal can be found in, e.g., U.S. patent application Ser No. 14/747,461 (filed Jun. 23, 2015), Ser. No. 14/948,221 (filed Nov. 20, 2015) and Ser. No. 14/974,623 (filed Dec. 18, 2015); in which all three applications are hereby incorporated herein by reference in their entireties.

In some embodiments, a non-human animal as described herein is a mammal. In some embodiments, a non-human animal as described herein is a small mammal, e.g., of the superfamily Dipodoidea or Muroidea. In some embodiments, a genetically modified animal as described herein is a rodent. In some embodiments, a rodent as described herein is selected from a mouse, a rat, and a hamster. In some embodiments, a rodent as described herein is selected from the superfamily Muroidea. In some embodiments, a genetically modified animal as described herein is from a family selected from Calomyscidae (e.g., mouse-like hamsters), Cricetidae (e.g., hamster, New World rats and mice, voles), Muridae (true mice and rats, gerbils, spiny mice, crested rats), Nesomyidae (climbing mice, rock mice, white-tailed rats, Malagasy rats and mice), Platacanthomyidae (e.g., spiny dormice), and Spalacidae (e.g., mole rats, bamboo rats, and zokors). In some certain embodiments, a genetically modified rodent as described herein is selected from a true mouse or rat (family Muridae), a gerbil, a spiny mouse, and a crested rat. In some certain embodiments, a genetically modified mouse as described herein is from a member of the family Muridae. In some embodiment, a non-human animal as described herein is a rodent. In some certain embodiments, a rodent as described herein is selected from a mouse and a rat. In some embodiments, a non-human animal as described herein is a mouse.

In some embodiments, a non-human animal as described herein is a mouse of a C57BL strain selected from C57BL/A, C57BL/An, C57BL/GrFa, C57BL/KaLwN, C57BL/6, C57BL/6J, C57BL/6ByJ, C57BL/6NJ, C57BL/10, C57BL/10ScSn, C57BL/10Cr, and C57BL/Ola. In some certain embodiments, a mouse as described herein is a 129 strain selected from the group consisting of a strain that is 129P1, 129P2, 129P3, 129X1, 129S1 (e.g., 129S1/SV, 129S1/SvIm), 129S2, 129S4, 129S5, 129S9/SvEvH, 129/SvJae, 129S6 (129/SvEvTac), 129S7, 129S8, 129T1, 129T2 (see, e.g., Festing et al., 1999, Mammalian Genome 10:836; Auerbach, W. et al., 2000, Biotechniques 29(5):1024-1028, 1030, 1032). In some certain embodiments, a genetically modified mouse as described herein is a mix of an aforementioned 129 strain and an aforementioned C57BL/6 strain. In some certain embodiments, a mouse as described herein is a mix of aforementioned 129 strains, or a mix of aforementioned BL/6 strains. In some certain embodiments, a 129 strain of the mix as described herein is a 129S6 (129/SvEvTac) strain. In some embodiments, a mouse as described herein is a BALB strain, e.g., BALB/c strain. In some embodiments, a mouse as described herein is a mix of a BALB strain and another aforementioned strain.

In some embodiments, a non-human animal as described herein is a rat. In some certain embodiments, a rat as described herein is selected from a Wistar rat, an LEA strain, a Sprague Dawley strain, a Fischer strain, F344, F6, and Dark Agouti. In some certain embodiments, a rat strain as described herein is a mix of two or more strains selected from the group consisting of Wistar, LEA, Sprague Dawley, Fischer, F344, F6, and Dark Agouti.

A rat pluripotent and/or totipotent cell can be from any rat strain, including, for example, an ACI rat strain, a Dark Agouti (DA) rat strain, a Wistar rat strain, a LEA rat strain, a Sprague Dawley (SD) rat strain, or a Fischer rat strain such as Fisher F344 or Fisher F6. Rat pluripotent and/or totipotent cells can also be obtained from a strain derived from a mix of two or more strains recited above. For example, the rat pluripotent and/or totipotent cell can be from a DA strain or an ACI strain. The ACI rat strain is characterized as having black agouti, with white belly and feet and an RT1av1 haplotype. Such strains are available from a variety of sources including Harlan Laboratories. An example of a rat ES cell line from an ACI rat is an ACI.G1 rat ES cell. The Dark Agouti (DA) rat strain is characterized as having an agouti coat and an RT1av1 haplotype. Such rats are available from a variety of sources including Charles River and Harlan Laboratories. Examples of a rat ES cell line from a DA rat are the DA.2B rat ES cell line and the DA.2C rat ES cell line. In some embodiments, the rat pluripotent and/or totipotent cells are from an inbred rat strain (see, e.g., U.S. Patent Application Publication No. 2014-0235933 A1, published Aug. 21, 2014, incorporated herein by reference in its entirety).

Specific Exemplary Embodiments—Engineered IgH Loci

In some embodiments, provided non-human animals comprise an engineered Igλ light chain locus as described herein and further comprise engineered IgH loci (or alleles) characterized by the presence of a plurality of human $V_H$, $D_H$ and $J_H$ gene segments arranged in germline configuration and operably linked to non-human IgH constant regions, enhancers and regulatory regions. In some embodiments, an engineered IgH locus (or allele) as described herein comprises one or more human $V_H$ gene segments, one or more human $D_H$ gene segments and one or more human $J_H$ gene segments operably linked to a non-human IgH constant region.

In some embodiments, an engineered IgH locus (or allele) comprises 5, 10, 15, 20, 25, 30, 35, 40 or more (e.g., 41, 42, 43, 44, 45, 46, 47, 48, 49, 50, 51, 52, etc.) human $V_H$ gene segments. In some certain embodiments, an engineered IgH locus (or allele) comprises all or substantially all the functional human $V_H$ gene segments found between human $V_H$3-74 and human $V_H$6-1 gene segments, inclusive, of a human IgH locus that appears in nature. In some certain embodiments, an engineered IgH locus (or allele) comprises at least human $V_H$ gene segments $V_H$3-74, $V_H$3-73, $V_H$3-72, $V_H$2-70, $V_H$1-69, $V_H$3-66, $V_H$3-64, $V_H$4-61, $V_H$4-59, $V_H$1-58, $V_H$3-53, $V_H$5-51, $V_H$3-49, $V_H$3-48, $V_H$1-46, $V_H$1-45, $V_H$3-43, $V_H$4-39, $V_H$4-34, $V_H$3-33, $V_H$4-31, $V_H$3-30, $V_H$4-28, $V_H$2-26, $V_H$1-24, $V_H$3-23, $V_H$3-21, $V_H$3-20, $V_H$1-18, $V_H$3-15, $V_H$3-13, $V_H$3-11, $V_H$3-9, $V_H$1-8, $V_H$3-7, $V_H$2-5, $V_H$7-4-1, $V_H$4-4, $V_H$1-3, $V_H$1-2 and $V_H$6-1.

In some embodiments, an engineered IgH locus (or allele) comprises 5, 10, 15, 20, 25 or more (e.g., 26, 27, etc.) human $D_H$ gene segments. In some certain embodiments, an engineered IgH locus (or allele) comprises all or substantially all of the functional human $D_H$ gene segment found between a human $D_H$1-1 and human $D_H$7-27 gene segment, inclusive, of a human IgH locus that appears in nature. In some certain embodiments, an engineered IgH locus (or allele) comprises at least human $D_H$ gene segments $D_H$1-1, $D_H$2-2, $D_H$3-3, $D_H$4-4, $D_H$5-5, $D_H$6-6, $D_H$1-7, $D_H$2-8, $D_H$3-9, $D_H$3-10, $D_H$5-12, $D_H$6-13, $D_H$2-15, $D_H$3-16, $D_H$4-17, $D_H$6-19, $D_H$1-20, $D_H$2-21, $D_H$3-22, $D_H$6-25, $D_H$1-26 and $D_H$7-27.

In some embodiments, an engineered IgH locus (or allele) comprises 1, 2, 3, 4, 5, 6 or more functional human $J_H$ gene segments. In some certain embodiments, an engineered IgH locus (or allele) comprises all or substantially all the functional human $J_H$ gene segments found between human $J_H$1 and human $J_H$6 gene segments, inclusive, of a human IgH locus that appears in nature. In some certain embodiments, an engineered IgH locus (or allele) comprises at least human $J_H$ gene segments $J_H$1, $J_H$2, $J_H$3, $J_H$4, $J_H$5 and $J_H$6.

In some embodiments, a non-human IgH constant region includes one or more non-human IgH constant region genes such as, for example, immunoglobulin M (IgM), immunoglobulin D (IgD), immunoglobulin G (IgG), immunoglobulin E (IgE) and immunoglobulin A (IgA). In some certain embodiments, a non-human IgH constant region includes a rodent IgM, rodent IgD, rodent IgG3, rodent IgG1, rodent IgG2b, rodent IgG2a, rodent IgE and rodent IgA constant region genes. In some embodiments, said human $V_H$, $D_H$ and $J_H$ gene segments are operably linked to one or more non-human IgH enhancers (i.e., enhancer sequences or enhancer regions). In some embodiments, said human $V_H$, $D_H$ and $J_H$ gene segments are operably linked to one or more non-human IgH regulatory regions (or regulatory sequences). In some embodiments, said human $V_H$, $D_H$ and $J_H$ gene segments are operably linked to one or more non-human IgH enhancers (or enhancer sequence) and one or more non-human IgH regulatory regions (or regulatory sequence).

In some embodiments, an engineered IgH locus as described herein does not contain an endogenous Adam6 gene. In some embodiments, an engineered IgH locus as described herein does not contain an endogenous Adam6 gene (or Adam6-encoding sequence) in the same germline genomic position as found in a germline genome of a wild-type non-human animal of the same species. In some embodiments, an engineered IgH locus as described herein does not contain a human Adam6 pseudogene. In some embodiments, an engineered IgH locus as described herein comprises insertion of at least one nucleotide sequence that encodes one or more non-human (e.g., rodent) Adam6 polypeptides. Said insertion may be outside of an engineered immunoglobulin heavy chain locus as described herein (e.g., upstream of a 5' most $V_H$ gene segment), within an engineered IgH locus or elsewhere in the germline genome of a non-human animal (e.g., a randomly introduced non-human Adam6-encoding sequence), cell or tissue.

In various embodiments, a provided non-human animal, non-human cell or non-human tissue as described herein does not detectably express, in whole or in part, an endogenous non-human $V_H$ region in an antibody molecule. In various embodiments, a provided non-human animal, non-human cell or non-human tissue as described herein does not contain (or lacks, or contains a deletion of) one or more nucleotide sequences that encode, in whole or in part, an endogenous non-human $V_H$ region (e.g., $V_H$, $D_H$ and/or $J_H$ in an antibody molecule. In various embodiments, a provided non-human animal, non-human cell or non-human tissue as described herein has a germline genome that includes a deletion of endogenous non-human $V_H$, $D_H$ and $J_H$ gene segments, in whole or in part. In various embodiments, a provided non-human animal is fertile.

Guidance for the creation of targeting vectors, non-human cells and animals harboring such engineered IgH loci (or alleles) can be found in, e.g., U.S. Pat. Nos. 8,642,835 and 8,697,940, which are incorporated by reference in their entireties. Persons of skill in the art are aware of a variety of technologies, known in the art, for accomplishing such genetic engineering and/or manipulation of non-human (e.g., mammalian) genomes or for otherwise preparing, providing, or manufacturing such sequences for introducing into the germline genome of non-human animals.

Specific Exemplary Embodiments—Engineered Igκ Light Chain Loci

In some embodiments, provided non-human animals comprise an engineered Igλ light chain locus as described herein and further comprise engineered Igκ light chain loci (or alleles) characterized by the presence of a plurality of human Vκ and Jκ gene segments arranged in germline configuration and operably linked to a non-human Igκ light chain constant region, Igκ enhancers and regulatory regions. In some embodiments, an engineered Igκ light chain locus (or allele) comprises one or more human Vκ gene segments and one or more human Jκ gene segments operably linked to a non-human Igκ constant region (Cκ).

In some certain embodiments, an engineered Igκ light chain locus (or allele) comprises at least human Vκ gene segments that appear in the distal variable cluster (or distal arm, or distal duplication) of a human Igκ light chain locus that appears in nature. In some certain embodiments, an engineered Igκ light chain locus (or allele) comprises at least human Vκ gene segments that appear in the proximal variable cluster (or proximal arm, or proximal duplication) of a human Igκ light chain locus that appears in nature. In some certain embodiments, an engineered Igκ light chain locus (or allele) comprises human Vκ gene segments that appear in the distal and proximal variable clusters of a human Igκ light chain locus that appears in nature. In some certain embodiments, an engineered Igκ light chain locus (or allele) comprises all or substantially all the functional human Vκ gene segments found between human Vκ2-40 (or Vκ3D-7) and human Vκ4-1 gene segments, inclusive, of a human Igκ light chain locus that appears in nature.

In some certain embodiments, an engineered Igκ light chain locus (or allele) comprises 5, 10, 15, 20, 25, 30, 35 or more (e.g., 36, 37, 38, 39, 40 etc.) human Vκ gene segments. In some certain embodiments, an engineered Igκ light chain locus (or allele) comprises human Vκ gene segments Vκ3D-7, Vκ1D-8, Vκ1D-43, Vκ3D-11, Vκ1D-12, Vκ1D-13, Vκ3D-15, Vκ1D-16, Vκ1D-17, Vκ3D-20, Vκ6D-21, Vκ2D-26, Vκ2D-28, Vκ2D-29, Vκ2D-30, Vκ1D-33, Vκ1D-39, Vκ2D-40, Vκ2-40, Vκ1-39, Vκ1-33, Vκ2-30, Vκ2-28, Vκ1-27, Vκ2-24, Vκ6-21, Vκ3-20, Vκ1-17, Vκ1-16, Vκ3-15, Vκ1-12, Vκ3-11, Vκ1-9, Vκ1-8, Vκ1-6, Vκ1-5, Vκ5-2 and Vκ4-1. In some certain embodiments, an engineered Igκ light chain locus (or allele) comprises at least human Vκ gene segments Vκ3D-7, Vκ1D-8, Vκ1D-43, Vκ3D-11, Vκ1D-12, Vκ1D-13, Vκ3D-15, Vκ1D-16, Vκ1D-17, Vκ3D-20, Vκ6D-21, Vκ2D-26, Vκ2D-28, Vκ2D-29, Vκ2D-30, Vκ1D-33, Vκ1D-39 and Vκ2D-40. In some certain embodiments, an engineered Igκ light chain locus (or allele) comprises at least human Vκ gene segments Vκ2-40, Vκ1-39, Vκ1-33, Vκ2-30, Vκ2-28, Vκ1-27, Vκ2-24, Vκ6-21, Vκ3-20, Vκ1-17, Vκ1-16, Vκ3-15, Vκ1-12, Vκ3-11, Vκ1-9, Vκ1-8, Vκ1-6, Vκ1-5, Vκ5-2 and Vκ4-1.

In some embodiments, an engineered Igκ light chain locus (or allele) comprises 1, 2, 3, 4, 5 or more functional human Jκ gene segments. In some certain embodiments, an engineered Igκ light chain locus (or allele) comprises all or substantially all the functional human Jκ gene segments found between human Jκ1 and human Jκ5 gene segments, inclusive, of a human Igκ light chain locus that appears in nature. In some certain embodiments, an engineered Igκ light chain locus (or allele) comprises at least human Jκ gene segments Jκ1, Jκ2, Jκ3, Jκ4 and Jκ5.

In some embodiments, said human Vκ and Jκ gene segments are operably linked to one or more non-human Igκ light chain enhancers (i.e., enhancer sequences or enhancer regions). In some embodiments, said human Vκ and Jκ gene segments are operably linked to one or more non-human Igκ light chain regulatory regions (or regulatory sequences). In some embodiments, said human Vκ and Jκ gene segments are operably linked to one or more non-human Igκ light chain enhancers (or enhancer sequences or enhancer regions) and one or more non-human Igκ light chain regulatory regions (or regulatory sequences).

In some embodiments, a non-human Cκ region of an engineered Igκ light chain locus (or allele) includes a rodent Cκ region such as, for example, a mouse Cκ region or a rat Cκ region. In some certain embodiments, a non-human Cκ region of an engineered Igκ light chain locus (or allele) is or comprises a mouse Cκ region from a genetic background that includes a 129 strain, a BALB/c strain, a C57BL/6 strain, a mixed 129×C57BL/6 strain or combinations thereof.

In some embodiments, provided non-human animals comprise an engineered Igλ light chain locus as described herein and further comprise an inactivated Igκ light chain loci (or alleles).

In various embodiments, a provided non-human animal, non-human cell or non-human tissue as described herein does not detectably express, in whole or in part, an endogenous non-human Vκ region in an antibody molecule. In various embodiments, a provided non-human animal, non-human cell or non-human tissue as described herein does not contain (or lacks, or contains a deletion of) one or more nucleotide sequences that encode, in whole or in part, an endogenous non-human Vκ region in an antibody molecule. In various embodiments, a provided non-human animal, non-human cell or non-human tissue as described herein has a germline genome that includes a deletion of endogenous non-human Vκ and Jκ gene segments, in whole or in part.

Guidance for the creation of targeting vectors, non-human cells and animals harboring such engineered Igκ light chain loci (or alleles) can be found in, e.g., U.S. Pat. Nos. 8,642,835 and 8,697,940, which are hereby incorporated by reference in their entireties. Persons of skill in the art are aware of a variety of technologies, known in the art, for accomplishing such genetic engineering and/or manipulation of non-human (e.g., mammalian) genomes or for otherwise preparing, providing, or manufacturing such sequences for introducing into the germline genome of non-human animals.

Specific Exemplary Embodiments—Engineered Igλ Light Chain Loci

In some embodiments, provided non-human animals comprise an engineered Igλ light chain locus characterized by the presence of a plurality of human Vλ, Jλ and Cλ gene segments arranged in germline configuration and inserted upstream of, and operably linked to, a non-human Cλ gene segment (or Cλ region gene). As described herein, such engineered Igλ light chain locus further includes one or more human Igλ light chain enhancer regions (or enhancer sequences). In some embodiments, an engineered Igλ light chain locus comprises one or more human Vλ gene segments and one or more human Jλ gene segments operably linked to a non-human Igλ light chain constant (Cλ) region. In some certain embodiments, an engineered Igλ light chain locus (or allele) comprises human Vλ gene segments that appear in at least cluster A of a human Igλ light chain locus; in some embodiments, cluster A and cluster B of a human Igλ light chain locus; in some certain embodiments, cluster A, cluster B and cluster C of a human Igλ light chain locus.

In some embodiments, an engineered Igλ light chain locus (or allele) comprises 5, 10, 15, 20, 25, 30 or more (e.g., 31, 32, 33, 34, 35, etc.) human Vλ gene segments. In some certain embodiments, an engineered Igλ light chain locus (or allele) comprises all or substantially all the functional human Vλ gene segments found between human Vλ4-69 and human Vλ3-1 gene segments, inclusive, of a human Igλ light chain locus that appears in nature. In some certain embodiments, an engineered Igλ light chain locus (or allele) comprises all or substantially all the functional human Vλ gene segments found between human Vλ5-52 and human Vλ3-1 gene segments, inclusive, of a human Igλ light chain locus that appears in nature. In some certain embodiments, an engineered Igλ light chain locus (or allele) comprises all or substantially all the functional human Vλ gene segments found between human Vλ3-27 and human Vλ3-1 gene segments, inclusive, of a human Igλ light chain locus that appears in nature. In some certain embodiments, an engineered Igλ light chain locus (or allele) comprises human Vλ gene segments Vλ4-69, Vλ8-61, Vλ4-60, Vλ6-57, Vλ10-54, Vλ5-52, Vλ1-51, Vλ9-49, Vλ1-47, Vλ7-46, Vλ5-45, Vλ1-44, Vλ7-43, Vλ1-40, Vλ5-39, Vλ5-37, Vλ1-36, Vλ3-27, Vλ3-25, Vλ2-23, Vλ3-22, Vλ3-21, Vλ3-19, Vλ2-18, Vλ3-

16, Vλ2-14, Vλ3-12, Vλ2-11, Vλ3-10, Vλ3-9, Vλ2-8, Vλ4-3 and Vλ3-1. In some certain embodiments, an engineered Igλ light chain locus (or allele) comprises at least the functional human Vλ gene segments from Vλ5-52 to Vλ1-40 and from Vλ3-27 to Vλ3-1.

In some embodiments, an engineered Igλ light chain locus (or allele) comprises 1, 2, 3, 4, 5, 6, 7 or more functional human Jλ gene segments. In some certain embodiments, an engineered Igλ light chain locus (or allele) comprises all or substantially all the functional human Jλ gene segments found between human Jλ1 and human Jλ7 gene segments, inclusive, of a human Igλ light chain locus that appears in nature. In some certain embodiments, an engineered Igλ light chain locus (or allele) comprises at least human Jλ gene segments Jλ1, Jλ2, Jλ3, Jλ6 and Jλ7.

In some embodiments, an engineered Igλ light chain locus (or allele) comprises 1, 2, 3, 4, 5, 6, 7 or more functional human Cλ gene segments. In some certain embodiments, an engineered Igλ light chain locus (or allele) comprises all or substantially all the functional human Cλ gene segments found between human Cλ1 and human Cλ7 gene segments, inclusive, of a human Igλ light chain locus that appears in nature. In some certain embodiments, an engineered Igλ light chain locus (or allele) comprises at least human Cλ gene segments Cλ1, Cλ2, Cλ3 and Cλ6.

In some embodiments, an engineered Igλ light chain locus (or allele) does not contain the same non-human Igλ light chain enhancer regions (or enhancer sequences) that appear in a wild-type Igλ light chain locus (or allele). In some embodiments, an engineered Igλ light chain locus (or allele) lacks at least one non-human Igλ light chain enhancer region (or enhancer sequence), in whole or in part (e.g., an Igλ enhancer 2-4 or Eλ2-4).

In some embodiments, said human Vλ and Jλ gene segments are operably linked to one or more non-human Igλ light chain enhancers (i.e., enhancer sequences or enhancer regions) and one or more human Igλ light chain enhancers (i.e., enhancer sequences or enhancer regions). In some embodiments, said human Vλ and Jλ gene segments are operably linked to one or more non-human Igλ light chain regulatory regions (or regulatory sequences). In some embodiments, said human Vλ and Jλ gene segments are operably linked to one or more non-human Igλ light chain enhancers (or enhancer sequences or enhancer regions), one or more human Igλ light chain enhancers (i.e., enhancer sequences or enhancer regions) and one or more non-human Igλ light chain regulatory regions (or regulatory sequences).

In some embodiments, an engineered Igλ light chain locus (or allele) as described herein does not contain a human VpreB gene (or human VpreB gene-encoding sequence).

In some embodiments, a non-human Cλ region of an engineered Igλ light chain locus (or allele) includes a rodent Cλ region such as, for example, a mouse Cλ region or a rat Cλ region. In some certain embodiments, a non-human Cλ region of an engineered Igλ light chain locus (or allele) is or comprises a mouse Cλ region from a genetic background that includes a 129 strain, a BALB/c strain, a C57BL/6 strain, a mixed 129×C57BL/6 strain or combinations thereof.

In some embodiments, a non-human Cλ region of an engineered Igλ light chain locus (or allele) as described herein comprises a sequence that is at least 50%, at least 55%, at least 60%, at least 65%, at least 70%, at least 75%, at least 80%, at least 85%, at least 90%, at least 95%, or at least 98% identical to SEQ ID NO:1 (mouse Cλ1), SEQ ID NO:3 (mouse Cλ2) or SEQ ID NO:5 (mouse Cλ3). In some certain embodiments, a non-human Cλ region of an engineered Igλ light chain locus (or allele) as described herein comprises a sequence that is substantially identical or identical to SEQ ID NO:1 (mouse Cλ1), SEQ ID NO:3 (mouse Cλ2) or SEQ ID NO:5 (mouse Cλ3). In some certain embodiments, a non-human Cλ region of an engineered Igλ light chain locus (or allele) as described herein is or comprises the sequence of a mouse Cλ1 region.

In some embodiments, a non-human Cλ region encoded by a sequence positioned at an engineered Igλ light chain locus (or allele) as described herein comprises a sequence that is at least 50%, at least 55%, at least 60%, at least 65%, at least 70%, at least 75%, at least 80%, at least 85%, at least 90%, at least 95%, or at least 98% identical to SEQ ID NO:2 (mouse Cλ1), SEQ ID NO:4 (mouse Cλ2) or SEQ ID NO:6 (mouse Cλ3). In some certain embodiments, a non-human Cλ region encoded by a sequence positioned at an engineered Igλ light chain locus (or allele) as described herein comprises a sequence that is substantially identical or identical to SEQ ID NO:2 (mouse Cλ1), SEQ ID NO:4 (mouse Cλ2) or SEQ ID NO:6 (mouse Cλ3). In some certain embodiments, a non-human Cλ region encoded by a sequence positioned at an engineered Igλ light chain locus (or allele) as described herein is or comprises a mouse Cλ1 region polypeptide.

In some embodiments, a non-human Cλ region of an engineered Igλ light chain locus (or allele) as described herein comprises a sequence that is at least 50%, at least 55%, at least 60%, at least 65%, at least 70%, at least 75%, at least 80%, at least 85%, at least 90%, at least 95%, or at least 98% identical to SEQ ID NO:7 (rat Cλ1), SEQ ID NO:9 (rat Cλ2), SEQ ID NO:11 (rat Cλ3) or SEQ ID NO:13 (rat Cλ4). In some certain embodiments, a non-human Cλ region of an engineered Igλ light chain locus (or allele) as described herein comprises a sequence that is substantially identical or identical to SEQ ID NO:7 (rat Cλ1), SEQ ID NO:9 (rat Cλ2), SEQ ID NO:11 (rat Cλ3) or SEQ ID NO:13 (rat Cλ4). In some certain embodiments, a non-human Cλ region of an engineered Igλ light chain locus (or allele) as described herein is or comprises the sequence of a rat Cλ1 region.

In some embodiments, a non-human Cλ region encoded by a sequence positioned at an engineered Igλ light chain locus (or allele) as described herein comprises a sequence that is at least 50%, at least 55%, at least 60%, at least 65%, at least 70%, at least 75%, at least 80%, at least 85%, at least 90%, at least 95%, or at least 98% identical to SEQ ID NO:8 (rat Cλ1), SEQ ID NO:10 (rat Cλ2), SEQ ID NO:12 (rat Cλ3) or SEQ ID NO:14 (rat Cλ4). In some certain embodiments, a non-human Cλ region encoded by a sequence positioned at an engineered Igλ light chain locus (or allele) as described herein comprises a sequence that is substantially identical or identical to SEQ ID NO:8 (rat Cλ1), SEQ ID NO:10 (rat Cλ2), SEQ ID NO:12 (rat Cλ3) or SEQ ID NO:14 (rat Cλ4). In some certain embodiments, a non-human Cλ region encoded by a sequence positioned at an engineered Igλ light chain locus (or allele) as described herein is or comprises a rat Cλ1 region polypeptide.

In some embodiments, an engineered Igλ light chain locus (or allele) as described herein is characterized by the presence of one or more unique nucleotide sequence junctions (or combinations of unique sequence junctions) resulting from the insertion of human genetic material corresponding to a human Igλ light chain sequence (genomic or synthetic) in the place of or within a non-human Igλ light chain sequence at an endogenous locus. Exemplary nucleotide sequence junctions are set forth in SEQ ID NO:117, SEQ ID NO:118, SEQ ID NO:119, SEQ ID NO:120, SEQ ID NO:121, SEQ ID NO:122, SEQ ID NO:123, SEQ ID NO:124, SEQ ID NO:125, SEQ ID NO:126, SEQ ID NO:127, SEQ ID NO:128 and SEQ ID NO:129.

In some embodiments, an engineered Igλ light chain locus (or allele) as described herein comprises one or more of SEQ ID NO:117, SEQ ID NO:118, SEQ ID NO:119, SEQ ID NO:120, SEQ ID NO:121, SEQ ID NO:122, SEQ ID NO:123, SEQ ID NO:124, SEQ ID NO:125, SEQ ID NO:126, SEQ ID NO:127, SEQ ID NO:128 and SEQ ID NO:129.

In some embodiments, an engineered Igλ light chain locus (or allele) as described herein comprises SEQ ID NO:120, SEQ ID NO:121, SEQ ID NO:122 and SEQ ID NO:123.

In some embodiments, an engineered Igλ light chain locus (or allele) as described herein comprises SEQ ID NO:117, SEQ ID NO:118, SEQ ID NO:119, SEQ ID NO:120, SEQ ID NO:121, SEQ ID NO:122 and SEQ ID NO:123.

In some embodiments, an engineered Igλ light chain locus (or allele) as described herein comprises SEQ ID NO:120, SEQ ID NO:121, SEQ ID NO:122, SEQ ID NO:123, SEQ ID NO:128 and SEQ ID NO:129.

In some embodiments, an engineered Igλ light chain locus (or allele) as described herein comprises SEQ ID NO:120, SEQ ID NO:121, SEQ ID NO:122, SEQ ID NO:123, SEQ ID NO:126 and SEQ ID NO:127.

In some embodiments, an engineered Igλ light chain locus (or allele) as described herein comprises SEQ ID NO:120, SEQ ID NO:121, SEQ ID NO:122, SEQ ID NO:123, SEQ ID NO:124 and SEQ ID NO:125.

Guidance on human Vλ, Jλ and Cλ gene segments can be found in, e.g., Lefranc, M. P., 2000, Nomenclature of the human immunoglobulin lambda (IGL) genes, Current Protocols in Immunology, No. Supplement, 40:A.1p.1-A.1p.37. Among other things, the present disclosure demonstrates that the presence of human Vλ and Jλ gene segments at Igλ light chain loci (or alleles) increases the diversity of the light chain repertoire of a provided non-human animal as compared to the diversity of the light chains in the expressed antibody repertoire of a non-human animal that does not comprise such engineered Igλ light chain alleles.

Methods

In certain aspects, non-human animals as described herein may be employed for making a human antibody and/or nucleic acid sequences encoding human antibodies, which human antibody comprises variable domains derived from nucleic acid sequences encoded by genetic material of a cell of a non-human animal as described herein. For example, a non-human animal as described herein is immunized with an antigen of interest under conditions and for a time sufficient that the non-human animal develops an immune response to said antigen of interest. Antibodies are isolated from the non-human animal (or one or more cells, for example, one or more B cells) so immunized and characterized using various assays measuring, for example, affinity, specificity, epitope mapping, ability for blocking ligand-receptor interaction, inhibition receptor activation, etc. In various embodiments, antibodies produced by non-human animals as described herein comprise one or more human variable domains that are derived from one or more human variable region nucleotide sequences isolated from the non-human animal. In some embodiments, anti-drug antibodies (e.g., anti-idiotype antibody) may be raised in non-human animals as described herein.

In some embodiments, non-human animals as described herein provide an improved in vivo system and source of biological materials (e.g., cells) for producing human antibodies that are useful for a variety of assays. In various embodiments, non-human animals as described herein are used to develop therapeutics that target a polypeptide of interest (e.g., a transmembrane or secreted polypeptide) and/or modulate one or more activities associated with said polypeptide of interest and/or modulate interactions of said polypeptide of interest with other binding partners (e.g., a ligand or receptor polypeptide). For example, in various embodiments, non-human animals as described herein are used to develop therapeutics that target one or more receptor polypeptides, modulate receptor polypeptide activity and/or modulate receptor polypeptide interactions with other binding partners. In various embodiments, non-human animals as described herein are used to identify, screen and/or develop candidate therapeutics (e.g., antibodies, siRNA, etc.) that bind one or more polypeptides of interest. In various embodiments, non-human animals as described herein are used to screen and develop candidate therapeutics (e.g., antibodies, siRNA, etc.) that block activity of one or more polypeptides of interest or that block the activity of one or more receptor polypeptides of interest. In various embodiments, non-human animals as described herein are used to determine the binding profile of antagonists and/or agonists of one or more polypeptides of interest. In some embodiments, non-human animals as described herein are used to determine the epitope or epitopes of one or more candidate therapeutic antibodies that bind one or more polypeptides of interest.

In various embodiments, non-human animals as described herein are used to determine the pharmacokinetic profiles of one or more human antibody candidates. In various embodiments, one or more non-human animals as described herein and one or more control or reference non-human animals are each exposed to one or more human antibody candidates at various doses (e.g., 0.1 mg/kg, 0.2 mg/kg, 0.3 mg/kg, 0.4 mg/kg, 0.5 mg/kg, 1 mg/kg, 2 mg/kg, 3 mg/kg, 4 mg/kg, 5 mg/mg, 7.5 mg/kg, 10 mg/kg, 15 mg/kg, 20 mg/kg, 25 mg/kg, 30 mg/kg, 40 mg/kg, or 50 mg/kg or more). Candidate therapeutic antibodies may be dosed via any desired route of administration including parenteral and non-parenteral routes of administration. Parenteral routes include, e.g., intravenous, intraarterial, intraportal, intramuscular, subcutaneous, intraperitoneal, intraspinal, intrathecal, intracerebroventricular, intracranial, intrapleural or other routes of injection. Non-parenteral routes include, e.g., oral, nasal, transdermal, pulmonary, rectal, buccal, vaginal, ocular. Administration may also be by continuous infusion, local administration, sustained release from implants (gels, membranes or the like), and/or intravenous injection. Blood is isolated from non-human animals (humanized and control) at various time points (e.g., 0 hr, 6 hr, 1 day, 2 days, 3 days, 4 days, 5 days, 6 days, 7 days, 8 days, 9 days, 10 days, 11 days, or up to 30 or more days). Various assays may be performed to determine the pharmacokinetic profiles of administered candidate therapeutic antibodies using samples obtained from non-human animals as described herein including, but not limited to, total IgG, anti-therapeutic antibody response, agglutination, etc.

In various embodiments, non-human animals as described herein are used to measure the therapeutic effect of blocking or modulating the activity of a polypeptide of interest and the effect on gene expression as a result of cellular changes or, in the context of a receptor polypeptide, the density of a receptor polypeptide on the surface of cells in the non-human animals. In various embodiments, a non-human animal as described herein or cells isolated therefrom are exposed to a candidate therapeutic that binds a polypeptide of interest and, after a subsequent period of time, analyzed for effects on specific cellular processes that are associated with said polypeptide of interest, for example, ligand-receptor interactions or signal transduction.

In certain aspects, non-human animals as described herein express human antibody variable domains, thus cells, cell lines, and cell cultures can be generated to serve as a source of human antibody variable domains for use in binding and functional assays, e.g., to assay for binding or function of an antagonist or agonist, particularly where the antagonist or agonist is specific for a human antigen of interest or specific for an epitope that functions in ligand-receptor interaction (binding). In various embodiments, epitopes bound by candidate therapeutic antibodies or siRNAs can be determined using cells isolated from non-human animals as described herein.

Cells from provided non-human animals can be isolated and used on an ad hoc basis, or can be maintained in culture for many generations. In various embodiments, cells from a provided non-human animal are immortalized (e.g., via use of a virus) and maintained in culture indefinitely (e.g., in serial cultures).

In some embodiments, non-human animals as described herein provide an in vivo system for the generation of variants of human antibody variable domains that binds a polypeptide of interest (e.g., human Vλ domain variants). Such variants include human antibody variable domains having a desired functionality, specificity, low cross-reactivity to a common epitope shared by two or more variants of a polypeptide of interest. In some embodiments, non-human animals as described herein are employed to generate panels of human antibody variable domains that contain a series of variant variable domains that are screened for a desired or improved functionality.

In certain aspects, non-human animals as described herein provide an in vivo system for generating human antibody variable region libraries (e.g., a human Vλ domain library). Such libraries provide a source for heavy and/or light chain variable region sequences that may be grafted onto different Fc regions based on a desired effector function, used as a source for affinity maturation of the variable region sequence using techniques known in the art (e.g., site-directed mutagenesis, error-prone PCR, etc.) and/or used as a source of antibody components for the generation of antibody-based therapeutic molecules such as, for example, chimeric antigen receptors (i.e., a molecule engineered using antibody components, e.g., an scFv), multi-specific binding agents (e.g., bi-specific binding agents) and fusion proteins (e.g., single domain antibodies, scFvs, etc.).

In some aspects, non-human animals as described herein provide an in vivo system for the analysis and testing of a drug or vaccine. In various embodiments, a candidate drug or vaccine may be delivered to one or more non-human animals as described herein, followed by monitoring of the non-human animals to determine one or more of the immune response to the drug or vaccine, the safety profile of the drug or vaccine, or the effect on a disease or condition and/or one or more symptoms of a disease or condition. Exemplary methods used to determine the safety profile include measurements of toxicity, optimal dose concentration, antibody (i.e., anti-drug) response, efficacy of the drug or vaccine and possible risk factors. Such drugs or vaccines may be improved and/or developed in such non-human animals.

Vaccine efficacy may be determined in a number of ways. Briefly, non-human animals as described herein are vaccinated using methods known in the art and then challenged with a vaccine or a vaccine is administered to already-infected non-human animals. The response of a non-human animal(s) to a vaccine may be measured by monitoring of, and/or performing one or more assays on, the non-human animal(s) (or cells isolated therefrom) to determine the efficacy of the vaccine. The response of a non-human animal(s) to the vaccine is then compared with control animals, using one or more measures known in the art and/or described herein.

Vaccine efficacy may further be determined by viral neutralization assays. Briefly, non-human animals as described herein are immunized and serum is collected on various days post-immunization. Serial dilutions of serum are pre-incubated with a virus during which time antibodies in the serum that are specific for the virus will bind to it. The virus/serum mixture is then added to permissive cells to determine infectivity by a plaque assay or microneutralization assay. If antibodies in the serum neutralize the virus, there are fewer plaques or lower relative luciferase units compared to a control group.

In some embodiments, non-human animals as described herein produce human antibody variable domains and, therefore, provide an in vivo system for the production of human antibodies for use in diagnostic applications (e.g., immunology, serology, microbiology, cellular pathology, etc.). In various embodiments, non-human animals as described herein may be used to produce human antibody variable domains that bind relevant antigenic sites for identification of cellular changes such as, for example, expression of specific cell surface markers indicative of pathological changes. Such antibodies can be conjugated to various chemical entities (e.g., a radioactive tracer) and be employed in various in vivo and/or in vitro assays as desired.

In some embodiments, non-human animals as described herein provide an improved in vivo system for development and selection of human antibodies for use in oncology and/or infectious diseases. In various embodiments, non-human animals as described herein and control non-human animals (e.g., having a genetic modification that is different than as described herein or no genetic modification, i.e., wild-type) may be implanted with a tumor (or tumor cells) or infected with a virus (e.g., influenza, HIV, HCV, HPV, etc.). Following implantation or infection, non-human animals may be administered a candidate therapeutic. The tumor or virus may be allowed sufficient time to be established in one or more locations within the non-human animals prior to administration of a candidate therapeutic. Alternatively, and/or additionally, the immune response may be monitored in such non-human animals so as to characterize and select potential human antibodies that may be developed as a therapeutic.

Kits

In some aspects, the present disclosure further provides a pack or kit comprising one or more containers filled with at least one non-human animal, non-human cell, DNA fragment, targeting vector, or any combination thereof, as described herein. Kits may be used in any applicable method (e.g., a research method). Optionally associated with such container(s) can be a notice in the form prescribed by a governmental agency regulating the manufacture, use or sale of pharmaceuticals or biological products, which notice reflects (a) approval by the agency of manufacture, use or sale for human administration, (b) directions for use, and/or (c) a contract that governs the transfer of materials and/or biological products (e.g., a non-human animal or non-human cell as described herein) between two or more entities and combinations thereof.

Other features of certain embodiments will become apparent in the course of the following descriptions of exemplary embodiments, which are given for illustration and are not intended to be limiting thereof.

Additional Exemplary Embodiments

In exemplary embodiment 1, provided herein is a rodent whose germline genome comprises an endogenous immunoglobulin λ light chain locus comprising (a) one or more human Vλ gene segments, (b) one or more human Jλ gene segments, and (c) one or more human Cλ gene segments, wherein (a) and (b) are operably linked to (c) and a rodent Cλ gene segment, and wherein the endogenous immunoglobulin λ light chain locus further comprises: one or more rodent immunoglobulin λ light chain enhancers (Eλ), and one or more human immunoglobulin λ light chain enhancers (Eλ).

In exemplary embodiment 2, provided herein is the rodent of embodiment 1, wherein the endogenous immunoglobulin λ light chain locus comprises two rodent Eλs.

In exemplary embodiment 3, provided herein is the rodent of embodiment 2, wherein the two rodent Eλs are a mouse Eλ and a mouse Eλ3-1.

In exemplary embodiment 4, provided herein is the rodent of any one of embodiments 1-3, wherein the endogenous immunoglobulin λ light chain locus comprises three human Eλs.

In exemplary embodiment 5, provided herein is the rodent of any one of embodiments 1-4, wherein the germline genome further comprises (i) an endogenous immunoglobulin heavy chain locus comprising insertion of one or more human $V_H$ gene segments, one or more human $D_H$ gene segments and one or more human $J_H$ gene segments, which human $V_H$, $D_H$ and $J_H$ gene segments are operably linked to a rodent immunoglobulin heavy chain constant region; or (ii) an endogenous immunoglobulin heavy chain locus comprising insertion of one or more human $V_H$ gene segments, one or more human $D_H$ gene segments and one or more human $J_H$ gene segments, which human $V_H$, $D_H$ and $J_H$ gene segments are operably linked to a rodent immunoglobulin heavy chain constant region, and an endogenous immunoglobulin κ light chain locus comprising insertion of one or more human Vκ gene segments and one or more human Jκ gene segments, which human Vκ and Jκ gene segments are operably linked to a rodent immunoglobulin Cκ region.

In exemplary embodiment 6, provided herein is the rodent of embodiment 5, wherein the insertion of one or more human $V_H$ gene segments, one or more human $D_H$ gene segments and one or more human $J_H$ gene segments replace rodent $V_H$, $D_H$ gene segments.

In exemplary embodiment 7, provided herein is the rodent of embodiments 6, wherein the insertion includes human non-coding DNA that naturally appears between human $V_H$, $D_H$, and $J_H$ gene segments, and combinations thereof.

In exemplary embodiment 8, provided herein is the rodent of embodiments 5 or 6, wherein the insertion of one or more human Vκ gene segments and one or more human Jκ gene segments replace rodent Vκ and Jκ gene segments.

In exemplary embodiment 9, provided herein is the rodent of embodiment 8, wherein the insertion includes human non-coding DNA that naturally appears between human Vκ and Jκ gene segments, and combinations thereof.

In exemplary embodiment 10, provided herein is the rodent of any one of embodiments 5-8, wherein the rodent immunoglobulin heavy chain constant region is an endogenous rodent immunoglobulin heavy chain constant region.

In exemplary embodiment 11, provided herein is the rodent of any one of embodiments 5-10, wherein the rodent Cκ region is an endogenous rodent Cκ region.

In exemplary embodiment 12, provided herein is the rodent of any one of embodiments 1-9, wherein the endogenous immunoglobulin λ light chain locus comprises a deletion of endogenous Vλ and Jλ gene segments, in whole or in part.

In exemplary embodiment 13, provided herein is the rodent of embodiment 12, wherein the endogenous immunoglobulin λ light chain locus comprises a deletion of Vλ2-Vλ3-Jλ2-Cλ2 gene segments and Vλ1-Jλ3-Cλ3-Jλ1 gene segments.

In exemplary embodiment 14, provided herein is the rodent of embodiment 12, wherein the endogenous immunoglobulin λ light chain locus comprises a deletion of Vλ2-Vλ3-Jλ2-Cλ2-Jλ4P-Cλ4P gene segments and Vλ1-Jλ3-Jλ3P-Cλ3-Jλ1 gene segments.

In exemplary embodiment 15, provided herein is the rodent of any one of embodiments 1-14, wherein the rodent Cλ gene segment is a mouse Cλ1 gene segment.

In exemplary embodiment 16, provided herein is the rodent of any one of embodiments 1-13, wherein the endogenous immunoglobulin λ light chain locus comprises a deletion of a rodent Eλ2-4.

In exemplary embodiment 17, provided herein is the rodent of any one of embodiments 1-16, wherein the rodent does not detectably express endogenous immunoglobulin λ light chains.

In exemplary embodiment 18, provided herein is the rodent of any one of embodiments 5-17, wherein the immunoglobulin heavy chain locus comprises insertion of the human $V_H$ gene segments from $V_H$3-74 to $V_H$6-1, the human $D_H$ gene segments from $D_H$1-1 to $D_H$7-27, and the human $J_H$ gene segments $J_H$1-$J_H$6.

In exemplary embodiment 19, provided herein is the rodent of embodiment 18, wherein the insertion includes human non-coding DNA that naturally appears between human $V_H$3-74 to $V_H$6-1, human non-coding DNA that naturally appears between human $D_H$1-1 to $D_H$7-27, and human non-coding DNA that naturally appears between human $J_H$1-$J_H$6.

In exemplary embodiment 20, provided herein is the rodent of any one of embodiments 5-19, wherein the immunoglobulin κ light chain locus comprises insertion of the proximal Vκ duplication, in whole or in part, of a human immunoglobulin κ light chain locus.

In exemplary embodiment 21, provided herein is the rodent of embodiment 20, wherein the immunoglobulin κ light chain locus comprises insertion of the human Vκ gene segments from Vκ2-40 to Vκ4-1 and the human Jκ gene segments from Jκ1-Jκ5.

In exemplary embodiment 22, provided herein is the rodent of embodiment 21, wherein the insertion includes human non-coding DNA that naturally appears between human Vκ2-40 to Vκ4-1, and human non-coding DNA that naturally appears between Jκ1-Jκ5.

In exemplary embodiment 23, provided herein is the rodent of any one of embodiments 1-22, wherein the endogenous immunoglobulin λ light chain locus comprises insertion of the human Vλ gene segments Vλ5-52 to Vλ1-40 and Vλ3-27 to Vλ3-1, at least the human Jλ-Cλ gene segment pairs Jλ1-Cλ1, Jλ2-Cλ2, Jλ3-Cλ3, Jλ6-Cλ6, the human Jλ gene segment Jλ7 and a rodent Cλ1 gene segment.

In exemplary embodiment 24, provided herein is the rodent of embodiments 23, wherein the insertion includes human non-coding DNA that naturally appears between human Vλ5-52 to Vλ1-40 and Vλ3-27 to Vλ3-1, human non-coding DNA that naturally appears between human Jκ-Cλ gene segment pairs Jλ1-Cλ1, Jλ2-Cλ2, Jλ3-Cλ3 and Jλ6-Cλ6, and human non-coding DNA that naturally appears upstream (or 5') of human Jλ gene segment Jλ7.

In exemplary embodiment 25, provided herein is the rodent of any one of embodiments 5-24, wherein the immunoglobulin heavy chain locus lacks an endogenous rodent Adam6 gene.

In exemplary embodiment 26, provided herein is the rodent of any one of embodiments 5-25, wherein the immunoglobulin heavy chain locus further comprises insertion of one or more nucleotide sequences encoding one or more rodent Adam6 polypeptides.

In exemplary embodiment 27, provided herein is the rodent of embodiment 26, wherein the one or more nucleotide sequences are inserted between a first and a second human $V_H$ gene segment.

In exemplary embodiment 28, provided herein is the rodent of embodiment 26, wherein the one or more nucleotide sequences are inserted in the place of a human Adam6 pseudogene.

In exemplary embodiment 29, provided herein is the rodent of embodiment 27, wherein the first human $V_H$ gene segment is human $V_H$1-2 and the second human $V_H$ gene segment is human $V_H$6-1.

In exemplary embodiment 30, provided herein is the rodent of embodiment 26, wherein the one or more nucleotide sequences are inserted between a human $V_H$ gene segment and a human $D_H$ gene segment.

In exemplary embodiment 31, provided herein is the rodent of any one of embodiments 5-30, wherein the rodent is heterozygous or homozygous for the endogenous immunoglobulin heavy chain locus.

In exemplary embodiment 32, provided herein is the rodent of any one of embodiments 5-31, wherein the rodent is heterozygous or homozygous for the endogenous immunoglobulin light chain locus.

In exemplary embodiment 33, provided herein is the rodent of any one of embodiments 1-32, wherein the rodent is heterozygous or homozygous for the endogenous immunoglobulin light chain locus.

In exemplary embodiment 34, provided herein is the rodent of any one of embodiments 1-33, wherein the rodent is a rat or a mouse.

In exemplary embodiment 35, provided herein is an isolated rodent cell whose germline genome comprises an endogenous immunoglobulin λ light chain locus comprising: (a) one or more human Vλ gene segments, (b) one or more human Jλ gene segments, and (c) one or more human Cλ gene segments, (i) wherein (a) and (b) are operably linked to (c) and a rodent Cλ gene segment, and (ii) wherein the endogenous immunoglobulin λ light chain locus further comprises: one or more rodent immunoglobulin λ light chain enhancers (Eλ) and one or more human immunoglobulin light chain enhancers (Eλ).

In exemplary embodiment 36, provided herein is an immortalized cell made from the rodent cell of embodiment 35.

In exemplary embodiment 37, provided herein is the isolated rodent cell of embodiment 35, wherein the rodent cell is a rodent embryonic stem cell.

In exemplary embodiment 38, provided herein is a rodent embryo generated from the rodent embryonic stem cell of embodiment 35.

In exemplary embodiment 39, provided herein is a method of making a rodent whose germline genome comprises an engineered endogenous immunoglobulin λ light chain locus, the method comprising (a) introducing a DNA fragment into a rodent embryonic stem cell, said DNA fragment comprising a nucleotide sequence that includes (i) one or more human Vλ gene segments, (ii) one or more human Jλ gene segments, and (iii) one or more human Cλ gene segments, wherein (i)-(iii) are operably linked to a rodent Cλ gene segment, and wherein the nucleotide sequence further comprises one or more human immunoglobulin λ light chain enhancers (Eλ); (b) obtaining the rodent embryonic stem cell generated in (a); and (c) creating a rodent using the rodent embryonic stem cell of (b).

In exemplary embodiment 40, provided herein is the method of embodiment 39, wherein the nucleotide sequence further includes and one or more human immunoglobulin λ light chain enhancers (Eλ).

In exemplary embodiment 41, provided herein is a method of making a rodent whose germline genome comprises an engineered endogenous immunoglobulin λ light chain locus, which engineered endogenous immunoglobulin λ light chain locus comprises insertion of one or more human Vλ gene segments, one or more human Jλ gene segments and one or more human Cλ gene segments, which human Vλ and Jλ gene segments are operably linked to a rodent or a human Cλ gene segment, and which endogenous immunoglobulin λ light chain locus further comprises one or more rodent immunoglobulin λ light chain enhancers (Eλ), and one or more human immunoglobulin λ light chain enhancers (Eλ), the method comprising modifying the germline genome of a rodent so that it comprises an engineered immunoglobulin λ light chain locus that includes insertion of one or more human Vλ gene segments, one or more human Jλ gene segments and one or more human Cλ gene segments, which human Vλ and Jλ gene segments are operably linked to a rodent or a human Cλ gene segment, and which endogenous immunoglobulin λ light chain locus further comprises one or more rodent immunoglobulin λ light chain enhancers (Eλ), and one or more human immunoglobulin λ light chain enhancers (Eλ), thereby making said rodent.

In exemplary embodiment 42, provided herein is the method of embodiment 39 or 41, wherein the one or more human Vλ gene segments include Vλ5-52 to Vλ1-40 and/or Vλ3-27 to Vλ3-1.

In exemplary embodiment 43, provided herein is the method of embodiment 42, wherein the one or more human Vλ gene segments include human non-coding DNA that naturally appears between human Vλ5-52 to Vλ1-40 and/or Vλ3-27 to Vλ3-1.

In exemplary embodiment 44, provided herein is the method of any one of embodiments 39-43, wherein the one or more human Jλ gene segments and the one or more human Cλ gene segments include the human Jλ-Cλ gene segment pairs Jλ1-Cλ1, Jλ2-Cλ2, Jλ3-Cλ3, Jλ6-Cλ6 and the human Jλ7 gene segment.

In exemplary embodiment 45, provided herein is the method of embodiment 44, wherein the human Jλ-Cλ gene segment pairs Jλ1-Cλ1, Jλ2-Cλ2, Jλ3-Cλ3 and Jλ6-Cλ6 include human non-coding DNA that naturally appears between the human Jλ and Cλ gene segment pairs, and the human Jλ7 gene segment includes human non-coding DNA that naturally appears upstream (or 5') of human Jλ7.

In exemplary embodiment 46, provided herein is the method of any one of embodiments 39-45, wherein the rodent Cλ gene segment is a mouse Cλ1 gene segment.

In exemplary embodiment 47, provided herein is the method of any one of embodiments 39-46, wherein the endogenous immunoglobulin λ light chain locus comprises three human Eλs.

In exemplary embodiment 48, provided herein is the method of any one of embodiments 39-46, wherein endogenous immunoglobulin λ light chain locus comprises two rodent Eλs.

In exemplary embodiment 49, provided herein is the method of embodiment 48, wherein the two rodent Eλs are a mouse Eλ and a mouse Eλ3-1.

In exemplary embodiment 50, provided herein is the method of any one of embodiments 38 and 42-49, wherein the DNA fragment further comprises one or more selection markers.

In exemplary embodiment 51, provided herein is the method of any one of embodiments 39 and 42-50, wherein the DNA fragment further comprises one or more site-specific recombination sites.

In exemplary embodiment 52, provided herein is the method of any one of embodiments 39 and 42-51, wherein the DNA fragment of (a) is introduced into a rodent embryonic stem cell whose germline genome comprises an endogenous immunoglobulin heavy chain locus comprising insertion of one or more human $V_H$ gene segments, one or more human $D_H$ gene segments and one or more human $J_H$ gene segments, which human $V_H$, $D_H$ and $J_H$ gene segments are operably linked to a rodent immunoglobulin heavy chain constant region; or an endogenous immunoglobulin heavy chain locus comprising insertion of one or more human $V_H$ gene segments, one or more human $D_H$ gene segments and one or more human $J_H$ gene segments, which human $V_H$, $D_H$ and $J_H$ gene segments are operably linked to a rodent immunoglobulin heavy chain constant region, and an endogenous immunoglobulin κ light chain locus comprising insertion of one or more human Vκ gene segments and one or more human Jκ gene segments, which human Vκ and Jκ gene segments are operably linked to a rodent immunoglobulin Cκ region.

In exemplary embodiment 53, provided herein is the method of any one of embodiments 39 and 42-51, wherein the DNA fragment of (a) is introduced into a rodent embryonic stem cell whose germline genome comprises a wild-type endogenous immunoglobulin heavy chain locus; or a wild-type endogenous immunoglobulin heavy chain locus and a wild-type endogenous immunoglobulin κ light chain locus; and wherein the method further comprises a step of breeding a mouse produced from said non-human embryonic stem cell with a second mouse.

In exemplary embodiment 54, provided herein is the method of any one of embodiments 47-49, wherein the modifying the germline genome of a rodent so that it comprises an engineered immunoglobulin λ light chain locus is carried out in a rodent embryonic stem cell whose germline genome further comprises an endogenous immunoglobulin heavy chain locus comprising insertion of one or more human $V_H$ gene segments, one or more human $D_H$ gene segments and one or more human $J_H$ gene segments, which human $V_H$, $D_H$ and $J_H$ gene segments are operably linked to a rodent immunoglobulin heavy chain constant region; or an endogenous immunoglobulin heavy chain locus comprising insertion of one or more human $V_H$ gene segments, one or more human $D_H$ gene segments and one or more human $J_H$ gene segments, which human $V_H$, $D_H$ and $J_H$ gene segments are operably linked to a rodent immunoglobulin heavy chain constant region, and an endogenous immunoglobulin κ light chain locus comprising insertion of one or more human Vκ gene segments and one or more human Jκ gene segments, which human Vκ and Jκ gene segments are operably linked to a rodent immunoglobulin Cκ region.

In exemplary embodiment 55, provided herein is the method of embodiment 52 or 54, wherein the insertion of one or more human $V_H$ gene segments, one or more human $D_H$ gene segments and one or more human $J_H$ gene segments includes human non-coding DNA that naturally appears between the one or more human $V_H$ gene segments, human non-coding DNA that naturally appears between the one or more human $D_H$ gene segments and human non-coding DNA that naturally appears between the one or more human $J_H$ gene segments.

In exemplary embodiment 56, provided herein is the method of embodiment 52 or 54, wherein the insertion of one or more human Vκ gene segments and one or more human Jκ gene segments includes human non-coding DNA that naturally appears between the one or more human Vκ gene segments and human non-coding DNA that naturally appears between the one or more human Jκ gene segments.

In exemplary embodiment 57, provided herein is the method of any one of embodiments 41-49, wherein the modifying the germline genome of a non-human animal so that it comprises an engineered immunoglobulin λ light chain locus is carried out in a non-human embryonic stem cell whose germline genome comprises a wild-type endogenous immunoglobulin heavy chain locus; or a wild-type endogenous immunoglobulin heavy chain locus and a wild-type endogenous immunoglobulin κ light chain locus; and wherein the method further comprises a step of breeding a mouse produced from said non-human embryonic stem cell with a second mouse.

In exemplary embodiment 58, provided herein is the method of embodiment 53 or 57, wherein the second mouse has a germline genome comprising wild-type IgH and Igκ loci.

In exemplary embodiment 59, provided herein is the method of embodiment 53 or 57, wherein the second mouse has a germline genome comprising homozygous or heterozygous humanized IgH and Igκ loci, which homozygous or heterozygous humanized IgH locus contains an inserted rodent Adam6-encoding sequence.

In exemplary embodiment 60, provided herein is the method of embodiment 53 or 57, wherein the second mouse has a germline genome comprising a homozygous or heterozygous humanized IgH locus and a homozygous or heterozygous inactivated Igκ locus.

In exemplary embodiment 61, provided herein is a method of producing an antibody in a rodent, the method comprising the steps of (1) immunizing a rodent with an antigen of interest, which rodent has a germline genome comprising an endogenous immunoglobulin λ light chain locus comprising (ai) one or more human Vλ gene segments, (b) one or more human Jλ gene segments, and (c) one or more human Cλ gene segments, wherein (a) and (b) are operably linked to (c) and a rodent Cλ gene segment, and wherein the endogenous immunoglobulin λ light chain locus further comprises: one or more rodent immunoglobulin λ light chain enhancers (Eλ) and one or more human immunoglobulin λ light chain enhancers (Eλ); (2) maintaining the rodent under conditions sufficient that the rodent produces an immune response to the antigen of interest; and (3) recovering an antibody from the rodent, or a rodent cell, that binds the antigen of interest.

In exemplary embodiment 62, provided herein is the method of embodiment 61, wherein the rodent has a germline genome further comprising: an endogenous immunoglobulin heavy chain locus comprising insertion of one or more human $V_H$ gene segments, one or more human $D_H$ gene segments and one or more human $J_H$ gene segments, which human $V_H$, $D_H$ and $J_H$ gene segments are operably linked to a rodent immunoglobulin heavy chain constant region; or an endogenous immunoglobulin heavy chain locus comprising insertion of one or more human $V_H$ gene segments, one or more human $D_H$ gene segments and one or more human $J_H$ gene segments, which human $V_H$, $D_H$ and $J_H$ gene segments are operably linked to a rodent immunoglobulin heavy chain constant region, and an endogenous immunoglobulin κ light chain locus comprising insertion of one or more human Vκ gene segments and one or more human Jκ gene segments, which human Vκ and Jκ gene segments are operably linked to a rodent immunoglobulin Cκ region.

In exemplary embodiment 63, provided herein is the method of embodiment 61 or 62, wherein the rodent cell is a B cell.

In exemplary embodiment 64, provided herein is the method of embodiment 61 or 62, wherein the rodent cell is a hybridoma.

In exemplary embodiment 65, provided herein is the method of any one of embodiments 61-64, wherein the endogenous immunoglobulin λ light chain locus comprises insertion of the human Vλ gene segments Vλ5-52 to Vλ1-40 and Vλ3-27 to Vλ3-1, the human Jλ-Cλ gene segment pairs Jλ1-Cλ1, Jλ2-Cλ2, Jλ3-Cλ3, Jλ6-Cλ6 and the human Jλ gene segment Jλ7.

In exemplary embodiment 66, provided herein is the method of embodiment 65, wherein the insertion includes human non-coding DNA that naturally appears between human Vλ Vλ5-52 to Vλ1-40 and Vλ3-27 to Vλ3-1, human non-coding DNA that naturally appears between human Jλ-Cλ gene segment pairs Jλ1-Cλ1, Jλ2-Cλ2, Jλ3-Cλ3 and Jλ6-Cλ6, and human non-coding DNA that naturally appears upstream (or 5') of human Jλ gene segment Jλ7.

In exemplary embodiment 67, provided herein is the method of any one of embodiments 61-66, wherein the rodent Cλ gene segment is a mouse Cλ1 gene segment.

In exemplary embodiment 68, provided herein is the method of any one of embodiments 62-67, wherein the immunoglobulin heavy chain locus comprises insertion of the human $V_H$ gene segments from $V_H$3-74 to $V_H$6-1, the human $D_H$ gene segments from $D_H$1-1 to $D_H$7-27 and the human $J_H$ gene segments $J_H$1-$J_H$6, and which human $V_H$, $D_H$ and $J_H$ gene segments are operably linked to an endogenous rodent immunoglobulin heavy chain constant region.

In exemplary embodiment 69, provided herein is the method of embodiment 68, wherein the insertion includes human non-coding DNA that naturally appears between human $V_H$3-74 to $V_H$6-1, human non-coding DNA that naturally appears between human $D_H$1-1 to $D_H$7-27, and human non-coding DNA that naturally appears between human $J_H$1-$J_H$6.

In exemplary embodiment 70, provided herein is the method of embodiment 68, wherein the human $V_H$, $D_H$ and $J_H$ gene segments replace rodent $V_H$, $D_H$ and $J_H$ gene segments.

In exemplary embodiment 71, provided herein is the method of any one of embodiments 62-70, wherein the immunoglobulin κ light chain locus comprises insertion of the human Vκ gene segments from Vκ2-40 to Vκ4-1 and the human Jκ gene segments from Jκ1-Jκ5, and which human Vκ and Jκ gene segments are operably linked to an endogenous rodent immunoglobulin Cκ region.

In exemplary embodiment 72, provided herein is the method of embodiment 71, wherein the insertion includes human non-coding DNA that naturally appears between human Vκ2-40 to Vκ4-1, and human non-coding DNA that naturally appears between human Jκ1-Jκ5.

In exemplary embodiment 73, provided herein is the method of embodiment 71, wherein the human Vκ and Jκ gene segments replace rodent Vκ and Jκ gene segments.

In exemplary embodiment 74, provided herein is the method of any one of embodiments 61-73, wherein the germline genome of the rodent further comprises insertion of one or more nucleotide sequences encoding one or more rodent Adam6 polypeptides.

In exemplary embodiment 75, provided herein is the method of any one of embodiments 62-74, wherein the immunoglobulin heavy chain locus lacks an endogenous rodent Adam6 gene.

In exemplary embodiment 76, provided herein is the method of embodiment 75, wherein the immunoglobulin heavy chain locus further comprises insertion of one or more nucleotide sequences encoding one or more rodent Adam6 polypeptides.

In exemplary embodiment 77, provided herein is the method of embodiment 76, wherein the one or more nucleotide sequences encoding one or more rodent Adam6 polypeptides are inserted between a first and a second human $V_H$ gene segment.

In exemplary embodiment 78, provided herein is the method of embodiment 77, wherein the first human $V_H$ gene segment is human $V_H$1-2 and the second human $V_H$ gene segment is human $V_H$6-1.

In exemplary embodiment 79, provided herein is the method of embodiment 76, wherein the one or more nucleotide sequences encoding one or more rodent Adam6 polypeptides are inserted in the place of a human Adam6 pseudogene.

In exemplary embodiment 80, provided herein is the method of embodiment 76, wherein the one or more nucleotide sequences encoding one or more rodent Adam6 polypeptides are inserted between a human $V_H$ gene segment and a human $D_H$ gene segment.

In exemplary embodiment 81, provided herein is the method of any one of embodiments 61-80, wherein the antibody recovered from the rodent, or a rodent cell, that binds the antigen of interest comprises a human heavy chain variable domain and a human lambda light chain variable domain.

In exemplary embodiment 82, provided herein is the method of embodiment 81, wherein the human heavy chain variable domain includes a rearranged human $V_H$ gene segment selected from the group consisting of $V_H$3-74, $V_H$3-73, $V_H$3-72, $V_H$2-70, $V_H$1-69, $V_H$3-66, $V_H$3-64, $V_H$4-61, $V_H$4-59, $V_H$1-58, $V_H$3-53, $V_H$5-51, $V_H$3-49, $V_H$3-48, $V_H$1-46, $V_H$1-45, $V_H$3-43, $V_H$4-39, $V_H$4-34, $V_H$3-33, $V_H$4-31, $V_H$3-30, $V_H$4-28, $V_H$2-26, $V_H$1-24, $V_H$3-23, $V_H$3-21, $V_H$3-20, $V_H$1-18, $V_H$3-15, $V_H$3-13, $V_H$3-11, $V_H$3-9, $V_H$1-8, $V_H$3-7, $V_H$2-5, $V_H$7-4-1, $V_H$4-4, $V_H$1-3, $V_H$1-2 and $V_H$6-1.

In exemplary embodiment 83, provided herein is the method of embodiment 81 or 82, wherein the human lambda light chain variable domain includes a rearranged human Vλ gene segment selected from the group consisting of Vλ4-69, Vλ8-61, Vλ4-60, Vλ6-57, Vλ10-54, Vλ5-52, Vλ1-51, Vλ9-49, Vλ1-47, Vλ7-46, Vλ5-45, Vλ1-44, Vλ7-43, Vλ1-40, Vλ5-39, Vλ5-37, Vλ1-36, Vλ3-27, Vλ3-25, Vλ2-23, Vλ3-22, Vλ3-21, Vλ3-19, Vλ2-18, Vλ3-16, Vλ2-14, Vλ3-12, Vλ2-11, Vλ3-10, Vλ3-9, Vλ2-8, Vλ4-3 and Vλ3-1.

In exemplary embodiment 84, provided herein is the method of any one of embodiments 39-83, wherein the rodent is a mouse or a rat.

In exemplary embodiment 85, provided herein is a rodent whose germline genome comprises a homozygous endogenous immunoglobulin λ light chain locus comprising: (i) human Vλ gene segments Vλ5-52 to Vλ1-40 and Vλ3-27 to Vλ3-1, (ii) human Jλ-Cλ gene segment pairs Jλ1-Cλ1, Jλ2-Cλ2, Jλ3-Cλ3 and Jλ6-Cλ6, (iii) human Jλ gene segment Jλ7, and (iv) three human immunoglobulin λ light chain enhancers; wherein (i)-(iv) are operably linked to each other and (i)-(iii) are upstream of a rodent Cλ gene segment, and wherein the endogenous immunoglobulin light chain locus lacks an endogenous rodent immunoglobulin Eλ2-4, the human Vλ gene segments Vλ5-52 to Vλ1-40 and Vλ3-27 to Vλ3-1 includes human non-coding DNA that naturally appears between the human Vλ gene segments, the human Jλ-Cλ gene segments pairs Jλ1-Cλ1, Jλ2-Cλ2, Jλ3-Cλ3 and Jλ6-Cλ6 includes human non-coding DNA that naturally appears between the human Jλ-Cλ gene segments pairs, and the human Jλ gene segment Jλ7 includes human non-coding DNA that naturally appears upstream (or 5') of human Jλ7.

In exemplary embodiment 86, provided herein is the rodent of embodiment 85, wherein the rodent Cλ gene segment is a mouse Cλ1 gene segment.

In exemplary embodiment 87, provided herein is the rodent of embodiment 85 or 86, wherein the endogenous immunoglobulin λ light chain locus further comprises endogenous rodent immunoglobulin λ light chain enhancers Eλ and Eλ3-1.

In exemplary embodiment 88, provided herein is the rodent of any one of embodiments 85-87, wherein the endogenous immunoglobulin λ light chain locus comprises a deletion of endogenous rodent Vλ2-Vλ3-Jλ2-Cλ2-Jλ4P-Cλ4P gene segments and Vλ1-Jλ3-Jλ3P-Cλ3-Jλ1 gene segments.

In exemplary embodiment 89, provided herein is the rodent of any one of embodiments 85-88, wherein the rodent is a rat or a mouse.

In some embodiments, provided herein is a rodent whose germline genome comprises an endogenous immunoglobulin λ light chain locus comprising (a) one or more human Vλ gene segments, (b) one or more human Jλ gene segments, and (c) one or more human Cλ gene segments, wherein (a) and (b) are operably linked to (c) and a rodent Cλ gene segment, and wherein the endogenous immunoglobulin λ light chain locus further comprises: one or more rodent immunoglobulin λ light chain enhancers (Eλ), and one or more human immunoglobulin λ light chain enhancers (Eλ).

In some embodiments, the endogenous immunoglobulin λ light chain locus comprises two rodent Eλs.

In some embodiments, the two rodent Eλs are a mouse Eλ and a mouse Eλ3-1.

In some embodiments, the endogenous immunoglobulin λ light chain locus comprises three human Eλs.

In some embodiments, the germline genome further comprises (i) an endogenous immunoglobulin heavy chain locus comprising insertion of one or more human $V_H$ gene segments, one or more human $D_H$ gene segments and one or more human $J_H$ gene segments, which human $V_H$, $D_H$ and $J_H$ gene segments are operably linked to a rodent immunoglobulin heavy chain constant region; or (ii) an endogenous immunoglobulin heavy chain locus comprising insertion of one or more human $V_H$ gene segments, one or more human $D_H$ gene segments and one or more human $J_H$ gene segments, which human $V_H$, $D_H$ and $J_H$ gene segments are operably linked to a rodent immunoglobulin heavy chain constant region, and an endogenous immunoglobulin κ light chain locus comprising insertion of one or more human Vκ gene segments and one or more human Jκ gene segments, which human Vκ and Jκ gene segments are operably linked to a rodent immunoglobulin Cκ region.

In some embodiments, the insertion of one or more human $V_H$ gene segments, one or more human $D_H$ gene segments and one or more human $J_H$ gene segments replace rodent $V_H$, $D_H$ gene segments.

In some embodiments, the insertion includes human non-coding DNA that naturally appears between human $V_H$, $D_H$, and $J_H$ gene segments, and combinations thereof.

In some embodiments, the insertion of one or more human Vκ gene segments and one or more human Jκ gene segments replace rodent Vκ and Jκ gene segments.

In some embodiments, the insertion includes human non-coding DNA that naturally appears between human Vκ and Jκ gene segments, and combinations thereof.

In some embodiments, the rodent immunoglobulin heavy chain constant region is an endogenous rodent immunoglobulin heavy chain constant region.

In some embodiments, wherein the rodent Cκ region is an endogenous rodent Cκ region.

In some embodiments, the endogenous immunoglobulin λ light chain locus comprises a deletion of endogenous Vλ and Jλ gene segments, in whole or in part.

In some embodiments, the endogenous immunoglobulin λ light chain locus comprises a deletion of Vλ2-Vλ3-Jλ2-Cλ2 gene segments and Vλ1-Jλ3-Cλ3-Jλ1 gene segments.

In some embodiments, the endogenous immunoglobulin λ light chain locus comprises a deletion of Vλ2-Vλ3-Jλ2-Cλ2-Jλ4P-Cλ4P gene segments and Vλ1-Jλ3-Jλ3P-Cλ3-Jλ1 gene segments.

In some embodiments, the rodent Cλ gene segment is a mouse Cλ1 gene segment.

In some embodiments, the endogenous immunoglobulin λ light chain locus comprises a deletion of a rodent Eλ2-4.

In some embodiments, the rodent does not detectably express endogenous immunoglobulin λ light chains.

In some embodiments, the immunoglobulin heavy chain locus comprises insertion of the human $V_H$ gene segments from $V_H$3-74 to $V_H$6-1, the human $D_H$ gene segments from $D_H$1-1 to $D_H$7-27, and the human $J_H$ gene segments $J_H$1-$J_H$6.

In some embodiments, the insertion includes human non-coding DNA that naturally appears between human $V_H$3-74 to $V_H$6-1, human non-coding DNA that naturally appears between human $D_H$1-1 to $D_H$7-27, and human non-coding DNA that naturally appears between human $J_H$1-$J_H$6.

In some embodiments, the immunoglobulin κ light chain locus comprises insertion of the proximal Vκ duplication, in whole or in part, of a human immunoglobulin κ light chain locus.

In some embodiments, the immunoglobulin κ light chain locus comprises insertion of the human Vκ gene segments from Vκ2-40 to Vκ4-1 and the human Jκ gene segments from Jκ1-Jκ5.

In some embodiments, the insertion includes human non-coding DNA that naturally appears between human Vκ2-40 to Vκ4-1, and human non-coding DNA that naturally appears between human Jκ1-Jκ5.

In some embodiments, the endogenous immunoglobulin λ light chain locus comprises insertion of the human Vλ gene segments Vλ5-52 to Vλ1-40 and Vλ3-27 to Vλ3-1, at least the human Jλ-Cλ gene segment pairs Jλ1-Cλ1, Jλ2-Cλ2, Jλ3-Cλ3, Jλ6-Cλ6, the human Jλ gene segment Jλ7 and a rodent Cλ1 gene segment.

In some embodiments, the insertion includes human non-coding DNA that naturally appears between human Vλ5-52 to Vλ1-40 and Vλ3-27 to Vλ3-1, human non-coding DNA that naturally appears between human Jλ-Cλ gene segment pairs Jλ1-Cλ1, Jλ2-Cλ2, Jλ3-Cλ3 and Jλ6-Cλ6, and human non-coding DNA that naturally appears upstream (or 5') of human Jλ gene segment Jλ7.

In some embodiments, the immunoglobulin heavy chain locus lacks an endogenous rodent Adam6 gene.

In some embodiments, the immunoglobulin heavy chain locus further comprises insertion of one or more nucleotide sequences encoding one or more rodent Adam6 polypeptides.

In some embodiments, the one or more nucleotide sequences are inserted between a first and a second human $V_H$ gene segment.

In some embodiments, the one or more nucleotide sequences are inserted in the place of a human Adam6 pseudogene.

In some embodiments, the first human $V_H$ gene segment is human $V_H$1-2 and the second human $V_H$ gene segment is human $V_H$6-1.

In some embodiments, the one or more nucleotide sequences are inserted between a human $V_H$ gene segment and a human $D_H$ gene segment.

In some embodiments, the rodent is heterozygous or homozygous for the endogenous immunoglobulin heavy chain locus.

In some embodiments, the rodent is heterozygous or homozygous for the endogenous immunoglobulin κ light chain locus.

In some embodiments, the rodent is heterozygous or homozygous for the endogenous immunoglobulin λ light chain locus.

In some embodiments, the rodent is a rat or a mouse.

In some embodiments, provided herein is an isolated rodent cell whose germline genome comprises an endogenous immunoglobulin λ light chain locus comprising: (a) one or more human Vλ gene segments, (b) one or more human Jλ gene segments, and (c) one or more human Cλ gene segments, (i) wherein (a) and (b) are operably linked to (c) and a rodent Cλ gene segment, and (ii) wherein the endogenous immunoglobulin λ light chain locus further comprises: one or more rodent immunoglobulin λ light chain enhancers (Eλ) and one or more human immunoglobulin λ light chain enhancers (Eλ).

In some embodiments, provided herein is an immortalized cell made from a rodent cell provided herein.

In some embodiments, the rodent cell is a rodent embryonic stem cell.

In some embodiments, provided herein is a rodent embryo generated from a rodent embryonic stem cell provided herein.

In some embodiments, provided herein is a method of making a rodent whose germline genome comprises an engineered endogenous immunoglobulin λ light chain locus, the method comprising (a) introducing a DNA fragment into a rodent embryonic stem cell, said DNA fragment comprising a nucleotide sequence that includes (i) one or more human Vλ gene segments, (ii) one or more human Jλ gene segments, and (iii) one or more human Cλ gene segments, wherein (i)-(iii) are operably linked to a rodent Cλ gene segment, and wherein the nucleotide sequence further comprises one or more human immunoglobulin λ light chain enhancers (Eλ); (b) obtaining the rodent embryonic stem cell generated in (a); and (c) creating a rodent using the rodent embryonic stem cell of (b).

In some embodiments, the nucleotide sequence further includes and one or more human immunoglobulin λ light chain enhancers (Eλ).

In some embodiments, provided herein is a method of making a rodent whose germline genome comprises an engineered endogenous immunoglobulin λ light chain locus, which engineered endogenous immunoglobulin λ light chain locus comprises insertion of one or more human Vλ gene segments, one or more human Jλ gene segments and one or more human Cλ gene segments, which human Vλ and Jλ gene segments are operably linked to a rodent or a human Cλ gene segment, and which endogenous immunoglobulin λ light chain locus further comprises one or more rodent immunoglobulin λ light chain enhancers (Eλ), and one or more human immunoglobulin λ light chain enhancers (Eλ), the method comprising modifying the germline genome of a rodent so that it comprises an engineered immunoglobulin λ light chain locus that includes insertion of one or more human Vλ gene segments, one or more human Jλ gene segments and one or more human Cλ gene segments, which human Vλ and Jλ gene segments are operably linked to a rodent or a human Cλ gene segment, and which endogenous immunoglobulin λ light chain locus further comprises one or more rodent immunoglobulin λ light chain enhancers (Eλ), and one or more human immunoglobulin λ light chain enhancers (Eλ), thereby making said rodent.

In some embodiments, the one or more human Vλ gene segments include Vλ5-52 to Vλ1-40 and/or Vλ3-27 to Vλ3-1.

In some embodiments, the one or more human Vλ gene segments include human non-coding DNA that naturally appears between human Vλ5-52 to Vλ1-40 and/or Vλ3-27 to Vλ3-1.

In some embodiments, the one or more human Jλ gene segments and the one or more human Cλ gene segments include the human Jλ-Cλ gene segment pairs Jλ1-Cλ1, Jλ2-Cλ2, Jλ3-Cλ3, Jλ6-Cλ6 and the human Jλ7 gene segment.

In some embodiments, the human Jλ-Cλ gene segment pairs Jλ1-Cλ1, Jλ2-Cλ2, Jλ3-Cλ3 and Jλ6-Cλ6 include human non-coding DNA that naturally appears between the human Jλ and Cλ gene segment pairs, and the human Jλ7 gene segment includes human non-coding DNA that naturally appears upstream (or 5') of human Jλ7.

In some embodiments, the rodent Cλ gene segment is a mouse Cλ1 gene segment.

In some embodiments, the endogenous immunoglobulin λ light chain locus comprises three human Eλs.

In some embodiments, the endogenous immunoglobulin λ light chain locus comprises two rodent Eλs.

In some embodiments, the two rodent Eλs are a mouse Eλ and a mouse Eλ3-1.

In some embodiments, the DNA fragment further comprises one or more selection markers.

In some embodiments, the DNA fragment further comprises one or more site-specific recombination sites.

In some embodiments, the DNA fragment of (a) is introduced into a rodent embryonic stem cell whose germline genome comprises an endogenous immunoglobulin heavy chain locus comprising insertion of one or more human $V_H$ gene segments, one or more human $D_H$ gene segments and one or more human $J_H$ gene segments, which human $V_H$, $D_H$ and $J_H$ gene segments are operably linked to a rodent immunoglobulin heavy chain constant region; or an endogenous immunoglobulin heavy chain locus comprising insertion of one or more human $V_H$ gene segments, one or more human $D_H$ gene segments and one or more human $J_H$ gene segments, which human $V_H$, $D_H$ and $J_H$ gene segments are operably linked to a rodent immunoglobulin heavy chain constant region, and an endogenous immunoglobulin κ light chain locus comprising insertion of one or more human Vκ gene segments and one or more human Jκ gene segments, which human Vκ and Jκ gene segments are operably linked to a rodent immunoglobulin Cκ region.

In some embodiments, the DNA fragment of (a) is introduced into a rodent embryonic stem cell whose germline genome comprises a wild-type endogenous immunoglobulin heavy chain locus; or a wild-type endogenous immunoglobulin heavy chain locus and a wild-type endogenous immunoglobulin κ light chain locus; and wherein the method further comprises a step of breeding a mouse produced from said non-human embryonic stem cell with a second mouse.

In some embodiments, the modifying the germline genome of a rodent so that it comprises an engineered immunoglobulin λ light chain locus is carried out in a rodent embryonic stem cell whose germline genome further comprises an endogenous immunoglobulin heavy chain locus comprising insertion of one or more human $V_H$ gene segments, one or more human $D_H$ gene segments and one or more human $J_H$ gene segments, which human $V_H$, $D_H$ and $J_H$ gene segments are operably linked to a rodent immunoglobulin heavy chain constant region; or an endogenous immunoglobulin heavy chain locus comprising insertion of one or more human $V_H$ gene segments, one or more human $D_H$ gene segments and one or more human $J_H$ gene segments, which human $V_H$, $D_H$ and $J_H$ gene segments are operably linked to a rodent immunoglobulin heavy chain constant region, and an endogenous immunoglobulin κ light chain locus comprising insertion of one or more human Vκ gene segments and one or more human Jκ gene segments, which human Vκ and Jκ gene segments are operably linked to a rodent immunoglobulin Cκ region.

In some embodiments, the insertion of one or more human $V_H$ gene segments, one or more human $D_H$ gene segments and one or more human $J_H$ gene segments includes human non-coding DNA that naturally appears between the one or more human $V_H$ gene segments, human non-coding DNA that naturally appears between the one or more human $D_H$ gene segments and human non-coding DNA that naturally appears between the one or more human $J_H$ gene segments.

In some embodiments, the insertion of one or more human Vκ gene segments and one or more human Jκ gene segments includes human non-coding DNA that naturally appears between the one or more human Vκ gene segments and human non-coding DNA that naturally appears between the one or more human Jκ gene segments.

In some embodiments, the modifying the germline genome of a non-human animal so that it comprises an engineered immunoglobulin λ light chain locus is carried out in a non-human embryonic stem cell whose germline genome comprises a wild-type endogenous immunoglobulin heavy chain locus; or a wild-type endogenous immunoglobulin heavy chain locus and a wild-type endogenous immunoglobulin κ light chain locus; and wherein the method further comprises a step of breeding a mouse produced from said non-human embryonic stem cell with a second mouse.

In some embodiments, the second mouse has a germline genome comprising wild-type IgH and Igκ loci.

In some embodiments, the second mouse has a germline genome comprising homozygous or heterozygous humanized IgH and Igκ loci, which homozygous or heterozygous humanized IgH locus contains an inserted rodent Adam6-encoding sequence.

In some embodiments, the second mouse has a germline genome comprising a homozygous or heterozygous humanized IgH locus and a homozygous or heterozygous inactivated Igκ locus.

In some embodiments, provided herein is a method of producing an antibody in a rodent, the method comprising the steps of (1) immunizing a rodent with an antigen of interest, which rodent has a germline genome comprising an endogenous immunoglobulin λ light chain locus comprising (ai) one or more human Vλ gene segments, (b) one or more human Jλ gene segments, and (c) one or more human Cλ gene segments, wherein (a) and (b) are operably linked to (c) and a rodent Cλ gene segment, and wherein the endogenous immunoglobulin λ light chain locus further comprises: one or more rodent immunoglobulin λ light chain enhancers (Eλ) and one or more human immunoglobulin λ light chain enhancers (Eλ); (2) maintaining the rodent under conditions sufficient that the rodent produces an immune response to the antigen of interest; and (3) recovering an antibody from the rodent, or a rodent cell, that binds the antigen of interest.

In some embodiments, the rodent has a germline genome further comprising: an endogenous immunoglobulin heavy chain locus comprising insertion of one or more human $V_H$ gene segments, one or more human $D_H$ gene segments and one or more human $J_H$ gene segments, which human $V_H$, $D_H$ and $J_H$ gene segments are operably linked to a rodent immunoglobulin heavy chain constant region; or an endogenous immunoglobulin heavy chain locus comprising insertion of one or more human $V_H$ gene segments, one or more human $D_H$ gene segments and one or more human $J_H$ gene segments, which human $V_H$, $D_H$ and $J_H$ gene segments are operably linked to a rodent immunoglobulin heavy chain constant region, and an endogenous immunoglobulin κ light chain locus comprising insertion of one or more human Vκ gene segments and one or more human Jκ gene segments, which human Vκ and Jκ gene segments are operably linked to a rodent immunoglobulin Cκ region.

In some embodiments, the rodent cell is a B cell.

In some embodiments, the rodent cell is a hybridoma.

In some embodiments, the endogenous immunoglobulin λ light chain locus comprises insertion of the human Vλ gene segments Vλ5-52 to Vλ1-40 and Vλ3-27 to Vλ3-1, the human Jλ-Cλ gene segment pairs Jλ1-Cλ1, Jλ2-Cλ2, Jλ3-Cλ3, Jλ6-Cλ6 and the human Jλ gene segment Jλ7.

In some embodiments, the insertion includes human non-coding DNA that naturally appears between human Vλ Vλ5-52 to Vλ1-40 and Vλ3-27 to Vλ3-1, human non-coding DNA that naturally appears between human Jλ-Cλ gene segment pairs Jλ1-Cλ1, Jλ2-Cλ2, Jλ3-Cλ3 and Jλ6-Cλ6, and human non-coding DNA that naturally appears upstream (or 5') of human Jλ gene segment Jλ7.

In some embodiments, the rodent Cλ gene segment is a mouse Cλ1 gene segment.

In some embodiments, the immunoglobulin heavy chain locus comprises insertion of the human $V_H$ gene segments from $V_H$3-74 to $V_H$6-1, the human $D_H$ gene segments from $D_H$1-1 to $D_H$7-27 and the human $J_H$ gene segments $J_H$1-$J_H$6, and which human $V_H$, $D_H$ and $J_H$ gene segments are operably linked to an endogenous rodent immunoglobulin heavy chain constant region.

In some embodiments, the insertion includes human non-coding DNA that naturally appears between human $V_H$3-74 to $V_H$6-1, human non-coding DNA that naturally appears between human $D_H1$-1 to $D_H7$-27, and human non-coding DNA that naturally appears between human $J_H1$-$J_H6$.

In some embodiments, the human $V_H$, $D_H$ and $J_H$ gene segments replace rodent $V_H$, $D_H$ and $J_H$ gene segments.

In some embodiments, the immunoglobulin κ light chain locus comprises insertion of the human Vκ gene segments from Vκ2-40 to Vκ4-1 and the human Jκ gene segments from Jκ1-Jκ5, and which human Vκ and Jκ gene segments are operably linked to an endogenous rodent immunoglobulin Cκ region.

In some embodiments, the insertion includes human non-coding DNA that naturally appears between human Vκ2-40 to Vκ4-1, and human non-coding DNA that naturally appears between human Jκ1-Jκ5.

In some embodiments, the human Vκ and Jκ gene segments replace rodent Vκ and Jκ gene segments.

In some embodiments, the germline genome of the rodent further comprises insertion of one or more nucleotide sequences encoding one or more rodent Adam6 polypeptides.

In some embodiments, the immunoglobulin heavy chain locus lacks an endogenous rodent Adam6 gene.

In some embodiments, the immunoglobulin heavy chain locus further comprises insertion of one or more nucleotide sequences encoding one or more rodent Adam6 polypeptides.

In some embodiments, the one or more nucleotide sequences encoding one or more rodent Adam6 polypeptides are inserted between a first and a second human $V_H$ gene segment.

In some embodiments, the first human $V_H$ gene segment is human $V_H1$-2 and the second human $V_H$ gene segment is human $V_H6$-1.

In some embodiments, the one or more nucleotide sequences encoding one or more rodent Adam6 polypeptides are inserted in the place of a human Adam6 pseudogene.

In some embodiments, the one or more nucleotide sequences encoding one or more rodent Adam6 polypeptides are inserted between a human $V_H$ gene segment and a human $D_H$ gene segment.

In some embodiments, the antibody recovered from the rodent, or a rodent cell, that binds the antigen of interest comprises a human heavy chain variable domain and a human lambda light chain variable domain.

In some embodiments, the human heavy chain variable domain includes a rearranged human $V_H$ gene segment selected from the group consisting of $V_H3$-74, $V_H3$-73, $V_H3$-72, $V_H2$-70, $V_H1$-69, $V_H3$-66, $V_H3$-64, $V_H4$-61, $V_H4$-59, $V_H1$-58, $V_H3$-53, $V_H5$-51, $V_H3$-49, $V_H3$-48, $V_H1$-46, $V_H1$-45, $V_H3$-43, $V_H4$-39, $V_H4$-34, $V_H3$-33, $V_H4$-31, $V_H3$-30, $V_H4$-28, $V_H2$-26, $V_H1$-24, $V_H3$-23, $V_H3$-21, $V_H3$-20, $V_H1$-18, $V_H3$-15, $V_H3$-13, $V_H3$-11, $V_H3$-9, $V_H1$-8, $V_H3$-7, $V_H2$-5, $V_H7$-4-1, $V_H4$-4, $V_H1$-3, $V_H1$-2 and $V_H6$-1.

In some embodiments, the human lambda light chain variable domain includes a rearranged human Vλ gene segment selected from the group consisting of Vλ4-69, Vλ8-61, Vλ4-60, Vλ6-57, Vλ10-54, Vλ5-52, Vλ1-51, Vλ9-49, Vλ1-47, Vλ7-46, Vλ5-45, Vλ1-44, Vλ7-43, Vλ1-40, Vλ5-39, Vλ5-37, Vλ1-36, Vλ3-27, Vλ3-25, Vλ2-23, Vλ3-22, Vλ3-21, Vλ3-19, Vλ2-18, Vλ3-16, Vλ2-14, Vλ3-12, Vλ2-11, Vλ3-10, Vλ3-9, Vλ2-8, Vλ4-3 and Vλ3-1.

In some embodiments, the rodent is a mouse or a rat.

In some embodiments, provided herein is a rodent whose germline genome comprises a homozygous endogenous immunoglobulin λ light chain locus comprising: (i) human Vλ gene segments Vλ5-52 to Vλ1-40 and Vλ3-27 to Vλ3-1, (ii) human Jλ-Cλ gene segment pairs Jλ1-Cλ1, Jλ2-Cλ2, Jλ3-Cλ3 and Jλ6-Cλ6, (iii) human Jλ gene segment Jλ7, and (iv) three human immunoglobulin λ light chain enhancers; wherein (i)-(iv) are operably linked to each other and (i)-(iii) are upstream of a rodent Cλ gene segment, and wherein the endogenous immunoglobulin light chain locus lacks an endogenous rodent immunoglobulin Eλ2-4, the human Vλ gene segments Vλ5-52 to Vλ1-40 and Vλ3-27 to Vλ3-1 includes human non-coding DNA that naturally appears between the human Vλ gene segments, the human Jλ-Cλ gene segments pairs Jλ1-Cλ1, Jλ2-Cλ2, Jλ3-Cλ3 and Jλ6-Cλ6 includes human non-coding DNA that naturally appears between the human Jλ-Cλ gene segments pairs, and the human Jλ gene segment Jλ7 includes human non-coding DNA that naturally appears upstream (or 5') of human Jλ7.

In some embodiments, the rodent Cλ gene segment is a mouse Cλ1 gene segment.

In some embodiments, the endogenous immunoglobulin λ light chain locus further comprises endogenous rodent immunoglobulin λ light chain enhancers Eλ and Eλ3-1.

In some embodiments, the endogenous immunoglobulin λ light chain locus comprises a deletion of endogenous rodent Vλ2-Vλ3-Jλ2-Cλ2-Jλ4P-Cλ4P gene segments and Vλ1-Jλ3-Jλ3P-Cλ3-Jλ1 gene segments.

In some embodiments, the rodent is a rat or a mouse.

EXAMPLES

The following examples are provided so as to describe to the skilled artisan how to make and use methods and compositions described herein, and are not intended to limit the scope of what the inventors of the present disclosure regard as their invention. Unless indicated otherwise, temperature is indicated in Celsius and pressure is at or near atmospheric.

Example 1

Construction of a Targeting Vector for Engineering a Rodent Igλ Light Chain Locus This example illustrates exemplary methods of constructing a targeting vector for insertion into the genome of a non-human animal such as a rodent (e.g., a mouse). The methods described in this example demonstrate the production of a non-human animal whose germline genome comprises an engineered Igλ light chain locus. In particular, this example demonstrates the construction of a series of targeting vectors for engineering an endogenous Igλ light chain locus in a non-human animal so that the non-human animal expresses and/or produces antibodies that include Igλ light chains having human variable domains and non-human or, in some embodiments, human constant domains from said endogenous Igλ light chain locus in the germline genome of the non-human animal. As described below, a series of targeting vectors containing varying amounts of genetic material corresponding to a human Igλ light chain locus (i.e., human Vλ Jλ Cλ and Igλ enhancer sequences) are inserted into an endogenous rodent Igλ light chain locus. In particular, said genetic material is inserted upstream of a rodent Cλ gene (or gene segment) so that human Vλ, Jλ and Cλ gene segments are operably linked to said rodent Cλ gene. The methods described in this example provide for retention and/or deletion of endogenous rodent Igλ gene segments (or sequences). An exemplary schematic illustration of a series of targeting vectors for constructing an engineered endogenous Igλ light chain locus is set forth in FIGS. 1-4.

A series of targeting vectors containing various amounts of human Vλ Jλ Cλ and Igλ enhancer sequences (or regions) for insertion into a rodent Igλ light chain locus were created using VELOCIGENE® technology (see, e.g., U.S. Pat. No. 6,586,251 and Valenzuela et al., 2003, Nature Biotech. 21(6):652-9; incorporated herein by reference in their entireties) and molecular biology techniques known in the art. The methods described in this example can be employed to utilize any human Vλ, Jλ, Cλ and Igλ enhancer sequences, or combination of sequences (or sequence fragments) as desired. Table 1 sets forth brief descriptions of each targeting vector illustrated in FIG. 1.

Briefly, about 12 kb (11,822 bp) of human Igλ genomic sequence from human bacterial artificial chromosome (BAC) clone CTD-2502m16 was ligated into mouse BAC clone RP23-60e14. This mouse BAC clone was engineered to shorten the BAC clone by about 90 kb, insert unique AsiSI and PI-SceI restriction enzyme recognition sites downstream of a mouse Cλ1 gene and replace the original Chloramphenicol resistance ($CM^R$) gene with a Spectinomycin resistance ($Spec^R$) gene and unique I-CeuI restriction site by two consecutive bacterial homologous recombination (BHR) steps prior to ligation with the human Igλ genomic sequence. The human BAC clone CTD-2502m16 was also modified by two consecutive BHR steps to trim about 53 kb of human sequence from the 3' end with a Neomycin selection cassette and a unique PI-SceI restriction site, and trim a $CM^R$ gene and about 101.5 kb of human sequence from the 5' end with a Hygromycin cassette and a unique AsiSI restriction site, thereby placing the AsiSI site and the Neomycin selection cassette about 2885 bp upstream and about 1418 bp downstream, respectively, of the modular human enhancer region (see, e.g., Asenbauer, H. and H. G. Klobeck, 1996, Eur. J. Immunol. 26(1):142-50, which is hereby incorporated by reference in its entirety). The human Igλ genomic sequence contained about 7.5 kb corresponding to a human Igλ enhancer (Eλ) region (or sequence), which is modular and contains three sequence elements (FIG. 1; Asenbauer, H. and H. G. Klobeck, 1996, Eur. J. Immunol. 26(1):142-50), and 2.9 kb and 1.4 kb of 5' and 3' flanking sequence, respectively, as well as a Neomycin selection cassette (i.e., a Neomycin resistance gene [$NEO^R$] under transcriptional control of a ubiquitin promoter and flanked by loxP sites). The modified human and mouse BAC clones were digested with AsiSI and PI-SceI sites and ligated together. After ligation to the engineered mouse BAC clone, the resulting targeting vector contained about 39,166 bp of mouse sequence as a 5' homology arm and included mouse Igλ gene segments Vλ1, Jλ3, Jλ3P, Cλ3, Jλ1, and Cλ1 (6286 targeting vector, FIG. 1). The 3' homology arm (about 30,395 bp) included a mouse Igλ enhancer (mEλ). For simplicity, in the depiction of 6286 targeting vector in FIG. 1, the mouse homology arms are not shown. Homologous recombination with this targeting vector resulted in the insertion of the three human Igλ enhancer sequences as well as the 5' and 3' flanking sequences without any deletion of mouse sequence. Recombinase-mediated deletion of the Neomycin selection cassette was achieved in ES cells by transient expression of Cre recombinase (see e.g., Lakso, M. et al., 1992, Proc. Natl. Acad. Sci. USA 89: 6232-6; Orban, P. C. et al., 1992, Proc. Natl. Acad. Sci. U.S.A. 89:6861-5; Gu, H. et al., 1993, Cell 73(6):1155-64; Araki, K. et al., 1995, Proc. Natl. Acad. Sci. U.S.A. 92:160-4; Dymecki, S. M., 1996, Proc. Natl. Acad. Sci. U.S.A. 93(12):6191-6; all of which are incorporated herein by reference in their entireties).

A second construct (6571 targeting vector) was engineered to include a group of five functional human Vλ gene segments and a substantially all of a human Jλ-Cλ cluster (i.e., human Jλ1-Cλ1-Jλ2-Cλ2-Jλ3-Cλ3-Jλ4-Cλ4-Jλ5-Cλ5-Jλ6-Cλ6-hJλ7) spanning about 125,473 bp, which was obtained from human BAC clone CTD-2079i4. To construct the targeting vector, a human Cλ7 gene in human BAC clone CTD-2079i4 was first replaced by BHR with a mouse Cλ1 gene and about 1588 bp of flanking sequence, which was amplified by PCR using mouse BAC clone RP23-60e14 as a template. A 5' homology arm containing about 37,161 bp of mouse sequence corresponding to sequence 5' of a mouse Cλ1 gene in mouse BAC clone RP23-60e14 was then ligated to the modified human BAC clone CTD-2079i4 containing the synthetic mouse Cλ1 gene using unique I-CeuI and PI-SceI restriction enzyme recognition sites separately introduced into both mouse and human BAC clones by BHR. This 5' homology arm contained mouse Vλ1, Jλ3, Jλ3P, Cλ3, and Jλ1 gene segments (FIG. 1). The 3' homology arm contained about 9,189 bp of human sequence corresponding to two of the human Eλs from the 6286 targeting vector (FIG. 1).

A third construct (6596 targeting vector) was engineered to contain an additional eleven functional human Vλ gene segments. This targeting vector contained about 171,458 bp of human sequence from BAC clone RP11-761L13. By design, the three human Vλ gene segments were included to provide 3' overlap homology (of about 33,469 bp) with the 6571 targeting vector. As described above, a 5' homology arm containing about 37,161 bp of mouse sequence was ligated to the 5' end of the DNA fragment containing the human Vλ gene segments using unique I-CeuI and AscI restriction enzyme recognition sites separately introduced into both mouse and human BAC clones by BHR.

A fourth construct (6597 targeting vector) was engineered to contain an additional nine functional human Vλ gene segments. This targeting vector contained about 121,188 bp of human sequence from two BAC clones, RP11-22L18 and RP11-761L13. As described above, the 3' end of this human sequence contained additional human Vλ gene segments that provided 3' overlap homology with the 6596 targeting vector (about 27,468 bp). As described above for the 6571 and 6596 targeting vectors, about 37,161 bp 5' homology arm containing mouse sequence from BAC clone RP23-60e14 was ligated to the 5' end of the human sequence using unique I-CeuI and AscI restriction enzyme recognition sites separately introduced into both mouse and human BAC clones by BHR.

In a similar manner, a fifth construct (6680 targeting vector) was engineered to contain the same additional nine functional human Vλ gene segments as the 6597 targeting vector, except that the 5' homology arm was changed to allow for deletion of the mouse Igλ light chain locus via homologous recombination. This 5' homology arm contained about 22,298 bp from mouse BAC clone RP23-15m16 and was ligated to the 5' end of the human sequence (~121,188 bp fragment, supra) using the unique I-CeuI and AscI restriction enzyme recognition sites separately introduced into both mouse and human BAC clones by BHR. This 5' homology arm contains mouse sequence 5' of a mouse Vλ2 gene segment, which, upon homologous recombination, effectively deletes the mouse Igλ light chain locus. This targeting vector contained the same 3' overlap homology as the 6597 targeting vector (described above). FIG. 2 illustrates the different alleles that result from insertion of the 6597 or 6680 targeting vectors.

In a similar manner, an additional engineered mouse strain was created via co-electroporation of two different targeting vectors into ES cells aided by the use of guide RNAs (gRNAs) using a CRISPR/Cas9 system (FIG. 3), see, e.g., U.S. Pat. No. 9,228,208 (granted Jan. 5, 2016) and U.S. Patent Application Publication Nos. U.S. 2015-0159174 A1 (filed Oct. 15, 2014), U.S. 2015-0376650 A1 (filed Jun. 5, 2015), U.S. 2015-0376628 A1 (filed Jun. 23, 2015), U.S. 2016-0060657 A1 (filed Oct. 30, 2015), U.S. 2016-0145646 A1 (filed Nov. 20, 2015), and U.S. 2016-0177339 A1 (filed Dec. 18, 2015); all of which are incorporated herein by reference in their entireties. The ES cells had a genome heterozygous for insertion of the 6571 targeting vector construct.

Figure 3:
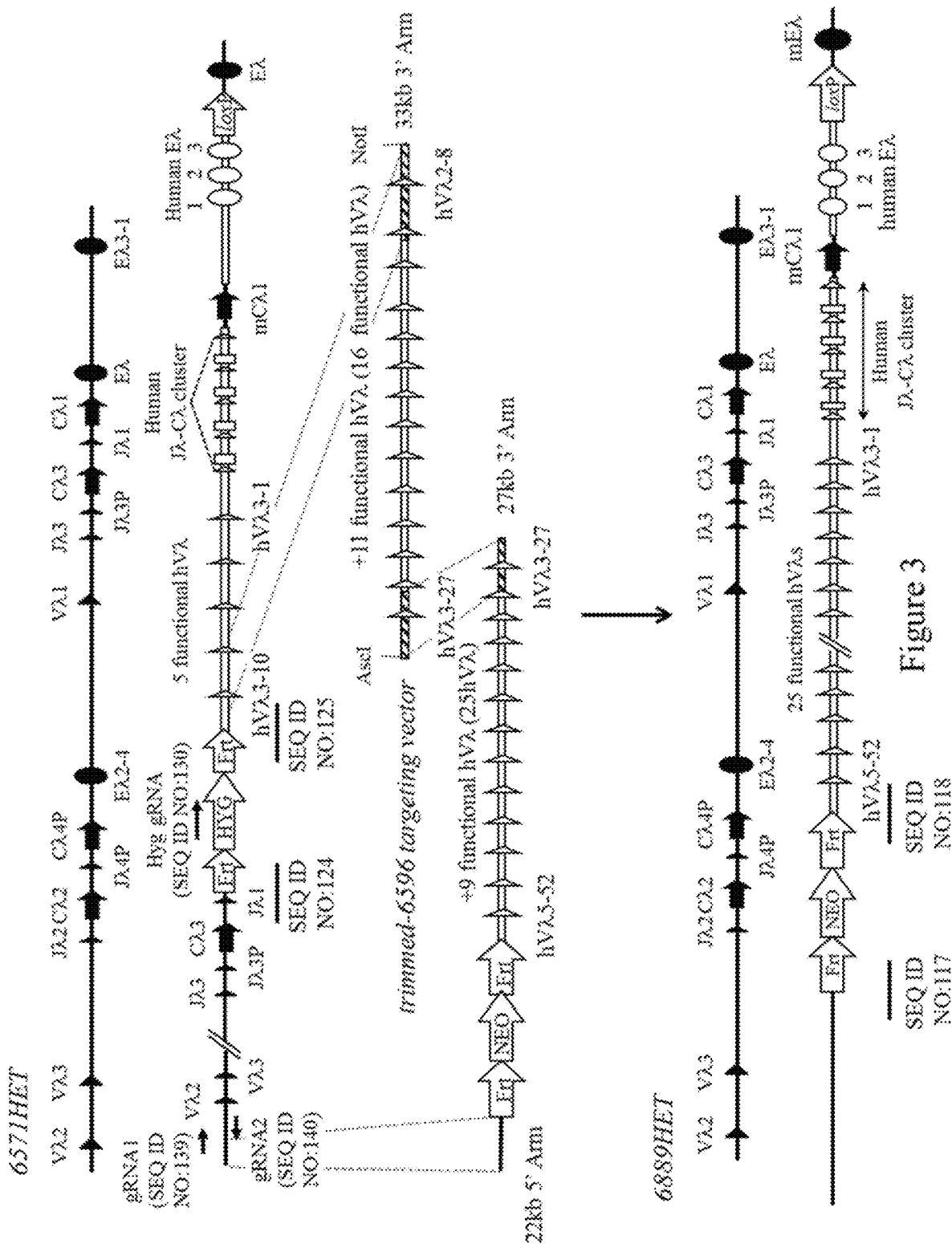
FIG. 3 shows a schematic illustration, not to scale, of an alternative exemplary strategy for construction of an engineered endogenous Igλ light chain locus in a rodent characterized by the presence of a plurality of human Vλ, Jλ and Cλ coding sequences that are operably linked to each other and operably linked to a rodent Cλ region. As depicted, two different targeting vectors are shown with various amounts of genetic material from a human Igλ light chain locus and are simultaneously inserted into an engineered rodent (e.g., mouse) Igλ light chain locus (shown at the top) that contains five human Vλ gene segments, a human Jλ-Cλ cluster, and a mouse Cλ1 gene. The 6596 targeting vector is modified to remove a Neomycin selection cassette and incorporate overlapping sequences (striped filled rectangles) at the 5' and 3' ends to provide regions of homology to facilitate recombination with a corresponding human sequence. A second targeting vector is designed to contain an overlap region on the 3'end of the construct (striped filled rectangles) that shares sequence homology with the modified 6596 targeting vector (trimmed-6596 targeting vector), which facilitates homologous recombination with the 5' end of the trimmed-6596 targeting vector. These two targeting vectors include further sets of additional human Vλ gene segments (eleven and nine, respectively) that sequentially add to the total human Vλ gene segment content of the endogenous mouse Igλ light chain locus after successful targeting of a first targeting vector. The second targeting vector included a 5' homology arm having a sequence that is identical to the sequence 5' (or upstream) of a rodent Vλ2 gene segment, thereby facilitating deletion of endogenous Vλ2-Vλ3-Jλ2-Cλ2-Jλ4P-Cλ4P-Eλ2-4-Vλ1-Jλ3-Jλ3P-Cλ3-Jλ1 gene segments upon homologous recombination with the targeting vector. The two targeting vectors are co-electroporated with guide RNAs (gRNA) to facilitate integration in the engineered Igλ light chain locus, which are marked with an arrow near each sequence location and each indicated by SEQ ID NO. Unless otherwise indicated, closed symbols indicate rodent gene segments and/or sequences, while open symbols indicate human gene segments and/or sequences. Site-specific recombination recognition sites (e.g., loxP, Frt) flanking selection cassettes (HYG: Hygromycin resistance gene [HYG$^R$] under transcriptional control of a ubiquitin promoter; NEO: Neomycin resistance gene [NEO$^R$] under transcriptional control of a ubiquitin promoter) are also shown. Selected nucleotide junction locations are marked with a line below each junction and each indicated by SEQ ID NO.

Briefly, as shown in FIG. 3, a trimmed 6596 targeting vector (i.e., without a 5' homology arm and cassette as described above) was designed to contain about 33 kb 3' homology arm that includes overlap sequence corresponding to three human Vλ gene segments in the 6571 targeting vector, about 111 kb sequence that comprises 11 additional human Vλ gene segments, and about 27 kb sequence that contains a single human Vλ gene segment and serves as an overlap region with the second targeting vector. The second targeting vector (6680 targeting vector) comprises the same about 27 kb overlap region sequence positioned on the 3' end of the targeting vector, about 94 kb sequence comprising an additional nine human Vλ gene segments, a Neomycin selection cassette (e.g., a Neomycin resistance gene [NEO$^R$] under transcriptional control of a ubiquitin promoter flanked by Frt recombination recognition sites) and about 22 kb 5' mouse λ homology arm. The ES cells employed in the electroporation of these two targeting vectors had a genome heterozygous for insertion of the 6571 targeting vector (FIG. 3). These ES cells were co-electroporated with the two targeting vectors described above along with a guide RNA (gRNA) that targets the Hygromycin resistance gene from the 6571 targeting vector at nucleotide sequence CGACCT-GATG CAGCTCTCGG (SEQ ID NO:130) and two gRNAs that target a region upstream of a mouse Vλ2 gene segment (i.e., 3' of a mouse Vλ2 gene segment on the minus strand; gRNA1: GTACATCTTG TCTTCAACGT, SEQ ID NO:139, about 1000 bp upstream of mouse Vλ2; gRNA2: GTCCATAATT AATGTAGTTA C, SEQ ID NO:140, about 380 bp upstream of mouse Vλ2) and promote double stranded breaks at these sequences. The two co-electroporated targeting vectors were inserted by homologous recombination into the genome of the ES cells at the Hygromycin sequence, replacing the region containing and surrounding the Hygromycin selection cassette. The resulting ES cells contained an engineered endogenous Igλ locus that included a human immunoglobulin variable region comprising 25 functional human Vλ gene segments operably linked to a human Jλ-Cλ cluster, a human Jλ7 gene segment and operably linked to a mouse Cλ1 gene (FIG. 3).

The targeting vectors described above were introduced into mouse embryonic stem (ES) cells to build the engineered Igλ light chain locus. Positive ES cell clones were confirmed after insertion of each targeting vector into the genome of ES cells (see below) prior to insertion of the next targeting vector. In some instances, intermediate strains were created for phenotypic analysis.

TABLE 1

Summary of Targeting Vectors

| Name | Approximate hIgλ sequence | Description |
|---|---|---|
| 6286 | 11,822 bp | Insertion of human Eλs into mouse Igλ locus |
| 6571 | 125,473 bp | Insertion of five functional human Vλ gene segments and portion of human Jλ-Cλ gene cluster |
| 6596 | 171,458 bp | Insertion of additional eleven functional human Vλ gene segments |
| 6597 | 121,188 bp | Insertion of additional nine functional human Vλ gene segments |
| 6680 | 121,188 bp | Insertion of additional nine functional human Vλ gene segments and deletion of mouse Igλ gene segments |
| 6889 | 121,188 bp | Insertion of additional nine functional human Vλ gene segments and deletion of mouse Igλ gene segments via simultaneous insertion of two targeting vectors and guide RNAs |

The nucleotide sequence across selected junction points after insertion of the targeting vectors described above was confirmed by sequencing. Selected junction points indicated in FIGS. 1-4 are provided below.

SEQ ID NO: 117
CCCTATTCACTGAGTTCTGGAAGCTCTGCTATTTCCATGATCGTTCA

CACTGACCCCTGTTGATCTTACCGGTACCGAAGTTCCTATTCCGAAG

TTCCTA

SEQ ID NO: 118
TTCTCTAGAAAGTATAGGAACTTCCTAGGGTTTCACCGGTGGCGCGC

CGATGTACATCAGTTCAGTCTGGAAAGGTGGAACAGCTCCAGGTGAA

GGCAGG

SEQ ID NO: 119
CTCTACGGGTGATGTTCATCTAAGGTGACAGGAGTCAGTGAGGGCTT

CTCAAGCTTTATCTATGTCGGGTGCGGAGAAAGAGGTAATGAAATGG

CACTCGAGCCCTGCTGGTGCCTTCTGTTGTATCCACGCCTTCAGTAG

ATTTGATGA

SEQ ID NO: 120
GAGTTTTTCCCTTTCCTGTCTGTCGAAGGCTAAGGTCTAAGCCTGTC

TGGTCACACTAGGTAAAGAATTTCTTTCTTCTCTAGATGCTTTGTCT

CATTTC

SEQ ID NO: 121
TATGTCACTGGAATTTAGAGTAGTGTGTGGAATGTCTTGGCAACCTG

GACACGCGTCCTGGCACCCAGTGAGAAAGTGGCCCTGAGGGAGAGGC

TCATAG

SEQ ID NO: 122
AGCAGCCGACATTTAGCAAAGAGGATTGGAAAATGAACCCCCCCTTA

-continued

AAATACAGTTAAACACAGAGGAGGGAGCAAACCGGTATAACTTCGTA

TAATGT

SEQ ID NO: 123
ATGCTATACGAAGTTATGTCGACCTCGAGGGGGGCCCGGTACCATC

TATGTCGGGTGCGGAGAAAGAGGTAATGAAATGGTCTCATTCCTTCC

CTGTCTCAAGGCATAATGGTTCAATATGCACCTGTA

SEQ ID NO: 124
TTCTCTCCAAGACTTGAGGTGCTTTTTGTTGTATACTTTCCCTTTCT

GTATTCTGCTTCATACCTATACTGGTACCGAAGTTCCTATTCCGAAG

TTCCTA

SEQ ID NO: 125
TTCTCTAGAAAGTATAGGAACTTCCTAGGGTTTCACCGGTGGCGCGC

CTGCCATTTCATTACCTCTTTCTCCGCACCCGACATAGATAAGCTTT

GGATTGGATTCAGTGAGCAAGAATTCACAAACACAATGGACTTATC

SEQ ID NO: 126
TTCTCTCCAAGACTTGAGGTGCTTTTTGTTGTATACTTTCCCTTTCT

GTATTCTGCTTCATACCTATACTGGTACCGAAGTTCCTATTCCGAAG

TTCCTA

SEQ ID NO: 127
TTCTCTAGAAAGTATAGGAACTTCCTAGGGTTTCACCGGTGGCGCGC

CCCCCTGCTGGTGCCTTTTGTTGTATCCACGCCTTCAGTAGATTTGA

TGATGC

SEQ ID NO: 128
TTCTCTCCAAGACTTGAGGTGCTTTTTGTTGTATACTTTCCCTTTCT

GTATTCTGCTTCATACCTATACTGGTACCGAAGTTCCTATTCCGAAG

TTCCTA

SEQ ID NO: 129
TTCTCTAGAAAGTATAGGAACTTCCTAGGGTTTCACCGGTGGCGCGC

CGATGTACATCAGTTCAGTCTGGAAAGGTGGAACAGCTCCAGGTGAA

GGCAGG

In the construction of engineered loci, in particular, engineered immunoglobulin loci, the inventors recognized that some human Vλ gene segments may be missing from certain haplotypes and, therefore, not represented in selected BAC clones spanning a human Igλ light chain locus. To give but one example, one report has provided evidence that more recently discovered alleles contain insertion/deletion of one or more human Vλ gene segments in cluster B of the human Igλ light chain locus as compared to previously reported alleles (e.g., human Vλ1-50, Vλ5-48, Vλ5-45 and Vλ5-39; see Moraes, J. C. and G. A. Passos, 2003, Immunogenetics 55(1):10-5). Thus, the inventors have designed a strategy to include human Vλ gene segments that are missing in a particular BAC clone used for targeting vector design and construction.

Briefly, human BAC clones are mapped to the human Igλ light chain locus by end sequencing. In particular, using the GRCh37/hg19 Assembly (UCSC Genome Browser, Human February 2009) human BAC clones RP11-346I4, CTD-2523F21 and CTD-2523E22 are identified to span a region of cluster B of the human Igλ light chain locus that includes human Vλ7-46 to Vλ1-36. For example, one or more missing human Vλ gene segments (e.g., Vλ5-39, Vλ5-37 and/or Vλ1-36) can be inserted into a targeting vector described above (6680 or 6889) using any one of these BAC clones identified to contain one or more human Vλ gene segments that are desired for insertion. For example, BAC clone CTD-2523F21 is modified by replacing the 3' with a selection cassette (e.g., Hygromycin resistance gene [HYG$^R$] under transcriptional control of a ubiquitin promoter) flanked by recombinase recognition sites (e.g., lox2372) and a ~27 kb 3' homology arm having overlapping sequence with the 6597 targeting vector (see above). The 5' end of human BAC clone serves as a 5' homology arm having overlapping sequence with the 6680 or 6889 targeting vector thereby facilitating homologous recombination and insertion of any missing human Vλ gene segments along with the selection cassette. An optional last step of transient expression of a recombinase (e.g., Cre) may be employed to remove the selection cassette.

Example 2

Generation of Rodents Having an Engineered Igλ Light Chain Locus

This example demonstrates the production of a non-human animal (e.g., rodent) whose germline genome comprises an endogenous Igλ light chain locus comprising insertion of a plurality of human Vλ, Jλ and Cλ sequences, which human Vλ, Jλ and Cλ sequences are operably linked to a rodent Cλ gene (or gene segment), and which endogenous Igλ light chain locus further includes one or more human Igλ enhancers (Eλs). In some embodiments, said endogenous Igλ light chain locus includes a deletion of one or more endogenous Igλ light chain enhancer regions (or sequences). Such non-human animals are characterized, in some embodiments, by expression of Igλ light chains that are fully human (i.e., human variable and constant domains).

Targeted insertion of targeting vectors described in Example 1 was confirmed by polymerase chain reaction. Targeted BAC DNA, confirmed by polymerase chain reaction, was then introduced into F1 hybrid (129S6SvEvTac/C57BL6NTac) mouse embryonic stem (ES) cells via electroporation followed by culturing in selection medium. In some embodiments, the ES cells used for electroporation of the series of targeting vectors may have a germline genome that includes wild-type IgH and Igκ loci, homozygous humanized IgH and Igκ loci, which homozygous humanized IgH locus contained an inserted rodent Adam6-encoding sequence (see, e.g., U.S. Pat. Nos. 8,642,835 and 8,697,940; hereby incorporated by reference in its entirety), or a homozygous humanized IgH locus (see, e.g., U.S. Pat. Nos. 8,642,835 and 8,697,940, supra) and a homozygous inactivated Igκ locus. In other embodiments, after targeted ES cells as described herein are used to generate mice (see below), resultant mice comprising an engineered human Igλ locus as described herein are used to breed with mice comprising humanized IgH and Igκ loci, which humanized IgH locus contains an inserted rodent Adam6-encoding sequence (see, e.g., U.S. Pat. Nos. 8,642,835 and 8,697,940, supra), or a humanized IgH locus (see, e.g., U.S. Pat. Nos. 8,642,835 and 8,697,940, supra) and an inactivated Igκ locus. Drug-resistant colonies were picked 10 days after electroporation and screened by TAQMAN™ and karyotyping for correct targeting as previously described (Valenzuela et al., supra; Frendewey, D. et al., 2010, Methods Enzymol. 476:295-307). Table 2 sets forth exemplary primers/probes sets used for screening positive ES cell clones (F: forward primer; R: reverse primer; P: probe).

The VELOCIMOUSE® method (DeChiara, T. M. et al., 2010, Methods Enzymol. 476:285-294; DeChiara, T. M., 2009, Methods Mol. Biol. 530:311-324; Poueymirou et al., 2007, Nat. Biotechnol. 25:91-99) was used, in which targeted ES cells were injected into uncompacted 8-cell stage Swiss Webster embryos, to produce healthy fully ES cell-derived F0 generation mice heterozygous for the engineered Igλ light chain allele. F0 generation heterozygous mice were crossed with C57B16/NTac mice to generate F1 heterozygotes that were intercrossed to produce F2 generation animals for phenotypic analyses.

Taken together, this example illustrates the generation of a rodent (e.g., a mouse) whose germline genome comprises an engineered Igλ light chain locus characterized by the presence of a plurality of human Vλ, Jλ and Cλ sequences operably linked to a rodent Cλ gene, which rodent engineered Igλ light chain locus includes endogenous rodent and human Igλ light chain enhancer sequences (or regions). The strategy described herein for inserting human Vλ, Jλ and Cλ sequences into an endogenous rodent Igλ light chain locus enables the construction of a rodent that expresses antibodies that contain human Vλ domains fused to either a human or rodent Cλ domain. As described herein, such human Vλ domains are expressed from endogenous Igλ light chain loci in the germline rodent genome.

TABLE 2

Representative primer/probe sets for screening positive ES cell clones

| Name | | Sequence (5'-3') |
|---|---|---|
| mIgLC1p3 | F | GCATGGCCTAGAGATAACAAGAC (SEQ ID NO: 15) |
| | R | GGCCTTGGATAACCTCAGGATAC (SEQ ID NO: 16) |
| | P | TCCATCCCAATAGATCTCATTCCTTCCC (SEQ ID NO: 17) |
| HSS1-1 | F | CCCTGTCAAGTCTCCAAGGTTG (SEQ ID NO: 18) |
| | R | CACTGTGGCCCAAGGATCAC (SEQ ID NO: 19) |
| | P | CACTCTGCCCAGGGAGTGTCTGG (SEQ ID NO: 20) |
| LoLjxn1 | F | GCATGGCCTAGAGATAACAAGACTG (SEQ ID NO: 21) |
| | R | GTGCTCTTCCCTTGGGAGA (SEQ ID NO: 22) |
| | P | TCCATCCCAATAGAGCGATCGCA (SEQ ID NO: 23) |
| Neo | F | GGTGGAGAGGCTATTCGGC (SEQ ID NO: 24) |
| | R | GAACACGGCGGCATCAG (SEQ ID NO: 25) |
| | P | TGGGCACAACAGACAATCGGCTG (SEQ ID NO: 26) |
| hIgL2 | F | AGCTGAATGGAAACAAGGCAA (SEQ ID NO: 27) |
| | R | GGAGACAATGCCCCAGTGA (SEQ ID NO: 28) |
| | P | TGACATGAACCATCTGTTTCTCTCTCGACAA (SEQ ID NO: 29) |
| hIgL4 | F | CCACCGCCAAGTTGACCTC (SEQ ID NO: 30) |
| | R | TGAAGGACTAAGGCCCAGGATAG (SEQ ID NO: 31) |

TABLE 2-continued

Representative primer/probe sets for screening positive ES cell clones

| Name | | Sequence (5'-3') |
|---|---|---|
| | P | AGTACAGCAAGGGCCCAGCCT (SEQ ID NO: 32) |
| hIgL5 | F | TGGCTCAGTGACAAGAGTC (SEQ ID NO: 33) |
| | R | CCAGGGACACAGCCTTTGC (SEQ ID NO: 34) |
| | P | TGCATTGCAGAGACCAGGGACC (SEQ ID NO: 35) |
| Hyg | F | TGCGGCCGATCTTAGCC (SEQ ID NO: 36) |
| | R | ACGAGCGGGTTCGGCCCATTC (SEQ ID NO: 37) |
| | P | TTGACCGATTCCTTGCGG (SEQ ID NO: 38) |
| Hyg D | F | TGTCGGCGTACACAAATCG (SEQ ID NO: 39) |
| | R | GGGCGTCGGTTTCCACTATC (SEQ ID NO: 40) |
| | P | CCGTCTGGACCGATGGCTGTGT (SEQ ID NO: 41) |
| Hyg U | F | CGACGTCTGTCGAGAAGTTTCTG (SEQ ID NO: 42) |
| | R | CACGCCCTCCTACATCGAA (SEQ ID NO: 43) |
| | P | AGTTCGACAGCGTGTCCGACCTGA (SEQ ID NO: 44) |
| mIgL1 | F | AACAACCGAGCTCCAGGTGT (SEQ ID NO: 45) |
| | R | AGGGCAGCCTTGTCTCCAA (SEQ ID NO: 46) |
| | P | CCTGCCAGATTCTCAGGCTCCCTG (SEQ ID NO: 47) |
| mIgL6 | F | GGAGGTCAGGAATGAGGGAC (SEQ ID NO: 48) |
| | R | CACTTGCTCACTGCAAAAGCA (SEQ ID NO: 49) |
| | P | TGTGGGATTTTGGAATTCTATCTCACTGATAGGAAAG (SEQ ID NO: 50) |
| mIgL10 | F | GCAGAGAGGATTCAAGAGCTGG (SEQ ID NO: 51) |
| | R | TTTTTGCAATGCTTCACCTGA (SEQ ID NO: 52) |
| | P | CAGGTGTCTGTATTGGAGGTCAATGGCA (SEQ ID NO: 53) |
| mIgL11 | F | GATTTGCTGAGGGCAGGGT (SEQ ID NO: 54) |
| | R | CCCCAAGTCTGATCCTTCCTT (SEQ ID NO: 55) |
| | P | CCTTCATACTCTTGCATCCTCCCTTCTCCA (SEQ ID NO: 56) |
| mIgL12 | F | GCTGACCAACGATCGCCTAA (SEQ ID NO: 57) |
| | R | TAAGCGCCACACTGCACCT (SEQ ID NO: 58) |
| | P | TTCCTTCTCTTCTGTGACTCAATTATTTGTGGACA (SEQ ID NO: 59) |
| mIgL13 | F | AACTGCTGATGCACTGGGC (SEQ ID NO: 60) |
| | R | TGAATGCATGGAGTTGGCC (SEQ ID NO: 61) |
| | P | TCTCCTTTGCAGTGGCTTAATTAGCTGAGTCA (SEQ ID NO: 62) |
| 1467hTI1 | F | CCCTGGTGAAGCATGTTTGC (SEQ ID NO: 63) |

TABLE 2-continued

Representative primer/probe sets for screening positive ES cell clones

| Name | | Sequence (5'-3') |
|---|---|---|
| | R | TGTGGCCTGTCTGCCTTACG (SEQ ID NO: 64) |
| | P | CCAAGCAGGAGGTGCTCAGTTCCCAA (SEQ ID NO: 65) |
| 1467hTI2 | F | GGGACAGGTGAAGGGCCTATC (SEQ ID NO: 66) |
| | R | TGGTCCACAGGATGCAGTTG (SEQ ID NO: 67) |
| | P | CGCACCTGTATCTAACCAGTCCCAGCATC (SEQ ID NO: 68) |
| 1467hTI3 | F | CACACCTAGACCCCGGAAGTC (SEQ ID NO: 69) |
| | R | TCGCTTTGCCAGTTGATTCTC (SEQ ID NO: 70) |
| | P | TCCACACTGTCGGCTGGGAGCTCA (SEQ ID NO: 71) |
| 1468h1 | F | CGCTTCAATGACCCAACCA (SEQ ID NO: 72) |
| | R | TGTTGAAACGTAATCCCCAATG (SEQ ID NO: 73) |
| | P | CTCCCACCAGGTGCCACATGCA (SEQ ID NO: 74) |
| 1468h2 | F | GGGCTACTTGAGGACCTTGCT (SEQ ID NO: 75) |
| | R | GACAGCCCTTACAGAGTTTGGAA (SEQ ID NO: 76) |
| | P | CAGGGCCTCCATCCCAGGCA (SEQ ID NO: 77) |
| 1468h3 | F | AGTGCAAACAGCAAGATGAGATCT (SEQ ID NO: 78) |
| | R | GGCGCTGAGCAGAAAACAA (SEQ ID NO: 79) |
| | P | AGACCACCAAGAAGGCCCAGAGTGACC (SEQ ID NO: 80) |
| 1468h5 | F | AAGACCAGGAGCTCTGCCTAAGT (SEQ ID NO: 81) |
| | R | CCCATCACGAACTGAAGTTGAG (SEQ ID NO: 82) |
| | P | CCCCAGTGTGTGAATCACTCTACCCTCC (SEQ ID NO: 83) |
| 1468h6 | F | CCCTTCATGATGCTTTGTCATC (SEQ ID NO: 84) |
| | R | GTAGTGGCAAAGGCAGATTCCT (SEQ ID NO: 85) |
| | P | CCTTCACTCCCCGAATGCCCTCC (SEQ ID NO: 86) |
| 6596V3-25-1 | F | GCCCTGCTCCAGTCTTATTCC (SEQ ID NO: 87) |
| | R | CTGCGTCTGGGCTTTGCT (SEQ ID NO: 88) |
| | P | CCACAGATCCCAAGTTGAGCCTGC (SEQ ID NO: 89) |
| 6596V3-22-1 | F | GTGAGCGGTACCCTGGAATC (SEQ ID NO: 90) |
| | R | AGCCTCGTCTTCGGTCAGGAC (SEQ ID NO: 91) |
| | P | TGAACGATTCTCTGGGTCCACC (SEQ ID NO: 92) |
| 6596V3-21-1 | F | CCTGAGCCAGGATGGAATGAAG (SEQ ID NO: 93) |
| | R | GGCCGTGATTTAAGAGGTTGTTAG (SEQ ID NO: 94) |
| | P | ACTGTGGACCCCAGATAATTCCCCTG (SEQ ID NO: 95) |

TABLE 2-continued

Representative primer/probe sets for screening positive ES cell clones

| Name | | Sequence (5'-3') |
|---|---|---|
| 6596VLdetect-1 | F | GAGTGCAGTGGCAGAATCTTG (SEQ ID NO: 96) |
| | R | GGCAGGGAGCATTGGTAGA (SEQ ID NO: 97) |
| | P | TACTGAAATCTCAGCCTCCCAGGC (SEQ ID NO: 98) |
| 6596V3-19-1 | F | TGGCTCCAGCTCAGGAAAV (SEQ ID NO: 99) |
| | R | CCCGGGAGTTACAGTAATAGTCA (SEQ ID NO: 100) |
| | P | CACAGCTTCCTTGACCATCACTGGG (SEQ ID NO: 101) |
| 6597_h3'arm1 | F | CCAGCCCACCCAATTATGCTA (SEQ ID NO: 102) |
| | R | GCGTTTAGGGCCAGGTACAAAT (SEQ ID NO: 103) |
| | P | TGGATCTGTCAAACACTTTCAGAGCA (SEQ ID NO: 104) |
| 6597_h3'arm2 | F | GAGGCTGCAGGGATGTAAC (SEQ ID NO: 105) |
| | R | CCCATTCCAGGTCCAATTCTCA (SEQ ID NO: 106) |
| | P | TTTGTAAAGTGCATAACACAGACCCTGA (SEQ ID NO: 107) |
| 66805'Arm1 | F | GGGTACAATGAGACAAGAATCAGA (SEQ ID NO: 108) |
| | R | GAAAGGCAAACACAAGTCACAGATG (SEQ ID NO: 109) |
| | P | TCAGCCCTCTGGAATGTAAGGATCA (SEQ ID NO: 110) |
| 66805'Arm2 | F | GCTGCATCTTCTCAAGTCTTTAAGT (SEQ ID NO: 111) |
| | R | GGGAACCAGTCAGGAACTCATAC (SEQ ID NO: 112) |
| | P | TAAGCAGACCTATGCATCGCTCA (SEQ ID NO: 113) |
| hIgLVpre2-8 | F | GTGCTCCTTGTTCCCTTCACAG (SEQ ID NO: 114) |
| | R | CTGAAGCATCTGCACCATCAAATC (SEQ ID NO: 115) |
| | P | CCACCCACATGTGCCCGTGTG (SEQ ID NO: 116) |

Example 3

Phenotypic Assessment of Rodents Having an Engineered Igλ Light Chain Locus

This example demonstrates the characterization of various immune cell populations in rodents (e.g., mice) engineered to contain an endogenous Igλ light chain locus as described above. In particular, this example specifically demonstrates that rodents having an engineered endogenous Igλ light chain locus as described herein display similar B cell development as compared to wild-type littermates. In particular, several engineered rodents harboring different amounts of genetic material corresponding to a human Igλ light chain locus each detectably express Igλ light chains having human variable and human or rodent constant domains on the surface of rodent B cells.

Figure 4:
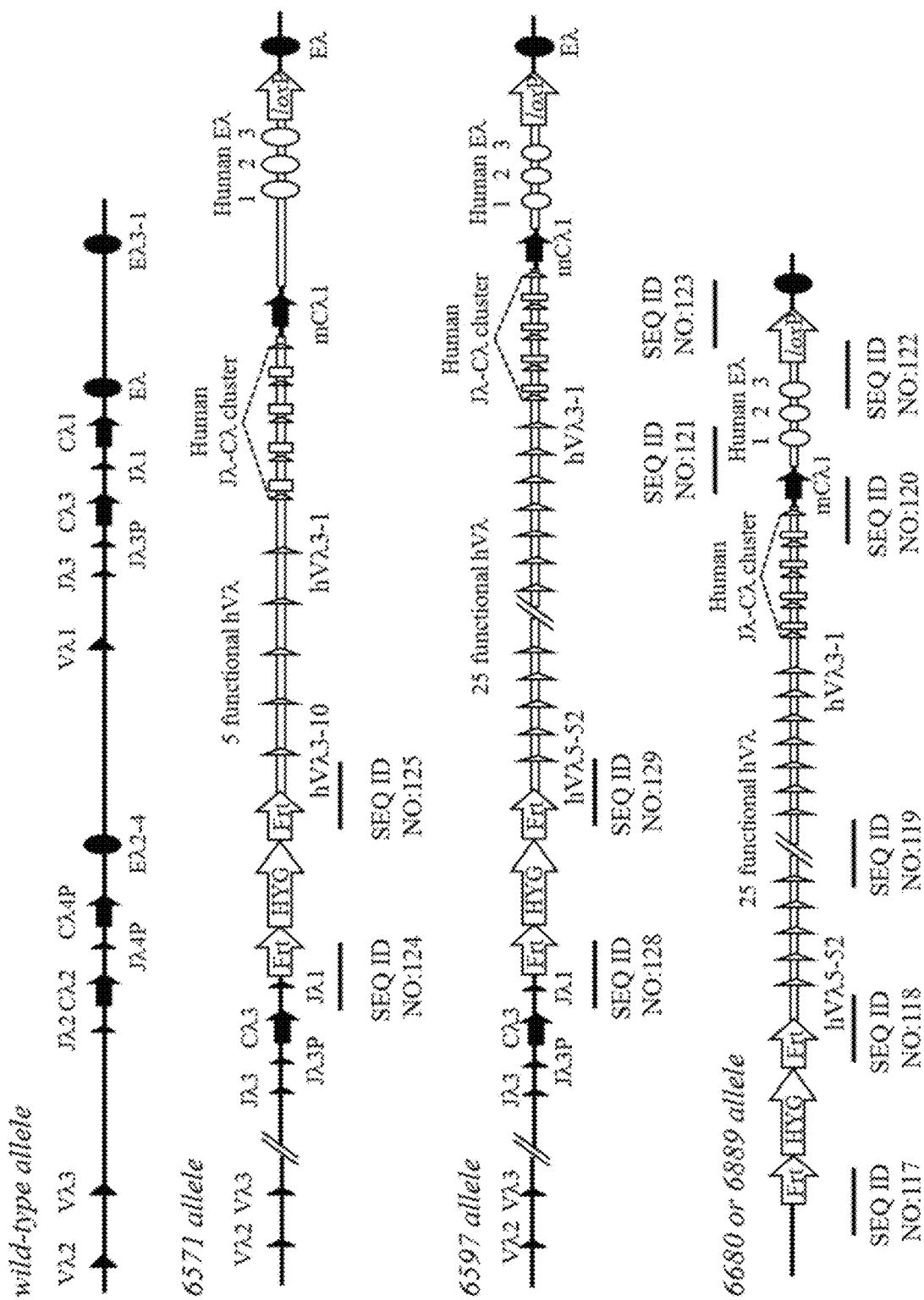
FIG. 4 shows a schematic illustration, not to scale, of wild-type and exemplary engineered rodent Igλ light chain alleles of rodents employed in the experiments described in Example 3. Wild-type allele: a wild-type mouse Igλ light chain locus (see also, e.g., FIG. 2 of U.S. Pat. No. 9,006, 511); 6571 allele: an Igλ light chain allele that contains 5 functional human Vλ gene segments, four functional human Jλ-Cλ gene segment pairs and a human Jλ7 gene segment operably linked to a rodent Cλ region (e.g., a mouse Cλ1 region), and which Igλ light chain locus further includes endogenous Vλ-Jλ-Cλ gene segments, three endogenous Igλ enhancer regions (or sequences) and a modular human Igλ enhancer region (or sequence, see above). 6597 allele: see above; 6680 allele: see above. Selected nucleotide junction locations are marked with a line below each junction and each indicated by SEQ ID NO.
Figure 5A:
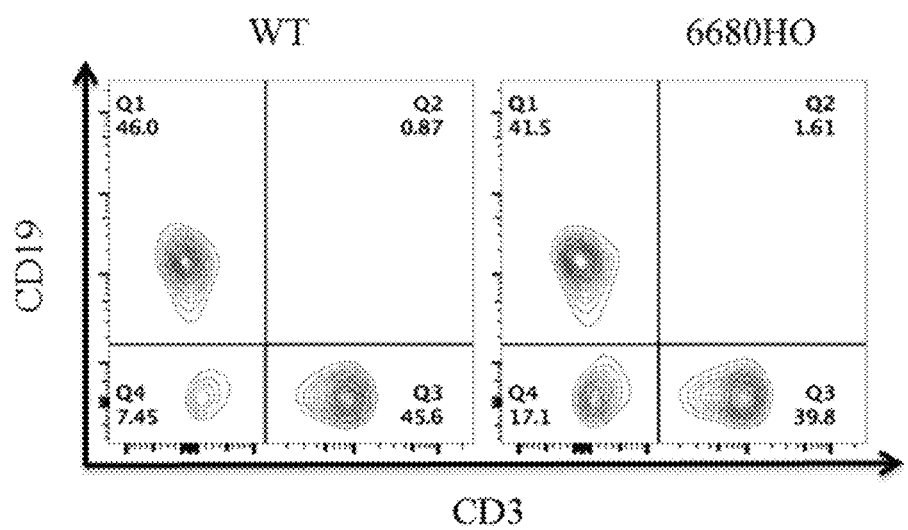
FIGS. 5A and 5B show representative contour plots indicating single cell-gated splenocytes (A) showing expression of CD19 (y-axis) and CD3 (x-axis), and absolute cell number per spleen (B) harvested from mice homozygous for insertion of the 6680 targeting vector (6680HO) and wild-type littermates (WT).
Figure 5B:
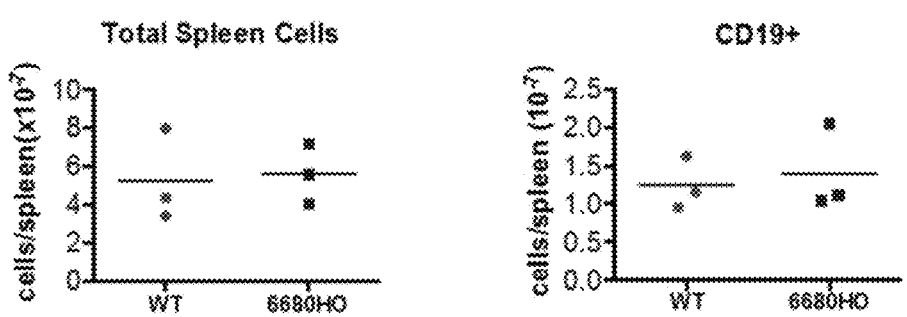
Figure 6A:
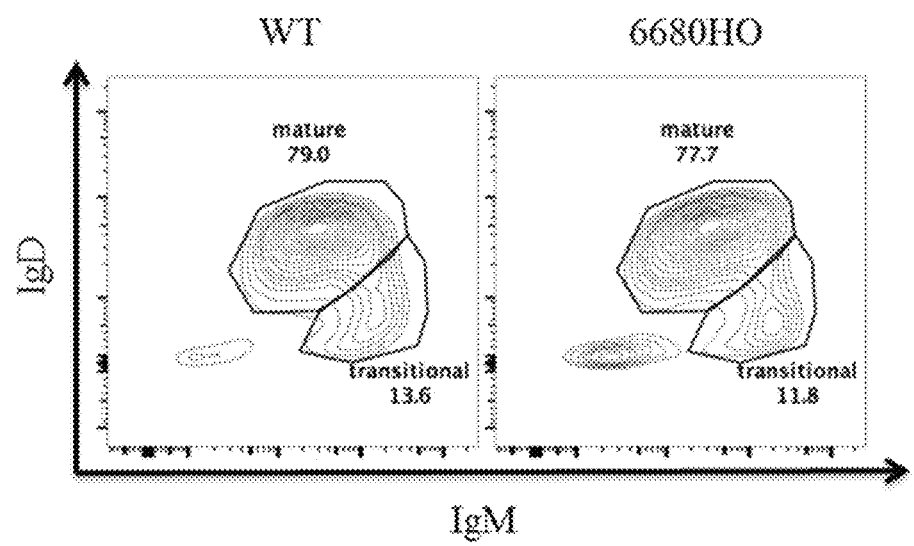
FIGS. 6A and 6B show representative contour plots indicating mature and transitional B cells in splenocytes gated on CD19$^+$ (A) showing expression of IgD (y-axis) and IgM (x-axis), and absolute cell number per spleen (B) harvested from mice homozygous for insertion of the 6680 targeting vector (6680HO) and wild-type littermates (WT). Specific B cell subpopulations are noted on each dot plot (e.g., mature, transitional).
Figure 6B:
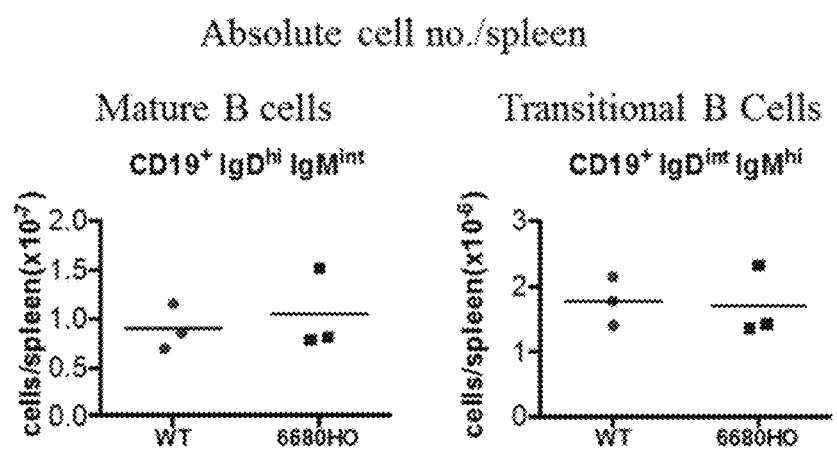
Figure 7A:
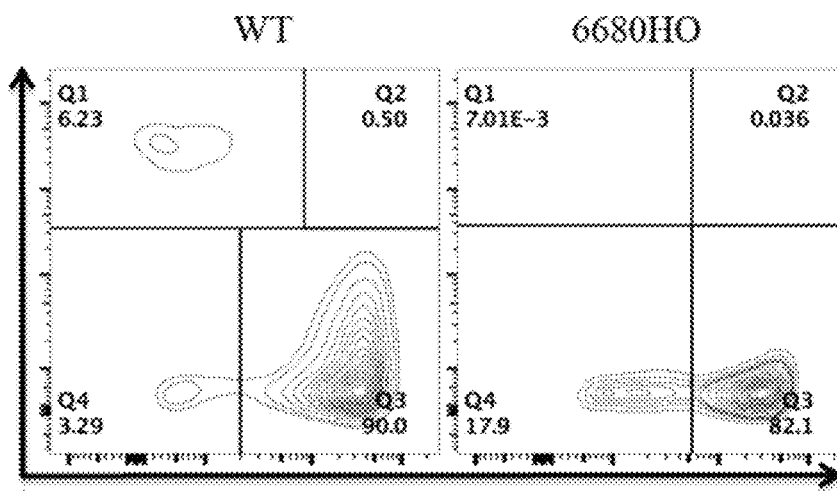
FIGS. 7A and 7B show representative contour plots indicating mouse Igλ (mIgλ, y-axis), mouse Igκ (mIgκ, x-axis) or human Igλ (hIgλ, y-axis) expression in CD19$^+$-gated splenocytes harvested from mice homozygous for insertion of the 6680 targeting vector (6680HO) and wild-type littermates (WT).
Figure 7B:
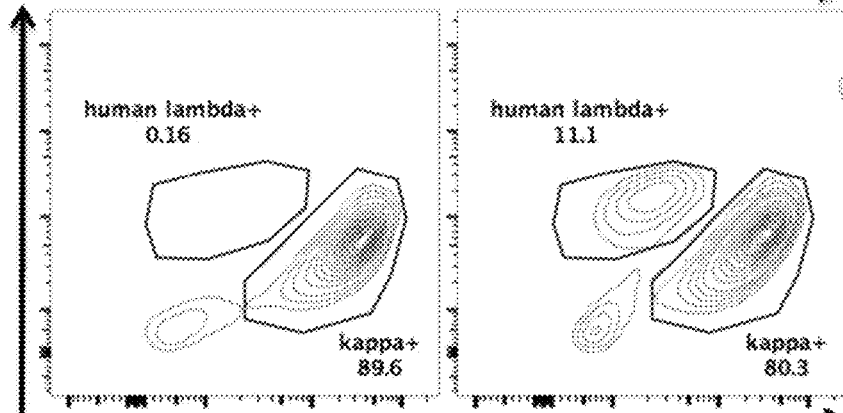
Figure 8A:
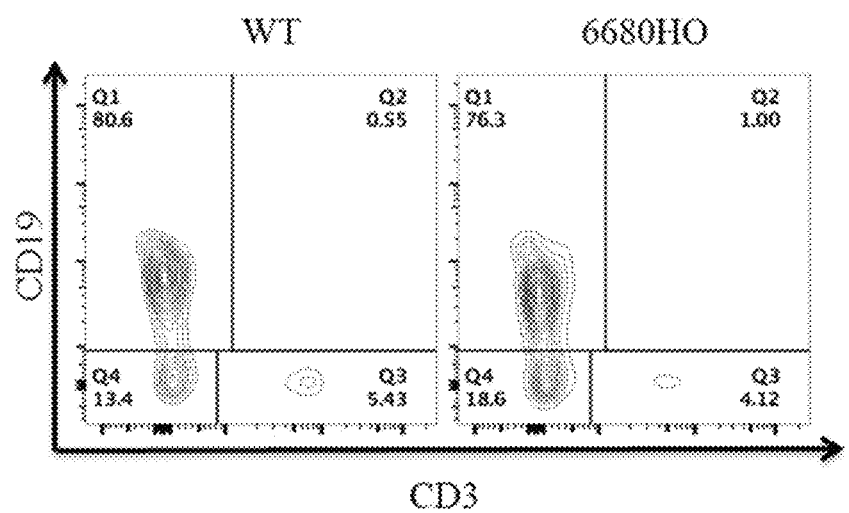
FIGS. 8A and 8B show representative contour plots indicating single cell-gated bone marrow (A) showing expression of CD19 (y-axis) and CD3 (x-axis), and absolute cell number per femur (B) harvested from mice homozygous for insertion of the 6680 targeting vector (6680HO) and wild-type littermates (WT).
Figure 8B:
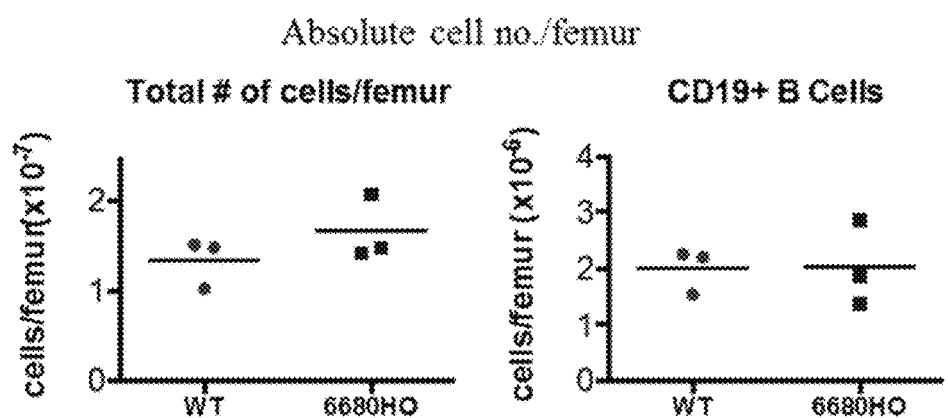
Figure 9A:
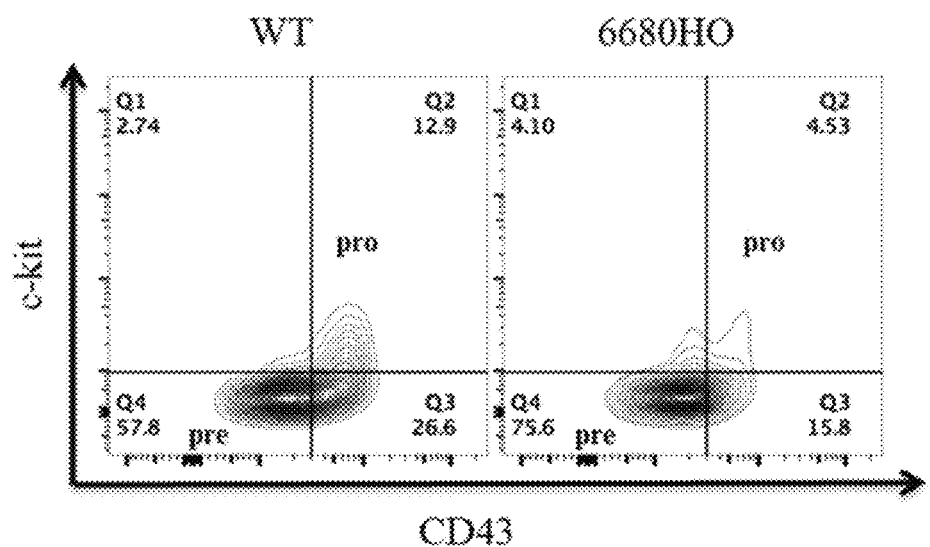
FIGS. 9A and 9B show representative contour plots indicating CD19$^+$IgM$^{low}$B220$^{int}$-gated bone marrow (A) showing expression of c-kit (y-axis) and CD43 (x-axis), and absolute cell number per femur (B) harvested from mice homozygous for insertion of the 6680 targeting vector (6680HO) and wild-type littermates (WT). Specific B cell subpopulations are noted on each dot plot (e.g., pro-B, pre-B).
Figure 9B:
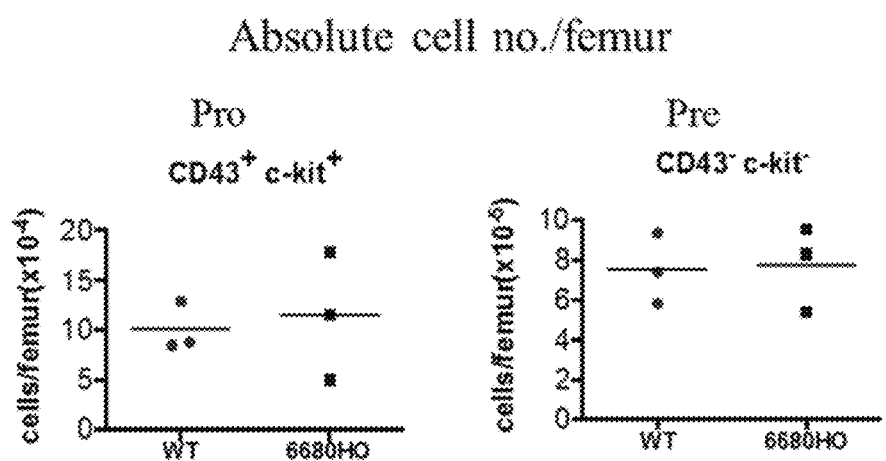
Figure 10A:
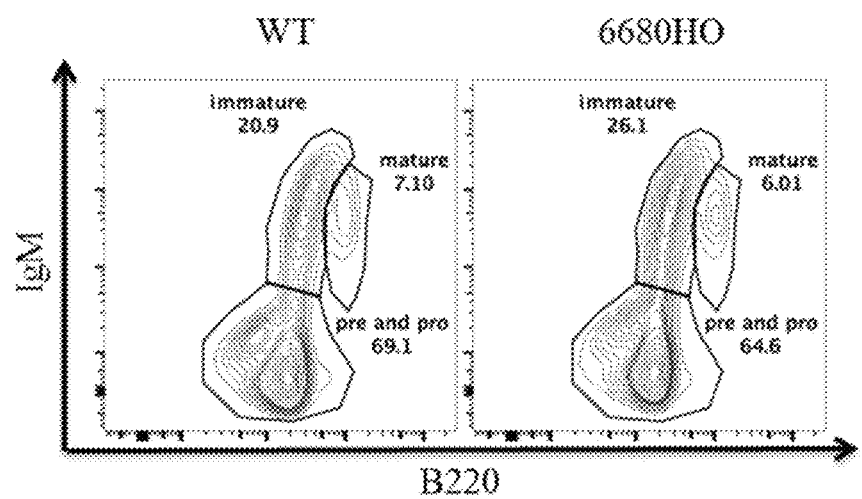
FIGS. 10A and 10B show representative contour plots indicating CD19$^+$-gated bone marrow (A) showing expression of IgM (y-axis) and B220 (x-axis), and absolute cell number per femur (B) harvested from mice homozygous for insertion of the 6680 targeting vector (6680HO) and wild-type littermates (WT). Specific B cell subpopulations are noted on each dot plot (e.g., immature, mature, pre- and pro-B).
Figure 10B:
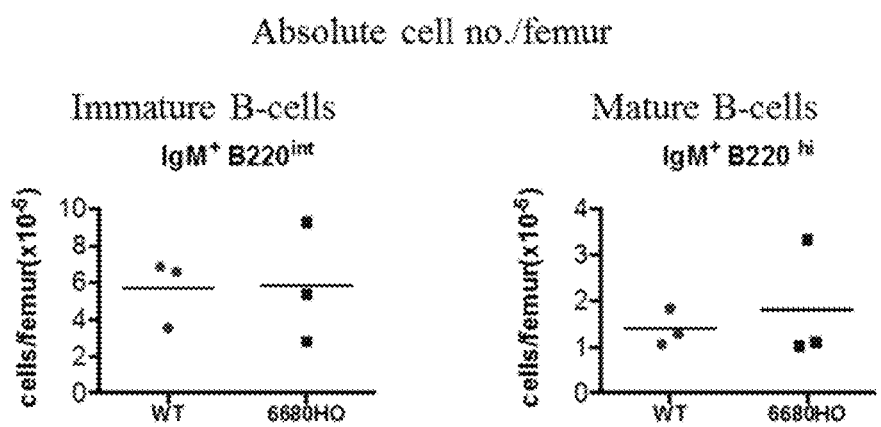

Briefly, spleens and femurs were harvested from selected engineered mouse strains homozygous or heterozygous for the Igλ light chain alleles depicted in FIG. 4 and wild-type littermates. Bone marrow was collected from femurs by flushing with 1× phosphate buffered saline (PBS, Gibco) with 2.0% fetal bovine serum (FBS). Red blood cells from spleen and bone marrow preparations were lysed with ACK lysis buffer (Gibco) followed by washing with 1×PBS with 2.0% FBS. Isolated cells (1×10⁶) were incubated with selected antibody cocktails for 30 min at +4° C. (see Table 3).

TABLE 3

Antibodies for cell staining analyzed by flow cytometry

| Antibody | Label | Vendor | Clone |
|---|---|---|---|
| Bone Marrow | | | |
| anti-mouse CD43 | FITC | BioLegend | 1B11 |
| anti-mouse c-Kit | PE | BioLegend | 2B8 |
| anti-mouse IgM | PeCy7 | eBiosciences | II/41 |
| anti-mouse IgD | PerCP-Cy5.5 | BioLegend | 11-26c.2a |
| anti-mouse CD3 | PB | BioLegend | 17-A2 |
| anti-mouse/-human B220 | APC | eBiosciences | RA3-6B2 |
| anti-mouse CD19 | APC-H7 | BD | 1D3 |
| anti-mouse Igκ | FITC | BD | 187.1 |
| anti-mouse Igλ | PE | BioLegend | RML-42 |
| anti-mouse IgM | PeCy7 | eBiosciences | II/41 |
| anti-mouse/-human B220 | PerCP-Cy5.5 | BD | RA3-6B2 |
| anti-mouse CD3 | PB | BioLegend | 17-A2 |
| anti-human Igλ | APC | Biolegend | MHL-38 |
| anti-mouse CD19 | APC-H7 | BD | 1D3 |
| Spleen | | | |
| anti-mouse Igκ | FITC | BD | 187.1 |
| anti-mouse Igλ | PE | BioLegend | RML-42 |
| anti-mouse IgM | PeCy7 | eBiosciences | II/41 |
| anti-mouse IgD | PerCP-Cy5.5 | BioLegend | 11-26c.2a |
| anti-mouse CD3 | PB | BioLegend | 17-A2 |
| anti-human Igλ | APC | Biolegend | MHL-38 |
| anti-mouse CD19 | APC-H7 | BD | 1D3 |

Following staining, cells were washed and fixed in 2% formaldehyde. Data acquisition was performed on a BD FORTESSA™ flow cytometer and analyzed with FLOWJO™ software. Representative results are set forth in FIGS. 5-13 and 18-21. Similar data was obtained for other strains depicted in FIG. 4, but only selected indicated strains are shown.

The results demonstrated that each strain harboring different amounts of genetic material corresponding to the human Igλ light chain locus demonstrated similar immune cell population profiles in the splenic and bone marrow compartments. In particular, as evident from the data shown in FIGS. 5-7, engineered mice demonstrated similar number of CD19⁻ splenic B cells, similar populations of mature and transitional B cell in the spleen, similar kappa usage in the spleen, and similar marginal zone and follicular B cell populations as their wild type littermate controls. Further, mice containing an engineered Igλ light chain locus as described herein in the presence of additional humanized IgH and humanized Igκ loci demonstrated no major differences in B cell development as compared with mice containing humanized IgH and humanized Igκ loci alone (e.g., see FIGS. 18A and 18B). Also, as shown in mice represented in FIGS. 8-12, engineered mice had similar CD19⁺, pro-, pre-, immature and mature B cell number and similar kappa usage in bone marrow as their wild type littermate controls. A summary of the light chain expression in selected engineered strains (homozygous—HO; heterozygous—HET) compared to their wild-type littermate controls is provided in FIG. 13. Mice homozygous for an engineered humanized Igλ locus as described herein, and also homozygous for humanized IgH and Igκ loci and homozygous for rodent Adam6-encoding sequence demonstrated increased utilization of lambda locus (about 40%) compared to the typical peripheral utilization (e.g., 5% in spleen) of lambda known for wild-type mice (see columns for 6680HO/VI HO/Adam6 HO and 6689HO/VI HO/Adam6 HO mice, FIG. 13). Also, a small proportion mouse Igλ-positive B cells was detected (~3-5%) in these mice, which confirms that the mouse Cλ gene within the engineered λ light chains locus is also expressed in the context of functional λ light chains in these mice.

Example 4

Antibody Expression in Rodents Having an Engineered Igλ Light Chain Locus

This example demonstrates the expression of antibodies from non-human animals, which antibodies contain light chains characterized by the presence of human Vλ regions and human or rodent Cλ regions, and which light chains are expressed from an engineered endogenous rodent Igλ light chain locus. In particular, this example specifically demonstrates the expression of antibodies in the serum of non-human animals (e.g., rodents) whose germline genome comprises an endogenous Igλ light chain locus comprising insertion of one or more human Vλ gene segments, one or more human Jλ gene segments and one or more human Cλ gene segments, which human Vλ, Jλ and Cλ gene segments are operably linked to a rodent Cλ gene, and which endogenous immunoglobulin λ light chain locus further comprises one or more rodent Igλ light chain enhancers (Eλ) and one or more human Igλ light chain enhancers (Eλ).

Figure 14A:
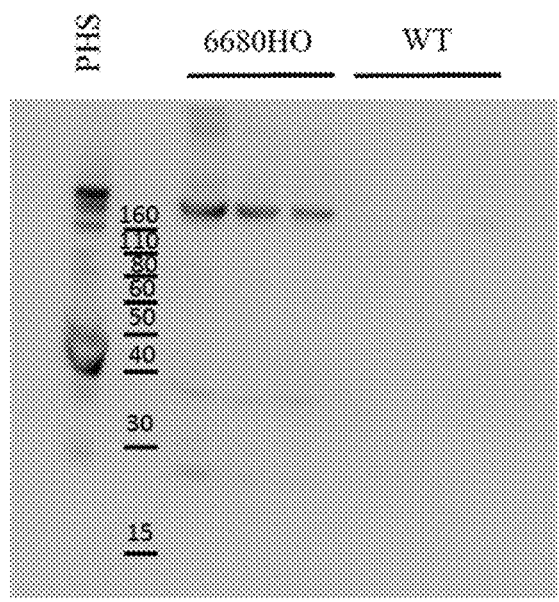
FIGS. 14A and 14B show representative immunoblots (Western blots) of SDS-PAGE under non-reducing conditions using serum isolated from engineered mice homozygous for insertion of the 6680 targeting vector (6680HO) and wild-type littermates (WT) indicating expression of mouse (B, right image) or human (A, left image) λ light chains; each sample was loaded into lanes at a volume of 1.5 μl serum. PHS: pooled human serum at a volume of 0.25 μl (Labquip Ltd Cat #9101A). Molecular weights in Kd are indicated on the right of each gel image.
Figure 14B:
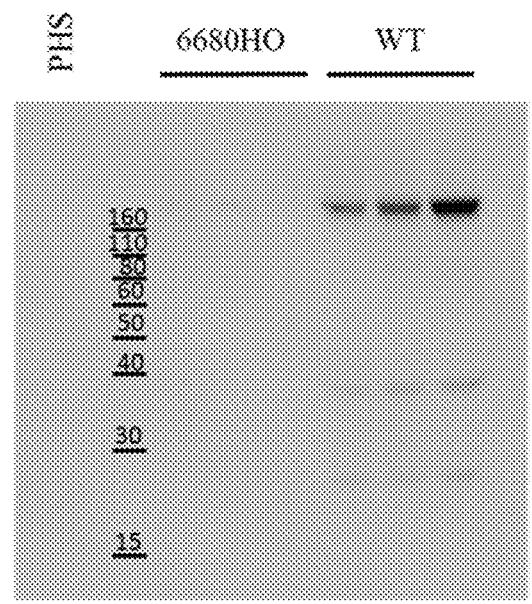

Briefly, blood was drawn from selected engineered mouse strains and wild-type littermates (see Example 3). Serum was separated from blood using Eppendorf tubes centrifuged at 9000 rcf for five minutes at 4° C. Collected serum was used for immunoblotting to identify Ig light chain expression of antibodies. Mouse sera were diluted 1.5:10 in PBS (without Ca²⁺ and Mg²⁺) and run on 4-20% Novex Tris-Glycine gels under reducing and non-reducing conditions. Gels were transferred to Polyvinylidene difluoride (PVDF) membranes according to manufacturer's specifications. Blots were blocked overnight with 5% nonfat milk in Tris-Buffered Saline with 0.05% Tween-20 (TBST, Sigma). PVDF membranes were exposed to different primary antibodies (mouse anti-hIgλ conjugated to HRP (Southern Biotech); goat anti-mIgλ conjugated to HRP, Southern Biotech) diluted 1:1,000 in 0.1% nonfat milk in TBST for one hour at room temperature. Blots were washed four times for ten minutes per wash and developed for one minute with Amersham ECL Western Blotting Detection Reagent (GE Healthcare Life Sciences) according to manufacturer's specifications. Blots were then imaged using GE Healthcare ImageQuant LAS-4000 Cooled CCD Camera Gel Documentation System. Images were captured at 15 second intervals until 20 images were captured or images were fully exposed, whichever came first. Representative results are set forth in FIGS. 14A and 14B. The results demonstrated that all engineered strains expressed detectable levels of human Igλ light chain containing antibodies in their sera (FIG. 14A and data not shown).

Example 5

Human Gene Segment Usage in Rodents Having an Engineered Igλ Light Chain Locus

This example demonstrates the human gene usage in light chains of antibodies expressed in rodents (e.g., mice) engineered to contain an endogenous Igλ light chain locus as described herein. Usage of human Igλ gene segments in selected engineered rodent strains described above was determined by Next Generation Sequencing antibody repertoire analysis.

Briefly, splenocytes were harvested from mice heterozygous for insertion of 25 functional human Vλ gene segments, 4 functional human Jλ-Cλ clusters, and a human Jλ7 gene segment upstream of a mouse Cλ1 gene, and a human Igλ enhancer inserted between the mouse Cλ1 gene and an endogenous mouse Igλ enhancer 3.1 (6889 heterozygous mice as in FIG. 4). B cells were positively enriched from total splenocytes by anti-mouse CD19 magnetic beads and MACS columns (Miltenyi Biotech). Total RNA was isolated from splenic B cells using the RNeasy Plus kit (Qiagen).

Reverse transcription with an oligo-dT primer followed by gene specific PCR was performed to generate cDNA containing human Igλ constant region sequences (Cλ1, Cλ2, Cλ3 and Cλ6), as well as cDNA containing mouse Cλ1 sequence, using SMARTer™ RACE cDNA Amplification Kit (Clontech). During reverse transcription, a specific DNA sequence (PITA: 5'-CCCATGTACT CTGCGTTGAT ACCACTGCTT-3', SEQ ID NO:133) was attached to the 3' end of the newly synthesized cDNAs. The cDNAs were purified by the NucleoSpin Gel and PCR Clean-Up Kit (Clontech), then further amplified using a primer reverse compliment to PIIA (5'-AAGCAGTGGT ATCAACGCAG AGTACAT-3', SEQ ID NO:141) paired with human Cλ specific primer (5'-CACYAGTGTG GCCTTGTTGG CTTG-3', SEQ ID NO:131) and mouse Cλ1 specific primer (5'-CACCAGTGTG GCCTTGTTAG TCTC-3', SEQ ID NO:132).

Purified amplicons were then amplified by PCR using a PIIA specific primer (5'-GTGACTGGAG TTCAGACGTG TGCTCTTCCG ATCTAAGCAG TGGTATCAAC GCA-GAGT-3', SEQ ID NO:134) and a nested human Cλ specific primer (5'-ACACTCTTTC CCTACACGAC GCTCTTC-CGA TCTCAGAGGA GGGCGGGAAC AGAGTG-3', SEQ ID NO:135) or a nested mouse Cλ1 specific primer (5'-ACACTCTTTC CCTACACGAC GCTCTTCCGA TCTAAGGTGG AAACAGGGTG ACTGATG-3', SEQ ID NO:136). PCR products between 450-690 bp were isolated and collected by Pippin Prep (SAGE Science). These fragments were further amplified by PCR using following primers: 5'-AATGATACGG CGACCACCGA GATCTACACX XXXXXACACT CTTTCCCTAC ACGACGCTCT TCCGATC-3', SEQ ID NO:137, and 5'-CAAGCAGAAG ACGGCATACG AGATXXXXXG TGACTGGAGT TCA-GACGTGT GCTCTTCCGA TCT-3', SEQ ID NO:138 ("XXXXXX" is a 6 bp index sequences to enable multiplexing samples for sequencing). PCR products between 490 bp-710 bp were isolated and collected by Pippin Prep, then quantified by qPCR using a KAPA Library Quantification Kit (KAPA Biosystems) before loading onto Miseq sequencer (Illumina) for sequencing (v3, 600-cycles).

Figure 15A:
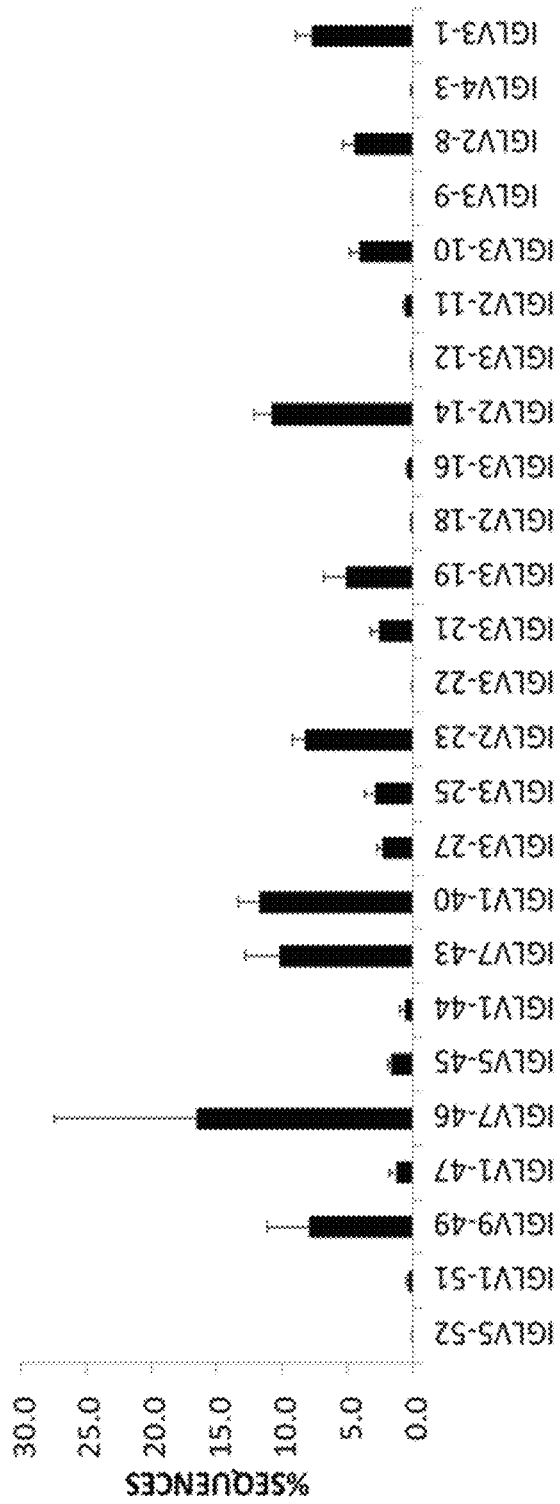
FIGS. 15A and 15B show representative human Vλ (FIG. 15A) and human Jλ (FIG. 15B) gene segment usage in human Cλ-primed sequences amplified from RNA isolated from splenocytes harvested from 6889HET mice (n=5).
Figure 15B:
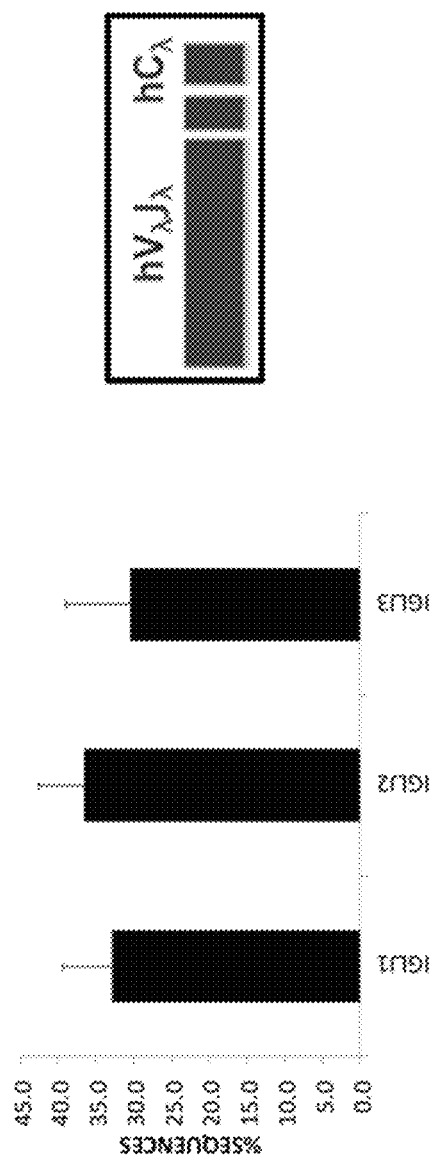
Figure 15C:
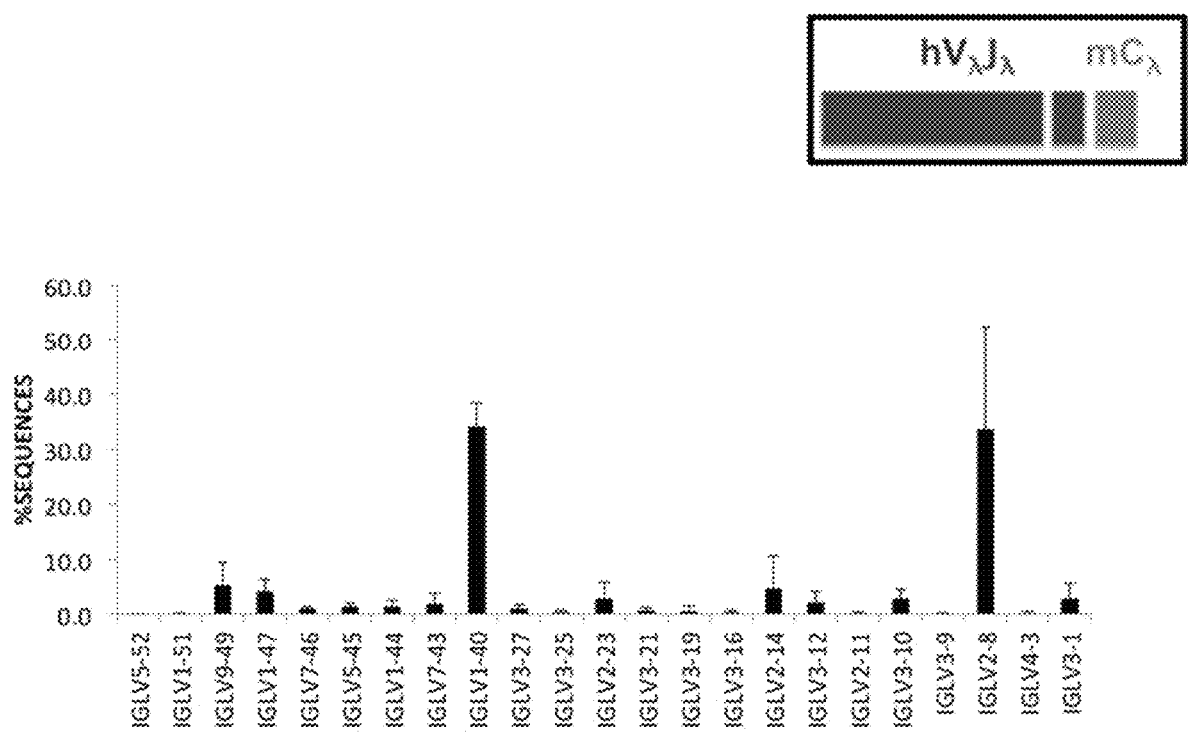
FIG. 15C shows representative human Vλ gene segment usage in mouse Cλ-primed sequences amplified from RNA isolated from splenocytes harvested from 6889HET mice (n=5).
Figure 15F:
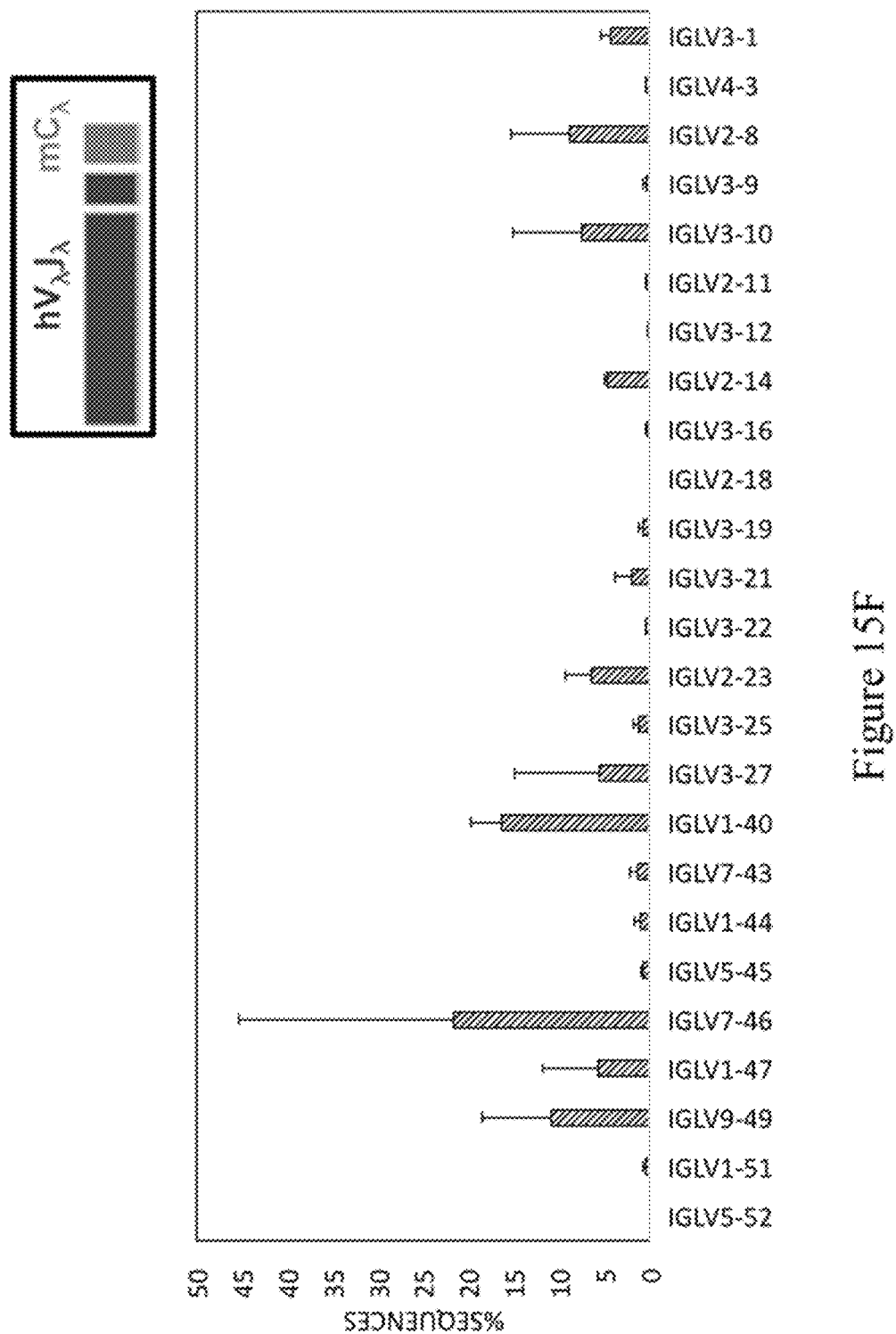
FIG. 15F shows representative human Vλ gene segment usage in mouse Cλ-primed sequences amplified from RNA isolated from splenocytes harvested from 6889HO/VI HO/Adam6 HO mice (n=6).

For bioinformatic analysis, the resulting Illumina sequences were demultiplexed and trimmed for quality. Overlapping paired-end reads were then assembled and annotated using local installation of igblast (NCBI, v2.2.25+). Reads were aligned to both human and mouse germline Vλ and Jλ segments database and sorted for the best hit. A sequence was marked as ambiguous and removed from analysis when multiple best hits with identical score were detected. A set of perl scripts was developed to analyze results and store data in mysql database. Representative results are set forth in FIGS. 15A-15B (human Cλ-primed) and 15C (mouse Cλ-primed).

In another experiment, splenic B cells harvested from mice (n=3) homozygous for insertion of the 6889 targeting vector (6889HO/VI HO/Adam6 HO, see above) were analyzed for usage of human Igλ gene segments by Next Generation Sequencing antibody repertoire analysis (described above). mRNA isolated from splenic B cells was amplified by 5'RACE using primers to mouse mCλ (n=3) and human hCλ (n=3) constant regions and sequenced using MiSeq. Representative results are set forth in FIGS. 15D-15E (human Cλ-primed) and 15F (mouse Cλ-primed).

Mice generated using the 6889 targeting vector (i.e., co-electroporation of two targeting vectors and gRNAs) demonstrated expression of all 25 functional human Vλ gene segments. Further, expression of human Vλ gene segments from B cells of these mice demonstrated similar frequencies in isolated B cells as compared to human Vλ gene segments observed in human cord blood. Taken together, this example demonstrates that rodents containing engineered Igλ light chain loci as described herein in their germline genomes express Igλ light chains containing human Igλ sequences in B cells. Further, such human Igλ sequences can be readily distinguished in light chains containing a mouse or human Cλ domain.

Example 6

Production of Antibodies in Engineered Rodents

This example demonstrates production of antibodies in a rodent that comprises an engineered endogenous Igλ light chain locus as described above using an antigen of interest (e.g., a single-pass or multi-pass membrane protein, etc.). The methods described in this example, or immunization methods well known in the art, can be used to immunize rodents containing an engineered endogenous Igλ light chain locus as described herein with polypeptides or fragments thereof (e.g., peptides derived from a desired epitope), or combination of polypeptides or fragments thereof, as desired.

Cohorts of mice having an engineered Igλ light chain locus as described herein and a humanized IgH locus (described above), or an engineered Igλ light chain locus as described herein and humanized IgH and Igκ light chain loci (described above), are challenged with an antigen of interest using immunization methods known in the art. The antibody immune response is monitored by an ELISA immunoassay (i.e., serum titer). When a desired immune response is achieved, splenocytes (and/or other lymphatic tissue) are harvested and fused with mouse myeloma cells to preserve their viability and form immortal hybridoma cell lines. The hybridoma cell lines are screened (e.g., by an ELISA assay) and selected to identify hybridoma cell lines that produce antigen-specific antibodies. Hybridomas may be further characterized for relative binding affinity and isotype as desired. Using this technique, and the immunogen described above, several antigen-specific chimeric antibodies (i.e., antibodies possessing human variable domains and rodent constant domains) are obtained.

DNA encoding the variable domains of heavy chain and light chains may be isolated and linked to desirable isotypes (constant domains) of the heavy chain and light chain for the preparation of fully-human antibodies. Such an antibody protein may be produced in a cell, such as a CHO cell. Fully human antibodies are then characterized for relative binding affinity and/or neutralizing activity of the antigen of interest.

DNA encoding the antigen-specific chimeric antibodies or the variable domains of light and heavy chains may be isolated directly from antigen-specific lymphocytes. Initially, high affinity chimeric antibodies are isolated having a human variable domain and a rodent constant domain and are characterized and selected for desirable characteristics, including affinity, selectivity, epitope, etc. Rodent constant domains are replaced with a desired human constant domain to generate fully-human antibodies. While the constant domain selected may vary according to specific use, high affinity antigen-binding and target specificity characteristics reside in the variable domain. Antigen-specific antibodies are also isolated directly from antigen-positive B cells (from immunized mice) without fusion to myeloma cells, as described in, e.g., U.S. Pat. No. 7,582,298, incorporated herein by reference in its entirety. Using this method, several fully human antigen-specific antibodies (i.e., antibodies possessing human variable domains and human constant domains) are made.

In one experiment, 6597het (n=6) and 6680het (n=6) mice were immunized via footpad administration with an extracellular domain (ECD) of receptor polypeptide to determine the immune response in engineered mice.

Briefly, mice were primed with 2.35 µg of antigen (receptor polypeptide ECD) plus 10 µg of CpG adjuvant (Invivogen ODN1826). Mice were boosted seven times with 2.35 λg of antigen (receptor polypeptide ECD), 10 µg of CpG adjuvant and 25 µg of Adju-Phos (Brenntag). Two days after the final injection, blood was drawn from selected engineered mouse strains and controls. Serum was separated from blood using Mictrotainer capillary blood collector tubes (BD cat #365967) with centrifugation at 9000 rcf for five minutes at 4° C. Serum ELISA assays were performed to determine total IgG (FIG. 16A), antigen-specific IgG (FIG. 16B), mIgκ (FIG. 17C) mIgλ (FIG. 17B) and hIgλ (FIG. 17A) titers.

For a total IgG ELISA assay, Maxisorp plates (Nunc) were coated with 1 µg/mL goat anti-mouse IgG+IgM+IgA H&L (Abcam) in DPBS (with Ca and Mg) per well and incubated overnight at 4° C. The following day, plates were washed four times in PBS-T (PBS without Ca or Mg plus 0.1% Tween-20) and blocked in PBS-T with 1% BSA for one hour at room temperature. Serum was diluted ten-fold (starting at 1:100 and ending at $1:10^9$) in PBS-T with 0.1% BSA and mouse IgG standard (Sigma) was diluted three-fold (starting at 1 µg/mL and ending at 0.05 ng/mL) in PBS-T with 0.1% BSA. 100 µl of each standard and sample dilution were added to the plate and incubated at room temperature for one hour, followed by washing four times in PBS-T. 100 µl of goat anti-mouse IgG human ads-HRP (Southern Biotech) diluted 1:2500 was added to each well, and plates were incubated an hour. Plates were washed four times in PBS-T, and 100 µl of TMB substrate reagent (BD Biosciences) was added to each well for ten minutes. The reaction was stopped with 100 µl of 1N Sulfuric Acid per well, and adsorption was measured at 450 nm. Data were analyzed in GraphPad Prism and fit to a four-parameter curve.

For an antigen-specific ELISA, Maxisorp plates (Nunc) were coated with 1 µg/mL antigen in DPBS (with Ca and Mg) per well and incubated overnight at 4° C. The following day, plates were washed four times in PBS-T and blocked in Sea Block (ThermoFisher) diluted 1:2 in PBS-T for one hour at room temperature. Serum was diluted (as above) in Sea Block diluted 1:5 in PBS-T. Each sample dilution was added to each plate and incubated at room temperature for one hour. Then plates were washed four times in PBS-T. 100 µl of either goat anti-mouse IgG human ads-HRP (Southern Biotech) diluted 1:2500, goat anti-mIgκ-HRP (Southern Biotech) diluted 1:4000, goat anti-mIgλ-HRP (Southern Biotech) diluted 1:4000, or goat anti-hIgλ mouse ads-HRP (Southern Biotech) diluted 1:4000 were added to each well, and plates were incubated for one hour. Plates were washed four times in PBS-T, and developed as described above. Representative results are set forth in FIGS. 16A-16B and 17A-17C.

Figure 17A:
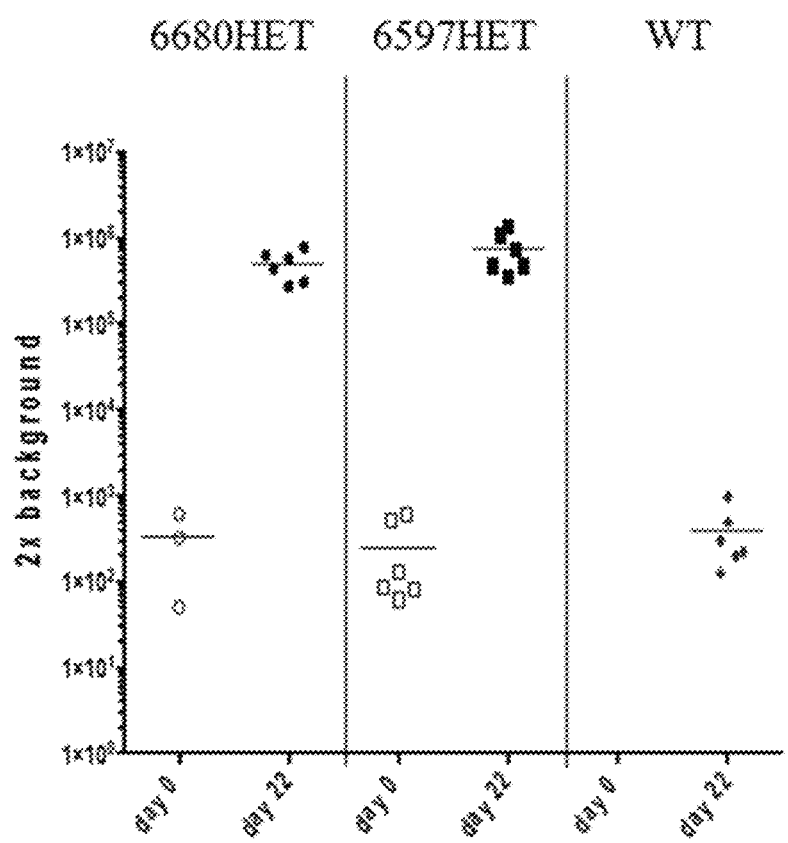
FIGS. 17A-C show representative human λ light chain (hIgλ, left), mouse λ light chain (mIgλ, middle) and mouse κ light chain (mIgκ, right) titers in antigen-specific IgG in serum at days 0 and 22 collected from immunized mice heterozygous for insertion of the 6597 (6597HET, n=6) or 6680 (6680HET, n=6) targeting vectors and immunized wild-type controls (WT, n=6).
Figure 17B:
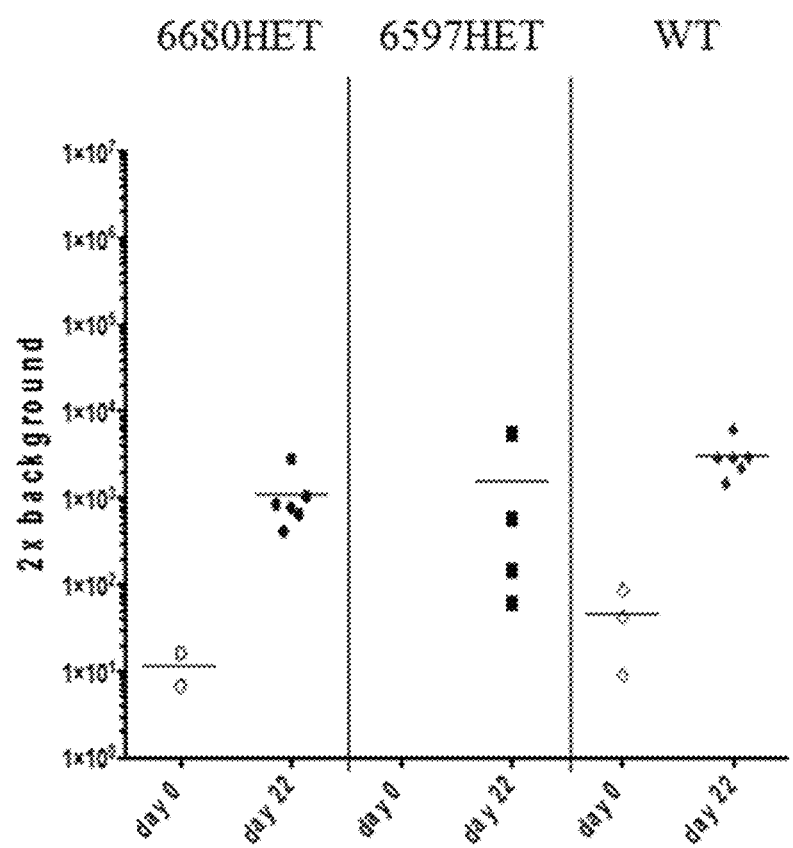
Figure 17C:
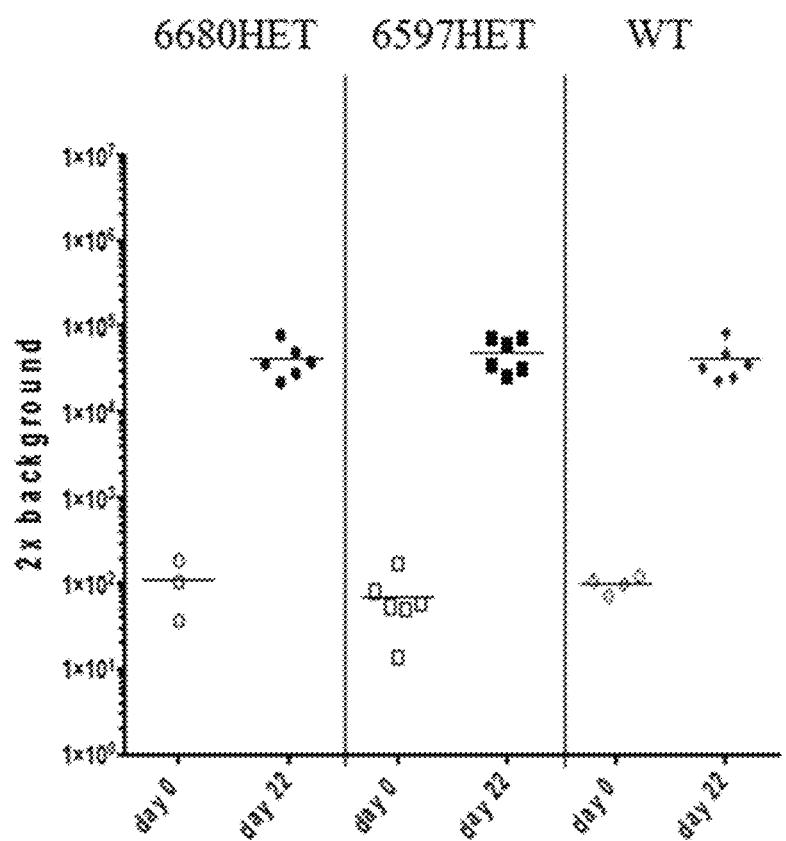
Figure 18B:
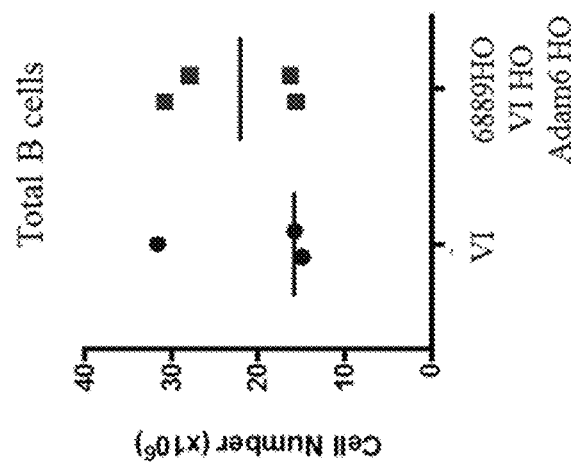
FIGS. 18A and 18B show representative contour plots indicating single cell-gated splenocytes (left) showing expression of CD19 (y-axis) and CD3 (x-axis), and total B cells per spleen (right) harvested from mice homozygous for insertion of the 6889 targeting vector (6889HO VI HO Adam6 HO) and reference engineered mice (VI). 6889HO/VI HO/Adam6 HO: see above; VI: an engineered mouse strain containing homozygous humanized IgH and Igκ loci, which homozygous humanized IgH locus contained an inserted rodent Adam6-encoding sequence (see, e.g., U.S. Pat. Nos. 8,642,835 and 8,697,940; hereby incorporated by reference in their entireties). Live single-cell splenocytes were defined by viability staining (Thermo Fisher).
Figure 18A:
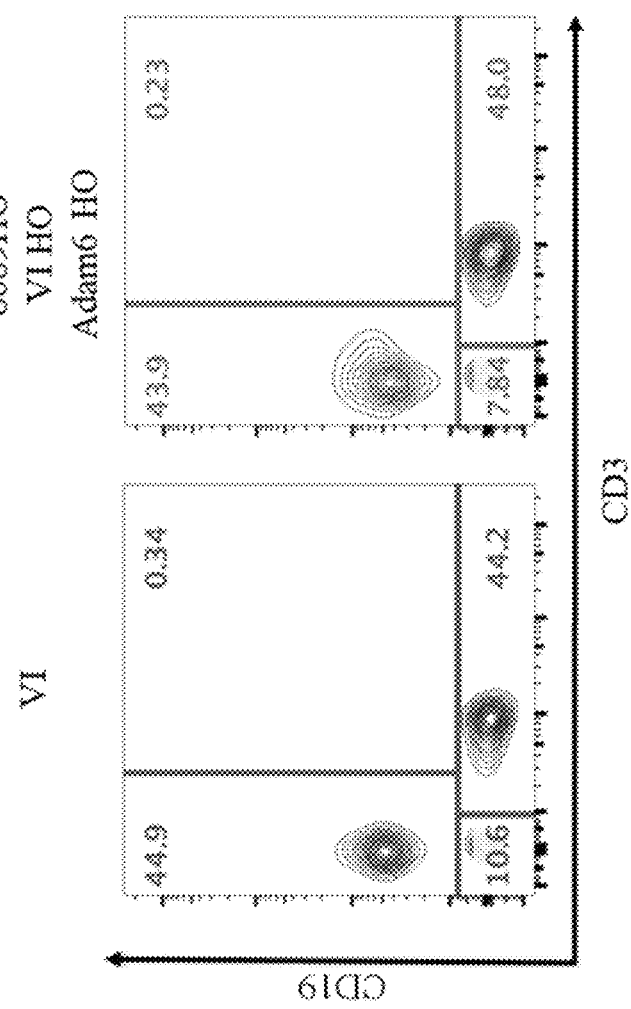
Figure 19:
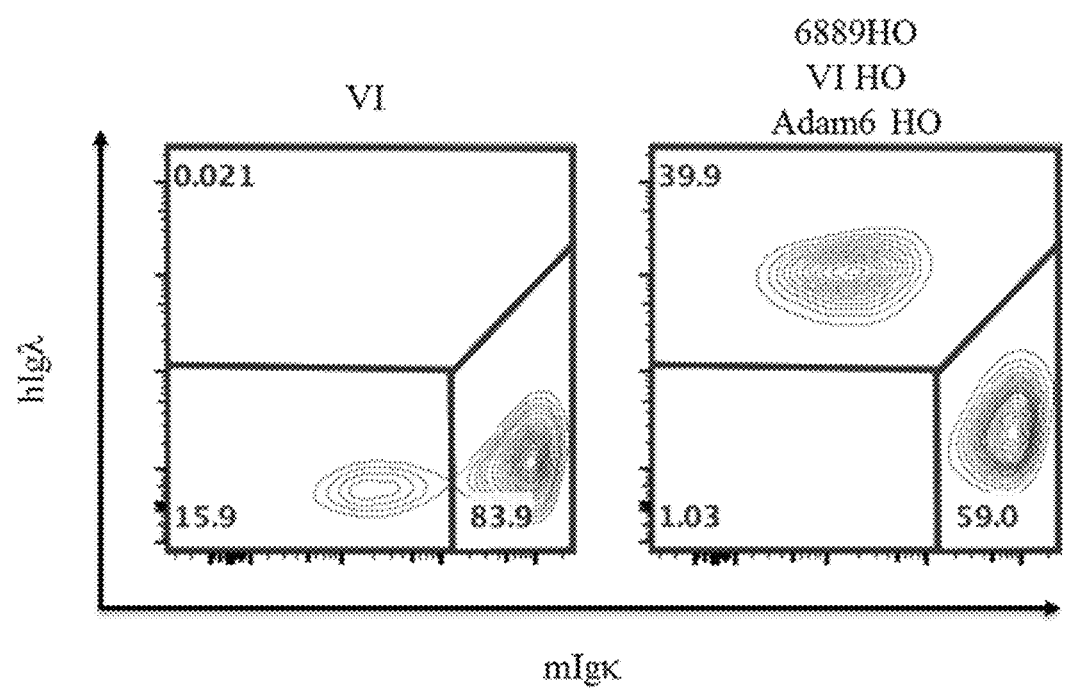
FIG. 19 shows representative contour plots indicating human Igλ (hIgλ, y-axis) and mouse Igκ (mIgκ, x-axis) expression in CD19+-gated splenocytes harvested from mice homozygous for insertion of the 6889 targeting vector (6889HO VI HO Adam6 HO) and reference engineered mice (VI). 6889HO/VI HO/Adam6 HO: see above; VI: see above.
Figure 20:
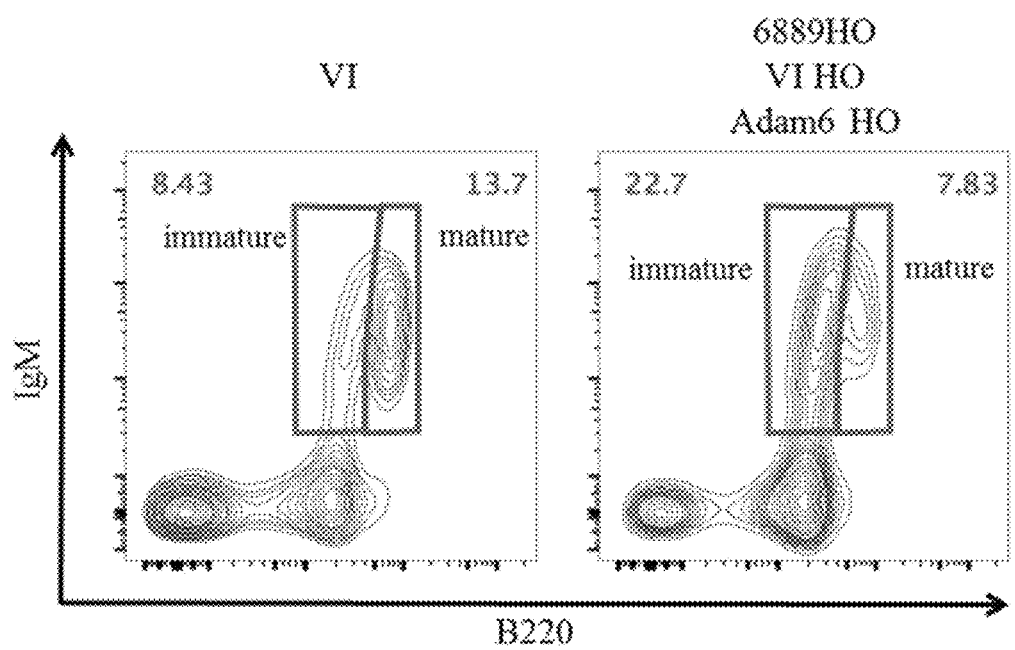
FIG. 20 shows representative contour plots indicating single cell-gated lymphocytes from bone marrow showing expression of IgM (y-axis) and B220 (x-axis) harvested from femurs of mice homozygous for insertion of the 6889 targeting vector (6889HO VI HO Adam6 HO) and reference engineered mice (VI). 6889HO/VI HO/Adam6 HO: see above; VI: see above. Immature and mature B cell subpopulations are noted on each contour plot.
Figure 21:
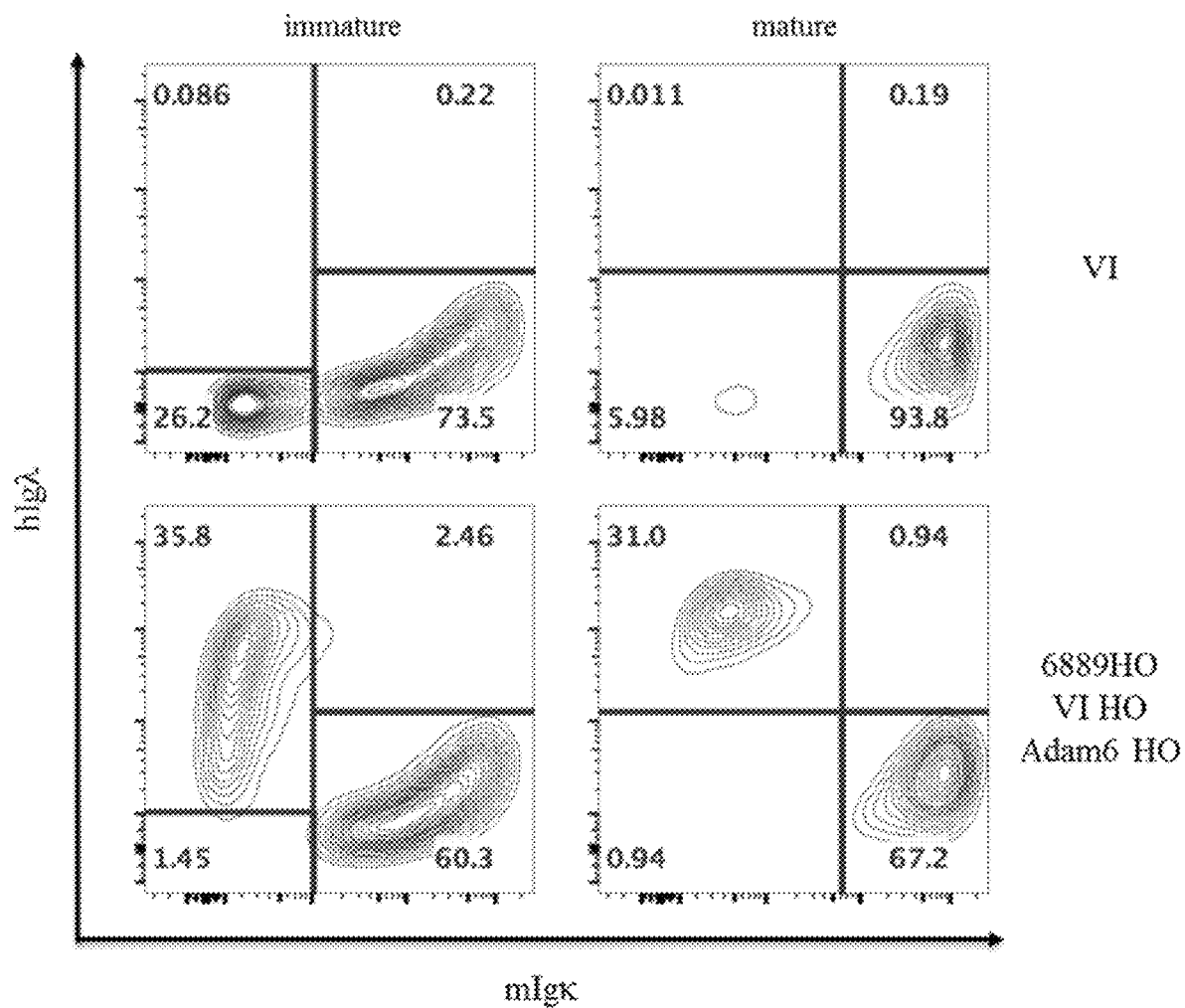
FIG. 21 shows representative contour plots indicating immature (CD19+IgM+B220$^{int}$-gated, left column) and mature (CD19+IgM+B220−-gated, right column) bone marrow showing expression of human Igλ (hIgλ, y-axis) and mouse Igκ (mIgκ, x-axis) from mice homozygous for insertion of the 6889 targeting vector (6889HO VI HO Adam6 HO) and reference engineered mice (VI). 6889HO/VI HO/Adam6 HO: see above; VI: see above.

Taken together, this example specifically demonstrates that rodents engineered to contain Igλ light chain loci as described herein generate strong antibody responses to immunization with an antigen of interest. Further, such engineered rodents demonstrate total and antigen-specific IgG levels comparable to wild-type controls, which confirms the capacity for a robust immune response in these engineered animals. Indeed, hIgλ titers were stronger than mIgλ titers upon immunization (FIGS. 17A and 17B). Thus, engineered rodents as described herein provide an improved in vivo system for the generation of antibodies for the development of human antibody-based therapeutics, in particular, human antibody-based therapeutics that utilize human Igλ light chain sequences.

EQUIVALENTS

It is to be appreciated by those skilled in the art that various alterations, modifications, and improvements to the present disclosure will readily occur to those skilled in the art. Such alterations, modifications, and improvements are intended to be part of the present disclosure, and are intended to be within the spirit and scope of the invention. Accordingly, the foregoing description and drawing are by way of example only and any invention described in the present disclosure if further described in detail by the claims that follow.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

The articles "a" and "an" in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or the entire group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. Where elements are presented as lists, (e.g., in Markush group or similar format) it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification.

Those skilled in the art will appreciate typical standards of deviation or error attributable to values obtained in assays or other processes as described herein. The publications, websites and other reference materials referenced herein to describe the background of the invention and to provide additional detail regarding its practice are hereby incorporated by reference in their entireties.

The invention claimed is:

1. A mouse whose germline genome comprises an endogenous immunoglobulin λ light chain locus comprising:
   (a) one or more human Vλ gene segments,
   (b) one or more human Jλ gene segments, and
   (c) one or more human Cλ gene segments,
wherein (a) and (b) are operably linked to (c) and a mouse Cλ gene segment, and wherein the endogenous immunoglobulin λ light chain locus further comprises: one or more mouse immunoglobulin λ light chain enhancers (Eλ), and one or more human immunoglobulin λ light chain enhancers (Eλ), and wherein the mouse expresses an immunoglobulin λ light chain comprising a human λ variable domain and either a human λ constant domain or a mouse λ constant domain.

2. The mouse of claim 1, wherein the endogenous immunoglobulin λ light chain locus comprises two mouse Eλs.

3. The mouse of claim 2, wherein the two mouse Eλs are a mouse Eλ and a mouse Eλ3-1.

4. The mouse of claim 1, wherein the endogenous immunoglobulin λ light chain locus comprises three human Eλs.

5. The mouse of claim 1, wherein the germline genome further comprises
   (i) an endogenous immunoglobulin heavy chain locus comprising insertion of one or more human $V_H$ gene segments, one or more human $D_H$ gene segments and one or more human $J_H$ gene segments, which human $V_H$, $D_H$ and $J_H$ gene segments are operably linked to a mouse immunoglobulin heavy chain constant region; or
   (ii) an endogenous immunoglobulin heavy chain locus comprising insertion of one or more human $V_H$ gene segments, one or more human $D_H$ gene segments and one or more human $J_H$ gene segments, which human $V_H$, $D_H$ and $J_H$ gene segments are operably linked to a mouse immunoglobulin heavy chain constant region, and an endogenous immunoglobulin κ light chain locus comprising insertion of one or more human Vκ gene segments and one or more human Jκ gene segments, which human Vκ and Jκ gene segments are operably linked to a mouse immunoglobulin Cκ region.

6. The mouse of claim 5, wherein the insertion of one or more human $V_H$ gene segments, one or more human $D_H$ gene segments and one or more human $J_H$ gene segments replace mouse $V_H$, $D_H$ gene segments.

7. The mouse of claim 6, wherein the insertion includes human non-coding DNA that naturally appears between human $V_H$, $D_H$, and $J_H$ gene segments, and combinations thereof.

8. The mouse of claim 5, wherein the insertion of one or more human Vκ gene segments and one or more human Jκ gene segments replace mouse Vκ and Jκ gene segments.

9. The mouse of claim 8, wherein the insertion includes human non-coding DNA that naturally appears between human Vκ and Jκ gene segments, and combinations thereof.

10. The mouse of claim 5, wherein the mouse immunoglobulin heavy chain constant region is an endogenous mouse immunoglobulin heavy chain constant region.

11. The mouse of claim 5, wherein the mouse Cκ region is an endogenous mouse Cκ region.

12. The mouse of claim 1, wherein the endogenous immunoglobulin λ light chain locus comprises a deletion of endogenous Vλ and Jλ gene segments, in whole or in part.

13. The mouse of claim 1, wherein the mouse Cλ gene segment is a mouse Cλ1 gene segment.

14. The mouse of claim 5, wherein the immunoglobulin κ light chain locus comprises insertion of the proximal Vκ duplication, in whole or in part, of a human immunoglobulin κ light chain locus.

15. The mouse of claim 5, wherein the immunoglobulin heavy chain locus lacks an endogenous mouse Adam6 gene.

16. The mouse of claim 15, wherein the immunoglobulin heavy chain locus further comprises insertion of one or more nucleotide sequences encoding one or more mouse Adam6 polypeptides.

17. The mouse of claim 5, wherein the mouse is homozygous for the endogenous immunoglobulin heavy chain locus.

18. The mouse of claim 5, wherein the mouse is homozygous for the endogenous immunoglobulin κ light chain locus.

19. The mouse of claim 1, wherein the mouse is homozygous for the endogenous immunoglobulin λ light chain locus.

20. A method of making a mouse whose germline genome comprises an engineered endogenous immunoglobulin λ light chain locus, the method comprising
   (a) introducing a DNA fragment into a mouse embryonic stem cell, said DNA fragment comprising a nucleotide sequence that includes
      (i) one or more human Vλ gene segments,
      (ii) one or more human Jλ gene segments, and
      (iii) one or more human Cλ gene segments,
      wherein (i)-(iii) are operably linked to a mouse Cλ gene segment, and
      wherein the nucleotide sequence further comprises one or more human immunoglobulin λ light chain enhancers (Eλ);
   (b) obtaining the mouse embryonic stem cell generated in (a); and
   (c) creating a mouse using the mouse embryonic stem cell of (b).

21. A method of making a mouse whose germline genome comprises an engineered endogenous immunoglobulin λ light chain locus, which engineered endogenous immunoglobulin λ light chain locus comprises insertion of one or more human Vλ gene segments, one or more human Jλ gene segments and one or more human Cλ gene segments, which human Vλ and Jλ gene segments are operably linked to a mouse or a human Cλ gene segment, and which endogenous immunoglobulin λ light chain locus further comprises one or more mouse immunoglobulin λ light chain enhancers (Eλ), and one or more human immunoglobulin λ light chain enhancers (Eλ), the method comprising
   modifying the germline genome of a mouse so that it comprises an engineered immunoglobulin λ light chain locus that includes insertion of one or more human Vλ gene segments, one or more human Jλ gene segments and one or more human Cλ gene segments, which human Vλ and Jλ gene segments are operably linked to a mouse or a human Cλ gene segment, and which endogenous immunoglobulin λ light chain locus further comprises one or more mouse immunoglobulin λ light chain enhancers (Eλ), and one or more human immunoglobulin λ light chain enhancers (Eλ), thereby making said mouse.

* * * * *

SEQUENCE LISTING

```
<160> NUMBER OF SEQ ID NOS: 141

<210> SEQ ID NO 1
<211> LENGTH: 317
<212> TYPE: DNA
<213> ORGANISM: Mus musculus

<400> SEQUENCE: 1
gccagcccaa gtcttcgcca tcagtcaccc tgtttccacc ttcctctgaa gagctcgaga      60
ctaacaaggc cacactggtg tgtacgatca ctgatttcta cccaggtgtg gtgacagtgg     120
actggaaggt agatggtacc cctgtcactc agggtatgga gacaacccag ccttccaaac     180
agagcaacaa caagtacatg gctagcagct acctgaccct gacagcaaga gcatgggaaa     240
ggcatagcag ttacagctgc caggtcactc atgaaggtca cactgtggag aagagtttgt     300
cccgtgctga ctgttcc                                                    317

<210> SEQ ID NO 2
<211> LENGTH: 106
<212> TYPE: PRT
<213> ORGANISM: Mus musculus

<400> SEQUENCE: 2

Gly Gln Pro Lys Ser Ser Pro Ser Val Thr Leu Phe Pro Pro Ser Ser
1               5                   10                  15

Glu Glu Leu Glu Thr Asn Lys Ala Thr Leu Val Cys Thr Ile Thr Asp
            20                  25                  30

Phe Tyr Pro Gly Val Val Thr Val Asp Trp Lys Val Asp Gly Thr Pro
        35                  40                  45

Val Thr Gln Gly Met Glu Thr Thr Gln Pro Ser Lys Gln Ser Asn Asn
    50                  55                  60

Lys Tyr Met Ala Ser Ser Tyr Leu Thr Leu Thr Ala Arg Ala Trp Glu
65                  70                  75                  80

Arg His Ser Ser Tyr Ser Cys Gln Val Thr His Glu Gly His Thr Val
                85                  90                  95

Glu Lys Ser Leu Ser Arg Ala Asp Cys Ser
            100                 105

<210> SEQ ID NO 3
<211> LENGTH: 314
<212> TYPE: DNA
<213> ORGANISM: Mus musculus

<400> SEQUENCE: 3
gtcagcccaa gtccactccc actctcaccg tgtttccacc ttcctctgag gagctcaagg      60
aaaacaaagc cacactggtg tgtctgattt ccaactttc cccgagtggt gtgacagtgg      120
cctggaaggc aaatggtaca cctatcaccc agggtgtgga cacttcaaat cccaccaaag     180
agggcaacaa gttcatggcc agcagcttcc tacatttgac atcggaccag tggagatctc     240
acaacagttt tacctgtcaa gttacacatg aagggacac tgtggagaag agtctgtctc      300
```

```
ctgcagaatg tctc                                                      314
```

<210> SEQ ID NO 4
<211> LENGTH: 105
<212> TYPE: PRT
<213> ORGANISM: Mus musculus

<400> SEQUENCE: 4

```
Gly Gln Pro Lys Ser Thr Pro Thr Leu Thr Val Phe Pro Pro Ser Ser
1               5                   10                  15

Glu Glu Leu Lys Glu Asn Lys Ala Thr Leu Val Cys Leu Ile Ser Asn
            20                  25                  30

Phe Ser Pro Ser Gly Val Thr Val Ala Trp Lys Ala Asn Gly Thr Pro
        35                  40                  45

Ile Thr Gln Gly Val Asp Thr Ser Asn Pro Thr Lys Glu Gly Asn Lys
    50                  55                  60

Phe Met Ala Ser Ser Phe Leu His Leu Thr Ser Asp Gln Trp Arg Ser
65                  70                  75                  80

His Asn Ser Phe Thr Cys Gln Val Thr His Glu Gly Asp Thr Val Glu
                85                  90                  95

Lys Ser Leu Ser Pro Ala Glu Cys Leu
            100                 105
```

<210> SEQ ID NO 5
<211> LENGTH: 314
<212> TYPE: DNA
<213> ORGANISM: Mus musculus

<400> SEQUENCE: 5

```
gtcagcccaa gtccactccc acactcacca tgtttccacc ttcccctgag gagctccagg    60
aaaacaaagc cacactcgtg tgtctgattt ccaattttc cccaagtggt gtgacagtgg    120
cctggaaggc aaatggtaca cctatcaccc agggtgtgga cacttcaaat cccaccaaag   180
aggacaacaa gtacatggcc agcagcttct tacatttgac atcggaccag tggagatctc   240
acaacagttt tacctgccaa gttacacatg aaggggacac tgtggagaag agtctgtctc   300
ctgcagaatg tctc                                                     314
```

<210> SEQ ID NO 6
<211> LENGTH: 105
<212> TYPE: PRT
<213> ORGANISM: Mus musculus

<400> SEQUENCE: 6

```
Gly Gln Pro Lys Ser Thr Pro Thr Leu Thr Met Phe Pro Pro Ser Pro
1               5                   10                  15

Glu Glu Leu Gln Glu Asn Lys Ala Thr Leu Val Cys Leu Ile Ser Asn
            20                  25                  30

Phe Ser Pro Ser Gly Val Thr Val Ala Trp Lys Ala Asn Gly Thr Pro
        35                  40                  45

Ile Thr Gln Gly Val Asp Thr Ser Asn Pro Thr Lys Glu Asp Asn Lys
    50                  55                  60

Tyr Met Ala Ser Ser Phe Leu His Leu Thr Ser Asp Gln Trp Arg Ser
65                  70                  75                  80

His Asn Ser Phe Thr Cys Gln Val Thr His Glu Gly Asp Thr Val Glu
                85                  90                  95

Lys Ser Leu Ser Pro Ala Glu Cys Leu
```

<210> SEQ ID NO 7
<211> LENGTH: 314
<212> TYPE: DNA
<213> ORGANISM: Rattus norvegicus

<400> SEQUENCE: 7

```
gtcagcccaa gtccactccc acactcacag tatttccacc ttcaactgag gagctccagg    60
gaaacaaagc cacactggtg tgtctgattt ctgatttcta cccgagtgat gtggaagtgg   120
cctggaaggc aaatggtgca cctatctccc agggtgtgga cactgcaaat cccaccaaac   180
agggcaacaa atacatcgcc agcagcttct tacgtttgac agcagaacag tggagatctc   240
gcaacagttt tacctgccaa gttacacatg aagggaacac tgtggagaag agtctgtctc   300
ctgcagaatg tgtc                                                     314
```

<210> SEQ ID NO 8
<211> LENGTH: 105
<212> TYPE: PRT
<213> ORGANISM: Rattus norvegicus

<400> SEQUENCE: 8

```
Gly Gln Pro Lys Ser Thr Pro Thr Leu Thr Val Phe Pro Pro Ser Thr
1               5                   10                  15

Glu Glu Leu Gln Gly Asn Lys Ala Thr Leu Val Cys Leu Ile Ser Asp
                20                  25                  30

Phe Tyr Pro Ser Asp Val Glu Val Ala Trp Lys Ala Asn Gly Ala Pro
            35                  40                  45

Ile Ser Gln Gly Val Asp Thr Ala Asn Pro Thr Lys Gln Gly Asn Lys
        50                  55                  60

Tyr Ile Ala Ser Ser Phe Leu Arg Leu Thr Ala Glu Gln Trp Arg Ser
65                  70                  75                  80

Arg Asn Ser Phe Thr Cys Gln Val Thr His Glu Gly Asn Thr Val Glu
                85                  90                  95

Lys Ser Leu Ser Pro Ala Glu Cys Val
            100                 105
```

<210> SEQ ID NO 9
<211> LENGTH: 314
<212> TYPE: DNA
<213> ORGANISM: Rattus norvegicus

<400> SEQUENCE: 9

```
accaacccaa ggctacgccc tcagtcaccc tgttcccacc ttcctctgaa gagctcaaga    60
ctgacaaggc tacactggtg tgtatggtga cagatttcta ccctggtgtt atgacagtgg   120
tctggaaggc agatggtacc cctatcactc agggtgtgga gactacccag cctttcaaac   180
agaacaacaa gtacatggct accagctacc tgcttttgac agcaaaagca tgggagactc   240
atagcaatta cagctgccag gtcactcacg aagagaacac tgtggagaag agtttgtccc   300
gtgctgagtg ttcc                                                     314
```

<210> SEQ ID NO 10
<211> LENGTH: 105
<212> TYPE: PRT
<213> ORGANISM: Rattus norvegicus

<400> SEQUENCE: 10

-continued

```
Asp Gln Pro Lys Ala Thr Pro Ser Val Thr Leu Phe Pro Pro Ser Ser
1               5                   10                  15

Glu Glu Leu Lys Thr Asp Lys Ala Thr Leu Val Cys Met Val Thr Asp
            20                  25                  30

Phe Tyr Pro Gly Val Met Thr Val Val Trp Lys Ala Asp Gly Thr Pro
        35                  40                  45

Ile Thr Gln Gly Val Glu Thr Gln Pro Phe Lys Gln Asn Asn Lys
    50                  55                  60

Tyr Met Ala Thr Ser Tyr Leu Leu Leu Thr Ala Lys Ala Trp Glu Thr
65                  70                  75                  80

His Ser Asn Tyr Ser Cys Gln Val Thr His Glu Glu Asn Thr Val Glu
                85                  90                  95

Lys Ser Leu Ser Arg Ala Glu Cys Ser
            100                 105
```

<210> SEQ ID NO 11
<211> LENGTH: 314
<212> TYPE: DNA
<213> ORGANISM: Rattus norvegicus

<400> SEQUENCE: 11

```
gtcagcccaa gtccactccc acactcacag tatttccacc ttcaactgag gagctccagg      60
gaaacaaagc cacactggtg tgtctgattt ctgatttcta cccgagtgat gtggaagtgg     120
cctggaaggc aaatggtgca cctatctccc agggtgtgga cactgcaaat cccaccaaac     180
agggcaacaa atacatcgcc agcagcttct acgtttgac agcagaacag tggagatctc     240
gcaacagttt tacctgccaa gttacacatg aagggaacac tgtggaaaag agtctgtctc     300
ctgcagagtg tgtc                                                      314
```

<210> SEQ ID NO 12
<211> LENGTH: 105
<212> TYPE: PRT
<213> ORGANISM: Rattus norvegicus

<400> SEQUENCE: 12

```
Gly Gln Pro Lys Ser Thr Pro Thr Leu Thr Val Phe Pro Pro Ser Thr
1               5                   10                  15

Glu Glu Leu Gln Gly Asn Lys Ala Thr Leu Val Cys Leu Ile Ser Asp
            20                  25                  30

Phe Tyr Pro Ser Asp Val Glu Val Ala Trp Lys Ala Asn Gly Ala Pro
        35                  40                  45

Ile Ser Gln Gly Val Asp Thr Ala Asn Pro Thr Lys Gln Gly Asn Lys
    50                  55                  60

Tyr Ile Ala Ser Ser Phe Leu Arg Leu Thr Ala Glu Gln Trp Arg Ser
65                  70                  75                  80

Arg Asn Ser Phe Thr Cys Gln Val Thr His Glu Gly Asn Thr Val Glu
                85                  90                  95

Lys Ser Leu Ser Pro Ala Glu Cys Val
            100                 105
```

<210> SEQ ID NO 13
<211> LENGTH: 314
<212> TYPE: DNA
<213> ORGANISM: Rattus norvegicus

<400> SEQUENCE: 13

```
accaacccaa ggctacgccc tcagtcaccc tgttcccacc ttcctctgaa gagctcaaga      60
```

```
ctgacaaggc tacactggtg tgtatggtga cagatttcta ccctggtgtt atgacagtgg    120
tctggaaggc agatggtacc cctatcactc agggtgtgga gactacccag cctttcaaac    180
agaacaacaa gtacatggct accagctacc tgcttttgac agcaaaagca tgggagactc    240
atagcaatta cagctgccag gtcactcacg aagagaacac tgtggagaag agtttgtccc    300
gtgctgagtg ttcc                                                      314
```

```
<210> SEQ ID NO 14
<211> LENGTH: 105
<212> TYPE: PRT
<213> ORGANISM: Rattus norvegicus

<400> SEQUENCE: 14
```

Asp Gln Pro Lys Ala Thr Pro Ser Val Thr Leu Phe Pro Pro Ser Ser
1               5                   10                  15

Glu Glu Leu Lys Thr Asp Lys Ala Thr Leu Val Cys Met Val Thr Asp
                20                  25                  30

Phe Tyr Pro Gly Val Met Thr Val Val Trp Lys Ala Asp Gly Thr Pro
            35                  40                  45

Ile Thr Gln Gly Val Glu Thr Thr Gln Pro Phe Lys Gln Asn Asn Lys
        50                  55                  60

Tyr Met Ala Thr Ser Tyr Leu Leu Leu Thr Ala Lys Ala Trp Glu Thr
65                  70                  75                  80

His Ser Asn Tyr Ser Cys Gln Val Thr His Glu Glu Asn Thr Val Glu
                85                  90                  95

Lys Ser Leu Ser Arg Ala Glu Cys Ser
            100                 105

```
<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gcatggccta gagataacaa gac                                             23

<210> SEQ ID NO 16
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ggccttggat aacctcagga tac                                             23

<210> SEQ ID NO 17
<211> LENGTH: 28
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 17
tccatcccaa tagatctcat tccttccc                                        28
```

<210> SEQ ID NO 18
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ccctgtcaag tctccaaggt tg                                              22

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
cactgtggcc caaggatcac                                                 20

<210> SEQ ID NO 20
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 20
cactctgccc agggagtgtc tgg                                             23

<210> SEQ ID NO 21
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
gcatggccta gagataacaa gactg                                           25

<210> SEQ ID NO 22
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
gtgctcttcc cttgggaga                                                  19

<210> SEQ ID NO 23
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 23
tccatcccaa tagagcgatc gca                                             23

-continued

<210> SEQ ID NO 24
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
ggtggagagg ctattcggc                                                  19

<210> SEQ ID NO 25
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
gaacacggcg gcatcag                                                    17

<210> SEQ ID NO 26
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 26
tgggcacaac agacaatcgg ctg                                             23

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
agctgaatgg aaacaaggca a                                               21

<210> SEQ ID NO 28
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
ggagacaatg ccccagtga                                                  19

<210> SEQ ID NO 29
<211> LENGTH: 31
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 29
tgacatgaac catctgtttc tctctcgaca a                                    31

<210> SEQ ID NO 30

```
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
ccaccgccaa gttgacctc                                                  19

<210> SEQ ID NO 31
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
tgaaggacta aggcccagga tag                                             23

<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 32
agtacagcaa gggcccagcc t                                               21

<210> SEQ ID NO 33
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
tggctcagtg acaagagtc                                                  19

<210> SEQ ID NO 34
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
ccagggacac agcctttgc                                                  19

<210> SEQ ID NO 35
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 35
tgcattgcag agaccaggga cc                                              22

<210> SEQ ID NO 36
<211> LENGTH: 17
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
tgcggccgat cttagcc                                                      17

<210> SEQ ID NO 37
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
acgagcgggt tcggcccatt c                                                 21

<210> SEQ ID NO 38
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 38
ttgaccgatt ccttgcgg                                                     18

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
tgtcgggcgt acacaaatcg                                                   20

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
gggcgtcggt ttccactatc                                                   20

<210> SEQ ID NO 41
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 41
ccgtctggac cgatggctgt gt                                                22

<210> SEQ ID NO 42
<211> LENGTH: 23
<212> TYPE: DNA
```

<213> ORGANISM: Artificial Sequence
<220> FEATURE:
<223> OTHER INFORMATION: Description of Artificial Sequence: Synthetic
      primer

<400> SEQUENCE: 42
cgacgtctgt cgagaagttt ctg                                              23

<210> SEQ ID NO 43
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
cacgccctcc tacatcgaa                                                   19

<210> SEQ ID NO 44
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 44
agttcgacag cgtgtccgac ctga                                             24

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
aacaaccgag ctccaggtgt                                                  20

<210> SEQ ID NO 46
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
agggcagcct tgtctccaa                                                   19

<210> SEQ ID NO 47
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 47
cctgccagat tctcaggctc cctg                                             24

<210> SEQ ID NO 48
<211> LENGTH: 20
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 48
ggaggtcagg aatgagggac                                              20

<210> SEQ ID NO 49
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
cacttgctca ctgcaaaagc a                                            21

<210> SEQ ID NO 50
<211> LENGTH: 37
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 50
tgtgggattt tggaattcta tctcactgat aggaaag                           37

<210> SEQ ID NO 51
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
gcagagagga ttcaagagct gg                                           22

<210> SEQ ID NO 52
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
tttttgcaat gcttcacctg a                                            21

<210> SEQ ID NO 53
<211> LENGTH: 28
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 53
caggtgtctg tattggaggt caatggca                                     28

<210> SEQ ID NO 54
<211> LENGTH: 19
<212> TYPE: DNA
<213> ORGANISM: Artificial Sequence
<220> FEATURE:
```

<223> OTHER INFORMATION: Description of Artificial Sequence: Synthetic
    primer

<400> SEQUENCE: 54
gatttgctga gggcagggt                                           19

<210> SEQ ID NO 55
<211> LENGTH: 21
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 55
ccccaagtct gatccttcct t                                        21

<210> SEQ ID NO 56
<211> LENGTH: 30
<212> TYPE: DNA
<213> ORGANISM: Artificial Sequence
<220> FEATURE:
<223> OTHER INFORMATION: Description of Artificial Sequence: Synthetic
    probe

<400> SEQUENCE: 56
ccttcatact cttgcatcct cccttctcca                               30

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 57
gctgaccaac gatcgcctaa                                          20

<210> SEQ ID NO 58
<211> LENGTH: 19
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 58
taagcgccac actgcacct                                           19

<210> SEQ ID NO 59
<211> LENGTH: 35
<212> TYPE: DNA
<213> ORGANISM: Artificial Sequence
<220> FEATURE:
<223> OTHER INFORMATION: Description of Artificial Sequence: Synthetic
    probe

<400> SEQUENCE: 59
ttccttctct tctgtgactc aattatttgt ggaca                         35

<210> SEQ ID NO 60
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 60
aactgctgat gcactgggc                                                    19

<210> SEQ ID NO 61
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
tgaatgcatg gagttggcc                                                    19

<210> SEQ ID NO 62
<211> LENGTH: 32
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 62
tctcctttgc agtggcttaa ttagctgagt ca                                     32

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
ccctggtgaa gcatgtttgc                                                   20

<210> SEQ ID NO 64
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
tgtggcctgt ctgccttacg                                                   20

<210> SEQ ID NO 65
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 65
ccaagcagga ggtgctcagt tcccaa                                            26

<210> SEQ ID NO 66
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
gggacaggtg aagggcctat c                                                    21

<210> SEQ ID NO 67
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
tggtccacag gatgcagttg                                                      20

<210> SEQ ID NO 68
<211> LENGTH: 29
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 68
cgcacctgta tctaaccagt cccagcatc                                            29

<210> SEQ ID NO 69
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
cacacctaga ccccggaagt c                                                    21

<210> SEQ ID NO 70
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
tcgctttgcc agttgattct c                                                    21

<210> SEQ ID NO 71
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 71
tccacactgt cggctgggag ctca                                                 24

<210> SEQ ID NO 72
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 72
cgcttcaatg acccaacca                                                    19

<210> SEQ ID NO 73
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
tgttgaaacg taatccccaa tg                                                22

<210> SEQ ID NO 74
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 74
ctcccaccag gtgccacatg ca                                                22

<210> SEQ ID NO 75
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
gggctacttg aggaccttgc t                                                 21

<210> SEQ ID NO 76
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76 gacagcccctt acagagtttg gaa                                              23

<210> SEQ ID NO 77
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 77
cagggcctcc atcccaggca                                                   20

<210> SEQ ID NO 78
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
```
agtgcaaaca gcaagatgag atct                                          24

<210> SEQ ID NO 79
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
ggcgctgagc agaaaacaa                                                19

<210> SEQ ID NO 80
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 80
agaccaccaa gaaggcccag agtgacc                                       27

<210> SEQ ID NO 81
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
aagaccagga gctctgccta agt                                           23

<210> SEQ ID NO 82
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
cccatcacga actgaagttg ag                                            22

<210> SEQ ID NO 83
<211> LENGTH: 28
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 83
ccccagtgtg tgaatcactc taccctcc                                      28

<210> SEQ ID NO 84
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
cccttcatga tgctttgtca tc                                              22

<210> SEQ ID NO 85
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
gtagtggcaa aggcagattc ct                                              22

<210> SEQ ID NO 86
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 86
ccttcactcc ccgaatgccc tcc                                             23

<210> SEQ ID NO 87
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
gccctgctcc agtcttattc c                                               21

<210> SEQ ID NO 88
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
ctgcgtctgg gctttgct                                                   18

<210> SEQ ID NO 89
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 89
ccacagatcc caagttgagc ctgc                                            24

<210> SEQ ID NO 90
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
gtgagcggta ccctggaatc                                                 20

<210> SEQ ID NO 91
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
agcctcgtct tcggtcagga c                                           21

<210> SEQ ID NO 92
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 92
tgaacgattc tctgggtcca cc                                          22

<210> SEQ ID NO 93
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
cctgagccag gatggaatga ag                                          22

<210> SEQ ID NO 94
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
ggccgtgatt taagaggttg ttag                                        24

<210> SEQ ID NO 95
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 95
actgtggacc ccagataatt cccctg                                      26

<210> SEQ ID NO 96
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96
gagtgcagtg gcagaatctt g                                           21

<210> SEQ ID NO 97
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 97
ggcagggagc attggtaga                                                    19

<210> SEQ ID NO 98
<211> LENGTH: 24
<212> TYPE: DNA
<213> ORGANISM: Artificial Sequence
<220> FEATURE:
<223> OTHER INFORMATION: Description of Artificial Sequence: Synthetic probe

<400> SEQUENCE: 98
tactgaaatc tcagcctccc aggc                                              24

<210> SEQ ID NO 99
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 99
tggctccagc tcaggaaav                                                    19

<210> SEQ ID NO 100
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 100
cccgggagtt acagtaatag tca                                               23

<210> SEQ ID NO 101
<211> LENGTH: 25
<212> TYPE: DNA
<213> ORGANISM: Artificial Sequence
<220> FEATURE:
<223> OTHER INFORMATION: Description of Artificial Sequence: Synthetic probe

<400> SEQUENCE: 101
cacagcttcc ttgaccatca ctggg                                             25

<210> SEQ ID NO 102
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 102
ccagcccacc caattatgct a                                                 21

```
<210> SEQ ID NO 103
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 103
gcgtttaggg ccaggtacaa at                                              22

<210> SEQ ID NO 104
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 104
tggatctgtc aaacactttc agagca                                          26

<210> SEQ ID NO 105
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 105
gaggctgcag ggatgtaac                                                  19

<210> SEQ ID NO 106
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 106
cccattccag gtccaattct ca                                              22

<210> SEQ ID NO 107
<211> LENGTH: 28
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 107
tttgtaaagt gcataacaca gaccctga                                        28

<210> SEQ ID NO 108
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 108
gggtacaatg agacaagaat caga                                            24

<210> SEQ ID NO 109
```

```
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 109
gaaaggcaaa cacaagtcac agatg                                          25

<210> SEQ ID NO 110
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 110
tcagccctct ggaatgtaag gatca                                          25

<210> SEQ ID NO 111
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 111
gctgcatctt ctcaagtctt taagt                                          25

<210> SEQ ID NO 112
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 112
gggaaccagt caggaactca tac                                            23

<210> SEQ ID NO 113
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 113
taagcagacc tatgcatcgc tca                                            23

<210> SEQ ID NO 114
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 114
gtgctccttg ttcccttcac ag                                             22

<210> SEQ ID NO 115
<211> LENGTH: 24
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 115
ctgaagcatc tgcaccatca aatc                                               24

<210> SEQ ID NO 116
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 116
ccacccacat gtgcccgtgt g                                                  21

<210> SEQ ID NO 117
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 117
ccctattcac tgagttctgg aagctctgct atttccatga tcgttcacac tgacccctgt        60
tgatcttacc ggtaccgaag ttcctattcc gaagttccta                             100

<210> SEQ ID NO 118
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 118
ttctctagaa agtataggaa cttcctaggg tttcaccggt ggcgcgccga tgtacatcag        60
ttcagtctgg aaaggtggaa cagctccagg tgaaggcagg                             100

<210> SEQ ID NO 119
<211> LENGTH: 150
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 119
ctctacgggt gatgttcatc taaggtgaca ggagtcagtg agggcttctc aagctttatc        60
tatgtcgggt gcggagaaag aggtaatgaa atggcactcg agccctgctg gtgccttctg       120
ttgtatccac gccttcagta gatttgatga                                        150

<210> SEQ ID NO 120
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 120 gagttttttcc ctttcctgtc tgtcgaaggc taaggtctaa gcctgtctgg tcacactagg    60
taaagaattt ctttcttctc tagatgcttt gtctcatttc                           100

<210> SEQ ID NO 121
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 121
tatgtcactg gaatttagag tagtgtgtgg aatgtcttgg caacctggac acgcgtcctg    60
gcacccagtg agaaagtggc cctgagggag aggctcatag                          100

<210> SEQ ID NO 122
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 122
agcagccgac atttagcaaa gaggattgga aaatgaaccc cccttaaaa tacagttaaa     60 cacagaggag ggagcaaacc ggtataactt cgtataatgt                          100

<210> SEQ ID NO 123
<211> LENGTH: 130
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 123
atgctatacg aagttatgtc gacctcgagg gggggcccgg taccatctat gtcgggtgcg    60
gagaaagagg taatgaaatg gtctcattcc ttccctgtct caaggcataa tggttcaata   120
tgcacctgta                                                           130

<210> SEQ ID NO 124
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 124
ttctctccaa gacttgaggt gcttttttgtt gtatactttc cctttctgta ttctgcttca    60
tacctatact ggtaccgaag ttcctattcc gaagttccta                          100

<210> SEQ ID NO 125
<211> LENGTH: 140
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 125

```
ttctctagaa agtataggaa cttcctaggg tttcaccggt ggcgcgcctg ccatttcatt      60
acctctttct ccgcacccga catagataag ctttggattg gattcagtga gcaagaattc     120
acaaacacaa tggacttatc                                                 140

<210> SEQ ID NO 126
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 126
ttctctccaa gacttgaggt gcttttttgtt gtatactttc cctttctgta ttctgcttca     60
tacctatact ggtaccgaag ttcctattcc gaagttccta                           100

<210> SEQ ID NO 127
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 127
ttctctagaa agtataggaa cttcctaggg tttcaccggt ggcgcgcccc cctgctggtg      60 cctttgttg tatccacgcc ttcagtagat ttgatgatgc                            100

<210> SEQ ID NO 128
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 128
ttctctccaa gacttgaggt gcttttttgtt gtatactttc cctttctgta ttctgcttca     60
tacctatact ggtaccgaag ttcctattcc gaagttccta                           100

<210> SEQ ID NO 129
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 129
ttctctagaa agtataggaa cttcctaggg tttcaccggt ggcgcgccga tgtacatcag      60
ttcagtctgg aaaggtggaa cagctccagg tgaaggcagg                           100

<210> SEQ ID NO 130
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 130
cgacctgatg cagctctcgg                                                  20
```

<210> SEQ ID NO 131
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 131
cacyagtgtg gccttgttgg cttg                                      24

<210> SEQ ID NO 132
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 132
caccagtgtg gccttgttag tctc                                      24

<210> SEQ ID NO 133
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 133
cccatgtact ctgcgttgat accactgctt                                30

<210> SEQ ID NO 134
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 134
gtgactggag ttcagacgtg tgctcttccg atctaagcag tggtatcaac gcagagt   57

<210> SEQ ID NO 135
<211> LENGTH: 56
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 135
acactctttc cctacacgac gctcttccga tctcagagga gggcgggaac agagtg    56

<210> SEQ ID NO 136
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 136
acactctttc cctacacgac gctcttccga tctaaggtgg aaacagggtg actgatg   57

```
<210> SEQ ID NO 137
<211> LENGTH: 67
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (30)..(35)
<223> OTHER INFORMATION: a, c, t, g, unknown or other

<400> SEQUENCE: 137
aatgatacgg cgaccaccga gatctacacn nnnnnacact ctttccctac acgacgctct    60
tccgatc                                                             67

<210> SEQ ID NO 138
<211> LENGTH: 63
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (25)..(29)
<223> OTHER INFORMATION: a, c, t, g, unknown or other

<400> SEQUENCE: 138
caagcagaag acggcatacg agatnnnnng tgactggagt tcagacgtgt gctcttccga    60
tct                                                                 63

<210> SEQ ID NO 139
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 139
gtacatcttg tcttcaacgt                                               20

<210> SEQ ID NO 140
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 140
gtccataatt aatgtagtta c                                             21

<210> SEQ ID NO 141
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 141
aagcagtggt atcaacgcag agtacat                                       27
```